(12) United States Patent
Pettit et al.

(10) Patent No.: US 9,266,927 B2
(45) Date of Patent: Feb. 23, 2016

(54) CYCLOSPORIN A ANALOGS

(71) Applicant: Allergan, Inc., Irvine, CA (US)

(72) Inventors: Simon N. Pettit, Colchester (GB);
Andrew D. Jones, Saffron Walden (GB);
Catherine Simone V. Frydrych,
Sawbridgeworth (GB); **William R.
Carling**, Bishops Stortford (GB);
Michael E. Garst, Newport Beach, CA
(US)

(73) Assignee: Allergan, Inc., Irvine, CA (US)

( * ) Notice: Subject to any disclaimer, the term of this patent is extended or adjusted under 35 U.S.C. 154(b) by 31 days.

(21) Appl. No.: 13/905,491

(22) Filed: May 30, 2013

(65) Prior Publication Data

US 2013/0324480 A1 Dec. 5, 2013

Related U.S. Application Data

(60) Provisional application No. 61/654,388, filed on Jun. 1, 2012.

(51) Int. Cl.
*A61K 38/13* (2006.01)
*C07K 7/64* (2006.01)
*A61K 38/00* (2006.01)

(52) U.S. Cl.
CPC ........ *C07K 7/645* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,798,823 | A | 1/1989 | Witzel |
| 4,885,276 | A | 12/1989 | Witzel |
| 5,214,130 | A | 5/1993 | Patchett et al. |
| 5,227,467 | A | 7/1993 | Durette et al. |
| 5,474,979 | A | 12/1995 | Ding et al. |
| 6,790,935 | B1 | 9/2004 | Mutter et al. |
| 7,297,679 | B2 | 11/2007 | Chang et al. |
| 7,511,013 | B2 | 3/2009 | Molino et al. |
| 7,538,084 | B2 | 5/2009 | Molino et al. |
| 7,696,166 | B2 | 4/2010 | Molino et al. |
| 7,718,767 | B2 | 5/2010 | Fliri et al. |
| 7,968,518 | B2 | 6/2011 | Hijikata et al. |
| 2003/0165545 | A1 | 9/2003 | Huth et al. |
| 2003/0186855 | A1 | 10/2003 | Or et al. |
| 2003/0212249 | A1 | 11/2003 | Naicker et al. |
| 2004/0110666 | A1 | 6/2004 | Or et al. |
| 2005/0059583 | A1 | 3/2005 | Acheampong et al. |
| 2005/0277584 | A1 | 12/2005 | Tien et al. |
| 2006/0069015 | A1 | 3/2006 | Molino et al. |
| 2006/0105944 | A1 | 5/2006 | Stern et al. |
| 2006/0105945 | A1 | 5/2006 | Stern et al. |
| 2007/0015694 | A1 | 1/2007 | Chang et al. |
| 2007/0027072 | A1 | 2/2007 | Chang et al. |
| 2007/0087962 | A1 | 4/2007 | Tien et al. |
| 2007/0191266 | A1 | 8/2007 | Brin |
| 2007/0207951 | A1 | 9/2007 | Schiffman |
| 2007/0299004 | A1 | 12/2007 | Acheampong et al. |
| 2008/0146497 | A1 | 6/2008 | Schiffman et al. |
| 2008/0207494 | A1 | 8/2008 | Chang et al. |
| 2009/0312300 | A1 | 12/2009 | Li et al. |
| 2010/0167996 | A1 | 7/2010 | Fliri et al. |
| 2010/0209390 | A1 | 8/2010 | Or et al. |
| 2011/0008284 | A1 | 1/2011 | Gao et al. |
| 2011/0008285 | A1 | 1/2011 | Long et al. |
| 2011/0008286 | A1 | 1/2011 | Wang et al. |
| 2011/0063295 | A1 | 3/2011 | Kuo |
| 2012/0088734 | A1 | 4/2012 | Frydrych et al. |
| 2012/0135939 | A1 | 5/2012 | Garst et al. |
| 2012/0190661 | A1 | 7/2012 | Trogden et al. |
| 2013/0122059 | A1 | 5/2013 | Gore et al. |
| 2013/0123193 | A1 | 5/2013 | Wu et al. |
| 2013/0123194 | A1 | 5/2013 | Blanda et al. |
| 2013/0123195 | A1 | 5/2013 | Blanda et al. |
| 2013/0210704 | A1 | 8/2013 | Su |

FOREIGN PATENT DOCUMENTS

| | | |
|---|---|---|
| EP | 0194972 | 7/1992 |
| WO | WO92-13545 | 8/1992 |
| WO | WO00-61168 | 10/2000 |
| WO | WO02-083143 | 10/2002 |
| WO | 03-033010 | 4/2003 |
| WO | 03-033526 | 4/2003 |
| WO | WO 2004/082629 | * 9/2004 |
| WO | WO2004-082629 | 9/2004 |
| WO | WO2006-039668 | 4/2006 |
| WO | WO2007-047334 | 4/2007 |
| WO | WO2007-008894 | 6/2007 |
| WO | WO2007-112345 | 10/2007 |
| WO | WO2007-136759 | 11/2007 |
| WO | WO2008-014200 | 1/2008 |
| WO | WO2008-137617 | 11/2008 |

(Continued)

OTHER PUBLICATIONS

Evers, 2003, Bioorganic & Medicinal Chemistry Letters, 13, 4415-4419, cited in IDS filed May 30, 2013.*
Levitsky, ChemBioChem 2005, 6, 890-899.*
Aebi et al, "Synthesis, conformation and immunosuppressive activity of a conformationally restricted cyclosporine lactam analogue", J. Med. Chem., 1988, vol. 31, pp. 1805-1815.
Bron et al. (2007) "Methodologies to Diagnose and Monitor Dry Eye Disease:Report of the Diagnostic Methodology Subcommittee of the International Dry Eye WorkShop (2007)" *Ocul. Surf.* 5(2):108-152.
Chen et al., "A sensitive enzyme immunoassay for cyclosporin A using antibodies generated against a novel hapten", Research Communications in Molecular Pathology and Pharmacology (1995), 88(3): 317-26.

(Continued)

*Primary Examiner* — Satyanarayana R Gudibande
(74) *Attorney, Agent, or Firm* — Barbara C. Potts

(57) ABSTRACT

The present invention relates to novel cyclosporin analogs, processes for preparing them, pharmaceutical compositions containing them, and methods for using these analogs and the compositions containing them for the treatment of medical conditions, including but not limited to ocular conditions such as dry eye.

17 Claims, No Drawings

(56) References Cited

FOREIGN PATENT DOCUMENTS

| WO | WO2008-143996 | 11/2008 |
|---|---|---|
| WO | WO2009-099467 | 8/2009 |
| WO | WO2009-148615 | 12/2009 |
| WO | WO2010-006117 | 1/2010 |
| WO | WO 2010-012073 | 2/2010 |
| WO | WO2010-076329 | 7/2010 |
| WO | WO2010-080913 | 7/2010 |
| WO | WO2010-080915 | 7/2010 |
| WO | WO2010-088573 | 7/2010 |
| WO | WO2010-120838 | 10/2010 |
| WO | WO2010/127301 | 11/2010 |
| WO | WO2010-138422 | 12/2010 |
| WO | WO2010-138423 | 12/2010 |
| WO | WO2011-020596 | 2/2011 |
| WO | WO2011-150102 | 12/2011 |
| WO | 2012009715 A2 | 1/2012 |
| WO | 2012021796 A2 | 2/2012 |
| WO | 2012051193 A1 | 4/2012 |
| WO | WO2012-051193 | 4/2012 |
| WO | 2012079172 A1 | 6/2012 |
| WO | WO2012-075494 | 6/2012 |
| WO | WO2012-079172 | 6/2012 |
| WO | WO2012-166610 | 12/2012 |
| WO | WO2013-052424 | 4/2013 |
| WO | 2014145686 A2 | 9/2014 |

OTHER PUBLICATIONS

Cross et al, "Rules for the Nomenclature of Organic Chemistry Section E: Stereochemistry", 1976, Pure & Appl. Chem. vol. 45, pp. 11-30.
Eberle et al, "Preparation and in Vitro Activities of Ethers of [D-Serine]8-cyclosporin", Journal of Medicinal Chemistry (1995), 38(11), 1853-64.
Eberle et al. << Synthesis of the Main Metabolite (OL-17) of Cyclosporin A >>, *J. Org. Chem.* 1992, 57, 2689-2691.
Enzo Life Sciences, << Calcineurin Phosphatase Assay Kit, A complete colorimetric assay kit for measuring calcineurin phosphatase activity >>, Instruction Manual BML-AK804, Feb. 16, 2012, 8 pages.
Evers et al, "Synthesis of non-immunosuppressive cyclophilin-cyclosporin A derivatives as potential anti-HIV-1 drugs", Bioorganic & Medicinal Chemistry Letters (2003), 13 (24, 4415-4419.
Fliri et al, << Cyclosporins Structure-Activity Relationships >>, Anals New York Academy of Sciences, Nov. 30, 1993; 47-53.
Greene et al, *Protective Groups in organic Synthesis* (1991), Wiley, New York. Table of Contents Only.
Handbook of Pharmaceutical Salts, P.Heinrich Stahal & Camille G. Wermuth (Eds), Verlag Helvetica Chemica Acta—Zürich, 2002, 329-345.
Hubler et al, << Synthetic routes to NetXaa$^4$-cyclosporin A derivatives as potential anti-HIV 2 drugs >>, *Tet. Lett.* 2000, 41, 7193-7196.
Kitahara et al, "Synthesis of the Enantiomers of Sclerosporin and Sclerosporal to Determine the Absolute Configuration of the Natural Products", Tetrahedron Letters, 1984, vol. 25, No. 41, 4685-4688.
Lawen et al, "Enzymatic biosynthesis of cyclosporine A and analogues", Biochimie (1992), 74, 511-516.
Lemp et al. (2007) "The Definition and Classification of Dry Eye Disease: Report of the Definition and Classification Subcommittee of the International Dry Eye Workshop" *Ocul. Surf.* 5:75-92.
Pflugfelder, Antiinflammatory therapy for dry eye, Am. J. Ophthalmol. 2004, 137(2) :337-342.
Quesniaux et al, << Cyclophilin binds to the region of cyclosporine involved in its immunosuppressive activity >>, Eur. J. Immunology, 1987, vol. 17, pp. 1359-1365.
Rao et al, ,, Synthesis of 2-(N-disubstituted amino)ethyltriphenylphosphonium bromides, Tetrahedron Letters 49, 2008, 824-826.
Seebach et al, ,, Modification of Cyclosporin A ($CS^H$): Generation of an Enolate at the Sarcosine Residue and Reactions with Electrophiles, Helvetica Chimica Acta, vol. 76 (1993), 1564-1590.
Sigal et al, "Is cyclophilin involved in the immunosuppressive and nephrotoxic mechanism of action of cyclosporine A?", J. Exp. Med., Mar. 1991, vol. 173, pp. 619-628.
Survase et al,"Cyclosporin A—A review on fermentative production, downstream processing and pharmacological applications", Biotechnology Advances, 29 (2011) 418-435.
Zuker et al, "Augmentation of mycophenolate mofetil in renal transplant patients receiving Prograf and Cellcept in combination therapy", Transplantation Proceedings (1997), 29(1/2), 334-336.
"Blepharitis", www.eyesite.org/cornea-and-eye-surface/blepharitis, 2000-2013, downloaded on May 28, 2013, 6 pages.
International Searching Authority—PCT/US2013/043266 International Filing Date May 30, 2013.
International Searching Authority—PCT/US2013/043266—International Filing Date May 30, 2013.

* cited by examiner

CYCLOSPORIN A ANALOGS

CROSS-REFERENCE TO RELATED APPLICATIONS

This application claims the benefit of U.S. Provisional Patent Application Ser. No. 61/654,388, filed on Jun. 1, 2012, the disclosure of which is incorporated herein by reference.

FIELD OF THE INVENTION

The present invention relates to novel cyclosporin analogs, processes for preparing them, pharmaceutical compositions containing them, and methods for using these analogs and the compositions containing them for the treatment of medical conditions, including but not limited to ocular conditions such as dry eye.

BACKGROUND OF THE INVENTION

Cyclosporins are a class of poly-N-methylated cyclic undecapeptides. The first cyclosporin to be isolated was cyclosporin A (CAS Registry Number: 59865-13-3), a naturally occurring fungal metabolite having the following structure:

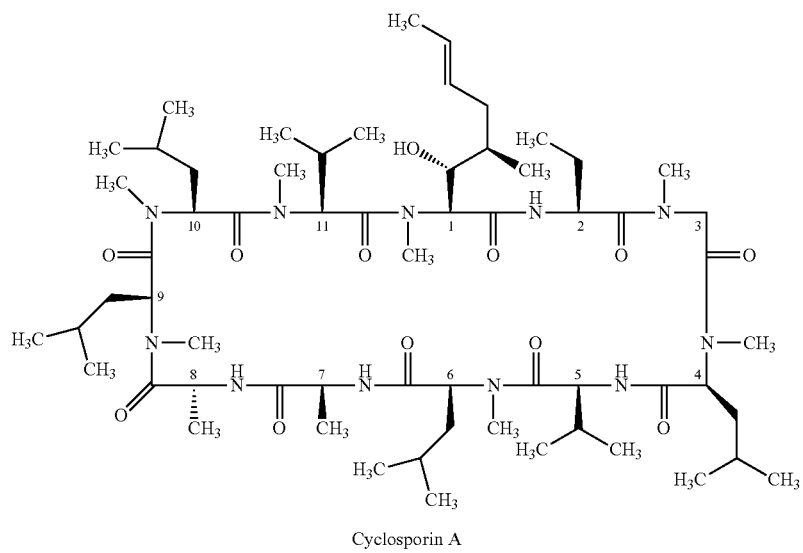 [SMILES: C/C=C/C[C@@H](C)[C@@H](O)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

Cyclosporin A

As shown by the structure above, Cyclosporin A consists of 11 amino acids and can be further represented as follows:

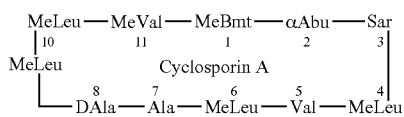

where:

MeBmt is (4R)-4-[(E)-2-butenyl]-4-methyl-L-threonine;

αAbu is L-α-aminobutyric acid;

Sar is sarcosine;

MeLeu is N-methyl-L-leucine;

Val is L-valine;

Ala is L-alanine;

DAla is D-alanine; and

MeVal is N-methyl-L-valine.

The numbers 1-11 are used to designate each of the eleven amino acids. Thus, MeBMT is the amino acid at position 1; sarcosine, the amino acid at position 3. In certain instances, the description herein may refer to the amino acid side chain at any one of positions 1-11. The carbon to which the amino acid side chain is attached is referred to as the alpha (α) carbon.

Cyclosporin A is best known for its immunosuppressive properties and is commonly prescribed for use in patients that have undergone bone marrow or organ transplantation. The present invention relates to the discovery of water-soluble analogs of cyclosporin A that are potent inhibitors of cyclophilin.

SUMMARY OF THE INVENTION

Accordingly, the present invention describes compounds having Formula I:

Formula I

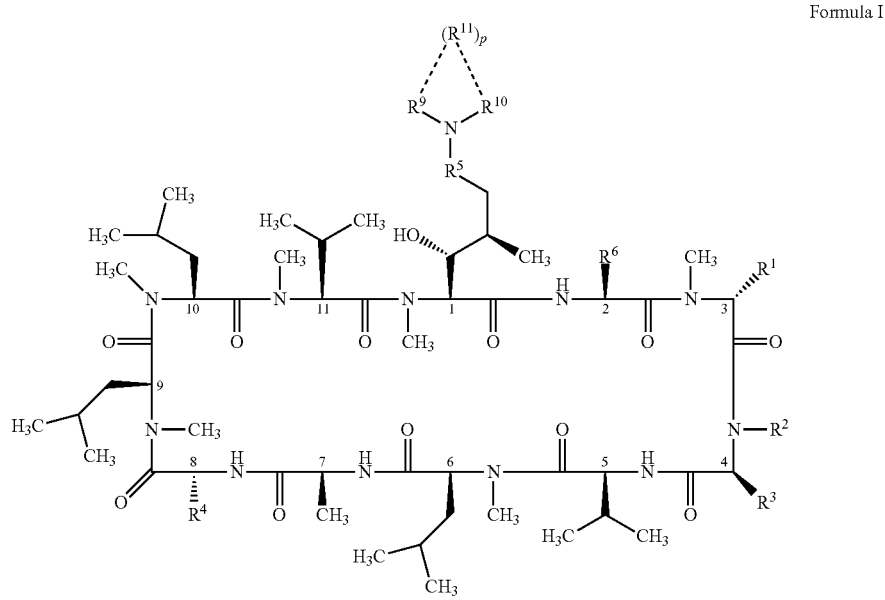

wherein:
$R^1$ is —H, —$C_{1-6}$alkyl, —$OC_{1-6}$alkyl, —$CH_2F$, —$CH_2OCH_3$, —$SC_{1-6}$alkyl, —$CH_3$, —$CH_2CH_3$, —$SCH(CH_3)_2$, —$CH_2OH$, —$SCH_3$, —$OCH_3$, —$R^{13}R^{14}$,

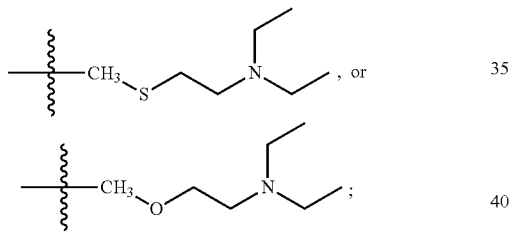

$R^2$ is —$CH_3$, —$CH_2CH_3$, or —$CH_2CH_2CH_3$;
$R^3$ is —$CH_2CH(CH_3)_2$, —$CH(CH_3)_2$, —$CH_2C(CH_3)_2(OH)$, —$CH(CH_3)(CH_2CH_3)$, or —$CH_2CH(R^7)(CH_2CH_3)$;
$R^4$ is —$CH_3$, or —$CH_2OH$;
$R^5$ is —$R^8(CH_2)_n(C=O)_m$—;
$R^6$ is —$CH_2CH_3$, —$CH(CH_3)(OH)$, —$CH(CH_3)_2$, or —$CH_2CH_2CH_3$;
$R^7$ is $OC_{1-5}$ alkyl;
$R^8$ is O, S, $CH_2O$, $CH_2S$, or $CH_2$;
$R^9$ is —H, —$C_{1-5}$ alkyl, —$C_{2-4}$fluoroalkyl, —$C_{1-5}$ alkyl-heterocycle, cyanoalkyl,

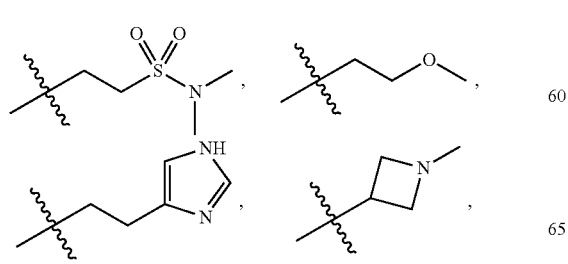

-continued

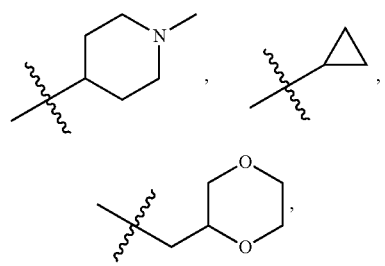

$C_{3-8}$cycloalkyl, heterocycle, aryl, or cycloalkenyl, or $R^9$ taken together with $R^{11}$, $R^{10}$, and the N to which $R^9$ and $R^{10}$ are attached forms a heterocycle;
$R^{10}$ is —H, —$C_{1-5}$ alkyl, —$C_{2-4}$fluoroalkyl, —$C_{1-5}$ alkyl-heterocycle, cyanoalkyl,

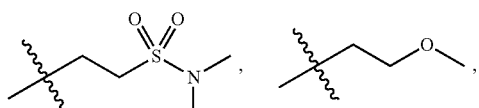

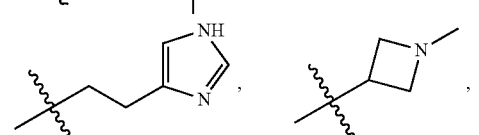

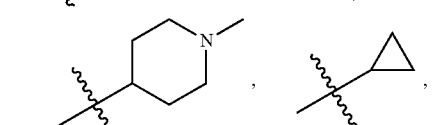

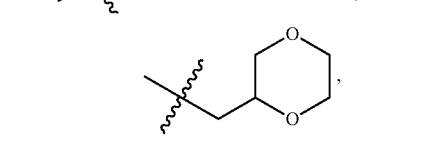

$C_{3-8}$cycloalkyl, heterocycle, aryl, or cycloalkenyl, or $R^{10}$ taken together with $R^{11}$, $R^9$, and the N to which $R^9$ and $R^{10}$ are attached forms a heterocycle;

$R^{11}$ is O, $NR^{12}$, $S(O)_q$, $CF_2$, $C_{1-5}$alkylene, $CH(OC_{1-6}$alkyl), divalent $C_{3-8}$cycloalkyl, divalent heterocycle, carbonyl, or taken together with $R^9$, $R^{10}$, and the N to which $R^9$ and $R^{10}$ are attached forms a heterocycle;

$R^{12}$ is H, $CH_3$, or $C_{1-5}$ alkyl;

$R^{13}$ is O, S, $CH_2O$, $CH_2S$, $CH_2SO$, or $CH_2SO_2$;

$R^{14}$ is H, $C_{1-6}$alkyl, $C_{2-6}$alkenyl, $C_{2-6}$alkynyl, $C_{3-8}$cycloalkyl, $CH_2CH_2N(CH_2CH_3)_2$, $CH_2CH_2NH(CH_2CH_3)$, heterocycle, or aryl;

n=0, 1, 2, 3, or 4;

m=0 or 1;

p=0 or 1; and q=0, 1, or 2;

wherein $R^{14}$ is optionally substituted with one or more groups independently selected from the group consisting of H, $C_{1-6}$alkyl, halogen, hydroxyl, ester, sulfonamide, ketone, aldehyde, cycloalkyl, heterocycle, aryl, amine, heterocycle, amide, and guanidinyl;

wherein the heterocycle comprising $R^9$, $R^{10}$, $R^{11}$, and the N to which $R^9$ and $R^{10}$ are attached is monocyclic or polycyclic;

wherein "- - - - - -" is a single bond or is absent; and with the provisos that when $R^8$ is O, S, $CH_2O$, or $CH_2S$ then n is not 0 or 1;

when p=0 then $R^{11}$ and "- - - - - -" are absent; and when $R^{11}$ and "- - - - - -" are absent then $R^9$ is not directly linked to $R^{10}$.

In another embodiment, the invention provides for a compound having Formula I, wherein:

$R^1$ is —H, —$C_{1-6}$alkyl, —$OC_{1-6}$alkyl, —$CH_2F$, —$CH_2OCH_3$, —$SC_{1-6}$alkyl, —$CH_3$, —$CH_2CH_3$, —$SCH(CH_3)_2$, —$CH_2OH$, —$SCH_3$, —$OCH_3$, —$R^{13}R^{14}$,

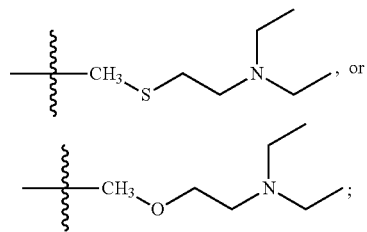, or

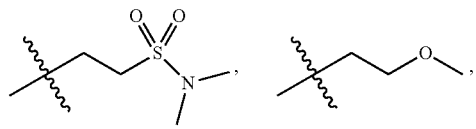;

$R^2$ is —$CH_3$, —$CH_2CH_3$, or —$CH_2CH_2CH_3$;

$R^3$ is —$CH_2CH(CH_3)_2$, —$CH(CH_3)_2$, —$CH_2C(CH_3)_2(OH)$, —$CH(CH_3)(CH_2CH_3)$, or —$CH_2CH(R^7)(CH_2CH_3)$;

$R^4$ is —$CH_3$, or —$CH_2OH$;

$R^5$ is —$R^8(CH_2)_n(C=O)_m$—;

$R^6$ is —$CH_2CH_3$, —$CH(CH_3)(OH)$, —$CH(CH_3)_2$, or —$CH_2CH_2CH_3$;

$R^7$ is $OC_{1-5}$ alkyl;

$R^8$ is O, S, $CH_2O$, $CH_2S$, or $CH_2$;

$R^9$ is —H, —$C_{1-5}$ alkyl,

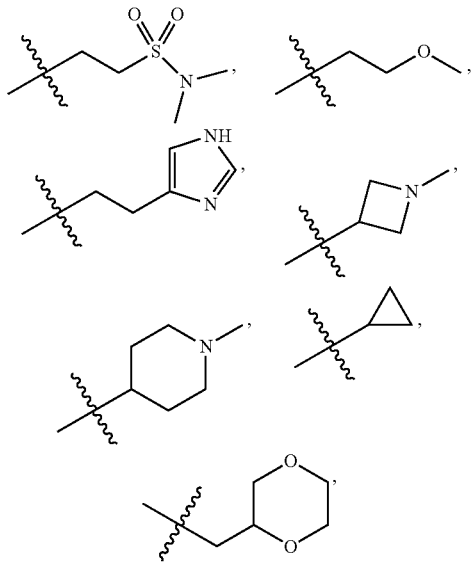

$C_{3-8}$cycloalkyl, heterocycle, aryl, or cycloalkenyl, or taken together with $R^{11}$, $R^{10}$, and the N to which $R^9$ and $R^{10}$ are attached forms a heterocycle;

$R^{10}$ is —H, —$C_{1-5}$ alkyl,

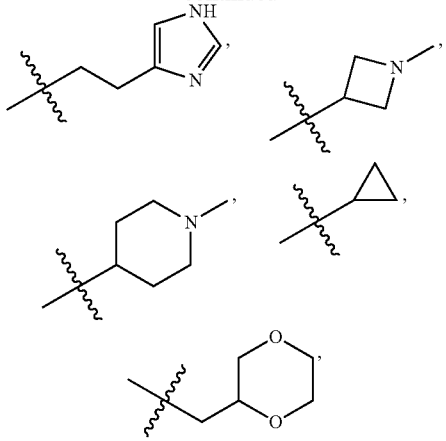

$C_{3-8}$cycloalkyl, heterocycle, aryl, or cycloalkenyl, or taken together with $R^{11}$, $R^9$, and the N to which $R^9$ and $R^{10}$ are attached forms a heterocycle;

$R^{11}$ is O, $NR^{12}$, $S(O)_q$, $C_{1-5}$alkylene, divalent $C_{3-8}$cycloalkyl, divalent heterocycle, carbonyl, or taken together with $R^9$, $R^{10}$, and the N to which $R^9$ and $R^{10}$ are attached forms a heterocycle;

$R^{12}$ is H, $CH_3$, or $C_{1-5}$ alkyl;

$R^{13}$ is O, S, $CH_2O$, $CH_2S$, $CH_2SO$, or $CH_2SO_2$;

$R^{14}$ is H, $C_{1-6}$alkyl, $C_{2-6}$alkenyl, $C_{2-6}$alkynyl, $C_{3-8}$cycloalkyl, $CH_2CH_2N(CH_2CH_3)_2$, $CH_2CH_2NH(CH_2CH_3)$, heterocycle, or aryl;

n=0, 1, 2, 3, or 4;

m=0 or 1;

p=0 or 1; and q=0, 1, or 2;

wherein $R^{14}$ is optionally substituted with one or more groups independently selected from the group consisting of H, $C_{1-6}$alkyl, halogen, hydroxyl, ester, sulfonamide, ketone, aldehyde, cycloalkyl, heterocycle, aryl, amine, heterocycle, amide, and guanidinyl;

wherein the heterocycle comprising $R^9$, $R^{10}$, $R^{11}$, and the N to which $R^9$ and $R^{10}$ are attached is monocyclic or polycyclic;

wherein "- - - - - -" is a single bond or is absent; and with the provisos that when $R^8$ is O, S, $CH_2O$, or $CH_2S$ then n is not 0 or 1;

when p=0 then $R^{11}$ and "- - - - - -" are absent; and when $R^{11}$ and "- - - - - -" are absent then $R^9$ is not directly linked to $R^{10}$.

A compound having Formula I according to any of the embodiments set forth above may further include the proviso that when $R^2$ is —$CH_3$, and $R^3$ is —$CH_2CH(CH_3)_2$, and $R^4$ is —$CH_3$, and $R^6$ is —$CH_2CH_3$, then the group

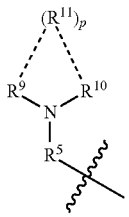

is not —$CH_2CH_2CH_2(C=O)N(CH_2CH_3)_2$, —$CH_2CH_2CH_2(C=O)N(CH_3)_2$, —$CH_2CH_2CH_2(C=O)NH_2$, —$CH_2CH_2CH_2CH_2CH_2NH(C=O)CH_3$, —$CH_2CH_2CH_2CH_2NH(C=O)CH_3$, —$CH_2CH_2CH_2CH_2CH_2NH(C=O)CH_2CH_3$, —$CH_2CH_2CH_2CH_2CH_2NH(C=O)CH_2CH_2CH_3$, —$CH_2CH_2CH_2CH_2NH(C=O)CH_3$, —$CH_2NHCH_2COOH$, or —$CH_2NH(CH_2)_5COOH$.

Additionally or alternatively, a compound according to any of the embodiments set forth above may further include the provisos that when m=1, and $R^2$ is —$CH_3$, and $R^3$ is —$CH_2CH(CH_3)_2$, and $R^4$ is —$CH_3$, and $R^6$ is —$CH_2CH_3$ then neither $R^9$ nor $R^{10}$ is —H or —$C_1$-$C_5$alkyl, and $R^9$, $R^{10}$, $R^{11}$, and the N to which $R^9$ and $R^{10}$ are attached taken together do not form morpholinyl.

A compound having Formula I may further include the provisos that when m=1 then neither $R^9$ nor $R^{10}$ is —H or —$C_1$-$C_5$alkyl, and $R^9$, $R^{10}$, $R^{11}$, and the N to which $R^9$ and $R^{10}$ are attached taken together do not form morpholinyl.

In one embodiment the invention provides a compound having Formula I, wherein $R^1$ is not hydrogen (H).

In another embodiment the invention provides a compound having Formula I, wherein when $R^1$ is H, then m=0.

In another embodiment the invention provides a compound having Formula I, wherein when $R^1$ is H, then m=0 and $R^9$, $R^{10}$, $R^{11}$, and the N to which $R^9$ and $R^{10}$ are attached together form a heterocycle.

In another embodiment the invention provides a compound having Formula I, wherein $R^6$ is —$CH_2CH_3$.

In another embodiment the invention provides a compound having Formula I, wherein $R^6$ is —$CH(CH_3)(OH)$.

In another embodiment the invention provides a compound having Formula I, wherein $R^6$ is —$CH(CH_3)_2$.

In another embodiment the invention provides a compound having Formula I, wherein $R^6$ is —$CH_2CH_2CH_3$.

In another embodiment the invention provides a compound having Formula I, wherein n=0, 1, 2, 3, or 4 and m=0.

In another embodiment the invention provides a compound having Formula I, wherein n=0, 1, 2, 3, or 4 and m=1.

In another embodiment the invention provides a compound having Formula I, wherein n=0, m=0, and p=1.

In another embodiment the invention provides a compound having Formula I, wherein n=1, m=1, and p=1.

In another embodiment the invention provides a compound having Formula I, wherein n=1, m=1, and p=0.

In another embodiment the invention provides a compound having Formula I, wherein n=3, m=0, and p=0.

In another embodiment the invention provides a compound having Formula I, wherein n=3, m=0, and p=1.

In another embodiment the invention provides a compound having Formula I, wherein n=2, m=0, and p=0.

In another embodiment the invention provides a compound having Formula I, wherein $R^8$ is $CH_2O$, n=2, and m=0.

In another embodiment the invention provides a compound having Formula I, wherein $R^1$ is —$CH_2CH_3$, $R^{11}$ is O, n=0, and p=1.

In another embodiment the invention provides a compound having Formula I, wherein $R^2$ is —$CH_3$ or —$CH_2CH_3$; $R^3$ is —$CH_2CH(CH_3)_2$, —$CH(CH_3)_2$, or —$CH_2C(CH_3)_2(OH)$; $R^4$ is —$CH_3$; $R^6$ is —$CH_2CH_3$; and $R^8$ is $CH_2$.

In another embodiment the invention provides a compound having Formula I, wherein $R^2$ is —$CH_3$; $R^3$ is —$CH_2CH(CH_3)_2$; $R^4$ is —$CH_3$; $R^6$ is —$CH_2CH_3$; and $R^8$ is $CH_2$.

In another embodiment the invention provides a compound having Formula I, wherein $R^1$ is —$CH_3$, —$CH_2CH_3$, or —$SCH_3$; $R^2$ is —$CH_3$; $R^3$ is —$CH_2CH(CH_3)_2$; $R^4$ is —$CH_3$; $R^6$ is —$CH_2CH_3$; and $R^8$ is $CH_2$.

In another embodiment the invention provides a compound having Formula I, wherein $R^1$ is —$SCH_3$, $R^{11}$ is O, n=0, m=0 and p=1, and wherein $R^9$, $R^{10}$, $R^{11}$, and the N to which $R^9$ and $R^{10}$ are attached taken together form a heterocycle.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^6$ is —$CH_2CH_3$, $R^8$ is $CH_2$, n=0, 1, 2, 3, or 4, m=0, and p=0.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^6$ is —$CH_2CH_3$, $R^8$ is $CH_2$, n=0, 1, 2, 3, or 4, m=0, and p=0.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2$—, $R^6$ is —$CH_2CH_3$, $R^8$ is $CH_2$, n=2, m=0, and p=0.

In another embodiment the invention provides a compound having Formula I, wherein $R^1$ is —$R^{13}R^{14}$, $R^{11}$ is O, $R^{13}$ is $CH_2S$, $R^{14}$ is —$CH_2CH_2N(CH_2CH_3)_2$, n=0, m=0 and p=1, and wherein $R^9$, $R^{10}$, $R^{11}$, and the N to which $R^9$ and $R^{10}$ are attached taken together form a heterocycle.

In another embodiment the invention provides a compound having Formula I, wherein $R^2$ is —$CH_3$, $R^3$ is —$CH_2CH(CH_3)_2$, $R^4$ is —$CH_3$, $R^6$ is —$CH_2CH_3$, and $R^8$ is $CH_2$.

In another embodiment the invention provides a compound having Formula I, wherein $R^2$ is —$CH_3$, $R^3$ is —$CH_2CH(CH_3)_2$, $R^4$ is —$CH_3$, $R^6$ is —$CH_2CH_3$, and $R^8$ is $CH_2O$.

In another embodiment the invention provides a compound having Formula I, wherein $R^2$ is —$CH_3$, $R^3$ is —$CH_2CH(CH_3)_2$, $R^4$ is —$CH_3$, $R^6$ is —$CH(CH_3)_2$, and $R^8$ is $CH_2$.

In one embodiment the invention provides a compound having Formula I, wherein p=1 and $R^9$, $R^{10}$, $R^{11}$ and the N to which $R^9$ and $R^{10}$ are attached taken together form a heterocycle.

In another embodiment the invention provides a compound having Formula I, wherein p=0 and $R^9$ is not directly linked to $R^{10}$.

In another embodiment the invention provides a compound having Formula I, wherein $R^1$ is —$CH_3$ and $R^6$ is —$CH_2CH_3$.

In another embodiment the invention provides a compound having Formula I, wherein $R^1$ is —$CH_3$, $R^6$ is —$CH_2CH_3$ or —$CH(CH_3)_2$, $R^8$ is $CH_2$, $R^{11}$ is O, n=0, 1, 2, 3, or 4, p=1, and $R^9$, $R^{10}$, $R^{11}$, and the N to which $R^9$ and $R^{10}$ are attached taken together form morpholine.

In another embodiment the invention provides a compound having Formula I, wherein $R^1$ is —$CH_3$, $R^6$ is —$CH_2CH_3$ or —$CH(CH_3)_2$, $R^8$ is $CH_2$, $R^{11}$ is $NR^{12}$, $R^{12}$ is $CH_3$, n=0, 1, 2, 3, or 4, p=1, and $R^9$, $R^{10}$, $R^{11}$, and the N to which $R^9$ and $R^{10}$ are attached taken together form N-methylpiperazine.

In another embodiment the invention provides a compound having Formula I, wherein $R^1$ is —$CH_3$, $R^6$ is —$CH_2CH_3$ or —$CH(CH_3)_2$, $R^8$ is $CH_2$, $R^{11}$ is $NR^{12}$, $R^{12}$ is H, n=0, 1, 2, 3, or 4, p=1, and $R^9$, $R^{10}$, $R^{11}$, and the N to which $R^9$ and $R^{10}$ are attached taken together form

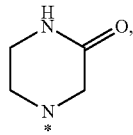

wherein "*" represents the point of attachment to $R^5$.

In another embodiment the invention provides a compound having Formula I, wherein $R^1$ is —$CH_3$, $R^2$ is —$CH_3$ or —$CH_2CH_3$, $R^3$ is —$CH_2CH(CH_3)_2$ or —$CH(CH_3)_2$, $R^4$ is —$CH_3$, $R^6$ is —$CH_2CH_3$, $R^8$ is $CH_2$, $R^{11}$ is O or $NR^{12}$, $R^{12}$ is $CH_3$, m=1, n=2, and p=1, and wherein $R^9$, $R^{10}$, $R^{11}$ and the N to which $R^9$ and $R^{10}$ are attached taken together form a heterocycle.

In another embodiment the invention provides a compound having Formula I, wherein $R^1$ is —H, $R^2$ is —$CH_3$, $R^3$ is —$CH_2CH(CH_3)_2$, $R^4$ is —$CH_3$, $R^6$ is —$CH_2CH_3$, $R^8$ is $CH_2$, $R^{11}$ is O, n=3, m=0, and p=1, and wherein $R^9$, $R^{10}$, $R^{11}$ and the N to which $R^9$ and $R^{10}$ are attached taken together form a heterocycle.

In another embodiment the invention provides a compound having Formula I, wherein m=1, p=1, and wherein $R^9$, $R^{10}$, $R^{11}$ and the N to which $R^9$ and $R^{10}$ are attached taken together form

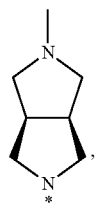

wherein "*" represents the point of attachment to $R^5$.

In another embodiment the invention provides a compound having Formula I, wherein $R^9$ is —H, $R^{10}$ is

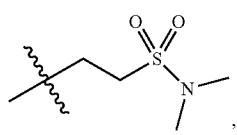 [SMILES: *CCS(=O)(=O)N(C)C]

and m=1.

In another embodiment the invention provides a compound having Formula I, wherein $R^9$ is —H, $R^{10}$ is

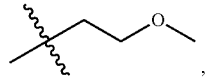 [SMILES: *CCOC]

and m=1.

In another embodiment the invention provides a compound having Formula I, wherein $R^9$ is —H, $R^{10}$ is

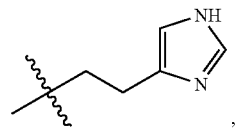

and m=1.

In another embodiment the invention provides a compound having Formula I, wherein $R^9$ is —$CH_2CH_3$, $R^{10}$ is —$CH_2CH_3$, m=1, and p=0.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2$—, $R^6$ is —$CH_2CH_3$, $R^8$ is $CH_2$, n=1, m=1, and p=0.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2$—, $R^6$ is —$CH_2CH_3$, $R^8$ is $CH_2$, n=2, m=0, and p=0.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2OCH_2CH_2$—, $R^6$ is —$CH_2CH_3$, $R^8$ is $CH_2O$, n=2, m=0, and p=0.

In another embodiment the invention provides a compound having Formula I, wherein $R^1$ is —$CH_2CH_3$, $R^2$ is —$CH_3$, $R^3$ is —$CH_2CH(CH_3)_2$, $R^4$ is —$CH_3$, $R^5$ is —$CH_2$—, $R^6$ is —$CH_2CH_3$, $R^8$ is $CH_2$, $R^{11}$ is O, n=0, m=0, and p=1, and wherein $R^9$, $R^{10}$, $R^{11}$, and the N to which $R^9$ and $R^{10}$ are attached taken together form

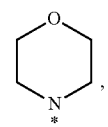

wherein "*" represents the point of attachment to $R^5$.

In another embodiment the invention provides a compound having Formula I, wherein $R^1$ is —$SCH_3$, $R^2$ is —$CH_3$, $R^3$ is —$CH_2CH(CH_3)_2$, $R^4$ is —$CH_3$, $R^5$ is —$CH_2$—, $R^6$ is —$CH_2CH_3$, $R^8$ is $CH_2$, $R^{11}$ is O, n=0, m=0, and p=1, and wherein $R^9$, $R^{10}$, $R^{11}$, and the N to which $R^9$ and $R^{10}$ are attached taken together form

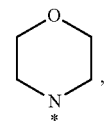

wherein "*" represents the point of attachment to $R^5$.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2$—, $R^6$ is —$CH_2CH_3$, $R^8$ is $CH_2$, n=2, m=0, and p=0.

In another embodiment the invention provides a compound having Formula I, wherein $R^1$ is —$R^{13}R^{14}$, $R^2$ is —$CH_3$, $R^3$ is —$CH_2CH(CH_3)_2$, $R^4$ is —$CH_3$, $R^5$ is —$CH_2$—, $R^6$ is —$CH_2CH_3$, $R^8$ is $CH_2$, $R^{11}$ is O, $R^{13}$ is $CH_2S$, $R^{14}$ is —$CH_2CH_2N(CH_2CH_3)_2$, n=0, m=0 and p=1, and wherein $R^9$, $R^{10}$, $R^{11}$, and the N to which $R^9$ and $R^{10}$ are attached taken together form

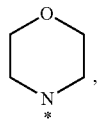, wherein "*" represents the point of attachment to $R^5$.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2$—, $R^6$ is —$CH(CH_3)_2$, $R^8$ is $CH_2$, $R^{11}$ is O, n=0, m=0, and p=1, and wherein $R^9$, $R^{10}$, $R^{11}$, and the N to which $R^9$ and $R^{10}$ are attached taken together form

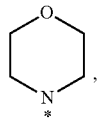, wherein "*" represents the point of attachment to $R^5$.

In another embodiment the invention provides a compound having Formula I, wherein $R^1$ is —$OCH_3$, $R^2$ is —$CH_3$, $R^3$ is —$CH_2CH(CH_3)_2$, $R^4$ is —$CH_3$, $R^5$ is —$CH_2$—, $R^6$ is —$CH_2CH_3$, $R^8$ is $CH_2$, $R^{11}$ is O, n=0, m=0, and p=1, and wherein $R^9$, $R^{10}$, $R^{11}$, and the N to which $R^9$ and $R^{10}$ are attached taken together form

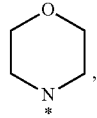, wherein "*" represents the point of attachment to $R^5$.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2CH_2$—, $R^6$ is —$CH(CH_3)_2$, $R^8$ is $CH_2$, $R^{11}$ is O, n=3, m=0, and p=1, and wherein $R^9$, $R^{10}$, $R^{11}$, and the N to which $R^9$ and $R^{10}$ are attached taken together form

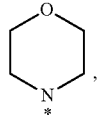, wherein "*" represents the point of attachment to $R^5$.

In another embodiment the invention provides a compound having Formula I, wherein $R^1$ is —H, $R^2$ is —$CH_3$, $R^3$ is —$CH_2CH(CH_3)_2$, $R^4$ is —$CH_3$, $R^5$ is —$CH_2CH_2CH_2CH_2$—, $R^6$ is —$CH(CH_3)_2$, $R^8$ is $CH_2$, $R^{11}$ is O, n=3, m=0, and p=1, and wherein $R^9$, $R^{10}$, $R^{11}$, and the N to which $R^9$ and $R^{10}$ are attached taken together form

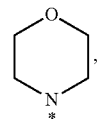, wherein "- - - - - -" represents the point of attachment to $R^5$.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2$—, $R^6$ is —$CH_2CH_3$, $R^8$ is $CH_2$, $R^{11}$ is O, n=0, m=0, and p=1, and wherein $R^9$, $R^{10}$, $R^{11}$, and the N to which $R^9$ and $R^{10}$ are attached taken together form

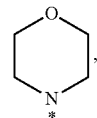, wherein "*" represents the point of attachment to $R^5$.

In another embodiment the invention provides a compound having Formula I, wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2CH_2$—, $R^6$ is —$CH_2CH_3$, $R^8$ is $CH_2$, $R^{11}$ is O, n=3, m=0, and p=1, and wherein $R^9$, $R^{10}$, $R^{11}$, and the N to which $R^9$ and $R^{10}$ are attached taken together form

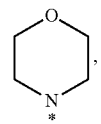, wherein "*" represents the point of attachment to $R^5$.

In some embodiments, $R^2$ is —$CH_3$, $R^3$ is —$CH_2CH(CH_3)_2$, $R^4$ is —$CH_3$, and $R^6$ is —$CH_2CH_3$.

In some embodiments $R^5$ is —$R^8(CH_2)_n(C=O)_m$—, which is attached to the nitrogen bearing the $R^9$ and $R^{10}$ groups through the (C=O), $R^8$ is $CH_2$, n=0, 1, 2, or 3, and m=0. Thus, in some embodiments $R^5$ is —$CH_2$, —$CH_2CH_2$—, —$CH_2CH_2CH_2$—, or —$CH_2CH_2CH_2CH_2$—. In some embodiments $R^8$ is $CH_2$, n=1, and m=1. Accordingly, in some embodiments $R^5$ is —$CH_2CH_2(C=O)$—, for example. In some embodiments $R^8$ is $CH_2O$, n=2, and m=0. Accordingly, in some embodiments $R^5$ is —$CH_2OCH_2CH_2$—, for example.

Non-limiting examples of $R^{11}$ include O, $NCH_3$, NH, $SO_2$, S, $CH_2$, $CF_2$, and $CH(OCH_3)$.

Non-limiting examples of a $C_{1-6}$alkyl-heterocycle include —$CH_2$Pyrid-2-yl, —$CH_2$Pyrid-3-yl, —$CH_2$Pyrimidin-2-yl, —$CH_2$Pyrazin-2-yl, —$CH_2$-3-Me-Imidazol-4-yl, —$CH_2$-2-Me-Pyrazol-3-yl, —$CH_2$Pyrid-4-yl, —$CH_2$-1-Me-Pyrazol-4-yl, and —$CH_2$-1-Me-3-$CF_3$-Pyrazol-5-yl.

A non-limiting example of a cyanoalkyl includes —$CH_2CH(CH_3)CN$.

In some embodiments, $R^9$, $R^{10}$, $R^{11}$, and the N to which $R^9$ and $R^{10}$ are attached taken together form a heterocycle. In some embodiments the heterocycle is a non-aromatic heterocycle. In other embodiments the heterocycle is an aromatic heterocycle.

Non-limiting examples of compounds having Formula I include those in which m=0 and $R^1$ is not H, and/or in which p=1 and $R^9$, $R^{10}$, $R^{11}$, and the N to which $R^9$ and $R^{10}$ are attached together form a heterocycle. Other non-limiting examples of compounds having Formula I include those wherein $R^1$ is —CH$_3$, —SCH$_3$, —OCH$_3$, or —CH$_2$OH; $R^8$ is CH$_2$; n=0, 1, 2, 3, or 4; m=0; p=1, and $R^9$, $R^{10}$, $R^{11}$, and the N to which $R^9$ and $R^{10}$ are attached taken together form a heterocycle. Additional examples of compounds include those wherein n=0, 1, 2, 3, or 4, m=0, p=0 or 1, and $R^1$ is —C$_{1-6}$alkyl, —OC$_{1-6}$alkyl, or —SC$_{1-6}$alkyl.

In some embodiments, the $R^9$ and $R^{10}$ heterocycle, or the heterocycle formed from $R^9$, $R^{10}$, and the N to which $R^9$ and $R^{10}$ are attached is independently selected from the group consisting of piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl,

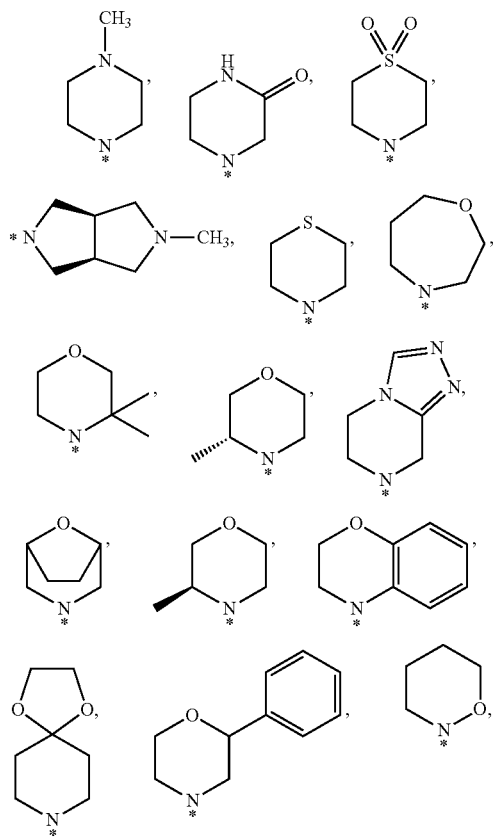

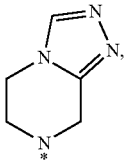 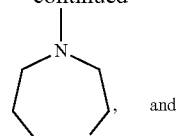 and 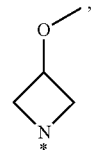

wherein "*" indicates the point of attachment to $R^5$.

The heterocycle formed by $R^9$, $R^{10}$, $R^{11}$, and the N to which $R^9$ and $R^{10}$ are attached taken together may be optionally substituted by an alkyl, halogen, or haloalkyl. One example of a haloalkyl is —CF$_3$. In some embodiments one or more hydrogen atoms on the heterocycle is replaced with fluorine (F). In specific embodiments, the fluorinated heterocycle is a saturated, non-aromatic heterocycle. In a more specific embodiment the fluorinated heterocycle is

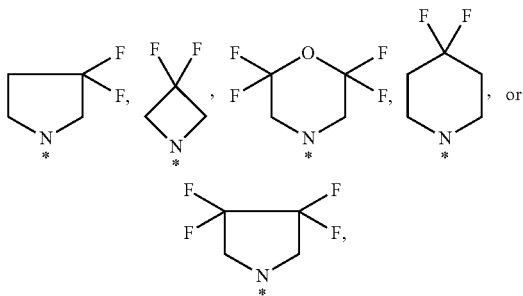

wherein "*" represents the point of attachment to $R^5$.

In some embodiments, the compound having Formula I is any one of those listed in Tables 1-27. Accordingly, non-limiting examples of a compound according to the present invention include any of the compounds listed in Tables 1-27. The present invention also provides for a pharmaceutical composition comprising or consisting of a therapeutically effective amount of a compound having Formula I and a pharmaceutically acceptable excipient.

For example, one embodiment is a compound having Formula I, wherein $R^1$=—CH$_3$, $R^2$=—CH$_3$, $R^3$=—CH$_2$CH(CH$_3$)$_2$, $R^4$=—CH$_3$, $R^6$=—CH$_2$CH$_3$, $R^8$=CH$_2$, $R^{11}$ is O, n=0, m=0, p=1, and $R^9$, $R^{10}$, $R^{11}$, and the N to which $R^9$ and $R^{10}$ are attached taken together form:

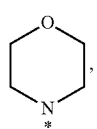

wherein "*" represents the point of attachment to $R^5$ (Compound F).

Another embodiment is a compound having Formula I, wherein $R^1$=—CH$_3$, $R^2$=—CH$_3$, $R^3$=—CH$_2$CH(CH$_3$)$_2$, $R^4$=—CH$_3$, $R^6$=—CH$_2$CH$_3$, $R^8$=CH$_2$, $R^9$=—H, $R^{10}$ is

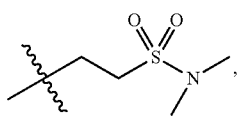 [SMILES: *CCS(=O)(=O)N(C)C]

n=1, m=1, and p=0 (Compound W).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=1, m=1, p=1, q=2, $R^{11}$ is $S(O)_q$, and $R^9$, $R^{10}$, $R^{11}$, and the N to which $R^9$ and $R^{10}$ are attached taken together form:

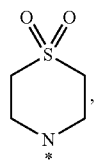

wherein "*" represents the point of attachment to $R^5$ (Compound Z).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=1, m=1, p=1, and $R^9$, $R^{10}$, $R^{11}$, and the N to which $R^9$ and $R^{10}$ are attached taken together form:

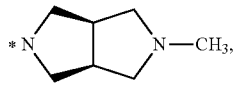

wherein "*" represents the point of attachment to $R^5$ (Compound ZZ).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=1, and $R^9$, $R^{10}$, $R^{11}$, and the N to which $R^9$ and $R^{10}$ are attached taken together form:

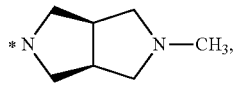

wherein "*" represents the point of attachment to $R^5$ (Compound O).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, $R^{11}$ is O, n=2, m=0, p=1, $R^{11}$ is O, and $R^9$, $R^{10}$, $R^{11}$, and the N to which $R^9$ and $R^{10}$ are attached taken together form:

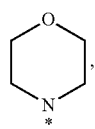

wherein "*" represents the point of attachment to $R^5$ (Compound KG).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=1, $R^{11}$ is O; and $R^9$, $R^{10}$, $R^{11}$, and the N to which $R^9$ and $R^{10}$ are attached taken together form:

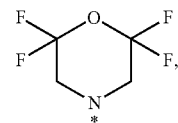

wherein "*" represents the point of attachment to $R^5$ (Compound EK).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=1, $R^{11}$ is $CF_2$, and $R^9$, $R^{10}$, $R^{11}$, and the N to which $R^9$ and $R^{10}$ are attached taken together form:

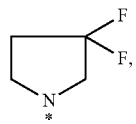

wherein "*" represents the point of attachment to $R^5$ (Compound EL).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=1, $R^{11}$ is $CF_2$, and $R^9$, $R^{10}$, $R^{11}$, and the N to which $R^9$ and $R^{10}$ are attached taken together form:

wherein "*" represents the point of attachment to $R^5$ (Compound EM).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=1, $R^{11}$ is $CF_2$, and $R^9$, $R^{10}$, $R^{11}$, and the N to which $R^9$ and $R^{10}$ are attached taken together form:

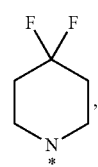

wherein "*" represents the point of attachment to $R^5$ (Compound EN).

Another embodiment is a compound having Formula I, wherein $R^1$=—$CH_3$, $R^2$=—$CH_3$, $R^3$=—$CH_2CH(CH_3)_2$, $R^4$=—$CH_3$, $R^6$=—$CH_2CH_3$, $R^8$=$CH_2$, n=0, m=0, p=0, $R^9$=—$CH_2CH_2CF_3$, and $R^{10}$=—$CH_2CH_2CF_3$ (Compound EQ).

Compounds of the present invention include but are not limited to the following:

[(3R,4R,5S)-4-(hydroxy)-3-methyl-5-(methylamino)-1-(morpholin-4-yl)hexanoic acid]$^1$[(R)-Me-Sar]$^3$cyclosporin A (Compound F);

[(3R,4R,5S)-4-hydroxy-3-methyl-5-(methylamino)-1-(4-methylpiperazino)-hexanoic acid]$^1$[(R)-Me-Sar]$^3$cyclosporin A (Compound L);

[(3R,4R,5S)-4-hydroxy-3-methyl-5-(methylamino)-1-N-diethylamino-hexanoic acid]$^1$[(R)-Me-Sar]$^3$cyclosporin A (Compound M);

[(3R,4R,5S)-4-hydroxy-3-methyl-5-(methylamino)-1-(N-3-piperazinone)-hexanoic acid]$^1$[(R)-Me-Sar]$^3$cyclosporin A (Compound N);

[(3R,4R,5S)-4-Hydroxy-3-methyl-5-(methylamino)-1-(2-{1H-imidazol-4-yl}-ethylamino)-hexanoic acid]$^1$[(R)-methyl-Sar]$^3$cyclosporin A (Compound AK);

[(3R,4R,5S)-4-Hydroxy-3-methyl-5-(methylamino)-1-(2-methoxyethylamino)-hexanoic acid]$^1$[(R)-methyl-Sar]$^3$ cyclosporin A (Compound AF);

[(3R,4R,5S)-4-Hydroxy-3-methyl-5-(methylamino)-1-(2-methoxyethyl)methylamino)-hexanoic acid]$^1$[(R)-methyl-Sar]$^3$cyclosporin A (Compound AG);

[(3R,4R,5S)-4-Hydroxy-3-methyl-5-(methylamino)-1-(N-(3aR*,6aS*)-2-methyloctahydropyrrolo[3,4-c]pyrrolo)-hexanoic acid]$^1$[(R)-methyl-Sar]$^3$cyclosporin A (Compound O);

[(3R,4R,5S)-4-Hydroxy-3-methyl-5-(methylamino)-1-(1,4-dioxan-2-ylmethyl)methylamino-hexanoic acid]$^1$[(R)-methyl-Sar]$^3$cyclosporin A (Compound AJ);

[(3R,4R,5S)-4-Hydroxy-3-methyl-5-(methylamino)-1-(thiomorpholino)-hexanoic acid]$^1$[(R)-Me-Sar]$^3$cyclosporin A (Compound J);

[(3R,4R,5S)-4-Hydroxy-3-methyl-5-(methylamino)-1-(1,1-dioxo-thiomorpholino)-hexanoic acid]$^1$[(R)-Me-Sar]$^3$cyclosporin A (Compound P);

[[(3R,4R,5S)-4-Hydroxy-3-methyl-5-(methylamino)-1-N-homomorpholino-hexanoic acid]$^1$[(R)-methyl-Sar]$^3$cyclosporin A (Compound X);

[(6R,7R,8S)-7-hydroxy-6-methyl-8-(methylamino)-1-N-morpholino-nonanoic acid]$^1$[(R)-methyl-Sar]$^3$cyclosporin A (Compound G);

[(6R,7R,8S)-7-Hydroxy-6-methyl-8-(methylamino)-1-N-diethylamino-nonanoic acid]$^1$[(R)-methyl-Sar]$^3$cyclosporin A (Compound AH);

[(6R,7R,8S)-7-Hydroxy-6-methyl-8-(methylamino)-1-N-(2-methoxy)ethylamino-nonanoic acid]$^1$[(R)-methyl-Sar]$^3$ cyclosporin A (Compound AI);

[(5R,6R,7S)-6-hydroxy-5-methyl-7-(methylamino)-1-N-morpholino-1-oxo-octanoic acid]$^1$[(R)-methyl-Sar]$^3$cyclosporin A (Compound H);

[(5R,6R,7S)-6-hydroxy-5-methyl-7-(methylamino)-1-(4-methylpiperazin-1-yl)-1-oxo-octanoic acid]$^1$[(R)-methyl-Sar]$^3$cyclosporin A (Compound T);

[(5R,6R,7S)-6-hydroxy-5-methyl-7-(methylamino)-1-diethylamino-1-oxo-octanoic acid]$^1$[(R)-methyl-Sar]$^3$cyclosporin A (Compound U);

[(5R,6R,7S)-6-hydroxy-5-methyl-7-(methylamino)-1-(2-{sulfonic acid dimethylamide}-ethylamino)-1-oxo-octanoic acid]$^1$[(R)-methyl-Sar]$^3$cyclosporin A (Compound W);

[(5R,6R,7S)-6-hydroxy-5-methyl-7-(methylamino)-1-(2-{1H-imidazol-4-yl}-ethylamino)-1-oxo-octanoic acid]$^1$[(R)-methyl-Sar]$^3$cyclosporin A (Compound Y);

[(5R,6R,7S)-6-hydroxy-5-methyl-7-(methylamino)-1-({1,1-dioxo}thiomorpholin-4-yl)-1-oxo-octanoic acid]$^1$[(R)-methyl-Sar]$^3$cyclosporin A (Compound Z);

[(5R,6R,7S)-6-hydroxy-5-methyl-7-(methylamino)-1-(N-(3aR*,6aS*)-2-methyloctahydropyrrolo[3,4-c]pyrrolo)-1-oxo-octanoic acid]1[(R)-methyl-Sar]3cyclosporin A (Compound ZZ);

[(5R,6R,7S)-6-hydroxy-5-methyl-7-(methylamino)-1-(2-methoxyethylamino)-1-oxo-octanoic acid]1[(R)-methyl-Sar]3cyclosporin A (Compound ZY);

[(5R,6R,7S)-6-hydroxy-5-methyl-7-(methylamino)-1-(1,4-dioxan-2-ylmethyl)amino)-1-oxo-octanoic acid]1[(R)-methyl-Sar]3cyclosporin A (Compound ZX);

[(5R,6R,7S)-6-Hydroxy-5-methyl-7-(methylamino)-1-piperidino-1-oxo-octanoic acid]$^1$[(R)-methyl-Sar]$^3$cyclosporin A (Compound Q);

[(3R,4R,5S)-4-Hydroxy-3-methyl-5-(methylamino)-1-2-(N,N-diethylamino)ethoxy-hexanoic acid]$^1$[(S)-thio-isopropyl-Sar]$^3$cyclosporin A (Compound AL);

[(3R,4R,5S)-4-hydroxy-3-methyl-5-(methylamino)-1-N-morpholino-hexanoic acid]$^1$[(R)-ethyl-Sar]$^3$cyclosporin A (Compound AB);

[(3R,4R,5S)-4-hydroxy-3-methyl-5-(methylamino)-1-N-morpholino-hexanoic acid]$^1$[(S)-thiomethyl-Sar]$^3$cyclosporin A (Compound K);

[(3R,4R,5S)-4-Hydroxy-3-methyl-5-(methylamino)-1-N-morpholino-hexanoic acid]$^1$[(S)-thio-isopropyl-Sar]$^3$cyclosporin A (Compound I);

[(3R,4R,5S)-4-Hydroxy-3-methyl-5-(methylamino)-1-N-morpholino-hexanoic acid]$^1$[(S)-methoxy-Sar]$^3$cyclosporin A (Compound B);

[(3R,4R,5S)-4-Hydroxy-3-methyl-5-(methylamino)-1-N-morpholino-hexanoic acid]$^1$[(R)-methoxymethylene-Sar]$^3$ cyclosporin A (Compound D);

[(3R,4R,5S)-4-Hydroxy-3-methyl-5-(methylamino)-1-N-morpholino-hexanoic acid]$^1$[(R)-hydroxymethyl-Sar]$^3$cyclosporin A (Compound V);

[(3R,4R,5S)-4-Hydroxy-3-methyl-5-(methylamino)-1-N-morpholino-hexanoic acid]$^1$[(R)-2-diethylamino ethyl oxymethyl-Sar]$^3$cyclosporin A (Compound S);

[(3R,4R,5S)-4-Hydroxy-3-methyl-5-(methylamino)-1-N-homomorpholino-hexanoic acid]$^1$[(R)-2-diethylamino ethyl oxymethyl-Sar]$^3$cyclosporin A (Compound AD);

[(5R,6R,7S)-1-(dimethylamino)-6-hydroxy-5-methyl-7-(methylamino)-octanoic acid]$^1$[(R)-methyl-Sar]$^3$cyclosporin A (Compound KF);

[(5R,6R,7S)-6-hydroxy-5-methyl-7-(methylamino)-1-(N-morpholino)-octanoic acid]$^1$[(R)-methyl-Sar]$^3$cyclosporin A (Compound KG);

[(3R,4R,5S)-4-Hydroxy-3-methyl-5-(methylamino)-1-N-morpholino-hexanoic acid]$^1$[(S)-2-diethylaminoethylthiomethyl-Sar]$^3$cyclosporin A cyclosporinA (Compound AC);

[(3R,4R,5S)-4-Hydroxy-3-methyl-5-(methylamino)-1-N-morpholino-hexanoic acid]$^1$[(S)-2-diethylaminoethylthiomethyl-Sar]$^3$cyclosporinA (Compound AC);

[(3R,4R,5S)-4-Hydroxy-3-methyl-5-(methylamino)-1-({pyridin-2-ylmethyl}-methylamino)-hexanoic acid]$^1$[(R)-methyl-Sar]$^3$cyclosporin A (Compound DA);

[(3R,4R,5S)-1-(Bis{pyridin-2-ylmethyl}amino)-4-hydroxy-3-methyl-5-(methylamino)-hexanoic acid]$^1$[(R)-methyl-Sar]$^3$cyclosporin A (Compound DB);

[(3R,4R,5S)-4-Hydroxy-3-methyl-5-(methylamino)-1-(methyl-phenyl-amino)-hexanoic acid]$^1$[(R)-methyl-Sar]$^3$cyclosporin A (Compound DC);

[(3R,4R,5S)-4-Hydroxy-3-methyl-5-(methylamino)-1-(methyl-pyridin-2-yl-amino)-hexanoic acid]$^1$[(R)-methyl-Sar]$^3$cyclosporin A (Compound DD);

[(3R,4R,5S)-4-Hydroxy-3-methyl-5-(methylamino)-1-(2-sulfamoyl-ethyl)-methyl-amino)-hexanoic acid][1][(R)-methyl-Sar][3]cyclosporin A (Compound DE);
[(3R,4R,5S)-4-Hydroxy-3-methyl-5-(methylamino)-1-({pyridin-3-ylmethyl}-methylamino)-hexanoic acid][1][(R)-methyl-Sar][3]cyclosporin A (Compound DF);
[(3R,4R,5S)-4-Hydroxy-3-methyl-5-(methylamino)-1-({pyrimidin-2-ylmethyl}-methylamino)-hexanoic acid][1][(R)-methyl-Sar][3]cyclosporin A (Compound DG);
[(3R,4R,5S)-4-Hydroxy-3-methyl-5-(methylamino)-1-({pyrazin-2-ylmethyl}-methylamino)-hexanoic acid][1][(R)-methyl-Sar][3]cyclosporin A (Compound DH);
[(3R,4R,5S)-4-Hydroxy-3-methyl-5-(methylamino)-1-({3-methyl-3H-imidazol-4-ylmethyl}-methylamino)-hexanoic acid][1][(R)-methyl-Sar][3]cyclosporin A (Compound DI);
[(3R,4R,5S)-4-Hydroxy-3-methyl-5-(methylamino)-1-({2-methyl-2H-pyrazol-3-ylmethyl}-methylamino)-hexanoic acid][1][(R)-methyl-Sar][3]cyclosporin A (Compound DJ);
[(3R,4R,5S)-1-({2-Cyano-propyl}-methyl-amino)-4-hydroxy-3-methyl-5-(methylamino)-hexanoic acid][1][(R)-methyl-Sar][3]cyclosporin A (Compound DK);
[(3R,4R,5S)-4-Hydroxy-3-methyl-5-(methylamino)-1-({pyridin-4-ylmethyl}-methylamino)-hexanoic acid][1][(R)-methyl-Sar][3]cyclosporin A (Compound DL);
[(3R,4R,5S)-4-Hydroxy-3-methyl-5-(methylamino)-1-({1-methyl-1H-pyrazol-4-ylmethyl}-methylamino)-hexanoic acid][1][(R)-methyl-Sar][3]cyclosporin A (Compound DM);
[(3R,4R,5S)-4-Hydroxy-3-methyl-5-(methylamino)-1-({3,3,3-trifluoropropyl}-methyl-amino)-hexanoic acid][1][(R)-methyl-Sar][3]cyclosporin A (Compound DN);
[(3R,4R,5S)-4-Hydroxy-3-methyl-5-(methylamino)-1-({1-methyl-3-trifluoromethyl-2H-pyrazol-5-ylmethyl}-methylamino)-hexanoic acid][1][(R)-methyl-Sar][3]cyclosporin A (Compound DO);
[(3R,4R,5S)-4-Hydroxy-3-methyl-5-(methylamino)-1-({5-fluoro-pyridin-2-ylmethyl}-methylamino)-hexanoic acid][1][(R)-methyl-Sar][3]cyclosporin A (Compound DP);
[(3R,4R,5S)-4-Hydroxy-3-methyl-5-(methylamino)-1-({5-chloro-pyridin-2-ylmethyl}-methylamino)-hexanoic acid][1][(R)-methyl-Sar][3]cyclosporin A (Compound DQ);
[(3R,4R,5S)-4-Hydroxy-3-methyl-5-(methylamino)-1-({3-trifluoromethyl-pyridin-2-ylmethyl}-methylamino)-hexanoic acid][1][(R)-methyl-Sar][3]cyclosporin A (Compound DR);
[(3R,4R,5S)-1-(3,3-Dimethyl-morpholin-4-yl)-4-hydroxy-3-methyl-5-(methylamino)-hexanoic acid][1][(R)-methyl-Sar][3]cyclosporin A (Compound DS);
[(3R,4R,5S)-4-Hydroxy-3-methyl-5-methylamino-((R)-3-methyl-morpholin-4-yl)-hexanoic acid][1][(R)-methyl-Sar][3]cyclosporin A (Compound DT);
[(3R,4R,5S)-1-(5,6-Dihydro-8H-[1,2,4]triazolo[4,3-a]pyrazin-7-yl)-4-Hydroxy-3-methyl-5-(methylamino)-hexanoic acid][1][(R)-methyl-Sar][3]cyclosporin A (Compound DU);
[(3R,4R,5S)-4-Hydroxy-3-methyl-5-(methylamino)-1-(8-oxa-3-aza-bicyclo[3.2.1]oct-3-yl)-hexanoic acid][1][(R)-methyl-Sar][3]cyclosporin A (Compound DV);
[(3R,4R,5S)-4-Hydroxy-3-methyl-5-(methylamino)-1-((S)-3-methyl-morpholin-4-yl)-hexanoic acid][1][(R)-methyl-Sar][3]cyclosporin A (Compound DW);
[(3R,4R,5S)-1-(2,3-Dihydro-benzo[1,4]oxazin-4-yl)-4-Hydroxy-3-methyl-5-(methylamino)-hexanoic acid][1][(R)-methyl-Sar][3]cyclosporin A (Compound DX);
[(3R,4R,5S)-1-(1,4-Dioxa-8-aza-spiro[4.5]dec-8-yl)-4-Hydroxy-3-methyl-5-(methylamino)-hexanoic acid][1][(R)-methyl-Sar][3]cyclosporin A (Compound DY);
[(3R,4R,5S)-4-Hydroxy-3-methyl-5-(methylamino)-1-(2-phenyl-morpholin-4-yl)-hexanoic acid][1][(R)-methyl-Sar][3] cyclosporin A (Compound DZ);
[(3R,4R,5S)-4-Hydroxy-3-methyl-5-(methylamino)-1-(piperidin-1-yl)-hexanoic acid][1][(R)-methyl-Sar][3]cyclosporin A (Compound EA);
[(3R,4R,5S)-4-Hydroxy-3-methyl-5-(methylamino)-1-(pyrrolidin-1-yl)-hexanoic acid][1][(R)-methyl-Sar][3]cyclosporin A (Compound EF);
[(3R,4R,5S)-4-Hydroxy-3-methyl-5-(methylamino)-1-(2-trifluoromethyl-piperidin-1-yl)-hexanoic acid][1][(R)-methyl-Sar][3]cyclosporin A (Compound EB);
[(3R,4R,5S)-4-Hydroxy-3-methyl-5-(methylamino)-1-(3-trifluoromethyl-morpholin-4-yl)-hexanoic acid][1][(R)-methyl-Sar][3]cyclosporin A (Compound EC);
[(3R,4R,5S)-4-Hydroxy-3-methyl-5-(methylamino)-1-([1,2]oxazinan-2-yl)-hexanoic acid][1][(R)-methyl-Sar][3]cyclosporin A (Compound ED);
[(3R,4R,5S)-4-Hydroxy-3-methyl-5-(methylamino)-1-(2-trifluoromethyl-5,6-dihydro-8H-imidazo[1,2-a]pyrazin-7-yl)-hexanoic acid][1][(R)-methyl-Sar][3]cyclosporin A (Compound EE);
[(3R,4R,5S)-4-Hydroxy-3-methyl-5-(methylamino)-1-(pyrrolidin-1-yl)-hexanoic acid][1][(R)-methyl-Sar][3]cyclosporin A (Compound EF);
[[(3R,4R,5S)-4-Hydroxy-3-methyl-5-(methylamino)-1-(4-methyl-[1,4]diazepan-1-yl)-hexanoic acid][1][(R)-methyl-Sar][3]cyclosporin A (Compound EG);
[[(3R,4R,5S)-4-Hydroxy-1-(3-methoxy-azetidin-1-yl)-3-methyl-5-(methylamino)-hexanoic acid][1][(R)-methyl-Sar][3]cyclosporin A (Compound EH);
[(4R,5R,6S)-5-Hydroxy-4-methyl-6-(methylamino)-1-(morpholin-4-yl)-heptanoic acid][1]cyclosporin A (Compound EI);
[(3R,4R,5S)-4-Hydroxy-3-methyl-1-(morpholin-4-yl)-hexanoic acid][1][(R)-methyl-Sar][3][Ethyl-Val][4]cyclosporin A (Compound EJ);
[(3R,4R,5S)-4-Hydroxy-3-methyl-5-(methylamino)-1-(2,2,6,6-tetrafluoro-morpholin-4-yl)-hexanoic acid][1][(R)-methyl-Sar][3]cyclosporin A (Compound EK);
[(3R,4R,5S)-(3,3-Difluoro-pyrrolidin-1-yl)-4-Hydroxy-3-methyl-5-(methylamino)-1-hexanoic acid][1][(R)-methyl-Sar][3]cyclosporin A (Compound EL);
[(3R,4R,5S)-(3,3-Difluoro-azetidin-1-yl)-4-hydroxy-3-methyl-5-(methylamino)-1-hexanoic acid][1][(R)-methyl-Sar][3] cyclosporin A (Compound EM);
[(3R,4R,5S)-(4,4-Difluoro-piperidin-1-yl)-4-hydroxy-3-methyl-5-(methylamino)-1-hexanoic acid][1][(R)-methyl-Sar][3]cyclosporin A (Compound EN);
[(3R,4R,5S)-4-Hydroxy-3-methyl-5-(methylamino)-1-(3,3,4,4-tetrafluoro-pyrrolidin-1-yl)-hexanoic acid][1][(R)-methyl-Sar][3]cyclosporin A (Compound ER);
[(3R,4R,5S)-4-Hydroxy-3-methyl-5-(methylamino)-1-(2,2,6,6-tetrafluoro-morpholin-4-yl)-hexanoic acid][1][(R)-hydroxymethyl-Sar][3]cyclosporin A (Compound EO);
(3R,4R,5S)-1-(3,3-Difluoro-pyrrolidin-1-yl)-4-hydroxy-3-methyl-5-(methylamino)-hexanoic acid][1][(R)-hydroxymethyl-Sar][3]cyclosporin A (Compound EP); and
(3R,4R,5S)-1-[Bis-(3,3,3-trifluoro-propyl)-amino]-[(4-Hydroxy-3-methyl-5-(methylamino)-hexanoic acid][1][(R)-methyl-Sar][3]cyclosporin A (Compound EQ).

In another embodiment there is provided a pharmaceutical composition comprising a compound having Formula I and a pharmaceutically acceptable excipient. The excipient can be an ophthalmically acceptable excipient.

The pharmaceutical composition can be in the form of a liquid, solid, or emulsion. For example, the pharmaceutical compositions can be in the form of an aqueous solution.

A compound of Formula I can be in a purified form. In one embodiment, the purified form is the form obtained from medium pressure liquid chromatography (MPLC).

The present invention includes pharmaceutically acceptable salts of any compound having Formula I.

The term "pharmaceutically acceptable salts" refers to salts or complexes that retain the desired biological activity of the compound of Formula I and exhibit minimal or no undesired toxicological effects to the patient, animal, or cell system to which they are administered. The "pharmaceutically acceptable salts" according to the invention include therapeutically active non-toxic base or acid salt forms of Formula I.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, or formic acid and the like (Handbook of Pharmaceutical Salts, P. Heinrich Stahal & Camille G. Wermuth (Eds), Verlag Helvetica Chemica Acta—Zürich, 2002, 329-345).

The base addition salt form of a compound of Formula I that occurs in its free form as an acid can be obtained by treating the acid with an appropriate base such as an inorganic base, for example, sodium hydroxide, magnesium hydroxide, potassium hydroxide, calcium hydroxide, ammonia and the like; or an organic base such as for example, L-arginine, ethanolamine, betaine, benzathine, morpholine and the like. (Handbook of Pharmaceutical Salts, P. Heinrich Stahal & Camille G. Wermuth (Eds), Verlag Helvetica Chemica Acta—Zürich, 2002, 329-345).

The present invention further concerns the use of a compound of Formula I, or a pharmaceutically acceptable salt thereof, for the manufacture of a pharmaceutical composition.

The present invention further encompasses a method for treating a medical condition in a patient in need thereof, the method comprising administering to the patient a therapeutically effective amount of a compound of Formula I, or a pharmaceutically acceptable salt thereof. In some forms of this method, the medical condition is selected from the group consisting of dry eye, dry eye disease, ocular surface inflammation, blepharitis, meibomian gland disease, allergic conjunctivitis, pterygia, ocular symptoms of graft versus host disease, ocular allergy, atopic keratoconjunctivitis, vernal keratoconjunctivitis, uveitis, anterior uveitis, Behcet's disease, Stevens Johnson syndrome, ocular cicatricial pemphigoid, chronic ocular surface inflammation caused by viral infection, herpes simplex keratitis, adenoviral keratoconjunctivitis, ocular rosacea, or pinguecula.

Another embodiment is a method for reducing corneal transplant rejection in a patient in need thereof, the method comprising administering to the patient a therapeutically effective amount of a compound of Formula I, or a pharmaceutically acceptable salt thereof.

Another embodiment is a method for reducing inflammation of the eye caused by an ocular surgery, the method comprising administering to the eye(s) of a patient who has received ocular surgery a therapeutically effective amount of a compound of Formula I, or a pharmaceutically acceptable salt thereof.

Another embodiment is a method for treating dry eye in a patient in need thereof, the method comprising administering to the eye(s) of the patient a therapeutically effective amount of a compound of Formula I, or a pharmaceutically acceptable salt thereof.

Another embodiment is a method for increasing tear production in a patient whose tear production is suppressed or presumed to be suppressed due to ocular inflammation associated with keratoconjunctivitis sicca, the method comprising administering to the eye(s) of the patient a therapeutically effective amount of a compound of Formula I, or a pharmaceutically acceptable salt thereof.

Another embodiment is a method for reducing or preventing an ocular condition in a patient, the method comprising administering a therapeutically effective amount of a compound of Formula I to the patient. In some forms of this method, the ocular condition is selected from the group consisting of dry eye, ocular surface inflammation, blepharitis, meibomian gland disease, allergic conjunctivitis, pterygia, ocular symptoms of graft versus host disease, ocular allergy, atopic keratoconjunctivitis, vernal keratoconjunctivitis, uveitis, anterior uveitis, ocular cicatricial pemphigoid, chronic ocular surface inflammation caused by viral infection, herpes simplex keratitis, adenoviral keratoconjunctivitis, ocular rosacea, and pinguecula.

A compound of Formula I may be administered in the form of a pharmaceutical composition, topically, orally, systemically, or by other suitable routes.

Many compounds having Formula I are potent inhibitors of cyclophilin A (CyP-A), and are non-immunosuppressive as measured by the Calcineurin phosphatase assay (IC50>10 µM) and mixed lymphocyte reaction (MLR) assay (>50 fold less active than Cyclosporin A). However, a sub-set of compounds of Formula I has been discovered that show immunosuppressive activity as measured by the Calcineurin phosphatase assay (IC50<4 µM) and MLR assay (<25 fold less active than Cyclosporin A).

The present invention includes, but is not limited to, the following embodiments 1-20:

1. A compound having Formula I

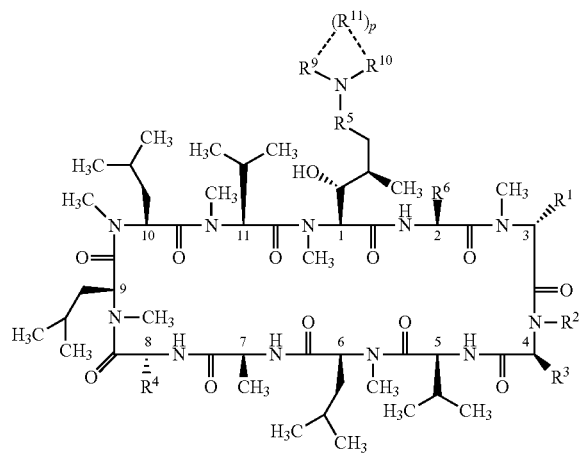

Formula I or a pharmaceutically acceptable salt thereof, wherein:

R$^1$ is —H, —C$_{1-6}$alkyl, —OC$_{1-6}$alkyl, —CH$_2$F, —CH$_2$OCH$_3$, —SC$_{1-6}$alkyl, —CH$_3$, —CH$_2$CH$_3$, —SCH(CH$_3$)$_2$, —CH$_2$OH, —SCH$_3$, —OCH$_3$, —R$^{13}$R$^{14}$,

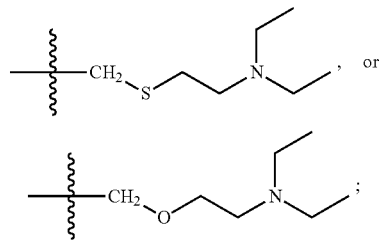

R$^2$ is —CH$_3$, —CH$_2$CH$_3$, or —CH$_2$CH$_2$CH$_3$;
R$^3$ is —CH$_2$CH(CH$_3$)$_2$, —CH(CH$_3$)$_2$, —CH$_2$C(CH$_3$)$_2$(OH), —CH(CH$_3$)(CH$_2$CH$_3$), or —CH$_2$CH(R$^7$)(CH$_2$CH$_3$);
R$^4$ is —CH$_3$ or —CH$_2$OH;
R$^5$ is —R$^8$(CH$_2$)$_n$(C=O)$_m$—;
R$^6$ is —CH$_2$CH$_3$, —CH(CH$_3$)(OH), —CH(CH$_3$)$_2$, or —CH$_2$CH$_2$CH$_3$;
R$^7$ is OC$_{1-5}$ alkyl;
R$^8$ is O, S, CH$_2$O, CH$_2$S, or CH$_2$;
R$^9$ is —H, —C$_{1-5}$ alkyl,

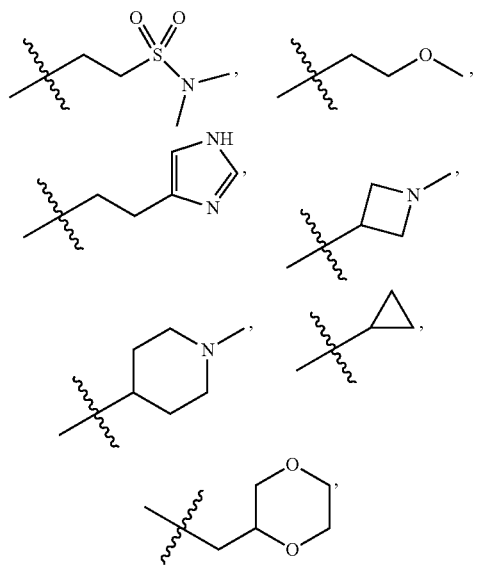

C$_{3-8}$cycloalkyl, heterocycle, aryl, or cycloalkenyl, or taken together with R$^{11}$, R$^{10}$, and the N to which R$^9$ and R$^{10}$ are attached forms a heterocycle;

R$^{10}$ is —H, —C$_{1-5}$ alkyl,

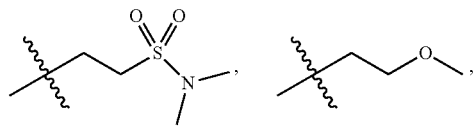

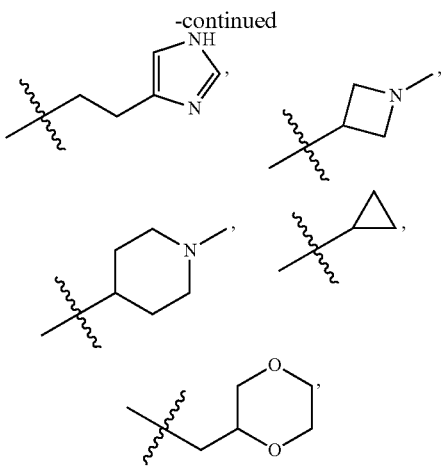

C$_{3-8}$cycloalkyl, heterocycle, aryl, or cycloalkenyl, or taken together with R$^{11}$, R$^9$, and the N to which R$^9$ and R$^{10}$ are attached forms a heterocycle;
R$^{11}$ is O, NR$^{12}$, S(O)$_q$, C$_{1-5}$alkylene, divalent C$_{3-8}$cycloalkyl, divalent heterocycle, carbonyl, or taken together with R$^9$, R$^{10}$, and the N to which R$^9$ and R$^{10}$ are attached forms a heterocycle;
R$^{12}$ is H, CH$_3$, or C$_{1-5}$ alkyl;
R$^{13}$ is O, S, CH$_2$O, CH$_2$S, CH$_2$SO, or CH$_2$SO$_2$;
R$^{14}$ is H, C$_{1-6}$alkyl, C$_{2-6}$alkenyl, C$_{2-6}$alkynyl, C$_{3-8}$cycloalkyl, CH$_2$CH$_2$N(CH$_2$CH$_3$)$_2$, CH$_2$CH$_2$NH(CH$_2$CH$_3$), heterocycle, or aryl;
n=0, 1, 2, 3, or 4;
m=0 or 1;
p=0 or 1; and
q=0, 1, or 2;
wherein R$^{14}$ is optionally substituted with one or more groups independently selected from the group consisting of H, C$_{1-6}$alkyl, halogen, hydroxyl, ester, sulfonamide, ketone, aldehyde, cycloalkyl, heterocycle, aryl, amine, heterocycle, amide, and guanidinyl;
wherein the heterocycle comprising R$^9$, R$^{10}$, R$^{11}$, and the N to which R$^9$ and R$^{10}$ are attached is monocyclic or polycyclic;
wherein "- - - - - -" is a single bond or is absent; and
with the provisos that
when R$^8$ is O, S, CH$_2$O, or CH$_2$S then n is not 0 or 1;
when p=0 then R$^{11}$ and "- - - - - -" are absent; and
when R$^{11}$ and "- - - - - -" are absent then R$^9$ is not directly linked to R$^{10}$.

2. A compound according to embodiment 1, above, wherein R$^1$ is not hydrogen (H).

3. A compound according to embodiment 1, wherein when R$^1$ is H then m=0.

4. A compound according to embodiment 1, wherein when R$^1$ is H, then m=0 and R$^9$, R$^{10}$, R$^{11}$, and the N to which R$^9$ and R$^{10}$ are attached together form a heterocycle.

5. A compound according to embodiment 1, wherein R$^2$ is —CH$_3$ or —CH$_2$CH$_3$; R$^3$ is —CH$_2$CH(CH$_3$)$_2$, —CH(CH$_3$)$_2$, or —CH$_2$C(CH$_3$)$_2$(OH); R$^4$ is —CH$_3$; R$^6$ is —CH$_2$CH$_3$; and R$^8$ is CH$_2$.

6. A compound according to embodiment 1, wherein R$^2$ is —CH$_3$; R$^3$ is —CH$_2$CH(CH$_3$)$_2$; R$^4$ is —CH$_3$; R$^6$ is —CH$_2$CH$_3$; and R$^8$ is CH$_2$.

7. A compound according to embodiment 1, wherein R$^1$ is —CH$_3$, —CH$_2$CH$_3$, or —SCH$_3$; R$^2$ is —CH$_3$; R$^3$ is —CH$_2$CH(CH$_3$)$_2$; R$^4$ is —CH$_3$; R$^6$ is —CH$_2$CH$_3$; and R$^8$ is CH$_2$.

8. A compound according to embodiment 1, wherein the compound is any one of those listed in Tables 1-20.

9. A pharmaceutical composition comprising as active ingredient a therapeutically effective amount of a compound according to any one of embodiments 1-8, or a pharmaceutically acceptable salt thereof, and a pharmaceutically acceptable excipient.

10. The pharmaceutical composition of embodiment 9, wherein the compound is present in the composition in an amount of from about 0.01% (w/v) to about 1% (w/v).

11. The pharmaceutical composition of embodiment 10, wherein the composition is in the form of an aqueous solution.

12. The pharmaceutical composition of embodiment 11, wherein the composition is acceptable for administration to the eye(s) of a mammal.

13. A method of treating a medical condition in a patient in need thereof, the method comprising administering to the patient a therapeutically effective amount of a compound, or a pharmaceutically acceptable salt thereof, according to any one of embodiments 1-8.

14. The method of embodiment 13, wherein the patient is a human patient.

15. The method of embodiment 13, wherein the medical condition is dry eye, dry eye disease, ocular surface inflammation, blepharitis, meibomian gland disease, allergic conjunctivitis, pterygia, ocular symptoms of graft versus host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, adenoviral keratoconjunctivitis, ocular rosacea, or pinguecula.

16. A method for reducing corneal transplant rejection in a patient in need thereof, the method comprising administering to the patient a therapeutically effective amount of a compound, or a pharmaceutically acceptable salt thereof, according to any one of embodiments 1-8.

17. A method for reducing inflammation of the eye caused by an ocular surgery, the method comprising administering to the eye(s) of a patient who has received ocular surgery a therapeutically effective amount of a compound, or a pharmaceutically acceptable salt thereof, according to any one of embodiments 1-8.

18. A method for treating dry eye in a patient in need thereof, the method comprising administering to the eye(s) of the patient a therapeutically effective amount of a compound, or a pharmaceutically acceptable salt thereof, according to any one of embodiments 1-8.

19. A method for increasing tear production in a patient whose tear production is suppressed or presumed to be suppressed due to ocular inflammation associated with keratoconjunctivitis sicca, the method comprising administering to the eye(s) of the patient a therapeutically effective amount of a compound according to any one of embodiments 1-8, or a pharmaceutically acceptable salt thereof.

20. The method of any one of embodiment 13, wherein the compound is administered to the patient topically, orally, or systemically.

The present invention further includes a method for making a compound having the formula:

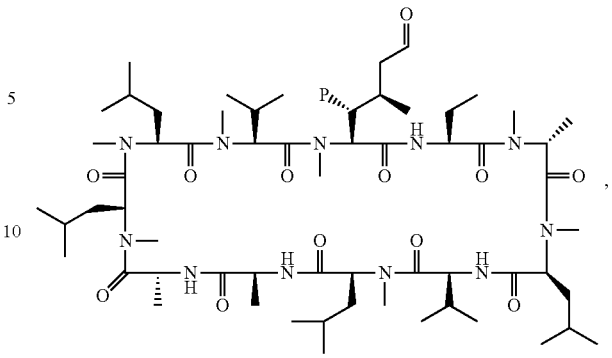

the method comprising
a) adding 10% palladium on carbon to a solution comprising

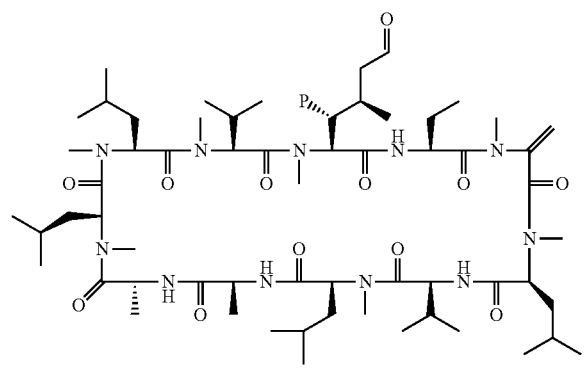

in ethanol, wherein P is a protecting group;
b) stirring the solution under a hydrogen atmosphere;
c) filtering the mixture from step b through a filter and collecting the filtrate;
d) washing the filter used in step c and collecting the filtrate together with the filtrate from step c;
e) evaporating the filtrate from step d to thereby obtain a compound having the formula shown above as the major product.

In some forms of this method for making, P is

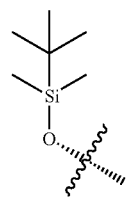

and the filter comprises celite. In yet more specific forms of this method washing the filter used in step c comprises washing the filter with ethyle acetate.

DEFINITIONS

A "patient in need in need of treatment" or "patient in need thereof" refers to a human or non-human mammal afflicted with a medical condition, as specified in context. Non-limiting examples of a non-human mammal include a horse, pig, monkey, dog, rabbit, guinea pig, rat, or mouse.

A "therapeutically effective amount" refers to the amount of a compound sufficient to reduce the severity of one or more symptoms associated with, accompanying, or resulting from a medical condition affecting a subject.

"Treating" and "to treat" refers to relieving or reducing at least one symptom associated with or accompanying a medical condition. For example, treatment of dry eye and relief of inflammation of the ocular surface, as may occur in an individual suffering from dry eye, may be observed or experienced as an improvement in vision, and/or as a reduction in swelling, pain, redness, dryness, scratchiness, grittiness, foreign body sensation, stinging, burning, or itching. Treating an inflammation of the ocular surface or ocular surface adnexa may improve the visual performance and the optical quality of the eye. Improvement in visual performance may include improved optical quality, improved tear film production, secretion, quality, and/or stability, reduced blurring, improved central and/or peripheral field vision, improved visual performance, acuity, or perception, and/or reduced blinking frequency. The symptom(s) positively affected by the treatment, will depend on the particular condition.

The term "inflammation" refers to the biological response of the living body to injury or other harmful insults. Symptoms of "an inflammation at the ocular surface" can include redness, swelling, heat, pain, and/or loss of function of glands or tissue in the ocular surface or ocular surface adnexa. Other symptoms may include sensations of (and lead a patient to complain of) dryness, burning, itching, or scratchiness. A subject may report a feeling of dust, dirt, sand, or gravel in the eye.

A "Medical condition" refers to a deviation from or interruption of the normal structure or function of any body part, tissue, organ, or system and that is characterized by an identifiable group of signs or symptoms whose etiology, pathology, and prognosis may be known or unknown. A medical condition of a body part, tissue, organ, or system of a human or non-human mammal may result from various causes, including but not limited to injury, surgical trauma, infection, nutritional deficiency, genetic defect, exposure to toxins or radiation, and environmental stress. Medical conditions include ocular conditions such as, for example, inflammation of the ocular surface, and dry eye; and dermatological conditions such as an inflammation of the skin.

An "ocular condition" is a disease, ailment or condition which affects or involves the eye or one or more parts or regions of the eye.

"Ocular surface condition" refers to a medical condition that affects or involves one or more parts, regions, or tissues of the ocular surface. An ocular surface condition can be an inflammation of an ocular surface tissue, and includes an acute, chronic, and surgically-induced inflammation of an ocular surface tissue.

The term "ocular surface" refers to the cornea, the corneal epithelium, the conjunctiva (palpebral, bulbar, and formiceal), the conjunctival blood vessels, Tenon's capsule, the sclera, and the limbus.

The term "ocular surface adnexa" refers to structures in close proximity to the ocular surface, including the lacrimal gland, the eye lids, eyelashes, and eyebrows, the orbital wall, the periocular or extraocular muscles, and the meibomian glands.

The "eye" is the sense organ for sight, and includes the eyeball, or globe, the orbital sense organ that receives light and transmits visual information to the central nervous system. Broadly speaking the eye includes the eyeball and the tissues and fluids which constitute the eyeball, the periocular muscles (such as the oblique and rectus muscles) and the portion of the optic nerve which is within or adjacent to the eyeball.

The "eye lids" are the structures covering the front of the eye that protect it, limit the amount of light entering the pupil, and help distribute tear film over the exposed corneal surface.

The term "biocompatible" means compatible with living tissue or a living system by not being toxic, injurious, or physiologically reactive and by causing minimal or no immunological reaction.

The term "alkyl", as used herein, refers to saturated monovalent or divalent hydrocarbon moieties having linear or branched moieties or combinations thereof and containing 1 to 6 carbon atoms. One methylene ($-CH_2-$) group, of the alkyl can be replaced by oxygen, sulfur, sulfoxide, nitrogen, carbonyl, carboxyl, sulfonyl, amide, sulfonamide, by a divalent $C_{3-6}$ cycloalkyl, by a divalent heterocycle, or by a divalent aryl group. Alkyl groups can be independently substituted by halogen, hydroxyl, cycloalkyl, amine groups, heterocyclic groups, carboxylic acid groups, phosphonic acid groups, sulphonic acid groups, phosphoric acid groups, nitro groups, amide groups, or sulfonamides groups. Non-limiting examples of suitable alkyl groups include methyl ($-CH_3$), ethyl ($-CH_2CH_3$), n-propyl ($-CH_2CH_2CH_3$), isopropyl ($-CH(CH_3)_2$), and t-butyl ($-C(CH_3)_3$).

An "alkylene" is a divalent alkyl. Non-limiting examples of an alkylene include methylene, ethylene ($-CH_2CH_2-$), and n-propylene ($-CH_2CH_2CH_2-$).

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen, nitro groups, cyano groups, $-OC_{1-6}$ alkyl groups, $-SC_{1-6}$ alkyl groups, $-C_{1-6}$ alkyl groups, $-C_{2-6}$ alkenyl groups, $-C_{2-6}$ alkynyl groups, $C_{3-8}$ cycloalkyl groups, carboxylic acid groups, ester groups, ketone groups, aldehyde groups, amide groups, amine groups, sulfonamide groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogennitro groups, cyano groups, $-OC_{1-6}$ alkyl groups, $-SC_{1-6}$ alkyl groups, $-C_{1-6}$ alkyl groups, $-C_{2-6}$ alkenyl groups, $-C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups.

The term "halogen", as used herein, refers to an atom of chlorine, bromine, fluorine, iodine.

The term "haloalkyl" refers to an alkyl in which one or more hydrogen atoms on the alkyl have been replaced with a halogen atom. Non-limiting examples of a haloalkyl include fluoroalkyls such as $-CF_3$ and $-CH_2CH_2CF_3$.

The term "heterocycle" as used herein, refers to a 3 to 10 membered ring, which can be aromatic or non-aromatic, monvalent or divalent, saturated or unsaturated, containing at least one heteroatom selected form O or N or S or combinations of at least two thereof, interrupting the carbocyclic ring structure. The heterocyclic ring can be interrupted by a C=O; the S and N heteroatoms can be oxidized. Heterocycles can be monocyclic or polycyclic. For example, a heterocycle can be bicyclic. The rings in a bicyclic or polycyclic heterocycle can be fused or non-fused. Heterocyclic ring moieties can be substituted by halogen, nitro groups, cyano groups, $-OC_{1-6}$ alkyl groups, $-SC_{1-6}$ alkyl groups, $-C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups, or hydroxyl groups.

The term "alkenyl", as used herein, refers to a monovalent or divalent hydrocarbon radical having 2 to 6 carbon atoms, derived from a saturated alkyl, having at least one double bond. A $C_{2-6}$ alkenyl can be in the E or Z configuration. Alkenyl groups can be substituted by $C_{1-3}$ alkyl, as defined above, or by halogen.

The term "alkynyl", as used herein, refers to a monovalent or divalent hydrocarbon radical having 2 to 6 carbon atoms, derived from a saturated alkyl, having at least one triple bond. Alkynyl groups can be substituted by $C_{1-3}$ alkyl, as defined above, or by halogen.

The term "aryl" as used herein, refers to an organic moiety derived from an aromatic hydrocarbon consisting of a ring containing 6 to 10 carbon atoms by removal of one hydrogen, which can be substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups. A non-limiting example of an aryl is phenyl. Preferred substitution site on aryl are the meta and the para positions. Most preferred substitution sites on aryl are the para positions.

The term "ketone" as used herein, represents an organic compound having a carbonyl group linked to a carbon atom such as —$(CO)R^x$ wherein $R^x$ can be alkyl, aryl, cycloalkyl, cycloalkenyl, heterocycle as defined herein.

The term "aldehyde" as used herein, represents a group of formula —$C(O)H$.

The term "ester" as used herein, represents a group of formula —$C(O)OR^x$, wherein $R^x$ can be alkyl, aryl, cycloalkyl, cycloalkenyl, heterocycle as defined herein.

The term "hydroxyl" as used herein, represents a group of formula —$OH$.

The term "carbonyl" as used herein, represents a group of formula —$C(O)$—, which may also be represented as and is equivalent to —$(C=O)$—.

The term "carboxyl" as used herein, represents a group of formula —$C(O)O$—.

The term "sulfonyl" as used herein, represents a group of formula —$SO_2$—.

The term "sulfate" as used herein, represents a group of formula —$O—S(O)_2—O$—.

The term "carboxylic acid" as used herein, represents a group of formula —$C(O)OH$.

The term "nitro" as used herein, represents a group of formula —$NO_2$.

The term "cyano" as used herein, represents a group of formula —$CN$.

The term "phosphonic acid" as used herein, represents a group of formula —$P(O)(OH)_2$.

The term "phosphoric acid" as used herein, represents a group of formula —$OP(O)(OH)_2$.

The term "amide" as used herein, represents a group of formula —$C(O)NR^xR^y$, wherein $R^x$ and $R^y$ can be the same or independently H, alkyl, aryl, cycloalkyl, cycloalkenyl, or heterocycle, as defined above.

The term "amine" as used herein, represents a group of formula —$NR^xR^y$, wherein $R^x$ and $R^y$ can be the same or independently H, alkyl, aryl, cycloalkyl, cycloalkenyl, or heterocycle as defined above.

The term "sulfonamide" as used herein, represents a group of formula —$S(O)_2NR^xR^y$ wherein $R^x$ and $R^y$ can be the same or independently H, alkyl, aryl, cycloalkyl, cycloalkenyl, heterocycle as defined above.

The term "sulfoxide" as used herein, represents a group of formula —$S(O)$—.

The term "sulphonic acid" as used herein, represents a group of formula —$S(O)_2OH$.

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

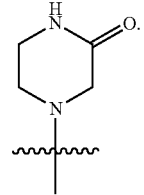 [SMILES: *N1CCNC(=O)C1]

The term "piperazinonyl" as used herein represents a group of formula

The term "morpholinyl" as used herein represents a group of formula

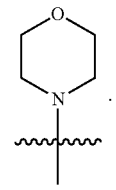

The term "N-methylpiperazinyl" as used herein represents a group of formula

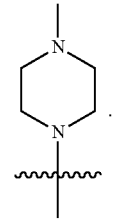

The term "guanidinyl" as used herein refers to a group of formula

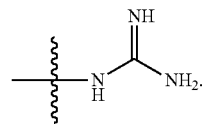 [SMILES: *NC(=N)N]

The term "substituted" means that one or more hydrogens on the designated atom is replaced with a selection from the indicated group, provided that the designated atom's normal valency under the existing circumstances is not exceeded, and that the substitution results in a stable compound.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art and in standard textbooks such as, for example, T. W. Greene et al, *Protective Groups in organic Synthesis* (1981), Wiley, New York.

DETAILED DESCRIPTION OF THE INVENTION

Therapeutic Uses

The present invention is directed in part to pharmaceutical compositions comprising a compound having Formula I.

A pharmaceutical composition comprising a compound of Formula I may be useful for treating dry eye, dry eye disease (i.e., keratoconjunctivitis sicca), ocular surface inflammation (i.e, inflammation of the ocular surface), blepharitis, meibomian gland disease, allergic conjunctivitis, pterygia, ocular symptoms of graft versus host disease, ocular allergy, atopic keratoconjunctivitis, vernal keratoconjunctivitis, uveitis, anterior uveitis, Behcet's disease, Stevens Johnson syndrome, ocular cicatricial pemphigoid, chronic ocular surface inflammation caused by viral infection, herpes simplex keratitis, adenoviral keratoconjunctivitis, ocular rosacea, and pinguecula, and to prevent or reduce the risk of corneal transplant rejection in a patient or subject in need thereof. Additionally, one embodiment of this invention is a method for administering a pharmaceutical composition of this invention to a patient before, during, or after ocular surgery (such as refractive surgery) to reduce and/or prevent inflammation of the eye or ocular surface caused by the surgery.

Pharmaceutical compositions of the invention may be useful for treating an inflammation of the ocular anterior segment of the eye. More specifically, the pharmaceutical compositions of the invention may be useful for treating an inflammation of the ocular surface or ocular surface adnexa.

In addition a pharmaceutical composition comprising a compound of Formula I may be useful for reducing one or symptoms associated with an inflammatory dermatological condition. One example of an inflammatory dermatological condition that may be subject to treatment is psoriasis. Additionally, a pharmaceutical composition comprising a compound of Formula I may be useful for treating a viral infection. Examples of viral infections may include Hepatitis C infection and Hepatitis B infection.

Accordingly, one embodiment is a method for reducing one or more or symptoms associated with an inflammatory dermatological condition in a patient in need thereof, comprising administering a pharmaceutical composition comprising a compound of Formula I to the patient. Another embodiment is a method for reducing or preventing an inflammatory dermatological condition in a patient, comprising administering a therapeutically effective amount of a compound of Formula I to the patient. The method may reduce one or more signs or symptoms of the inflammatory dermatological condition. One example of an inflammatory dermatological condition is psoriasis.

Another embodiment is a method for treating an inflammation of the skin in a patient in need thereof comprising administering a pharmaceutical composition comprising a compound of Formula I to the patient. Another embodiment is a method for reducing an inflammation of the skin in a patient, comprising administering a therapeutically effective amount of a compound of Formula I to the patient.

Another embodiment is a method for treating a viral infection in a patient in need thereof, comprising administering a pharmaceutical composition comprising a compound of Formula I to the patient. Another embodiment is a method for reducing one or more signs or symptoms of a viral infection, or for inhibiting the progress of a viral infection in a patient, comprising administering a pharmaceutical composition comprising a compound of Formula I to the patient.

One embodiment is a method for treating dry eye in a patient in need thereof, comprising administering a pharmaceutical composition comprising a compound of Formula I to the eye(s) of the patient.

Another embodiment is a method for increasing tear production in a patient whose tear production is suppressed (or presumed to be suppressed) due to ocular inflammation associated with keratoconjunctivitis sicca.

Another embodiment is a method for reducing ocular surface inflammation in a patient, comprising administering a therapeutically effective amount of a compound having Formula I to the patient. In one method, the ocular surface inflammation is associated with keratoconjunctivitis sicca. In some forms of this method, the compound having Formula I is administered topically to the patient's eye(s).

One embodiment is a method for reducing or preventing an ocular condition in a patient, the method comprising administering a therapeutically effective amount of a compound of Formula I to the patient. The method may reduce one or more signs or symptoms of the ocular condition.

"Dry eye" as used herein includes "dry eye disease" as defined by the International Dry Eye Workshop (DEWS) in Lemp et al. (2007) "The Definition and Classification of Dry Eye Disease: Report of the Definition and Classification Subcommittee of the International Dry Eye Workshop" *Ocul. Surf* 5:75-92. The International Dry Eye Workshop (DEWS) defines dry eye disease as "a multifactorial disease of the tears and ocular surface that results in symptoms of discomfort, visual disturbance, and tear film instability with potential damage to the ocular surface, accompanied by increased osmolarity of the tear film and inflammation of the ocular surface."

The term "dry eye disease" is considered to be synonymous with "dry eye syndrome" and "keratoconjunctivitis sicca." Dry eye disease includes the aqueous deficient (Sjogren and non-Sjogren) and evaporative categories of dry eye disease. An individual with dry eye disease may present with symptoms of both aqueous deficiency (e.g., insufficient tear production) and excessive evaporation of the tear film.

The pharmaceutical composition can be administered to a patient topically, orally, or systemically (including intravenously or intraarterially). Administration may be to the eye, such as the surface of the eye.

The actual amount of the compound to be administered in any given case will be determined by a physician taking into account the relevant circumstances, such as the severity of the condition, the age and weight of the patient, the patient's general physical condition, the cause of the condition, and the route of administration.

Accordingly, the present invention includes methods for treating any of the above ocular conditions in a patient in need thereof by administering a pharmaceutical composition comprising a compound of Formula I to the patient. The composition can be administered directly to the ocular surface of the eye or to an ocular region in the eye. Modes of direct administration to the eye can include topical delivery and intraocular injection.

Pharmaceutical compositions of the invention may also be useful for restoring corneal sensitivity that has been impaired due to surgery on the cornea or other surface of the eye. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients may actually be a form of corneal neuropathy that results when corneal nerves are severed by surgery or inflamed after viral infection.

A patient in need of treatment of an "ocular surface inflammation" or more specifically "dry eye" may complain of superficial scratchy pain, abrasiveness, eye dryness, foreign body sensation, scratchiness, ocular discomfort, ocular pain, burning, itching, decreased vision, visual blurriness or cloudiness, irritation or pain from bright light, or decreased visual acuity. Dryness may be experienced and reported as a feeling that moisture is absent, foreign body sensation, and/or as a feeling of dust, sand, or gravel in the eye. Accordingly, a patient with dry eye may experience one or more of the following symptoms: stinging and/or burning, dryness, sensation of foreign body (gritty or sandy feeling), itching, sensitivity to light, pain or soreness, intermittent blurred vision, tired or fatigued eyes, and frequent blinking.

Dry eye may be due to inadequate tear production, a disruption in tear secretion, decreased tear film quality, or excessive evaporation of the tear film at the ocular surface, any and all of which can lead to sensations of dry eye and eye dryness and/or be associated with dry eye disease.

An individual having dry eye may exhibit one or more of the characteristics or symptoms associated with dry eye disease (keratoconjunctivitis sicca). Methods for diagnosing and monitoring dry eye disease may include those described in Bron et al. (2007) "Methodologies to Diagnose and Monitor Dry Eye Disease:Report of the Diagnostic Methodology Subcommittee of the International Dry Eye WorkShop (2007)" *Ocul. Surf.* 5(2):108-152, and can include, but are not necessarily limited to, symptom questionnaires developed for use in dry eye diagnosis, the fluorescein tear film break up test, ocular surface staining grading with fluorescein/yellow filter, the Schirmer test, and tear osmolarity measurement.

A common feature of dry eye disease is an unstable tear film due to abnormal or deficient tear production, increased tear evaporation, or imbalance of tear components. An unstable tear film may lead to or promote inflammation of the ocular surface (Pflugfelder et al. 2004, Am. J. Ophthalmol. 137:337-342).

An individual suffering from or in need of treatment of "dry eye," for the present invention, can be one that presents with, is suffering from, or exhibits one or more symptoms of dry eye disease, or ocular surface dryness, or eye dryness, which depending on the individual may include sensations of dry eye (i.e., sensations of eye dryness), tear film instability, decreased tear secretion, delayed clearance, and altered tear composition, or tear hyperosmolarity.

For purposes of the present invention, "dry eye" that may potentially be treated with the present pharmaceutical compositions may be chronic or temporary, may occur in one or both eyes of an individual, and in particular patients may be due to or caused by changes in physiological condition; use of contact lenses; allergy to a medication; in response to an external environmental factor such as pollen, dust, particulates, or low humidity; due to a side effect of a medication; aging; low blink rate; vitamin A deficiency; a chemical burn; radiation; blepharitis; rosacea; reaction to the use preservative-containing topical eye drops, such as wetting drops; disorders of the lid aperature; meibomian oil deficiency; lacrimal deficiency; disruption or damage of the lacrimal gland or obstruction of the lacrimal gland duct; reflex block; infection; changes in hormonal balance; eye surgery, including but not limited to refractive laser eye surgery, including LASIK, LASEK, and PRK; or as a result of exposure to an environmental contaminant encountered during a recreational or occupational activity; or as a result of physical injury to the eye. Accordingly, pharmaceutical compositions of the present invention may reduce the severity of one or more symptoms associated with or accompanying dry eye.

In particular patients suffering from dry eye disease, to which the present method may be directed, the dry eye disease may be caused by nutritional disorders or deficiencies (including vitamins), pharmacologic side effects, eye stress and glandular and tissue destruction, environmental exposure to smog, smoke, excessively dry air, airborne particulates, autoimmune and immunodeficient disorders, and may be prevalent in patients who are unable to blink.

In other forms, the present invention may be directed to treating dry eye associated with rheumatoid arthritis, lupus erythematosus, polymyositis, rosacea, scleroderma, polyarteritis, thyroiditis, hepatobiliary disease, lymphoma, pulmonary fibrosis, macroglobulinemia, or coeliac disease.

Blepharitis is a disorder of the meibomian glands, which produce the lipid layer of tear film. With blepharitis, the glands may become inflamed. Symptoms of blepharitis may include eye irritation, soreness, redness and an accumulation of matter on the eyelids. Patients may also experience dry eye as well. Patients suffering from blepharitis may complain of a sandy or itchy feeling of their eyes. There is usually redness, thickening, and irregularity of the lid margins. Accordingly, blepharitis involves an inflammation of the eye lid margins. Blepharitis can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients may actually be a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperlasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, formix foreshortening, trichiasis, entropion, and madurosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA-DR.sup.+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

Uveitis, the inflammation of the uvea, is responsible for about 10% of the visual impairment in the United States. Phacoanaphylactic endophthalmitis is a human autoimmune disease. Panuveitis refers to inflammation of the entire uveal (vascular) layer of the eye. Posterior uveitis generally refers to chorioentinitis, and anterior uveitis refers to iridocyclitis.

The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, such as rheumatoid arthritis, Behcet's disease, ankylosing spondylitis, and sarcoidosis; as an isolated immune mediated ocular disorder, such as pars planitis, iridocyclitis etc., unassociated with known etiologies; and following certain systemic diseases which cause antibody-antigen complexes to be deposited in the uveal tissues. Together these disorders represent the non-infectious uveitities.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Uveitis is a prominent feature of Behcet's disease, a multisystem inflammatory disorder also characterized by oral and genital ulcers, cutaneous, vascular, joint, and neurological manifestations.

Rosacea is a chronic and common skin disorder with no identified cause or cure. The pathogenesis of rosacea is thought to have multiple factors. Possible factors include exposure to the demodex folliculorum mite, gastrointestinal disease or a vasodilation disorder, and other triggers such as diet or sunlight. Patients may present with a variety of symptoms, including inflammatory papules, edema, telangiectasia, rhinophyma and ocular symptoms.

The ocular signs of rosacea include blepharitis, including anterior blepharitis, conjunctivitis, iritis, iridocyclitis, keratitis, meibomian gland dysfunction, telangiectasia, erythema, chalazion, hordeolum, interpalpebral hyperemia, conjuctival hyperemia, ciliary base injection, bulbar injection, crusts, sleeves, and superficial punctuate keratopathy. The ocular symptoms are nonspecific and may include burning, tearing, decreased tear secretion, redness, and foreign body or gritty or dry sensation, irritation, Itchiness, Blurred vision, Photosensitivity, Watery eyes, bloodshot eyes, Burning, telangiectasia, irregularity of the lid margins, and meibomian gland dysfunction.

Pinguecula is a benign, yellowish brown proliferative growth that forms on the conjunctiva. Pinguecula may cause irritation and scratchiness of the eye, dry eye, inflammation of the conjunctiva and effect appearance of the eye. Inflamed pinguecula, which cause ocular irritation or become unsightly, may require surgical removal. However, the post-operation scar may be as cosmetically objectionable as the pinguecula and pinguecula regrowth may occur following surgical removal.

Allogeneic bone marrow transplantation (BMT) is a well-established treatment for malignant and non-malignant hematological diseases, and is performed in tens of thousands of patients each year. Mature donor T cells within the stem cell graft are the main mediators of the beneficial immune effects, but they are also responsible for the induction of graft-versus-host disease (GVHD), the major cause of morbidity and mortality in BMT patients. GVHD occurs when transplanted donor-derived T cells recognize proteins expressed by recipient antigen-presenting cells. Consequently, this recognition induces donor T-cell activation, proliferation, and differentiation, leading to a cellular and inflammatory attack on recipient target tissues. Acute or chronic GVHD occurs within a 100-day period post-BMT that leads to dermatitis, enteritis, and hepatitis. Ocular symptoms include blurry vision, foreign body sensation, burning sensation, severe light sensitivity, chronic conjunctivitis, dry eye, and eye pain.

Pharmaceutical Compositions

The present invention includes pharmaceutical compositions comprising, consisting of, or consisting essentially of a compound having Formula I, or a pharmaceutically acceptable salt thereof, in combination with one or more pharmaceutically acceptable excipients. A pharmaceutically acceptable excipient may improve the stability or effectiveness of the composition. A "pharmaceutically acceptable excipient" is one that is compatible with the compound of Formula I and that is not harmful to the person receiving the pharmaceutical composition. Mixtures of two or more of such suitable excipients may be used. A pharmaceutical composition may comprise two or more compounds having Formula I, or two or more salts thereof.

Pharmaceutical compositions of the present invention can be in the form of a liquid (such as an aqueous solution), solid, gel, or emulsion. The composition can be sterilized and therefore prepared in sterile form for pharmaceutical use.

The pharmaceutical composition may be prepared in a unit dosage form suitable for oral, systemic (arterial or intravenous), or topical administration to a patient. For example the pharmaceutical composition may be prepared in an aqueous liquid or emulsion form suitable or acceptable for administration or topical application to the eye(s) of the patient.

For topical ocular applications (such as administration to the eye), pharmaceutical compositions may be prepared by combining a therapeutically effective amount of a compound of Formula I, or a pharmaceutically acceptable salt thereof, as an active ingredient, with one or more pharmaceutically acceptable excipients. For ocular applications, the excipient is further preferably ophthalmically acceptable, that is, is causes little or no injury to the eye.

A therapeutically effective amount of a compound of Formula I can be from about 0.001% (w/v) to about 5% (w/v), from about 0.001% (w/v) to about 1.0% (w/v), from about 0.01% (w/v) to about 0.5% (w/v), from about 0.01% to about 1% (w/v), from about 0.1% to about 0.5% (w/v), or from about 0.5% to about 1% (w/v) in liquid and emulsion formulations. The actual dose of the active compounds of the present invention depends on the specific compound, and on the condition to be treated.

Emulsions may be prepared by combining a compound of Formula I in a sterile lipophilic vehicle or fixed oil. The lipophilic vehicle or fixed oil may be selected from the group consisting of synthetic mono- and diglycerides, fatty acids (including oleic acid), naturally occurring vegetable oils, sesame oil, coconut oil, peanut oil, cottonseed oil, castor oil, olive oil, mineral oil, synthetic fatty vehicles, and ethyl oleate. Buffers, emulsifiers, dispersing agents, preservatives, antioxidants, and the like can be incorporated as required.

Pharmaceutically acceptable excipients for use with the invention may include but are not limited to preservatives, buffering agents, antioxidants, lipophilic vehicles, hydrophilic vehicles, tonicity agents, electrolytes, thickeners, neutralizing agents, emulsifiers, dispersing agents, demulcents, plasticizers, occlusive agents, and film formers, and combinations thereof. Certain compositions may include both a buffer component and a tonicity component.

Useful preservatives may include benzalkonium chloride, PURITE®, sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, methyl and ethyl parabens, methylparaben, polyvinyl alcohol, benzyl alcohol, phenylethanol, hexetidine, chlorite components, such as stabilized chlorine dioxide, metal chlorite, and other ophthalmically acceptable preservatives. The concentration of the preservative component, if any, in the present compositions is a concentration effective to preserve the composition, and is often in a range of about 0.00001% to about 0.05% or about 0.1% (w/w) of the composition.

Acceptable buffering agents may include HEPES and those prepared from a suitable combination of the acid and/or base forms of acetates, citrates, phosphates, carbonates, succinates, and borates, such as sodium citrate dihydrate and boric acid. Phosphate buffers may be composed of sodium phosphate dibasic and sodium phosphate monobasic. Examples include monosodium phosphate, monohydrate, sodium phosphate dibasic heptahydrate, and sodium phosphate monobasic monohydrate. Buffering agents may be provided in any of the compositions in an amount effective to control the pH of the composition. The pH of the composition can be in a range of about 6 to about 8, about 7 to about 8, about 7 to about 7.6, or about 7.5 to about 8.

Useful tonicity agents may include glycerin, sugar alcohols, xylitol, sorbitol, glycerol, erythritol, mannitol, salts, potassium chloride and/or sodium chloride. Tonicity agents may be provided in an amount effective to control the tonicity or osmolality of the compositions. The osmolality of the composition can be in a range of about 200 to about 400, or about 250 to about 350, mOsmol/kg respectively. In one embodiment, the composition is isotonic. An isotonic solution is a solution that has the same solute concentration as that inside normal cells of the body and the blood. An isotonic solution in contact with a cell produces no net flow of water across the cell membrane. Useful lipophilic vehicles may include castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, cetyl alcohols, and stearyl alcohols. Useful hydrophilic vehicles include water. A pharmaceutical composition may optionally comprise an acceptable amount of dimethyl sulfoxide as an excipient. Additional examples of excipients that may be optionally included in the pharmaceutical compositions of the present invention may include those listed in Table A.

TABLE A

| Function | Ingredient |
| --- | --- |
| Active | Compound of Formula I |
| Thickener or polyelectrolyte | carbomer, sodium carboxymethylcellulose, methylcellulose, hydroxypropyl methylcellulose, polyvinyl alcohol, xanthan gum |
| Neutralizing Agent | sodium hydroxide, organic bases |
| Emulsifier or dispersing agent | polysorbate 20, polysorbate 40, polysorbate 60, polysorbate 80, POE-40-stearate, Pemulen ® and other polymeric emulsifiers. |
| Demulcent | carboxymethylcellulose sodium, hydroxypropyl methylcellulose hydroxyethyl cellulose, methylcellulose, polyvinyl alcohol, povidone, glycerin, propylene glycol, PEG 300, PEG 400 |
| Plasticizer | Silicone oils, isostearyl alcohol, cetyl alcohol, glycerin |
| Occlusive Agent | silicone oils, petrolatum, waxes |
| Film Former | acrylate/octylacrylamide copolymer, poly(ethyl acrylate, methyl methacrylate), chitosan, polyvinyl alcohol, polyisobutylene, polyvinylpyrrolidone-vinyl acetate copolymer, silicon gum, polyvinylpyrrolidone, other sustained release polymeric films |

U.S. Pat. No. 5,474,979, the entire contents of which are incorporated herein by reference, provides examples of emulsions that may be used to prepare pharmaceutical compositions of the present invention. The patent discloses the vehicle used in Restasis®, cyclosporin A 0.05%, manufactured by Allergan, Inc. This vehicle may be used to prepare pharmaceutical compositions of the present invention.

Methods of Preparation

The present invention includes processes (i.e., methods) for preparing compounds having Formula I. Compounds having Formula I may be prepared according to the following reaction schemes and accompanying discussions. Unless otherwise indicated, the $R^1$, $R^2$, $R^3$, $R^4$, $R^5$, $R^6$, $R^7$, $R^8$, $R^9$, $R^{10}$, $R^{12}$, $R^{13}$, and $R^{14}$, and m, n, p, and q variables; and structure of Formula I; in the following reaction schemes and discussion are as defined above in the Summary of the Invention.

The present invention includes isotopically-labeled compounds of Formula I. For Example, a compound having Formula I may contain one or more isotopic atoms such as deuterium $^2$H (or D) in place of proton $^1$H (or H) or $^{13}$C in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

Isotopically-labeled compounds of the present invention are identical to those recited herein, except that one or more atoms in the compound are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

The present invention can further include the Intermediates formed by the following schemes.

As shown in the following schemes, the starting material for compounds of Formula I is cyclosporin A (CAS Number 59865-13-3). Cyclosporin A may be obtained commercially from suppliers such as Sigma-Aldrich (St. Louis, Mo., United States) or TCI America (Portland, Oreg., United States). Other cyclosporin starting materials such as Cyclosporin D (CAS Registry Number 63775-96-2) may also be obtained through commercial suppliers such as Enzo Life Sciences (Ann Arbor, Mich., United States; Farmingdale, N.Y., United States). Other cyclosporin starting materials may be prepared from cyclosporin A as described by M. Mutter et al. *Tet. Lett.* 2000, 41, 7193-7196 and U.S. Pat. No. 5,214,130.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

In general, characterization of the compounds is performed according to the following methods: Proton nuclear magnetic resonance ($^1$H NMR, written occasionally as $^1$H NMR) and carbon nuclear magnetic resonance ($^{13}$C NMR, written occasionally as $^{13}$C NMR) spectra were recorded on a Bruker 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; bs, broad singlet; dd, doublet of doublets; and bt, broad triplet. Data were reported in the following format: chemical shift (multiplicity, integrated intensity, assignment).

Electron spray mass spectra (ESMS) were recorded on a Micromass ZQ.

The following abbreviations used in the following reaction schemes and accompanying discussions are defined as follows:

Ac acetyl, a group of formula "—(C═O)CH$_3$"
DCM dichoromethane
CH$_2$Cl$_2$ dichloromethane
LDA lithium diisopropylamide
THF tetrahydrofuran
NMO 4-Methylmorpholine N-oxide
CH$_3$CN acetonitrile
TPAP Tetrapropylammonium perruthenate
MeOH methanol
NaCNBH$_3$ sodium cyanoborohydride
CD$_3$OD deuterated methanol
DMSO-d6 deuterated dimethyl sulfoxide
NaOMe sodium methoxide
EtOH ethanol
NaBH$_4$ sodium borohydride
MgSO$_4$ magnesium sulfate
NH$_4$Cl ammonium chloride
HCl hydrochloric acid
DIBAL-H Diisobutylaluminium hydride
Et$_2$O ether
K$_2$CO$_3$ potassium carbonate
DMF N,N-dimethylformamide
Et$_3$N triethylamine
CuI copper iodide
PdCl$_2$(PPh$_3$)$_2$ Bis(triphenylphosphine)palladium(II) chloride
NaH sodium hydride
EtOAc ethylacetate
AcOH acetic acid
TFA trifluoroacetic acid
NH$_3$ ammonia
CDCl$_3$ deuterated chloroform
n-Bu$_4$NOH Tetrabutylammonium hydroxide
NH$_2$NH$_2$ hydrazine
LAH or LiAlH$_4$ Lithium aluminium hydride
DEAD diethyl azodicarboxylate
Ph$_3$P triphenylphosphine
M molar concentration (molarity)
MPLC Medium pressure liquid chromatography
DIPEA diisopropylethylamine
i-Pr isopropyl
n-Bu n-butyl
TBDMSOTf t-Butyldimethylsilyl trifluoromethanesulphonate
OTBDMS O-t-Butyldimethylsilyl
TBDMS t-Butyldimethylsilyl
10% Pd/C 10% Palladium on carbon
NaBH(OAc)$_3$ or NaBHOAc3 Sodium triacetoxyborohydride
TBAF tetrabutylammonium fluoride
n-BuLi n-Butyl lithium
i-Pr$_2$NH Diisopropylamine
ESMS MH$^+$ Electrospray mass spectrum positive ion
Grubbs II catalyst Grubbs catalyst second generation, also known as (1,3-Bis(2,4,6-trimethylphenyl)-2-imidazolidinylidene)dichloro (phenylmethylene)(tricyclohexylphosphine)ruthenium
HOBt-EDC N-hydroxybenzotriazole 1-ethyl-3-(3-dimethylaminopropyl) carbodiimide hydrochloride
Pd(PPh$_3$)$_4$ Tetrakis(triphenylphospine) palladium(0)
OTBDMS t-Butyldimethylsilyloxy
iBuOC(O)Cl Isobutyl chloroformate
MeSO2Cl Methane sulphonyl chloride

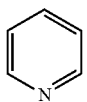

Pyridine
MeSSMe Dimethyl disulphide
DBU 1,8-Diazabicyclo[5.4.0]undec-7-ene
TBDMS t-Butyldimethylsilyl
H-cube Continuous flow hydrogenation apparatus
BuLi (same as n-BuLi above)
PhSSPh Diphenyl disulphide
DMAP 4-Dimethylaminopyridine
TEA Triethylamine
Hg(OAc)2 Mercury(II) acetate
CSA Camphor sulphonic acid
MeI Methyl iodide
BnNEt3$^+$Cl$^−$ Benzytriethylammonium chloride
aq. KOH Aqueous potassium hydroxide
Ac2O Acetic anhydride
NBS N-Bromosuccinimide
AIBN 2,2'-Azobis(2-methylpropionitrile)
H2 or H$_2$ Hydrogen gas
10% Pd/C 10% palladium on carbon

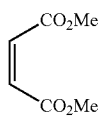

dimethyl maleate
O$_3$ ozone

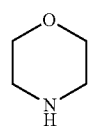

morpholine

ClCH$_2$CH$_2$Cl dichloroethane
n-BuLi n-butyllithium
i-Pr$_2$NH diisopropylamine
CO$_2$ carbon dioxide
ClCO$_2$CH$_2$Cl chloromethylchloroformate
ClCO$_2$CH$_2$CH$_2$Cl 2-chloroethylchloroformate

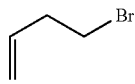

1-bromo-but-3-ene
Cs$_2$CO$_3$ cesium carbonate
LiOH lithium hydroxide
Pd(PPh$_3$)$_4$ tetrakistriphenylphosphine palladium(0)
PdCl$_2$(CH$_3$CN)$_2$ Bis(acetonitrile)dichloropalladium(II)
ClCO$_2$CHMeCl 1-chloroethylchloroformate
CCl$_4$ carbontetrachloride

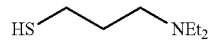

3-[(N,N-diethyl)amino]propan-1-thiol
Me methyl, a group of formula "—CH$_3$"
Et ethyl, a group of formula "—CH$_2$CH$_3$"
RT room temperature
o/n overnight The following synthetic schemes illustrate how compounds according to the invention can be made. Those skilled in the art will be routinely able to modify and/or adapt the following schemes to synthesize any compound of the invention covered by Formula I.

Scheme I

Procedure for Obtaining a Compound Having Formula I, Wherein n=0, m=0, and R$^8$ is CH$_2$

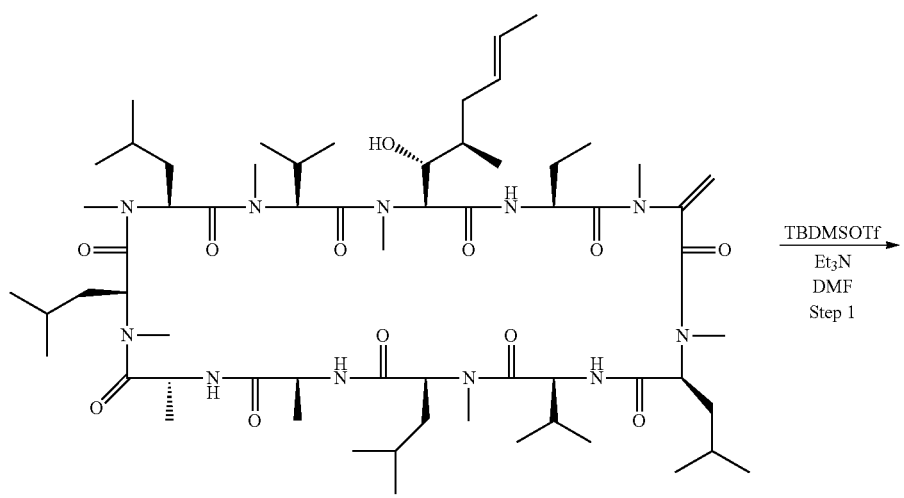

Intermediate 1

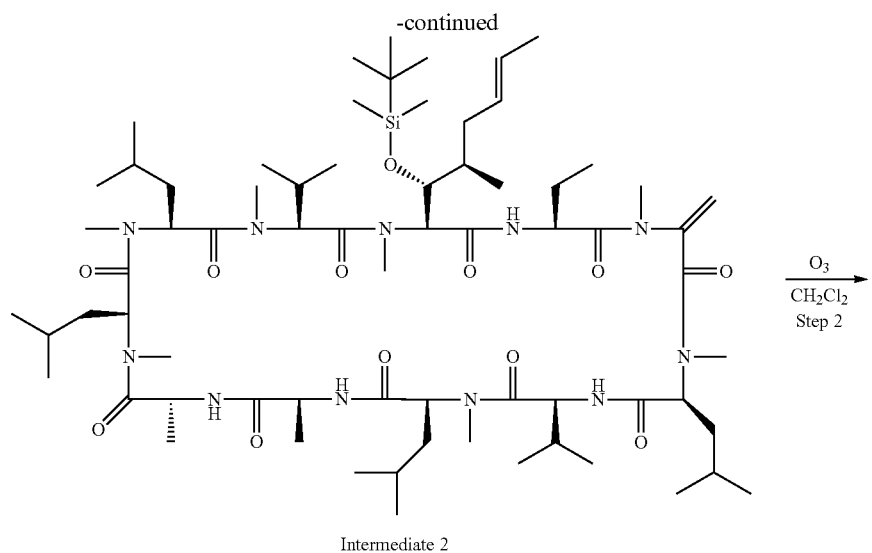
Intermediate 2
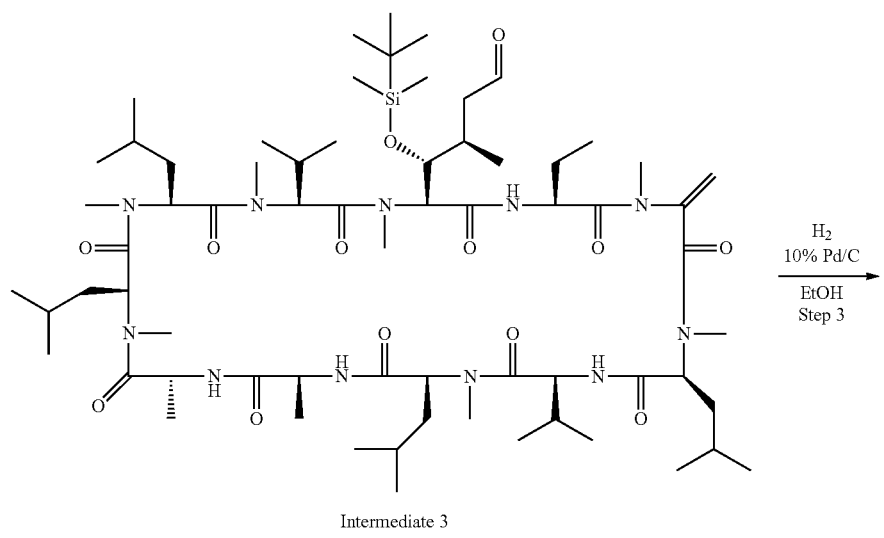
Intermediate 3
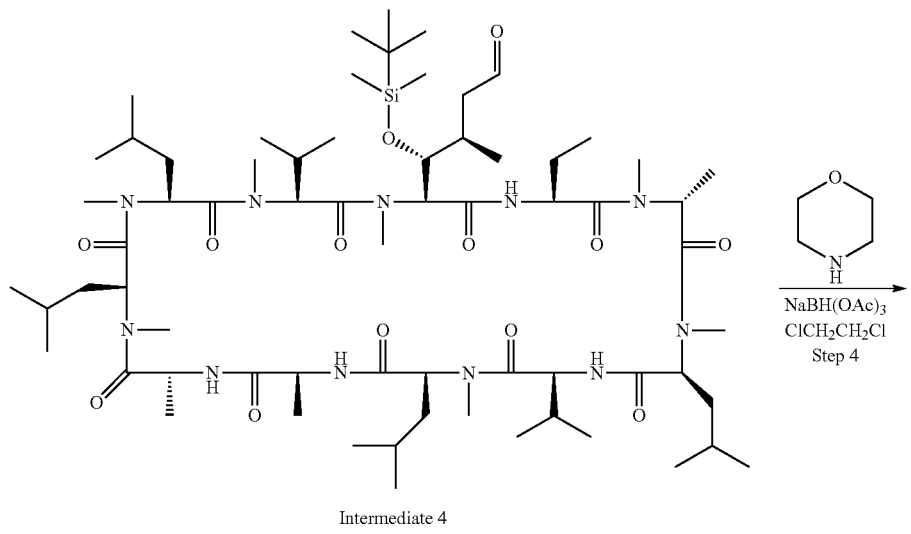
Intermediate 4

-continued
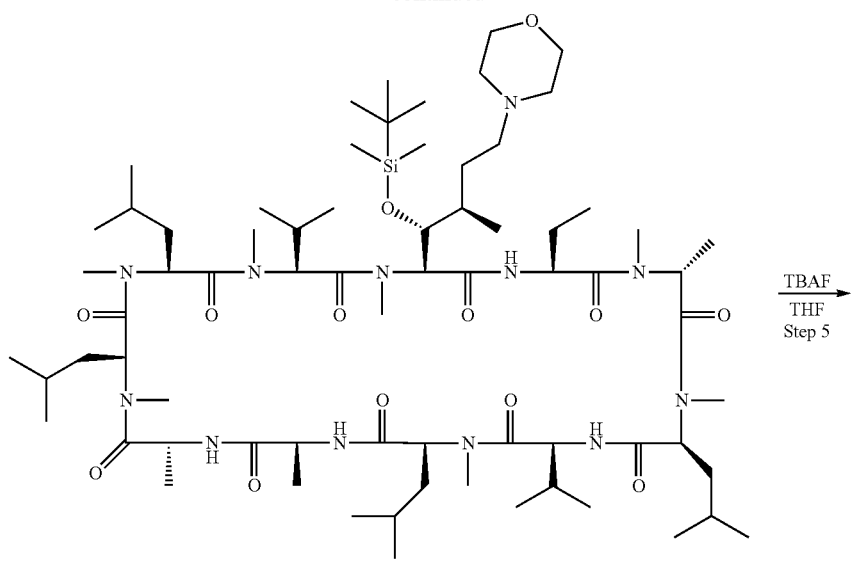
Intermediate 5
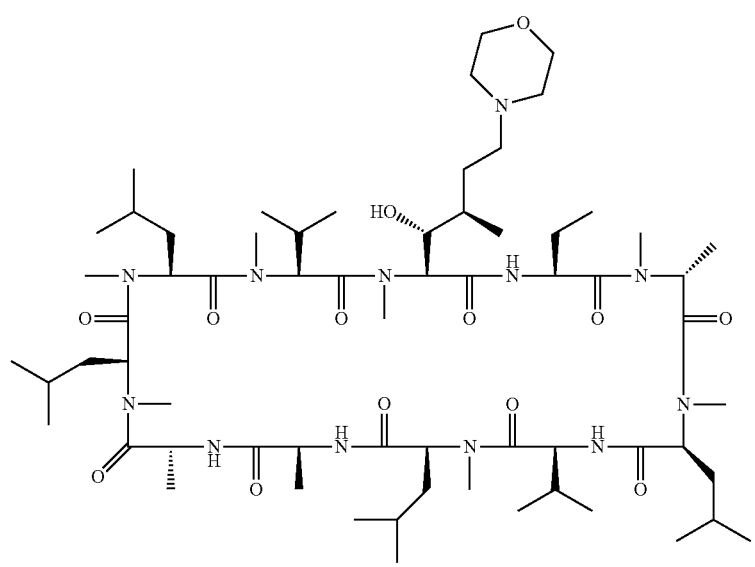
Compound of Formula I
(Compound F)

Preparation of Intermediate 1

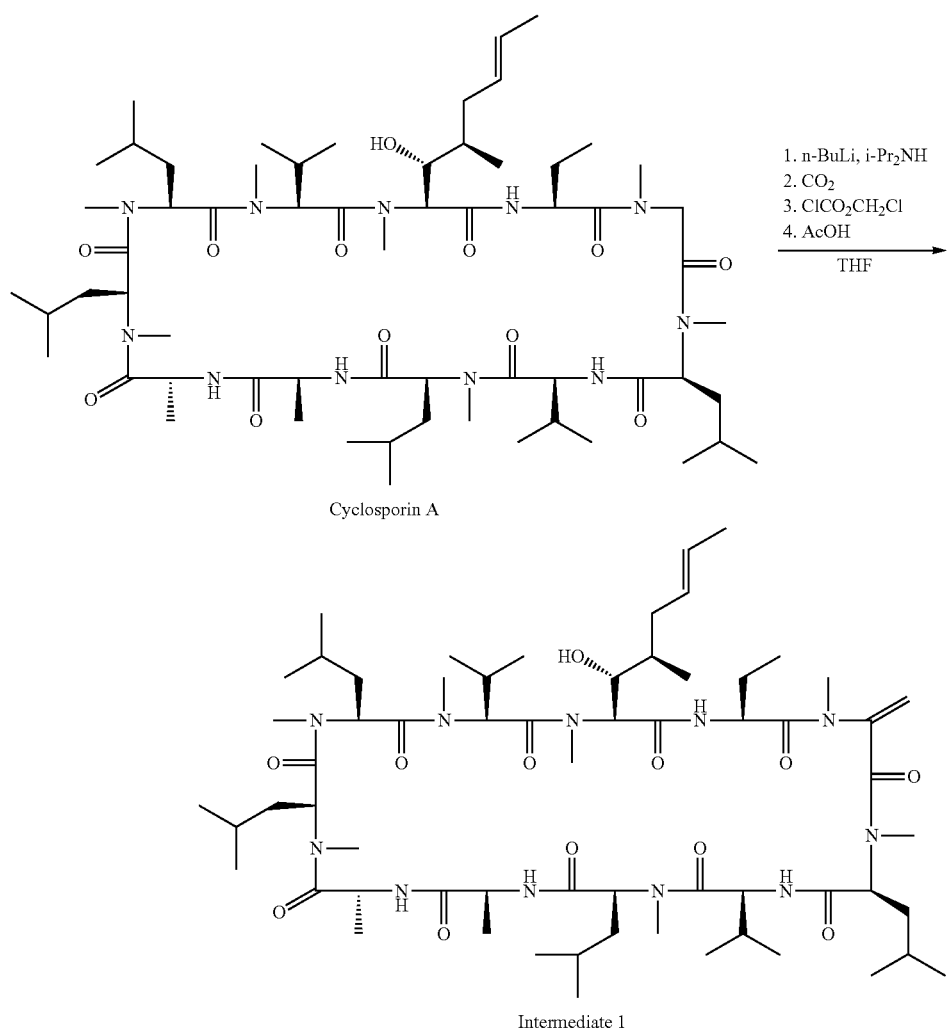

Intermediate 1, also known as [Methylene-Sar]³, is prepared as follows.

To a solution of diisopropylamine (11.2 ml, 80 mmol) in dry THF (240 ml) at −78° C. under an atmosphere of nitrogen was added dropwise n-butyl lithium (2.5 M in hexane, 32 ml, 80 mmol) and the resulting mixture was stirred at −78° C. for 60 minutes.

A solution of dry cyclosporine A (dried by azeotroping with 2×40 ml toluene then kept in dessicator o/n in presence of $P_2O_5$) (9.6 g, 8.0 mmol) in dry THF (40 ml) was added and the reaction was stirred under the same conditions for 2 h. A flow of carbon dioxide was bubbled through the reaction mixture for 30 minutes with temperature increasing to −50° C. The resulting mixture was allowed to warm to 15° C. over a period of 2 hours then cool back down to −50° C. before the addition of chloromethylchloroformate (7.1 ml, 80 mmol). The reaction mixture was allowed to warm to room temperature overnight then cooled to 0° C. and acetic acid (5 ml, 88 mmol) was added.

The mixture was allowed to warm to room temperature, the solvent evaporated and the resultant mixture was partitioned between ethyl acetate and brine. The organic phase was separated, dried ($Na_2SO_4$) and concentrated to give a yellow oil.

The crude product was purified by MPLC chromatography using a solvent gradient of 100% diethyl ether→96% diethyl ether/4% methanol to give [methylene-Sar]³cyclosporin A (Intermediate I).

ESMS MH⁺ 1214.8, MNa⁺ 1236.8

$^1$H NMR (CDCl$_3$, ppm) δ 4.98 (d, 1H, olefin CH$_2$), 5.25 (d, 1H, olefin CH$_2$), 7.17 (d, 1H, amide NH), 7.52 (d, 1H, amide NH), 7.59 (d, 1H, amide NH), 7.85 (d, 1H, amide NH).

$^{13}$C NMR (CDCl$_3$, ppm) δ 143.96 (olefin C), 108.09 (olefin CH$_2$).

By substituting chloroethylchloroformate for chloromethylchloroformate (reactant 3 in Preparation of Intermediate 1), Intermediate 16 can be produced (structure shown below). Intermediates 4 and 16 can serve as the starting material for the production of amines and amides of Formula I, as shown and described below.

Preparation of Intermediate 2

To a solution of [methylene-Sar]³cyclosporin A (5 g, 4.12 mmol) (Intermediate 1) in DMF (50 ml) at 0° C. under an atmosphere of nitrogen was added triethylamine (10 eq., 5.75 ml, 41.2 mmol) followed by a dropwise addition of TBDM-SOTf (5 eq, 4.5 ml, 20.6 mmol) (over 5 minutes) and the reaction mixture warmed to room temperature over 2 h. The reaction mixture was diluted with t-butyl methyl ether (200 ml), then washed with 2N HCl (100 ml), followed by $H_2O$ (100 ml). The aqueous extracts were extracted with t-butyl methyl ether (100 ml), and the combined organics washed with $H_2O$ (2×100 ml), brine (100 ml) then dried ($MgSO_4$), filtered and evaporated under reduced pressure to yield Intermediate 2 as a viscous oil. The crude product was used in the next step without further purification.

$^1$H NMR ($CDCl_3$, ppm) δ 7.40 (d, 1H, amide NH), 7.79 (d, 1H, amide NH), 7.90 (d, 1H, amide NH), 8.28 (d, 1H, amide NH).

Preparation of Intermediate 3

A solution of [(5R,6R,7S)-6-(t-butyldimethylsilanyloxy)-5-methyl-7-(methylamino)-octanoic acid]$^1$[methylene-Sar]$^3$ cyclosporin A (Intermediate 2) (9 g, approx 4 mmol) was dissolved in $CH_2Cl_2$ (200 ml) and added to a 3-neck flask equipped with inlet (for nitrogen/ozone addition) and outlet connected to a Dreschler bottle containing 2M KI solution. The reaction mixture was cooled to −78° C. over a solid $CO_2$/acetone bath, under a nitrogen atmosphere. When the temperature of the reaction vessel had stabilised, the nitrogen was removed and ozone bubbled through the reaction mixture until it became a pale blue colour (approx. 20 minutes). The ozone supply was removed and nitrogen bubbled through the reaction mixture until the blue colour had gone, then dimethylsulphide (0.8 ml) was added, and the reaction mixture warmed to room temperature over 2 hours. After this time, the reaction mixture was washed with $H_2O$ (3×200 ml), then dried ($MgSO_4$), filtered and evaporated under reduced pressure to yield the crude product as a clear, viscous oil.

The crude product was purified by MPLC chromatography using a solvent gradient of 100% hexane→40% ethyl acetate/60% hexane to give Intermediate 3 as a white solid.

ESMS MH$^+$ 1316.67

$^1$H NMR ($CDCl_3$, ppm) δ 7.53 (d, 1H, amide NH), 7.75 (d, 1H, amide NH), 7.84 (d, 1H, amide NH), 8.33 (d, 1H, amide NH), 9.63 (s, 1H, aldehyde H).

Preparation of Intermediate 4

To a solution of [(3R,4R,5S)-4-(t-butyldimethylsilanyloxy)-3-methyl-5-(methylamino)-1-oxo-hexanoic acid]$^1$ [methylene-Sar]$^3$cyclosporin A (Intermediate 3) (1 g) in ethanol was added 10% Palladium on Carbon (0.5 g) and the reaction stirred under a hydrogen atmosphere for 18 h. After this time, the reaction mixture was filtered through a pad of celite and washed with ethyl acetate. The solvent was evaporated to leave the Intermediate 4 as a fluffy white solid. Obtain a mixture of (R) and (S)-methyl, approx >7:1 (R):(S). The product can be used like this and purified later in the synthesis.

ESMS MH$^+$ 1318.77

$^1$H NMR ($CDCl_3$, ppm) δ 7.57 (d, 1H, amide NH), 7.65 (d, 1H, amide NH), 7.89 (d, 1H, amide NH), 8.47 (d, 1H, amide NH), 9.63 (s, 1H, aldehyde H).

Preparation of Intermediate 5

To a stirred solution of [(3R,4R,5S)-4-(t-butyldimethylsilanyloxy)-3-methyl-5-(methylamino)-1-oxo-hexanoic acid]$^1$ [(R)-methyl-Sar]$^3$cyclosporin A (Intermediate 4) (0.13 g, 0.1 mmol) in 1,2-dichloroethane (1 ml) was added morpholine (0.02 ml, 0.2 mmol) and sodium triacetoxyborohydride (0.038 g, 0.2 mmol) and the reaction mixture stirred at room temperature for 18 h. After this time, the reaction mixture was diluted with dichloromethane (5 ml) and washed with $H_2O$ (3×5 ml), then the organic phase was dried ($MgSO_4$), filtered and evaporated. Intermediate 5 was obtained as a white solid and not purified further at this stage.

ESMS MH$^+$ 1389.78

$^1$H NMR ($CDCl_3$, ppm) δ 7.57 (d, 1H, amide NH), 7.64 (d, 1H, amide NH), 7.96 (d, 1H, amide NH), 8.38 (d, 1H, amide NH).

Preparation of [(3R,4R,5S)-4-(hydroxy)-3-methyl-5-(methylamino)-1-(morpholin-4-yl) hexanoic acid]$^1$ [(R)-Me-Sar]$^3$cyclosporin A (Compound F)

To a stirred solution of [(3R,4R,5S)-4-(t-butyldimethylsilanyloxy)-3-methyl-5-(methylamino)-1-N-morpholino-hexanoic acid]$^1$[(R)-Me-Sar]$^3$cyclosporin A (Intermediate 5) (0.13 g, 0.1 mmol) in THF (2 ml) was added tetrabutylammonium fluoride TBAF (1.0M soln in THF, 0.2 ml, 0.2 mmol) and the reaction mixture stirred at room temperature for 8 h. After this time, the reaction solvent was evaporated, and the resulting residue redissolved in dichloromethane and washed with $H_2O$ (3×5 ml). The organic phase was dried ($MgSO_4$), filtered and evaporated to give a white solid. The crude product was first passed through a 5 g SCX (acidic) cartridge using methanol (collects TBDMS impurity) then 5% ammonia in methanol. The basic fractions were combined and evaporated to give [(3R,4R,5S)-4-(hydroxy)-3-methyl-5-(methylamino)-1-(morpholin-4-yl)hexanoic acid]$^1$[(R)-Me-Sar]$^3$ cyclosporin A (Compound F) as a pure white solid.

ESMS MH$^+$ 1275.69

$^1$H NMR ($CDCl_3$, ppm) δ 7.18 (d, 1H, amide NH), 7.39 (d, 1H, amide NH), 7.76 (d, 1H, amide NH), 7.89 (d, 1H, amide NH).

While Scheme I shows morpholine as the reactant at Step 4, Intermediate 4 can be reacted with other heterocycles or amines to produce a set of corresponding intermediates. Each of the resulting intermediates can then be separately deprotected according to Step 5 of Scheme I to produce a compound of Formula I. For instance, N-methylpiperazine, piperazinone, or diethylamine ($NH(CH_2CH_3)_2$) may be separately reacted with Intermediate 4 to produce three distinct compounds of Formula I wherein n=0 and m=0.

Preparation of Compound L

Thus, using the procedure shown in Scheme I with N-methylpiperazine as the reactant at Step 4, [(3R,4R,5S)-4-(t-butyldimethylsilanyloxy)-3-methyl-5-(methylamino)-1-(4-methylpiperazino)-hexanoic acid]$^1$[(R)-Me-Sar]$^3$ cyclosporin A (Intermediate 50) was obtained as a white solid (ESMS MH$^+$ 1402.81). Intermediate 50 was deprotected as shown in Step 5 to give Compound L ([(3R,4R,5S)-4-hydroxy-3-methyl-5-(methylamino)-1-(4-methylpiperazino)-hexanoic acid]$^1$[(R)-Me-Sar]$^3$cyclosporin A) as a white solid.

ESMS MH$^+$ 1288.74

$^1$H NMR ($CDCl_3$, ppm) δ 7.20 (d, 1H, amide NH), 7.38 (d, 1H, amide NH), 7.79 (d, 1H, amide NH), 7.89 (d, 1H, amide NH).

Preparation of Compound M

Using the procedure shown in Scheme I with diethylamine as the reactant at Step 4, [(3R,4R,5S)-4-(t-butyldimethylsilanyloxy)-3-methyl-5-(methylamino)-1-N-diethylamino-hexanoic acid]¹[(R)-Me-Sar]³cyclosporin A (Intermediate 51) was obtained as a white solid (ESMS MH⁺ 1375.87).

Intermediate 51 ([(3R,4R,5S)-4-(t-butyldimethylsilanyloxy)-3-methyl-5-(methylamino)-1-N-diethylamino-hexanoic acid]¹[(R)-Me-Sar]³cyclosporin A) was deprotected according to Step 5 in Scheme I to give Compound M ([(3R,4R,5S)-4-hydroxy-3-methyl-5-(methylamino)-1-N-diethylamino-hexanoic acid]¹[(R)-Me-Sar]³cyclosporin A) as a white solid.

ESMS MH⁺ 1261.82

¹H NMR (CDCl$_3$, ppm) δ 7.18 (d, 1H, amide NH), 7.39 (d, 1H, amide NH), 7.80 (d, 1H, amide NH), 7.82 (d, 1H, amide NH).

Preparation of Compound N

Using the procedure shown in Scheme I with diethylamine as the reactant at Step 4, [(3R,4R,5S)-4-(t-butyldimethylsilanyloxy)-3-methyl-5-(methylamino)-1-N-diethylamino-hexanoic acid]¹[(R)-Me-Sar]³cyclosporin A (Intermediate 52) was obtained as a white solid.

Intermediate 52 ([(3R,4R,5S)-4-(t-butyldimethylsilanyloxy)-3-methyl-5-(methylamino)-1-(N-3-piperazinone)-hexanoic acid]¹[(R)-Me-Sar]³cyclosporin A) was then deprotected according to Step 5 in Scheme I to give Compound N ([(3R,4R,5S)-4-hydroxy-3-methyl-5-(methylamino)-1-(N-3-piperazinone)-hexanoic acid]¹[(R)-Me-Sar]³cyclosporin A), as a white solid.

ESMS MH⁺ 1288.81

¹H NMR (CDCl$_3$, ppm) δ 7.12 (d, 1H, amide NH), 7.91 (d, 1H, amide NH), 8.10 (d, 1H, amide NH), 8.32 (d, 1H, amide NH).

Using the procedure shown in Scheme I with the appropriate amines the following compounds were prepared:

Compound AK (see Table 17) [(3R,4R,5S)-4-Hydroxy-3-methyl-5-(methylamino)-1-(2-{1H-imidazol-4-yl}-ethylamino)-hexanoic acid]¹[(R)-methyl-Sar]³cyclosporin A

ESMS MH⁺ 1300.4

¹H NMR (CDCl$_3$, ppm) δ 6.79 (bs, 1H, imidazole CH), 7.25 (d, 1H, amide NH), 7.54 (bs, 2H, imidazole CH and amide NH), 7.82 (d, 1H, amide NH), 8.04 (d, 1H, amide NH).

Compound AF (see Table 16) [(3R,4R,5S)-4-Hydroxy-3-methyl-5-(methylamino)-1-(2-methoxyethylamino)-hexanoic acid]¹[(R)-methyl-Sar]³cyclosporin A

ESMS MH⁺ 1263.6

¹H NMR (CDCl$_3$, ppm) δ 7.20 (d, 1H, amide NH), 7.40 (d, 1H, amide NH), 7.80 (d, 1H, amide NH), 7.89 (d, 1H, amide NH).

Compound AG (see Table 16) [(3R,4R,5S)-4-Hydroxy-3-methyl-5-(methylamino)-1-(2-methoxyethyl)methylamino)-hexanoic acid]¹[(R)-methyl-Sar]³cyclosporin A

ESMS MH⁺ 1277.6

¹H NMR (CDCl$_3$, ppm) δ 7.19 (d, 1H, amide NH), 7.41 (d, 1H, amide NH), 7.78 (d, 1H, amide NH), 7.89 (d, 1H, amide NH).

Compound O (see Table 9), [(3R,4R,5S)-4-Hydroxy-3-methyl-5-(methylamino)-1-(N-(3aR*,6aS*)-2-methyloctahydropyrrolo[3,4-c]pyrrolo)-hexanoic acid]¹[(R)-methyl-Sar]³cyclosporin A

ESMS MH⁺ 1314.7

¹H NMR (CDCl$_3$, ppm) δ 7.21 (d, 1H, amide NH), 7.41 (d, 1H, amide NH), 7.79 (d, 1H, amide NH), 7.79 (d, 1H, amide NH).

Compound AJ (see Table 16), [(3R,4R,5S)-4-Hydroxy-3-methyl-5-(methylamino)-1-(1,4-dioxan-2-ylmethyl)methylamino-hexanoic acid]¹[(R)-methyl-Sar]³cyclosporin A

ESMS MH⁺ 1319.6

¹H NMR (CDCl$_3$, ppm) δ 7.13 (d, 1H, amide NH), 7.44 (d, 1H, amide NH), 7.75 (d, 1H, amide NH), 7.91 (d, 1H, amide NH).

Compound J (see Table 10), [(3R,4R,5S)-4-Hydroxy-3-methyl-5-(methylamino)-1-(thiomorpholino)-hexanoic acid]¹[(R)-Me-Sar]³cyclosporin A

ESMS MH⁺ 1291.58

¹H NMR (CDCl$_3$, ppm) δ 7.18 (d, 1H, amide NH), 7.42 (d, 1H, amide NH), 7.76 (d, 1H, amide NH), 7.92 (d, 1H, amide NH).

Compound P (see Table 11), [(3R,4R,5S)-4-Hydroxy-3-methyl-5-(methylamino)-1-(1,1-dioxo-thiomorpholino)-hexanoic acid]¹[(R)-Me-Sar]³cyclosporin A

ESMS MH⁺ 1323.77

¹H NMR (CDCl$_3$, ppm) δ 7.14 (d, 1H, amide NH), 7.51 (d, 1H, amide NH), 7.71 (d, 1H, amide NH), 7.97 (d, 1H, amide NH).

Compound X (see Table 13), [[(3R,4R,5S)-4-Hydroxy-3-methyl-5-(methylamino)-1-N-homomorpholino-hexanoic acid]¹[(R)-methyl-Sar]³cyclosporin A

ESMS MH⁺ 1289.67

¹H NMR (CDCl$_3$, ppm) δ 7.19 (d, 1H, amide NH), 7.41 (d, 1H, amide NH), 7.78 (d, 1H, amide NH), 7.91 (d, 1H, amide NH).

Compound EK (see Table 13), [(3R,4R,5S)-4-Hydroxy-3-methyl-5-(methylamino)-1-(2,2,6,6-tetrafluoro-morpholin-4-yl)-hexanoic acid]¹[(R)-methyl-Sar]³cyclosporin A

ESMS MH⁺ 1347.67

¹H NMR (CDCl$_3$, ppm) δ 7.15 (d, 1H, amide NH), 7.53 (d, 1H, amide NH), 7.73 (d, 1H, amide NH), 8.08 (d, 1H, amide NH).

Compound EL [(3R,4R,5S)-(3,3-Difluoro-pyrrolidin-1-yl)-4-Hydroxy-3-methyl-5-(methylamino)-1-hexanoic acid]¹[(R)-methyl-Sar]³cyclosporin A

ESMS MH⁺ 1295.91

¹H NMR (CDCl$_3$, ppm) δ 7.17 (d, 1H, amide NH), 7.42 (d, 1H, amide NH), 7.75 (d, 1H, amide NH), 7.92 (d, 1H, amide NH).

Compound EM [(3R,4R,5S)-(3,3-Difluoro-azetidin-1-yl)-4-hydroxy-3-methyl-5-(methylamino)-1-hexanoic acid]¹[(R)-methyl-Sar]³cyclosporin A ESMS MH⁺ 1281.56
¹H NMR (CDCl₃, ppm) δ 7.19 (d, 1H, amide NH), 7.41 (d, 1H, amide NH), 7.76 (d, 1H, amide NH), 7.92 (d, 1H, amide NH).

Compound EN [(3R,4R,5S)-(4,4-Difluoro-piperidin-1-yl)-4-hydroxy-3-methyl-5-(methylamino)-1-hexanoic acid]¹[(R)-methyl-Sar]³cyclosporin A ESMS MH⁺ 1309.55
¹H NMR (CDCl₃, ppm) δ 7.16 (d, 1H, amide NH), 7.42 (d, 1H, amide NH), 7.75 (d, 1H, amide NH), 7.90 (d, 1H, amide NH).

Compound ER [(3R,4R,5S)-4-Hydroxy-3-methyl-5-(methylamino)-1-(3,3,4,4-tetrafluoro-pyrrolidin-1-yl)-hexanoic acid]¹[(R)-methyl-Sar]³cyclosporin A ESMS MH⁺ 1331.52
¹H NMR (CDCl₃, ppm) δ 7.16 (d, 1H, amide NH), 7.50 (d, 1H, amide NH), 7.73 (d, 1H, amide NH), 8.03 (d, 1H, amide NH).

Compound EQ (3R,4R,5S)-1-[Bis-(3,3,3-trifluoro-propyl)-amino]-[(4-Hydroxy-3-methyl-5-(methylamino)-hexanoic acid]¹[(R)-methyl-Sar]³cyclosporin A ES/MS: 1398.0 MH⁺
¹H NMR (CDCl₃, ppm) δ 7.11 (d, 1H, amide NH), 7.52 (d, 1H, amide NH), 7.73 (d, 1H, amide NH), 7.98 (d, 1H, amide NH).

Intermediate 50

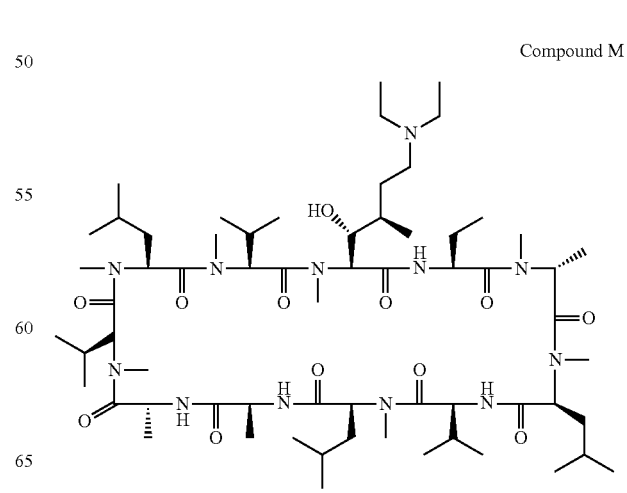

Compound L

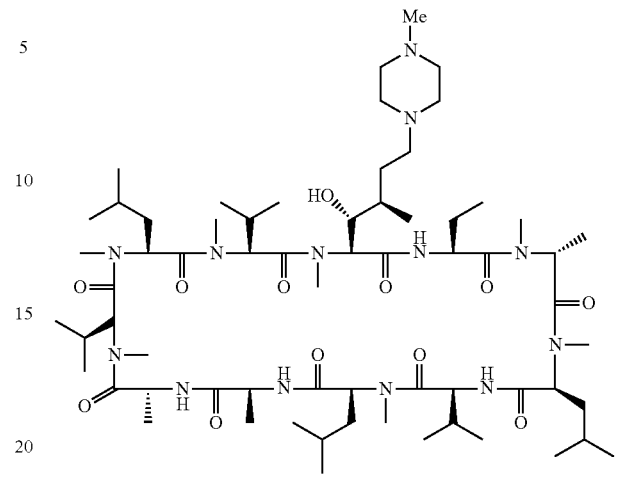

Intermediate 51

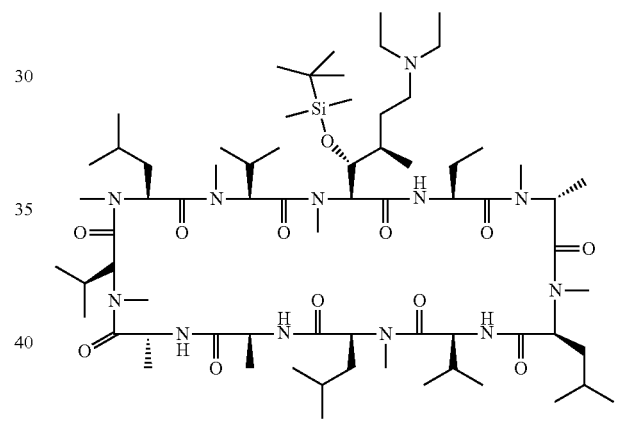

Compound M

Intermediate 52
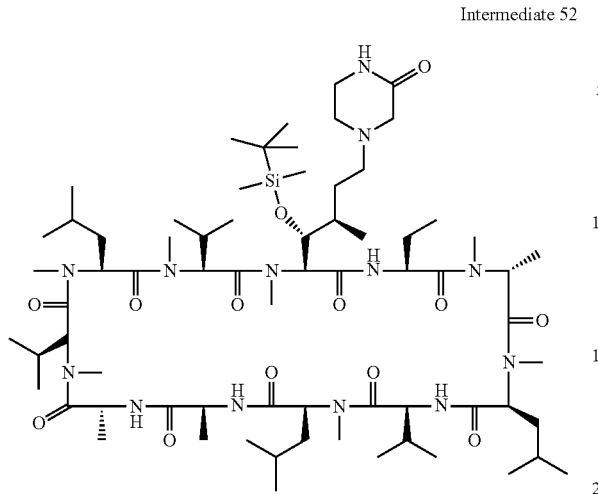
Compound AF
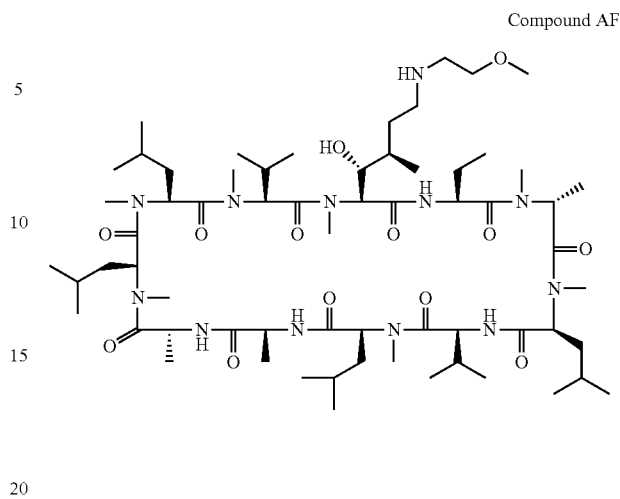
Compound N
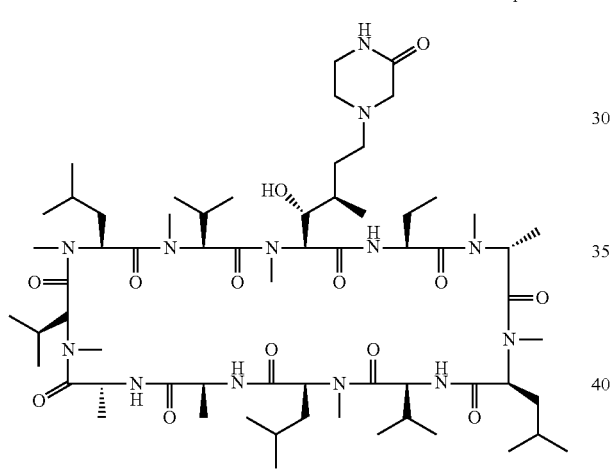
Compound AG
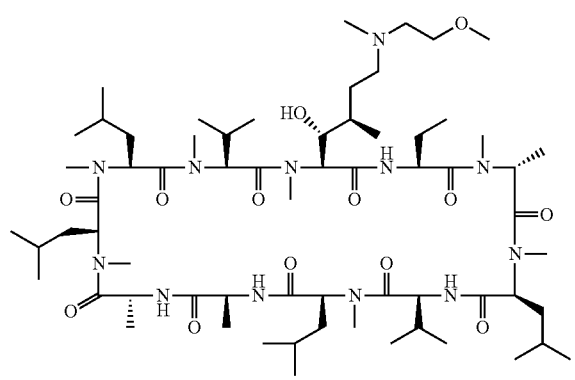
Compound AK
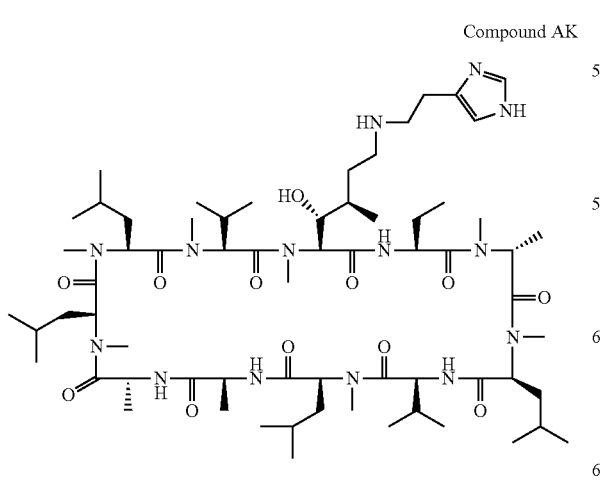
Compound O
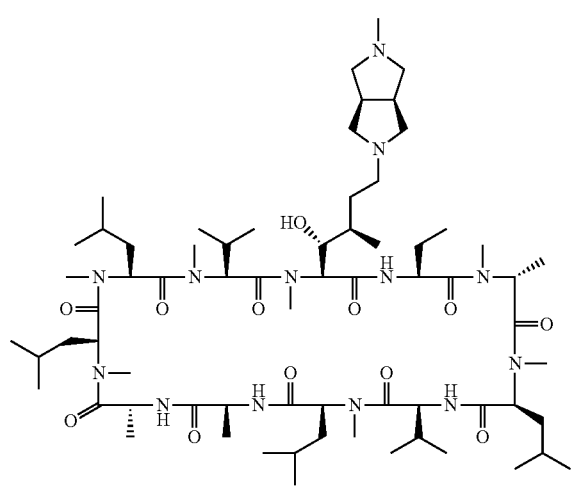

Compound AJ
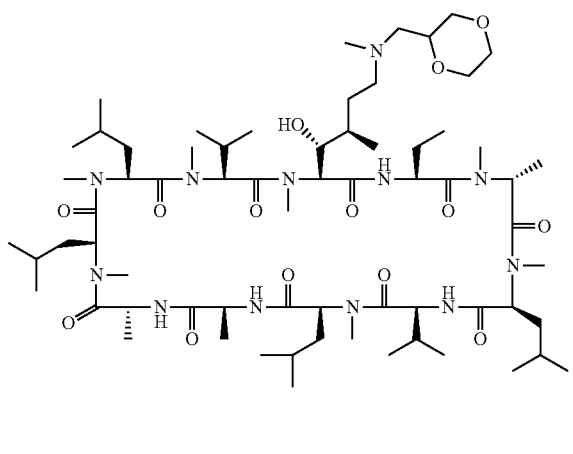
Compound P
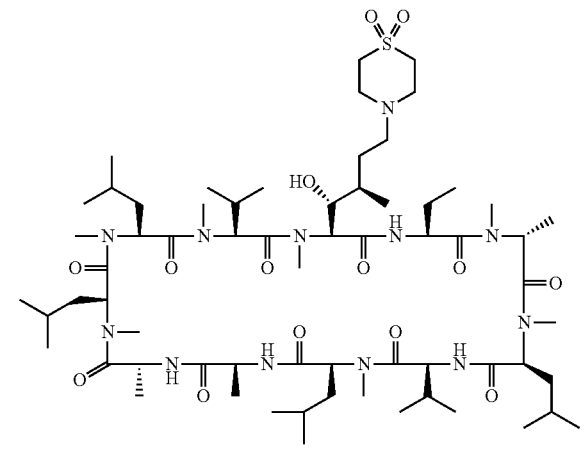
Compound J
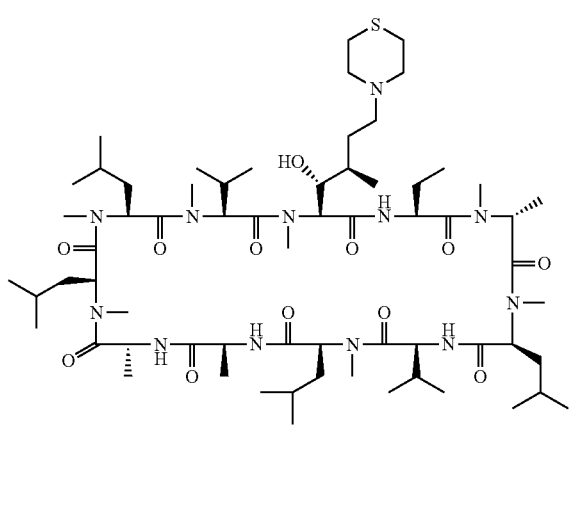
Compound EK
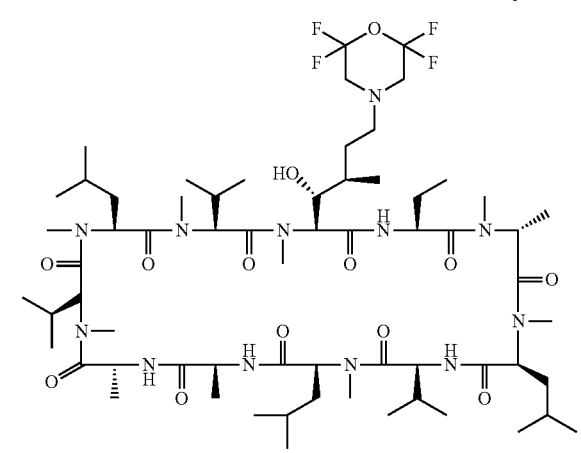
Compound X
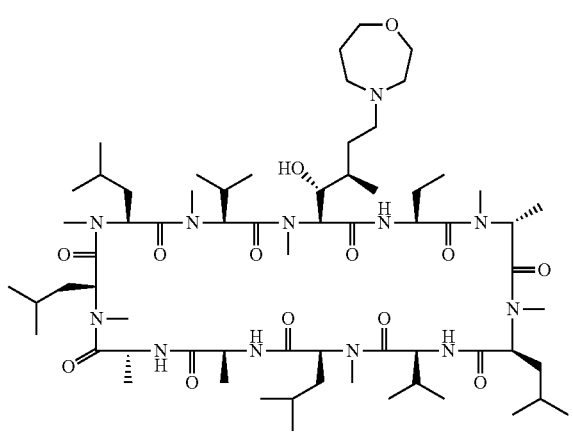
Compound EL
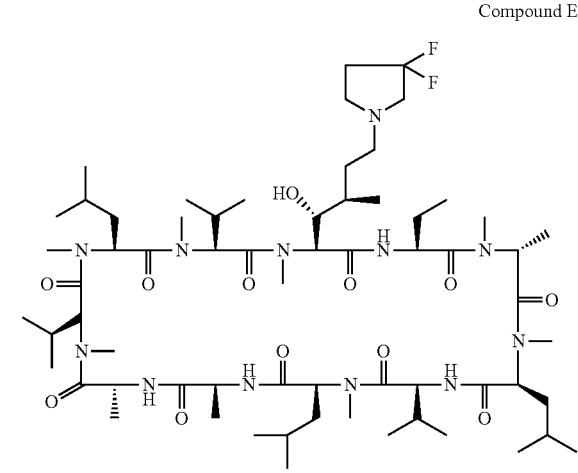

-continued

Compound EM

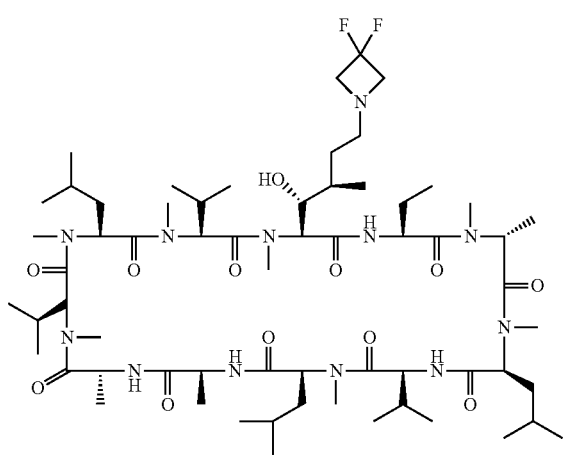

Compound ER

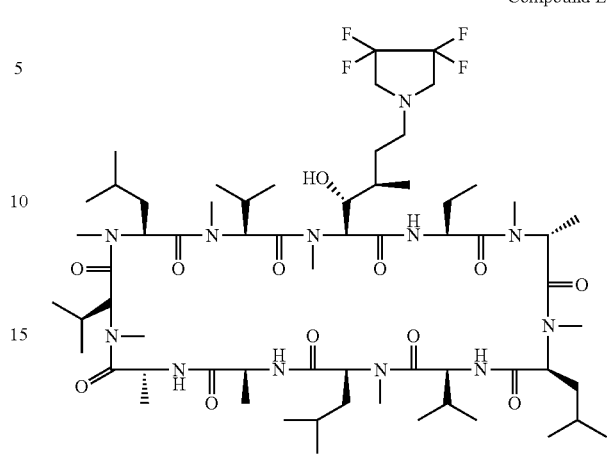

Compound EQ

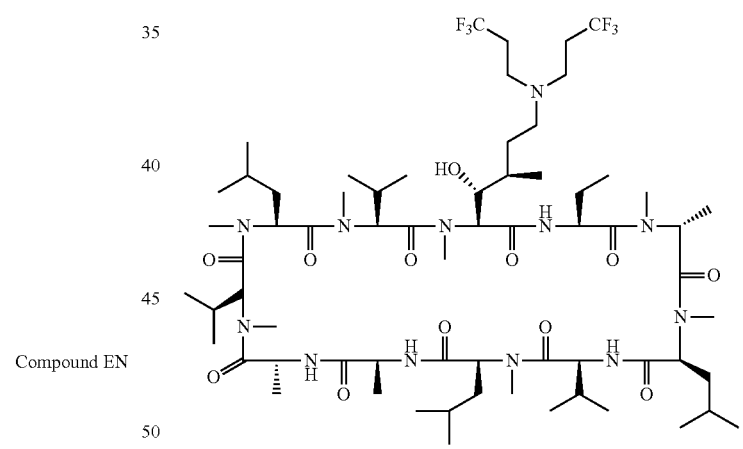

Compound EN

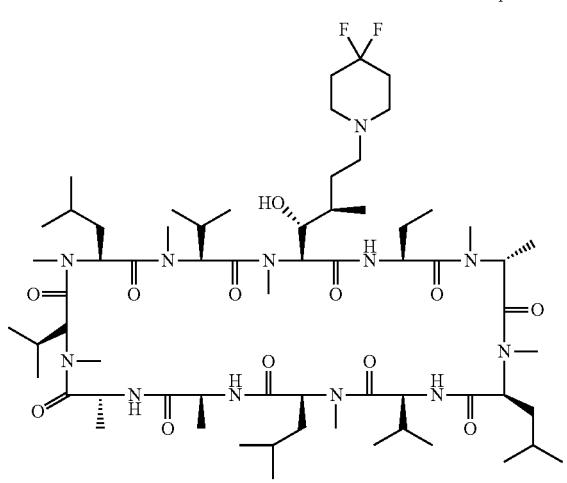

Scheme II

Procedure for Obtaining a Compound Having Formula I, Wherein n=3 and m=0

The distance between the amine in the side chain at position 1 and the cyclosporin scaffold can be varied (that is, the value of n can be adjusted between 0 and 4) according to the schemes set forth herein.

For example Scheme II enables the practitioner to obtain a compound of Formula I having an amine at the position 1 α-carbon in which n=3.

Scheme II
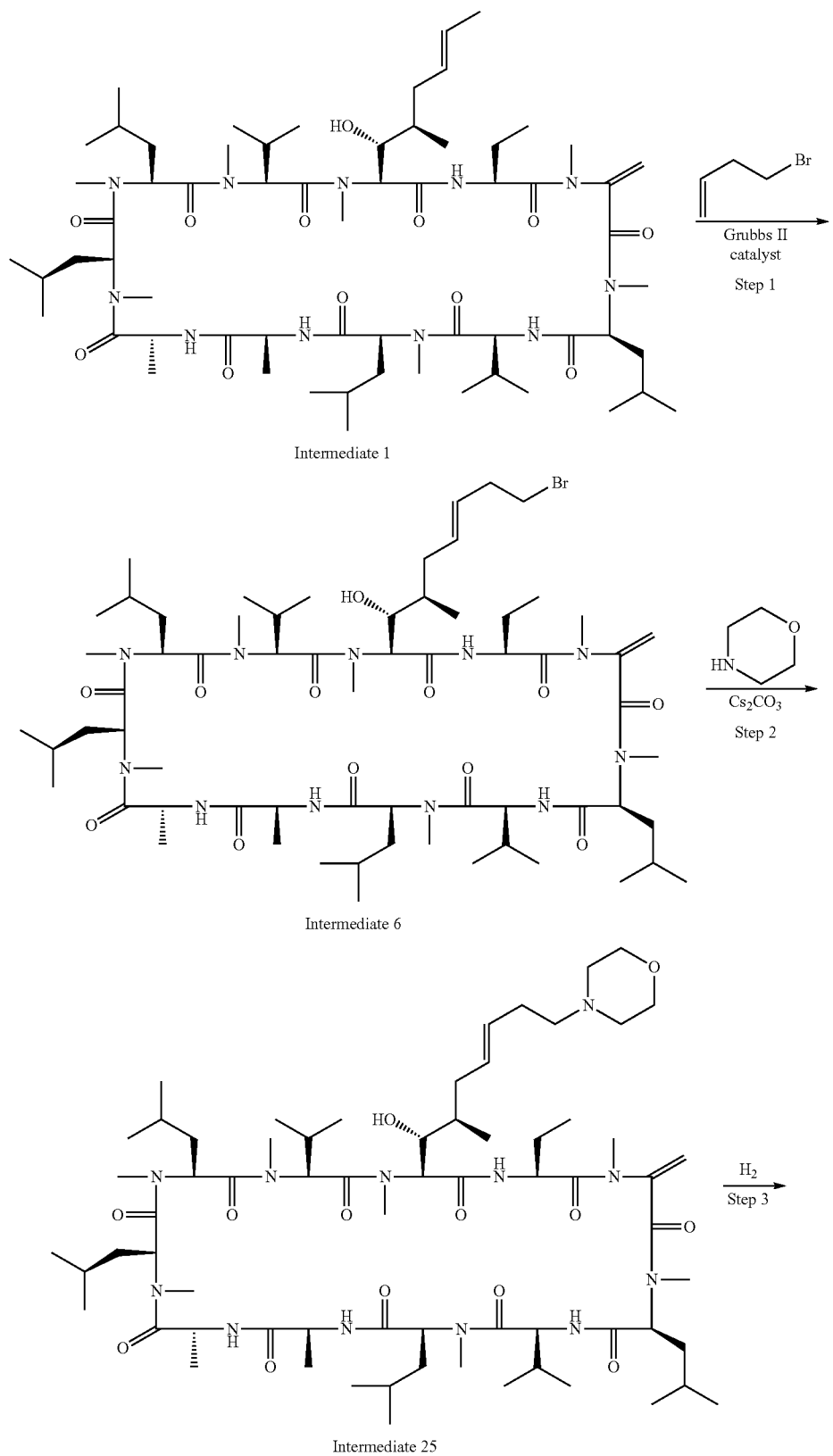

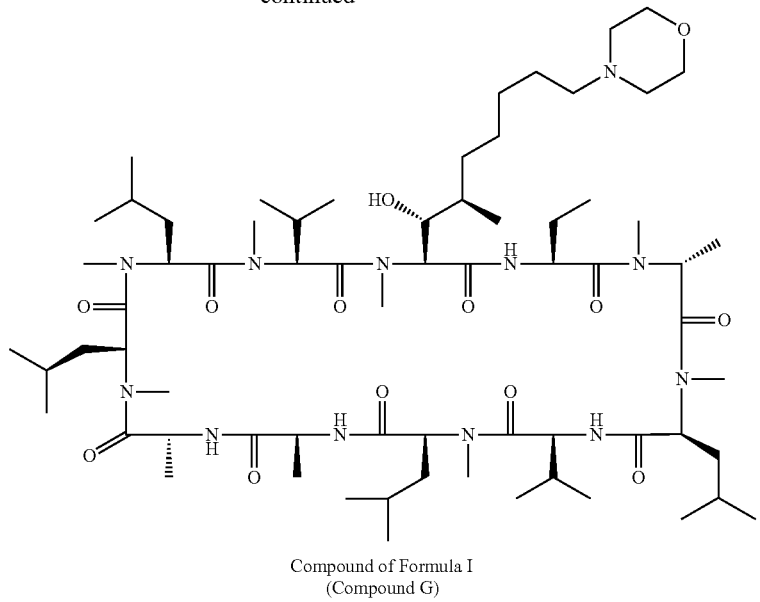

Compound of Formula I
(Compound G)

Preparation of Intermediate 6

[Methylene-Sar]³cyclosporin A (Intermediate 1) (242 mg, 0.2 mmol) and 4-bromo but-1-ene, (405 mg, 3.0 mmol) were dissolved in dry dichloromethane (4 mL). The mixture was purged with nitrogen before the addition of Grubbs catalyst second generation (40 mg, 0.048 mmol) then refluxed for 18 hours. The reaction mixture was cooled to room temperature then purified by silicagel chromatography using a solvent gradient of 100% dichloromethane→96% dichloromethane/4% methanol to provide [(3E,6R,7R,8S)-1-bromo-7-hydroxy-6-methyl-8-(methylamino)-non-3-enoic acid]¹cyclosporin A (Intermediate 6) as an off-white solid.

Grubbs' catalyst second generation (Grubbs II catalyst) is described in U.S. Patent Application Publication No. 2003/0186855. Longer chain brominated alkenes may be used at Step 1 if desired to produce a longer side chain at position 1.

ESMS MH⁺ 1306.7/1308.7

¹H NMR (CDCl₃, ppm) δ 7.19 (d, 1H, amide NH), 7.65 (d, 1H, amide NH), 7.70 (d, 1H, amide NH), 8.07 (d, 1H, amide NH).

Preparation of Intermediate 25

3E,6R,7R,8S) [(3E,6R,7R,8S)-1-bromo-7-hydroxy-6-methyl-8-(methylamino)-non-3-enoic acid]¹cyclosporin A (Intermediate 6) (260 mg, 0.2 mmol) was dissolved in acetonitrile. Morpholine (385 uL, 0.4 mmol), cesium carbonate (255 mg, 0.8 mmol) and a catalytic amount of potassium iodide were added. The reaction mixture was stirred at room temperature for 18 hours. Further amount of morpholine (100 uL, 0.1 mmol) was added and the reaction mixture stirred for 3 hours before evaporating the volatiles. The residue was purified by SCX chromatography using a solvent gradient of 100% methanol→0.21M ammonia in methanol. The material obtained was dissolved in ethyl acetate, washed three times with water, dried over sodium sulphate and concentrated to give [(3E,6R,7R,8S)-7-hydroxy-6-methyl-8-(methylamino)-1-N-morpholino-non-3-enoic acid]¹[methylene-Sar]³cyclosporin A (Intermediate 25) as a white solid.

ESMS MH⁺ 1313.8

¹H NMR (CDCl₃, ppm) δ 7.17 (d, 1H, amide NH), 7.62 (m, 2H, amide NH), 8.00 (d, 1H, amide NH).

Preparation of Compound G

[(3E,6R,7R,8S)-7-hydroxy-6-methyl-8-(methylamino)-1-N-morpholino-non-3-enoic acid]¹[methylene-Sar]³cyclosporin A (Intermediate 25) (68 mg, 0.054 mmol) was dissolved in ethanol (6 mL), treated with 10% palladium on carbon (68 mg) then placed under a 1 atm atmosphere of hydrogen for 65 hours. Fresh catalyst (68 mg) was added to the reaction mixture and hydrogenation carried on for an additional 24 hours. The reaction mixture was filtered through celite then concentrated in vacuo. The residue was purified by silicagel chromatography using a solvent gradient of 100% dichloromethane→95% dichloromethane/5% methanol to provide [(6R,7R,8S)-7-hydroxy-6-methyl-8-(methylamino)-1-N-morpholino-nonanoic acid]¹[(R)-methyl-Sar]³cyclosporin A (Compound G) as a white solid.

ESMS MH⁺ 1317.8

¹H NMR (CDCl₃, ppm) δ 7.17 (d, 1H, amide NH), 7.50 (d, 1H, amide NH), 7.69 (d, 1H, amide NH), 7.91 (d, 1H, amide NH).

Using the procedure shown in Scheme II with the appropriate amines the following compounds were prepared:

Compound AH (see Table 16) [(6R,7R,8S)-7-Hydroxy-6-methyl-8-(methylamino)-1-N-diethylamino-nonanoic acid]¹[(R)-methyl-Sar]³cyclosporin A

ESMS MH⁺ 1303.8

¹H NMR (CDCl₃, ppm) δ 7.14 (d, 1H, amide NH), 7.50 (d, 1H, amide NH), 7.67 (d, 1H, amide NH), 7.93 (d, 1H, amide NH).

Compound AI (see Table 16) [(6R,7R,8S)-7-Hydroxy-6-methyl-8-(methylamino)-1-N-(2-methoxy)ethylamino-nonanoic acid]¹[(R)-methyl-Sar]³cyclosporin A

ESMS MH⁺ 1305.7

¹H NMR (CDCl₃, ppm) δ 7.16 (d, 1H, amide NH), 7.51 (d, 1H, amide NH), 7.67 (d, 1H, amide NH), 7.93 (d, 1H, amide NH).

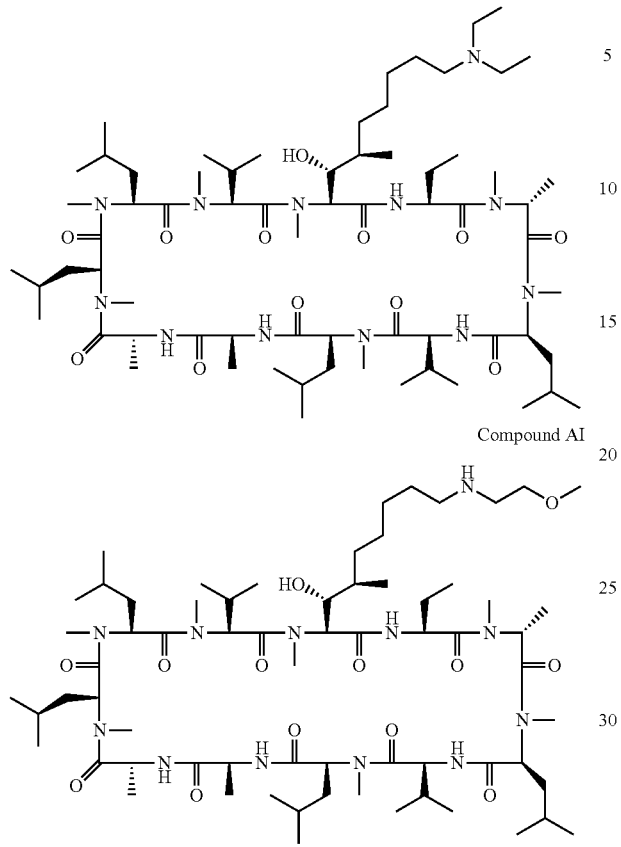

Compound AH

Compound AI

Compound C (see Table 4) [(6R,7R,8S)-7-Hydroxy-6-methyl-8-(methylamino)-1-N-morpholinyl-nonanoic acid]¹cyclosporin A

ESMS MH⁺ 1303.8

¹H NMR (CDCl₃, ppm) δ 7.15 (d, 1H, amide NH), 7.5 (d, 1H, amide NH), 7.7 (d, 1H, amide NH), 7.95 (d, 1H, amide NH).

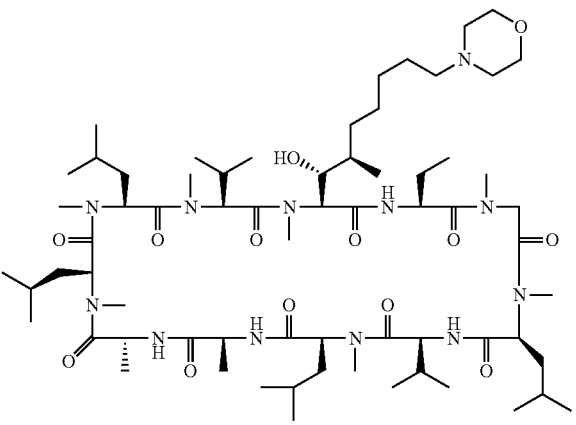

Compound C

Scheme III

Procedure for Obtaining a Compound Having Formula I where n=1, and m=1

Schemes III and IV describe efficient processes for the synthesis of amides of Formula I. Scheme III describes the use of metathesis using Grubbs II catalyst while Scheme IV describes the use of Wittig chemistry. The metathesis route (scheme III) is two steps shorter than the Wittig route (scheme IV) starting from intermediate 1.

Scheme III

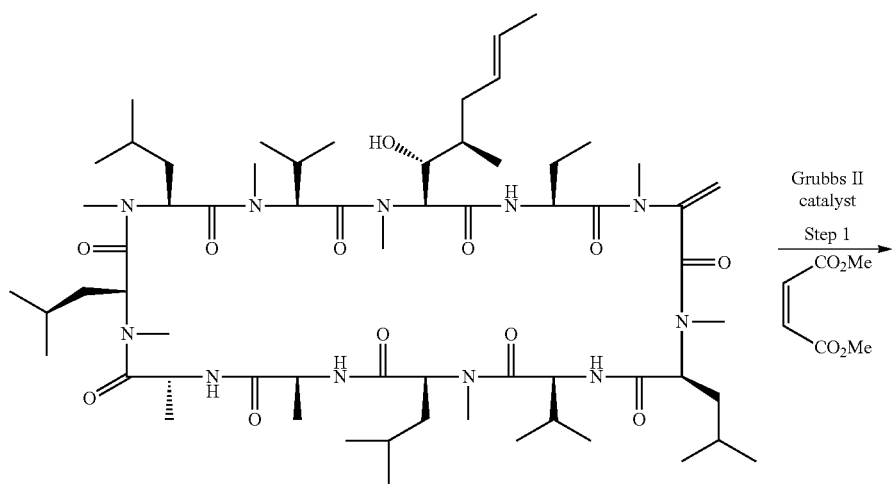

Intermediate 1

-continued
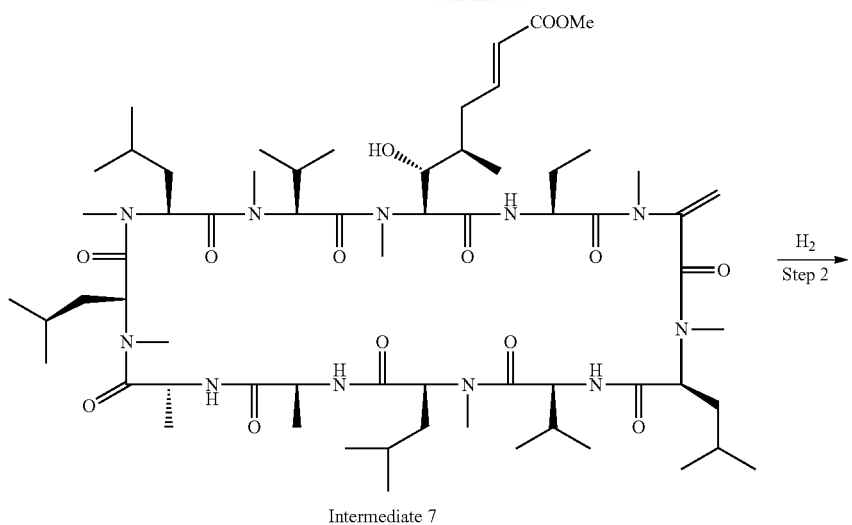
Intermediate 7
$\xrightarrow[\text{Step 2}]{\text{H}_2}$
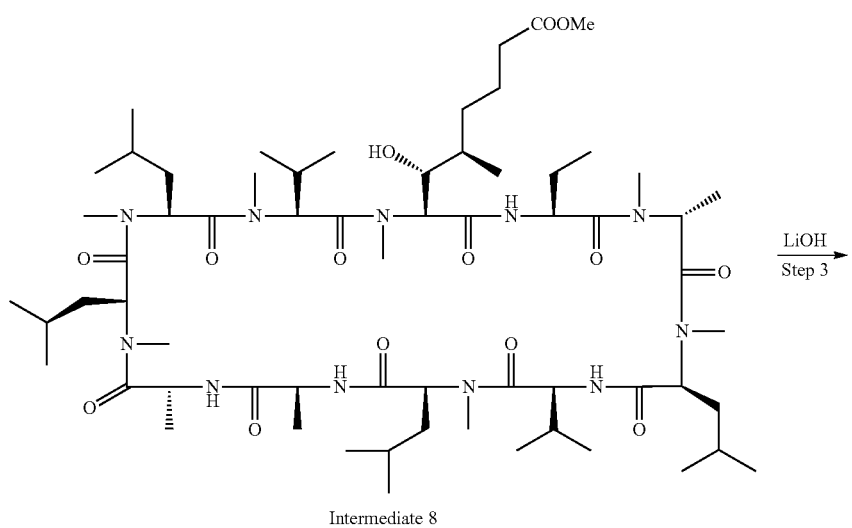
Intermediate 8
$\xrightarrow[\text{Step 3}]{\text{LiOH}}$
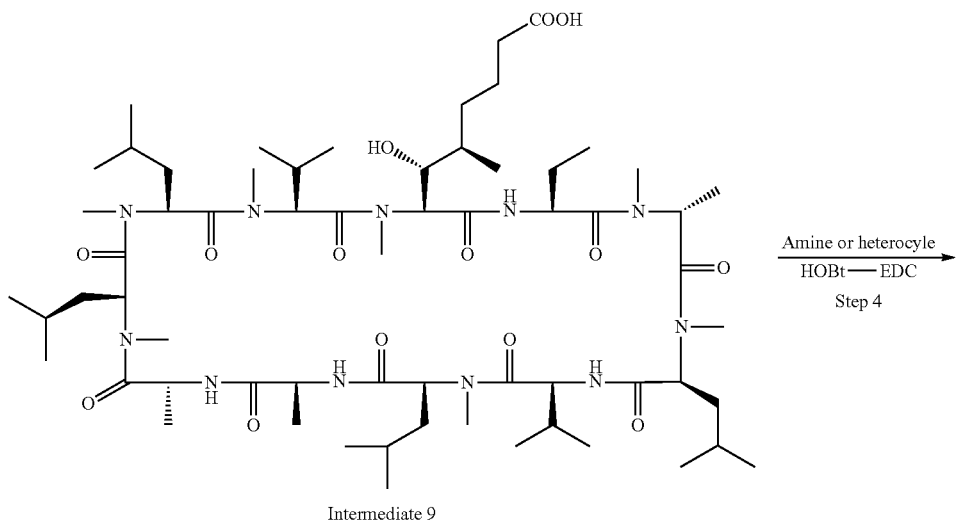
Intermediate 9
$\xrightarrow[\text{HOBt—EDC}]{\text{Amine or heterocyle}}$
Step 4

-continued

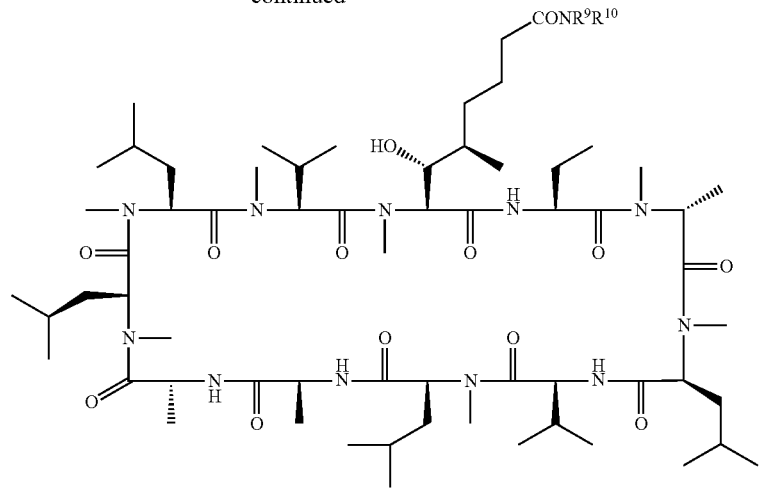

Compound of Formula I

Preparation of Intermediate 7

Methylene-Sar]³cyclosporin A (Intermediate 1) (242 mg, 0.2 mmol) and dimethyl maleate (376 uL, 3.0 mmol) were dissolved in dry dichloromethane (4 mL). The mixture was purged with nitrogen before the addition of Grubbs catalyst second generation (40 mg, 0.048 mmol) then refluxed for 18 hours. The reaction mixture was cooled to room temperature then purified by silicagel chromatography using a solvent gradient of 100% dichloromethane→96% dichloromethane/4% methanol to provide [[2E,5R,6R,7S)-6-hydroxy-5-methyl-7-(methylamino)-oct-2-enedioic acid]methyl ester]¹[methylene-Sar]³cyclosporin A (Intermediate 7) as an off-white solid.

ESMS MH⁺ 1258.98

¹H NMR (CDCl₃, ppm) δ 5.74 (d, 1H, olefin), 7.00 (dt, 1H, olefin), 7.18 (d, 1H, amide NH), 7.51 (d, 1H, amide NH), 7.60 (d, 1H, amide NH), 7.79 (d, 1H, amide NH).

Preparation of Intermediate 8

[[(2E,5R,6R,7S)-6-Hydroxy-5-methyl-7-(methylamino)-oct-2-enedioic acid]methyl ester]¹[methylene-Sar]³cyclosporin A (Intermediate 7) (68 mg, 0.054 mmol) was dissolved in ethanol (6 mL), treated with 10% palladium on carbon (68 mg) then placed under a 1 atm atmosphere of hydrogen for 65 hours. Fresh catalyst (68 mg) was added to the reaction mixture and hydrogenation carried on for an additional 24 hours. The reaction mixture was filtered through celite then concentrated in vacuo. The residue was purified by silicagel chromatography using a solvent gradient of 100% dichloromethane→95% dichloromethane/5% methanol to provide [[(5R,6R,7S)-6-hydroxy-5-methyl-7-(methylamino)-octanedioic acid]methyl ester]¹[(R)-methyl-Sar]³cyclosporin A (Intermediate 8) as a white solid.

ESMS MH⁺ 1262.71

¹H NMR (CDCl₃, ppm) δ 7.15 (d, 1H, amide NH), 7.48 (d, 1H, amide NH), 7.70 (d, 1H, amide NH), 7.78 (d, 1H, amide NH).

Preparation of Intermediate 9 from Intermediate 8

[[(5R,6R,7S)-6-Hydroxy-5-methyl-7-(methylamino)-octanedioic acid]methyl ester]¹[(R)-methyl-Sar]³cyclosporin A (Intermediate 8) (0.34 g, 0.27 mmol) was dissolved in tetrahydrofuran (30 mL) then treated with a solution of lithium hydroxide (64 mg, 1.5 mmol) in water (4 mL). The reaction mixture was stirred at room temperature for 25 hours then concentrated. The residue was treated with ethyl acetate and HCl 1N. The organic phase was washed with brine, dried (Na₂SO₄) and concentrated. The residue was purified by silicagel chromatography using a solvent gradient of 100% dichloromethane→95% dichloromethane/5% methanol to provide [(5R,6R,7S)-6-hydroxy-5-methyl-7-(methylamino)-octanedioic acid]¹[(R)-methyl-Sar]³cyclosporin A (Intermediate 9) as a white solid.

ESMS MH⁺ 1248.6

¹H NMR (CDCl₃, ppm) δ 7.21 (d, 1H, amide NH), 7.61 (d, 1H, amide NH), 7.69 (d, 1H, amide NH), 8.03 (d, 1H, amide NH).

As described below, the procedure shown in Scheme III can be generally adapted to produce a variety of Compounds of Formula I, depending on the structure of the amine or heterocycle reacted with Intermediate 9 at Step 4 in Scheme III.

Preparation of Compound H from Intermediate 9

[(5R,6R,7S)-6-Hydroxy-5-methyl-7-(methylamino)-octanedioic acid]¹[(R)-methyl-Sar]³cyclosporin A (Intermediate 9) (50 mg, 0.04 mmol) was dissolved in acetonitrile (2 mL) and stirred at 0° C. under nitrogen. Morpholine (8 uL, 0.09 mmol) then N-hydroxybenzotriazole (10 mg, 0.05 mmol) then 1-ethyl-3-(3-dimethylaminopropyl) carbodiimide hydrochloride (11 mg, 0.056 mmol) were added. The reaction mixture was left to stir at 0° C. for 30 minutes then allowed to warm up to room temperature and stirred for 17 hours. The volatiles were removed and the residue was partitioned between ethyl acetate and water, the organic phase was washed with water, brine then dried over sodium sulphate then concentrated in vacuo to give [(5R,6R,7S)-6-hydroxy-5-methyl-7-(methylamino)-1-N-morpholino-1-oxo-octanoic acid]¹[(R)-methyl-Sar]³cyclosporin A (Compound H) as a white solid.

ESMS MH⁺ 1318.0

¹H NMR (CDCl₃, ppm) δ 7.15 (d, 1H, amide NH), 7.52 (d, 1H, amide NH), 7.72 (d, 1H, amide NH), 8.01 (d, 1H, amide NH).

Preparation of Compound T from Intermediate 9

By substituting N-methyl piperazine for morpholine in the procedure described above to prepare Compound H, [(5R,6R,7S)-6-hydroxy-5-methyl-7-(methylamino)-1-(4-methylpiperazin-1-yl)-1-oxo-octanoic acid]$^1$[(R)-methyl-Sar]$^3$cyclosporin A (Compound T) was obtained as a white solid after purification by SCX chromatography using a solvent gradient of 100% methanol→0.14M ammonia in methanol.

ESMS MH$^+$ 1330.8

$^1$H NMR (CDCl$_3$, ppm) δ 7.14 (d, 1H, amide NH), 7.51 (d, 1H, amide NH), 7.71 (d, 1H, amide NH), 8.00 (d, 1H, amide NH).

Preparation of Compound U from Intermediate 9

By substituting diethylamine for morpholine in the procedure described above to prepare Compound H, [(5R,6R,7S)-6-hydroxy-5-methyl-7-(methylamino)-1-diethylamino-1-oxo-octanoic acid]$^1$[(R)-methyl-Sar]$^3$cyclosporin A (Compound U) was obtained as a white solid after purification by silicagel chromatography using a solvent gradient of 100% dichloromethane→95% dichloromethane/5% methanol.

ESMS MH$^+$ 1303.8

$^1$H NMR (CDCl$_3$, ppm) δ 7.12 (d, 1H, amide NH), 7.50 (d, 1H, amide NH), 7.69 (d, 1H, amide NH), 7.98 (d, 1H, amide NH).

Preparation of Compound W from Intermediate 9

By substituting 2-amino-ethanesulfonic acid dimethylamide for morpholine in the procedure described above to prepare Compound H, [(5R,6R,7S)-6-hydroxy-5-methyl-7-(methylamino)-1-(2-{sulfonic acid dimethylamide}-ethylamino)-1-oxo-octanoic acid]$^1$[(R)-methyl-Sar]$^3$cyclosporin A (Compound W) was obtained as a white solid after purification by SCX chromatography using methanol.

ESMS MH$^+$ 1382.6

$^1$H NMR (CDCl$_3$, ppm) δ 6.99 (t, 1H, amide NH), 7.23 (d, 1H, amide NH), 7.62 (d, 1H, amide NH), 7.80 (d, 1H, amide NH), 8.12 (d, 1H, amide NH).

Preparation of Compound Y from Intermediate 9

By substituting 2-(1H-imidazol-4-yl)-ethylamine for morpholine in the procedure described above to prepare Compound H, [(5R,6R,7S)-6-hydroxy-5-methyl-7-(methylamino)-1-(2-{1H-imidazol-4-yl}-ethylamino)-1-oxo-octanoic acid]$^1$[(R)-methyl-Sar]$^3$cyclosporin A (Compound Y) was obtained as a white solid after purification by SCX chromatography using a solvent gradient of 100% methanol→0.14M ammonia in methanol.

ESMS MH$^+$ 1341.9

$^1$H NMR (CDCl$_3$, ppm) δ 6.61 (m, 1H, amide NH), 6.82 (bs, 1H, imidazole CH), 7.22 (d, 1H, amide NH), 7.56 (bs, 1H, imidazole CH), 7.64 (d, 1H, amide NH), 7.78 (d, 1H, amide NH), 8.12 (d, 1H, amide NH).

Preparation of Compound Z from Intermediate 9

By substituting thiomorpholine 1,1-dioxide for morpholine in the procedure described above to prepare Compound H, [(5R,6R,7S)-6-hydroxy-5-methyl-7-(methylamino)-1-({1,1-dioxo}thiomorpholin-4-yl)-1-oxo-octanoic acid]$^1$[(R)-methyl-Sar]$^3$cyclosporin A (Compound Z) was obtained as a white solid after purification by SCX chromatography using methanol.

ESMS MH$^+$ 1365.3

$^1$H NMR (CDCl$_3$, ppm) δ 7.21 (d, 1H, amide NH), 7.58 (d, 1H, amide NH), 7.74 (d, 1H, amide NH), 8.08 (d, 1H, amide NH).

The chemical structures, and therefore formulas, of Compounds H, T, U, W, Y, and Z are shown below.

Preparation of Compound ZZ from Intermediate 9

By substituting (3aR*,6aS*)-2-methyloctahydropyrrolo[3,4-c]pyrrole for morpholine in the procedure described above to prepare Compound H, [(5R,6R,7S)-6-hydroxy-5-methyl-7-(methylamino)-1-(N-(3aR*,6aS*)-2-methyloctahydropyrrolo[3,4-c]pyrrolo)-1-oxo-octanoic acid]1[(R)-methyl-Sar]3cyclosporin A (Compound ZZ) was obtained as a white solid after purification by SCX chromatography using a solvent gradient of 100% methanol to 0.14M ammonia in methanol.

ESMS MH+1356.6

1H NMR (CDCl$_3$, ppm) δ 7.13 (d, 1H, amide NH), 7.50 (d, 1H, amide NH), 7.71 (d, 1H, amide NH), 8.00 (d, 1H, amide NH).

Preparation of Compound ZY from Intermediate 9

By substituting 2-methoxy-ethylamine for morpholine in the procedure described above to prepare Compound H, [(5R,6R,7S)-6-hydroxy-5-methyl-7-(methylamino)-1-(2-methoxyethylamino)-1-oxo-octanoic acid]1[(R)-methyl-Sar]3cyclosporin A (Compound ZY) was obtained as a white solid after purification by silica gel chromatography using a solvent gradient of 100% dichloromethane to 95% dichloromethane/5% methanol.

ESMS MH+1306.0

1H NMR (CDCl$_3$, ppm) δ 6.39 (bt, 1H, amide NH), 7.20 (d, 1H, amide NH), 7.59 (d, 1H, amide NH), 7.78 (d, 1H, amide NH), 8.11 (d, 1H, amide NH).

Preparation of Compound ZX from Intermediate 9

By substituting (1,4-dioxan-2-ylmethyl)amine for morpholine in the procedure described above to prepare Compound H, [(5R,6R,7S)-6-hydroxy-5-methyl-7-(methylamino)-1-(1,4-dioxan-2-ylmethyl)amino)-1-oxo-octanoic acid]1[(R)-methyl-Sar]3cyclosporin A (Compound ZX) was obtained as a white solid after purification by silica gel chromatography using a solvent gradient of 100% dichloromethane to 95% dichloromethane/5% methanol.

ESMS MH+1347.7

1H NMR (CDCl$_3$, ppm) δ 6.41 (dd, 1H, amide NH), 7.20 (d, 1H, amide NH), 7.62 (bs, 2H, amide NH), 7.78 (d, 1H, amide NH), 8.12 (d, 1H, amide NH).

Using the procedure described in scheme III with piperidine in step 4, compound Q was prepared.

Compound Q (see Table 11) [(5R,6R,7S)-6-hydroxy-5-methyl-7-(methylamino)-1-piperidino-1-oxo-octanoic acid]$^1$[(R)-methyl-Sar]$^3$cyclosporin A

ESMS MH$^+$ 1315.6

$^1$H NMR (CDCl$_3$, ppm) δ 7.14 (d, 1H, amide NH), 7.51 (d, 1H, amide NH), 7.71 (d, 1H, amide NH), 8.02 (d, 1H, amide NH).

Using the procedure described in scheme III with Cyclosporin A as the starting material and morpholine as the amine in step 4, compound E was prepared.

Compound E [(5R,6R,7S)-6-hydroxy-5-methyl-7-(methylamino)-1-N-morpholino-1-oxo-octanoic acid][1]cyclosporin A ESMS MH+ 1303.68
$^1$H NMR (CDCl$_3$, ppm) δ 7.15 (d, 1H, amide NH), 7.5 (d, 1H, amide NH), 7.75 (d, 1H, amide NH), 8.1 (d, 1H, amide NH).

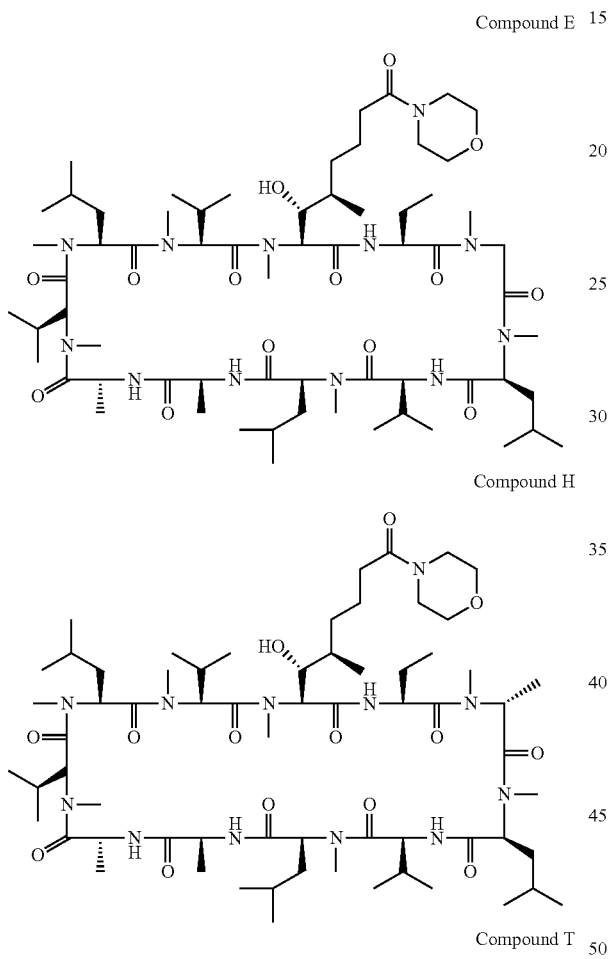

Compound E

Compound H

Compound T

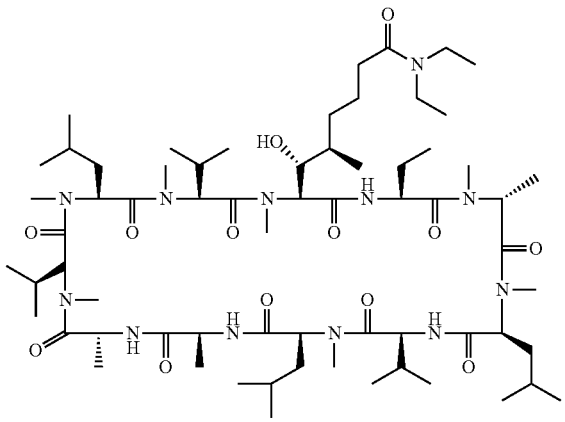

Compound U

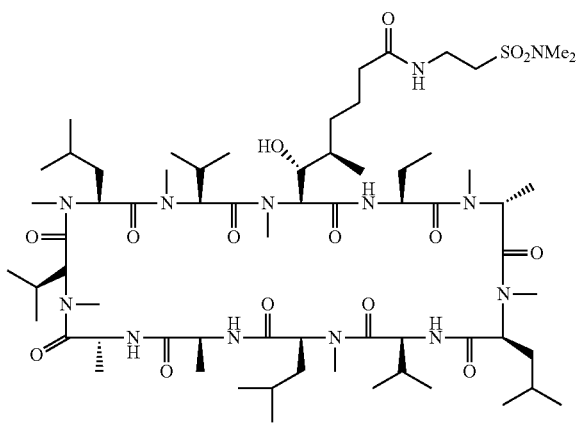

Compound W

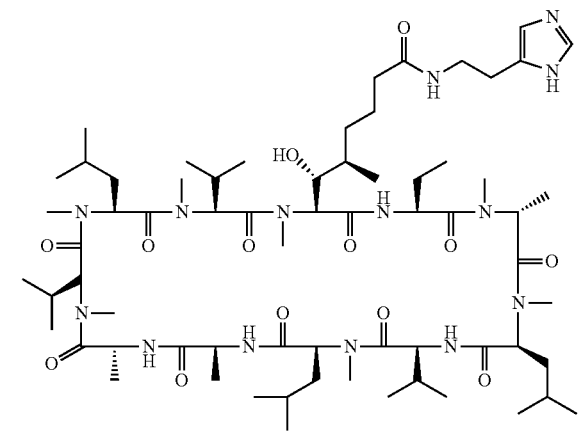

Compound Y

Compound Z
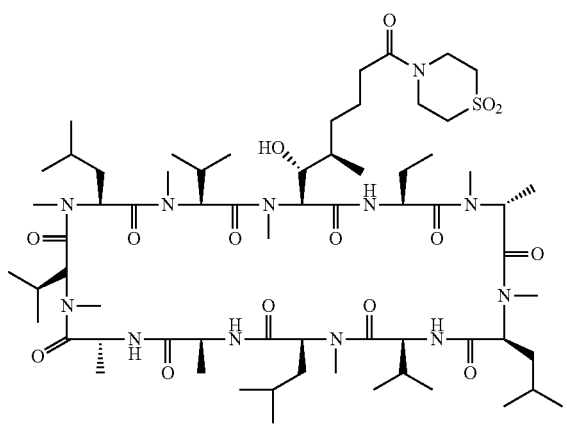
Compound ZX
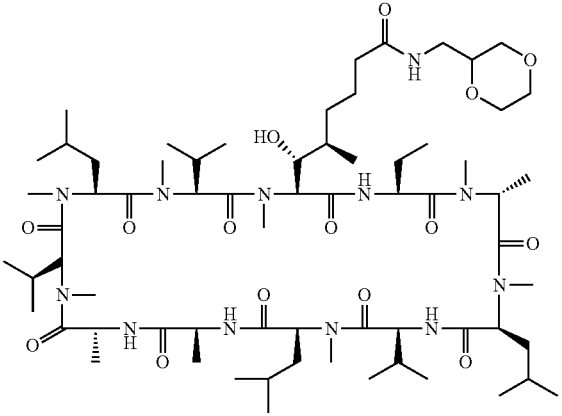
Compound ZZ
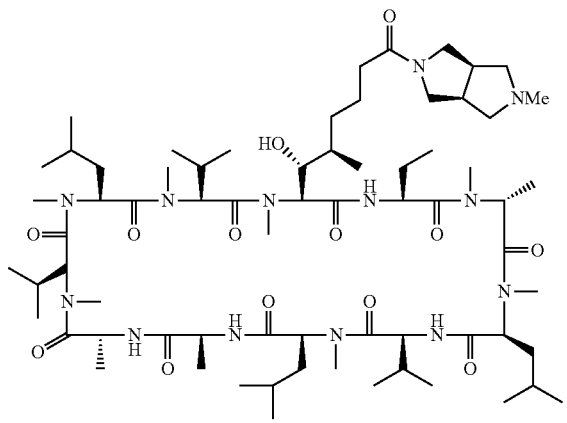
Compound Q
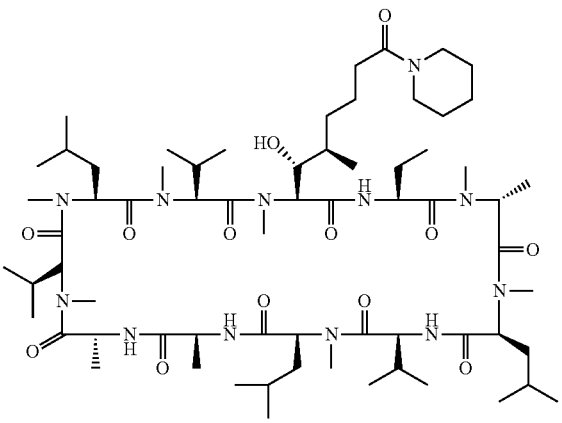
Compound ZY
Scheme IV
Procedure for Obtaining a Compound Having Formula I where n=1 and m=1

Scheme IV
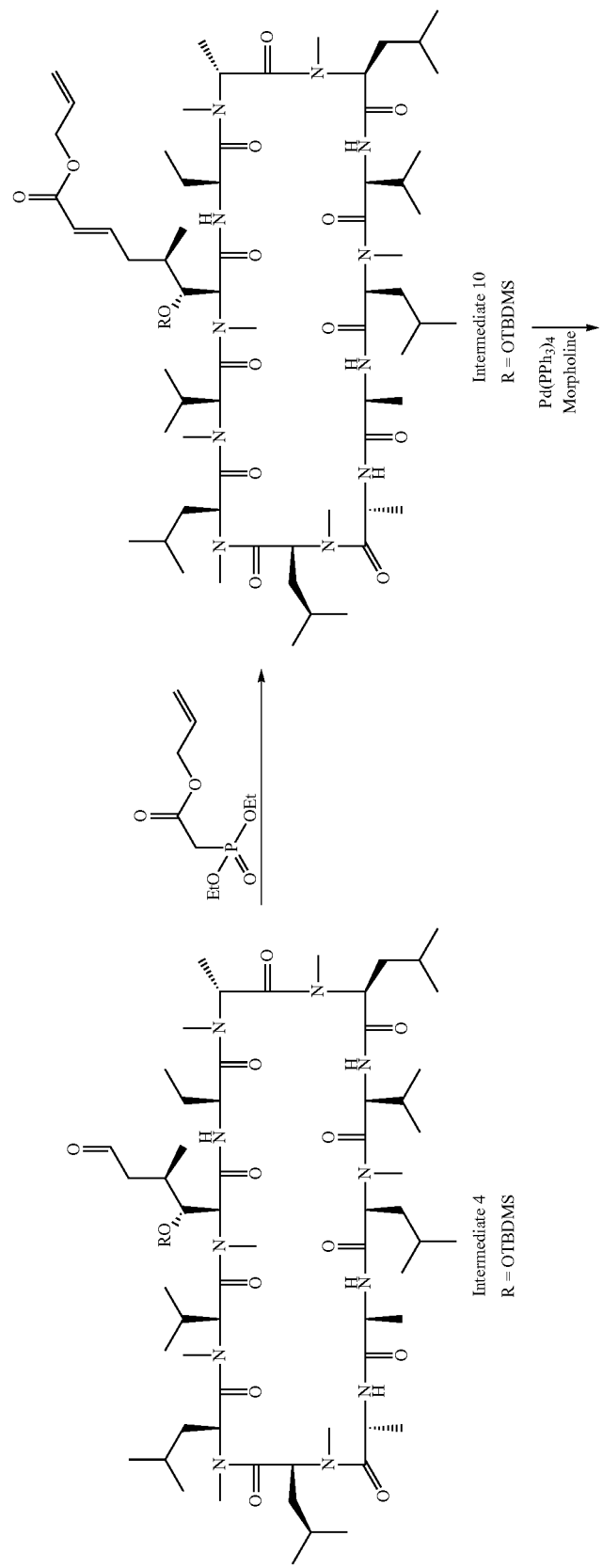

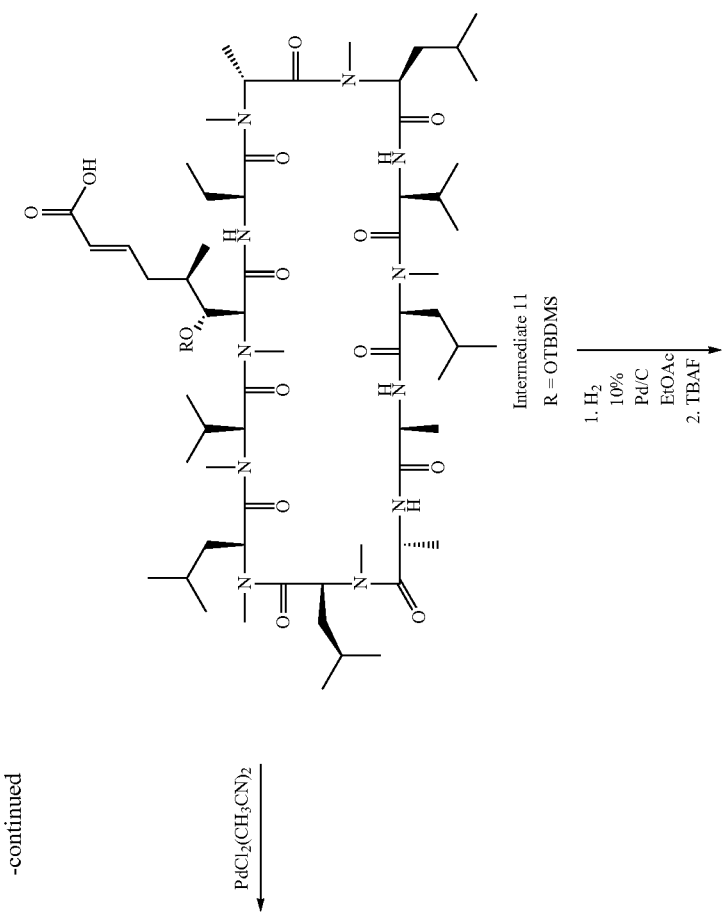
Intermediate 11
R = OTBDMS
1. H₂ 10% Pd/C EtOAc
2. TBAF
-continued
PdCl₂(CH₃CN)₂
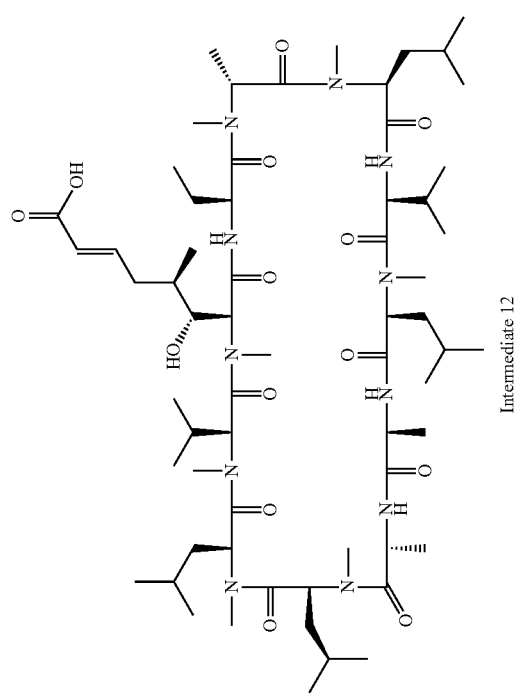
Intermediate 12

-continued
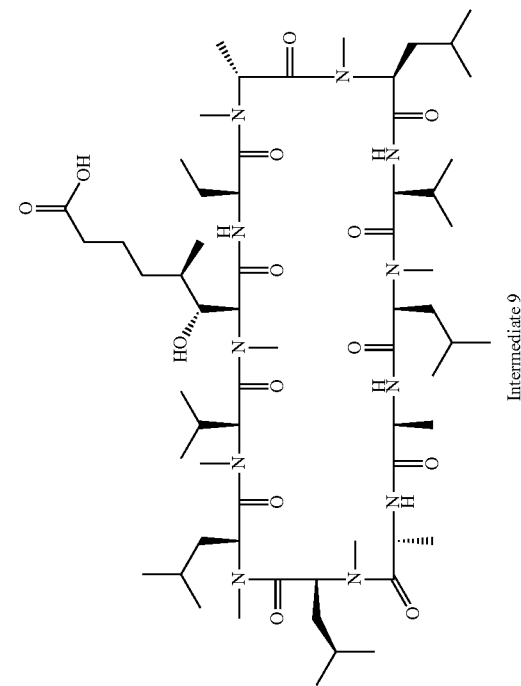
Intermediate 9
↓ HOBt —— EDC
   Amine
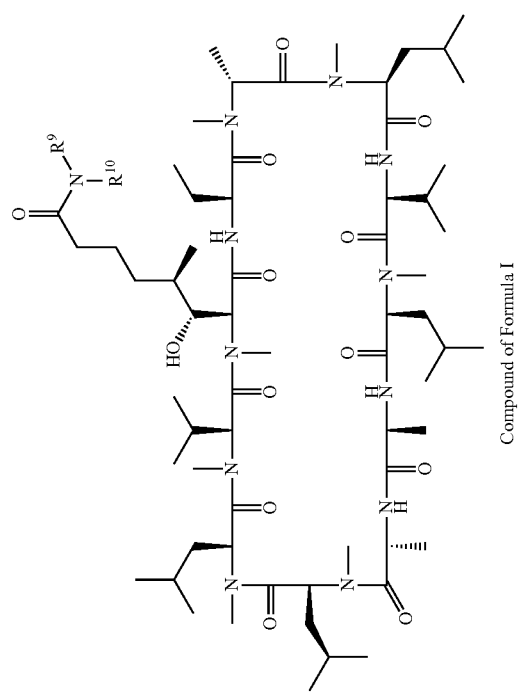
Compound of Formula I For Scheme IV, Intermediate 4 is prepared as described above in Scheme I.

Preparation of Intermediate 10 from Intermediate 4

To a suspension of lithium chloride (127 mg, 3 mmol) in acetonitrile (5 mL) was added successively diisopropylethylamine (522 uL, 3 mmol) and allyldiethylphosphono acetate (89 uL, 0.42 mmol). The mixture was stirred at room temperature for 15 minutes before the addition of a solution of [(3R,4R,5S)-4-(t-butyldimethylsilanyloxy)-3-methyl-5-(methylamino)-1-oxo-hexanoic acid]1[(R)-methyl-Sar]3cyclosporin A (Intermediate 4) (393 mg, 0.3 mmol) in acetonitrile/methanol (50/50, 8 mL). The reaction mixture was stirred at room temperature for 18 hours then concentrated in vacuo. The residue was partitioned between ethyl acetate and 1M HCl, the organic phase was washed twice with further 1M HCl then saturated aqueous sodium bicarbonate. The organic phase was dried over sodium sulphate then concentrated in vacuo. The residue was purified by silica gel chromatography using a solvent gradient of 100% dichloromethane to 95% dichloromethane/5% methanol to provide [(2E,5R,6R,7S)-6-(t-butyldimethylsilanyloxy)-5-methyl-7-(methylamino)-oct-2-enedioic acid]allyl ester]1[(R)-methyl-Sar]3cyclosporin A (Intermediate 10) as a white solid.

1H NMR (CDCl$_3$, ppm) δ 5.73 (d, 1H, olefin), 7.06 (dt, 1H, olefin), 7.5 (m, 2H, amide NH), 7.90 (d, 1H, amide NH), 8.37 (d, 1H, amide NH).

Preparation of Intermediate 11 from Intermediate 10

A solution of [[(2E,5R,6R,7S)-6-(t-butyldimethylsilanyloxy)-5-methyl-7-(methylamino)-octanedioic acid]allyl ester]1[(R)-methyl-Sar]3cyclosporin A (Intermediate 10) (97 mg, 0.069 mmol) in dry THF (4 mL) had nitrogen gas bubbled through for 5 minutes before and after the addition of tetrakis (triphenylphosphine)palladium (0) (16 mg, 0.0138 mmol). Morpholine (62 uL, 0.69 mmol) was then added and the reaction mixture was stirred at room temperature for 20 hours. The volatiles were removed and the residue was dissolved in ethyl acetate and washed twice with 1M HCl then once with brine. The organic phase was dried over sodium sulphate then concentrated in vacuo. NMR analysis indicated that the reaction was not complete and so the mixture was treated again as described above and this time stirred at room temperature for 3 days. The above work-up provided a residue which was purified by silica gel chromatography using a solvent gradient of 100% dichloromethane to 96% dichloromethane/4% methanol to provide [(2E,5R,6R,7S)-6-(t-butyldimethylsilanyloxy)-5-methyl-7-(methylamino)-oct-2-enedioic acid]1[(R)-methyl-Sar]3cyclosporin A (Intermediate 11) as a white solid.

1H NMR (CDCl$_3$, ppm) δ 7.49 (d, 1H, amide NH), 7.59 (d, 1H, amide NH), 7.78 (d, 1H, amide NH), 8.42 (d, 1H, amide NH).

Preparation of Intermediate 12 from Intermediate 11

A solution of [(2E,5R,6R,7S)-6-(t-butyldimethylsilanyloxy)-5-methyl-7-(methylamino)-oct-2-enedioic acid]1[(R)-methyl-Sar]3cyclosporin A (Intermediate 11) (56 mg, 0.041 mmol) in dry acetone (2 mL) had nitrogen gas bubbled through it for 5 minutes before the addition of bis(acetonitrile)dichloropalladium (II) (1 mg, 0.004 mmol). The reaction mixture was stirred at room temperature for 17 hours, then additional dry acetone (2 mL) and bis(acetonitrile)dichloropalladium (II) (1 mg, 0.004 mmol) were added and the reaction mixture was stirred for a further 3 days. The reaction mixture was filtered through celite using diethyl ether and methanol as solvents. The solvents were evaporated and the residue obtained was purified by silica gel chromatography using a solvent gradient of 100% dichloromethane to 95% dichloromethane/5% methanol to provide [(2E,5R,6R,7S)-6-hydroxy-5-methyl-7-(methylamino)-oct-2-enedioic acid]1 [(R)-methyl-Sar]3cyclosporin A (Intermediate 12) as a white solid.

ESMS MH+1246.7

1H NMR (CDCl$_3$, ppm) δ 7.19 (d, 1H, amide NH), 7.50 (d, 1H, amide NH), 7.65 (d, 1H, amide NH), 8.05 (d, 1H, amide NH).

Preparation of Intermediate 9 from Intermediate 11

[(2E,5R,6R,7S)-6-(t-Butyldimethylsilanyloxy)-5-methyl-7-(methylamino)-oct-2-enedioic acid]1[(R)-methyl-Sar] 3cyclosporin A (Intermediate 11) (100 mg, 0.073 mmol) was dissolved in methanol (20 mL), treated with 10% palladium on carbon (50 mg) then placed under a 1 atm atmosphere of hydrogen for 17 hours. The reaction mixture was filtered through celite then concentrated in vacuo to provide the dihydro version of intermediate 11 [[(5R,6R,7S)-6-(t-butyldimethylsilanyloxy)-5-methyl-7-(methylamino)-octanedioic acid]1[(R)-methyl-Sar]3 cyclosporin A (Intermediate 56) as a white solid.

1H NMR (CDCl$_3$, ppm) δ 7.49 (d, 1H, amide NH), 7.83 (m, 2H, amide NH), 8.30 (d, 1H, amide NH).

A solution of [(5R,6R,7S)-6-(t-butyldimethylsilanyloxy)-5-methyl-7-(methylamino)-octanedioic acid]1[(R)-methyl-Sar]3cyclosporin A (Intermediate 56) (95 mg, 0.07 mmol) in tetrahydrofuran (4 mL) was treated with a 1M solution of tetrabutylammonium fluoride in tetrahydrofuran (350 uL, 0.35 mmol). The reaction mixture was stirred at room temperature for 23 hours. The volatiles were removed and the residue was partitioned between ethyl acetate and water, the organic phase was washed twice with water then dried over sodium sulphate then concentrated in vacuo. The residue was purified by silicagel chromatography using a solvent gradient of 100% dichloromethane to 94% dichloromethane/6% methanol to provide

[(5R,6R,7S)-6-hydroxy-5-methyl-7-(methylamino)-octanedioic acid]1[(R)-methyl-Sar]3 cyclosporin A (Intermediate 9) as a white solid.

ESMS MH+1248.6

1H NMR (CDCl$_3$, ppm) δ 7.21 (d, 1H, amide NH), 7.61 (d, 1H, amide NH), 7.69 (d, 1H, amide NH), 8.03 (d, 1H, amide NH).

The final step in Scheme IV, the conversion of Intermediate 9 to a Compound of Formula I, is carried out as described above in Scheme III, step 4.

Scheme V
Procedure for Obtaining a Compound Having Formula I where n=2 and m=0
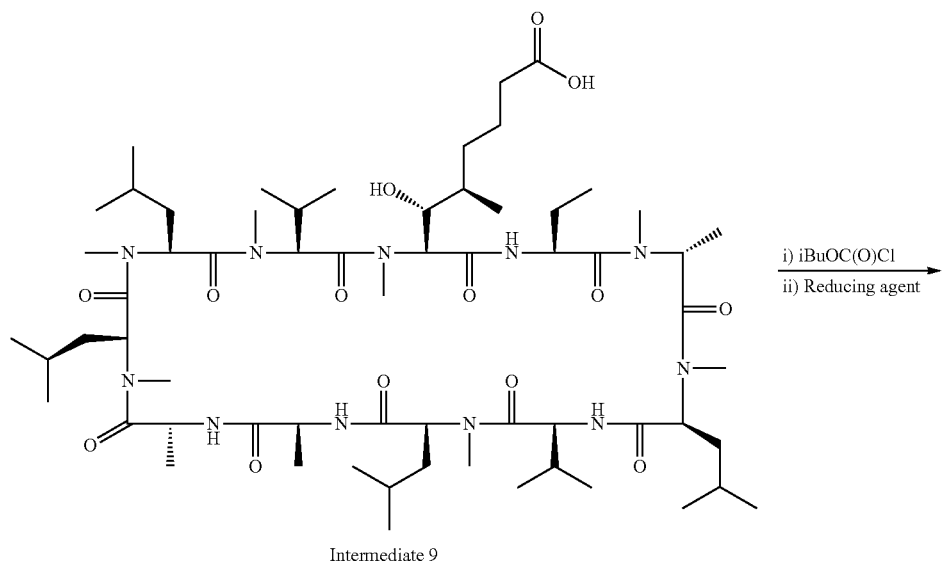
Intermediate 9
i) iBuOC(O)Cl
ii) Reducing agent
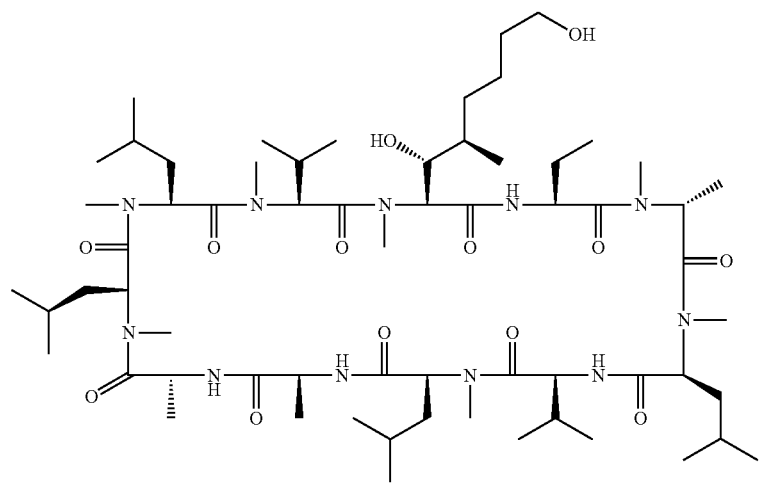
Intermediate 13
i) MeSO2Cl Pyridine ii) Amine -continued

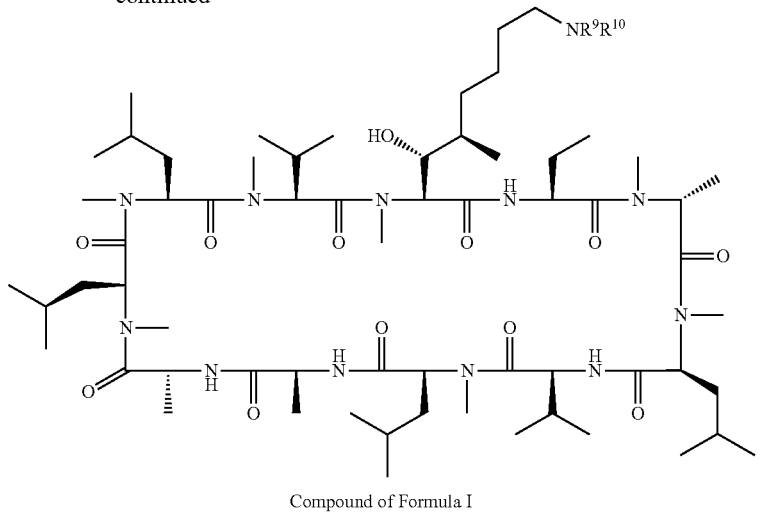

Compound of Formula I

Preparation of Intermediate 9

For purposes of Scheme V, Intermediate 9 is prepared as described in Scheme IV.

Preparation of Intermediate 13

To a solution of Intermediate 9 in a solvent such as dichloromethane is added isobutyl carbonyl chloride together with a base such as triethylamine. After removal of the solid by filtration the solvent is evaporated to give the anhydride. The anhydride is dissolved in a solvent such as dioxane and a reducing agent such as sodium borohydride is added in order to give the alcohol, intermediate 13.

Preparation of a Compound of Formula I from Intermediate 13

Intermediate 13 is dissolved in DCM and methanesulphonyl chloride and pyridine are added. The product is dissolved in a solvent such as acetonitrile and a base such as cesium carbonate is added. The required amine is added and the reaction mixture is stirred at a temperature between room temperature and 60° in order to give compounds of Formula I as shown in scheme V.

By using an alternative starting aldehyde, such as Intermediate 15, shown below, containing one less carbon and using the same chemistry described in Schemes IV and Xa, amines are prepared where n=1 and m=0, and amides are prepared where n=0 and m=1. The alternative starting aldehyde used for such syntheses can be prepared as shown below in Scheme VI.

Scheme VI

Preparation of Intermediate 15 (aldehyde)

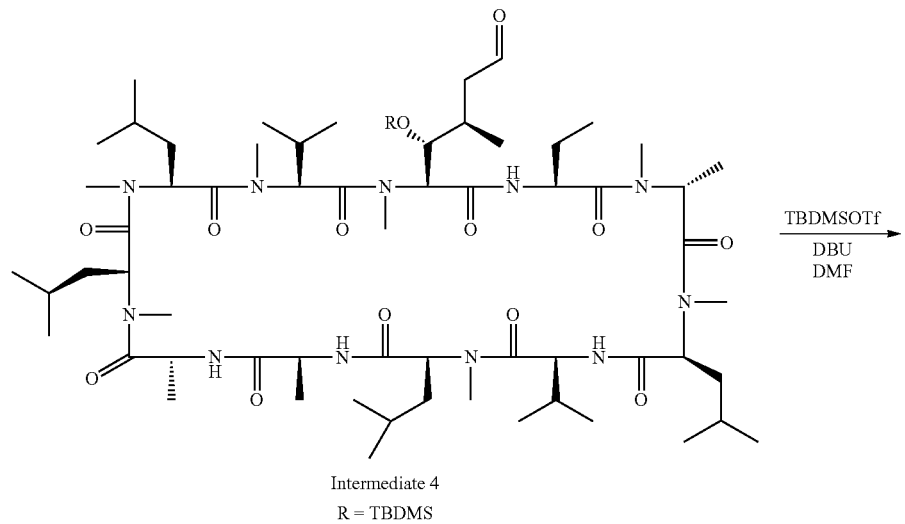

Intermediate 4
R = TBDMS

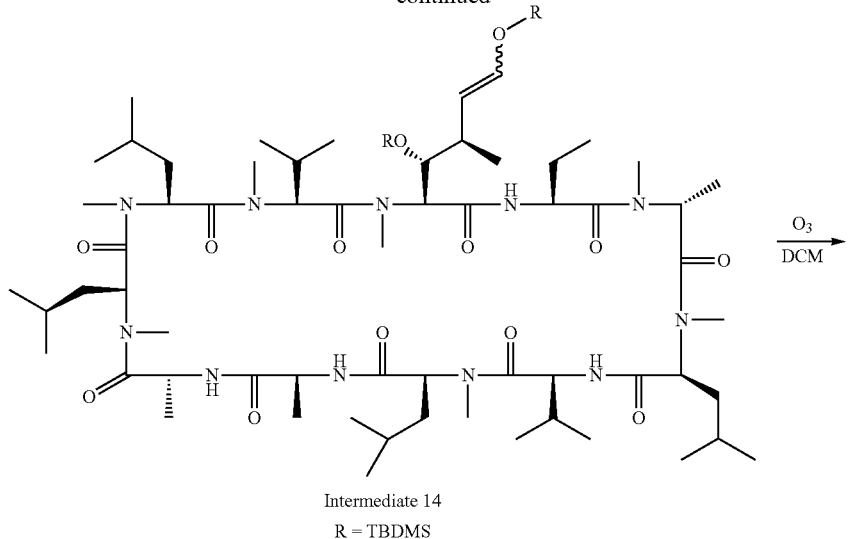

Intermediate 14
R = TBDMS

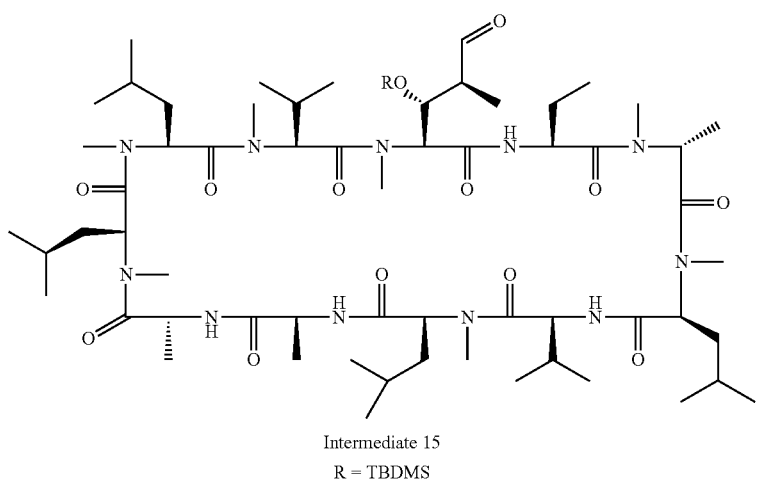

Intermediate 15
R = TBDMS

Preparation of Intermediate 4

For purposes of Scheme VI, Intermediate 4 is prepared according to Scheme I.

Preparation of Intermediate 14

To a solution of [(3R,4R,5S)-4-(t-butyldimethylsilanyloxy)-3-methyl-5-(methylamino)-1-oxo-hexanoic acid][1][methylene-Sar][3]cyclosporin A (Intermediate 4) (0.4 g) in DMF (1 ml) cooled to 0° C. was added DBU (0.5 ml) followed by a dropwise solution of TBDMSOTf (0.38 ml) in DMF (0.5 ml) and the reaction stirred under a nitrogen atmosphere for 18 h. After this time, the reaction mixture was diluted with ethyl acetate (10 ml) and $H_2O$ (10 ml). The organic layer was separated, dried, filtered and evaporated under reduced pressure.

The crude product was purified by MPLC chromatography using a solvent gradient of 100% dichloromethane→2% methanol/98% dichloromethane to give Intermediate 14 as a white solid.

$^1$H NMR (CDCl$_3$, ppm) δ 7.43 (d, 1H, amide NH), 7.58 (d, 1H, amide NH), 7.93 (d, 1H, amide NH), 8.58 (d, 1H, amide NH).

Preparation of Intermediate 15

A solution of Intermediate 14 (0.33 g, approx 0.23 mmol) was prepared according to the method used for the preparation of intermediate 3 (scheme 1, step 2) to give [(2R,3R,4S)-3-(t-butyldimethylsilanyloxy)-2-methyl-4-(methylamino)-1-oxo-pentanoic acid][1][methylene-Sar][3]cyclosporin A, intermediate 15 as a clear oil.

$^1$H NMR (CDCl$_3$, ppm) δ 7.44 (d, 1H, amide NH), 7.47 (d, 1H, amide NH), 7.97 (d, 1H, amide NH), 8.67 (d, 1H, amide NH), 9.52 (s, 1H, aldehyde H).

Scheme VII

Procedure for Obtaining a Compound Having Formula I where $R^8$ is $CH_2O$, n=2, and m=0

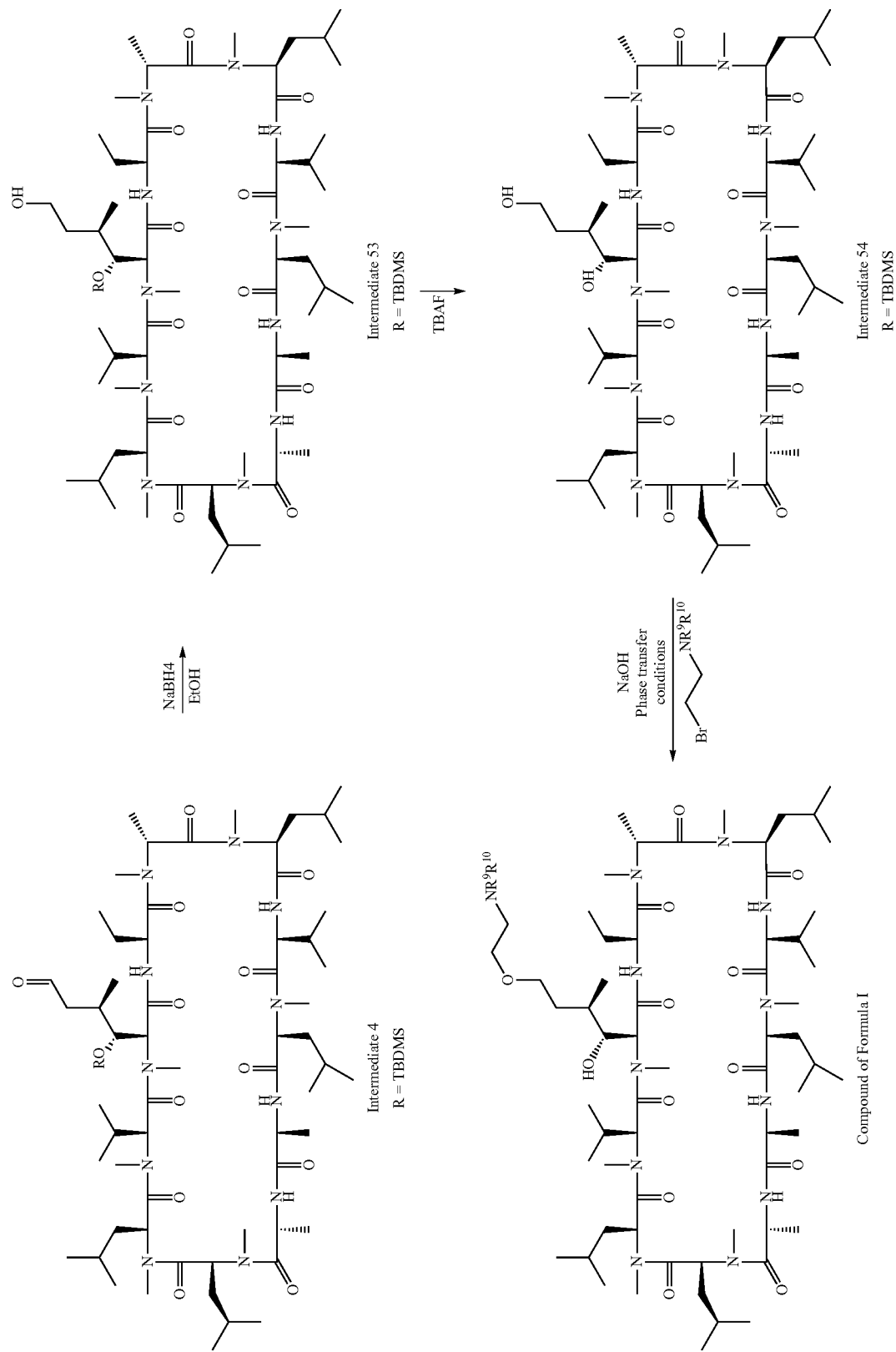

Preparation of Intermediate 53

Intermediate 53 was prepared by reduction of the aldehyde, Intermediate 4, using sodium borohydride in a solvent such as methanol, as described in US 2004/0110666.

Specifically, Intermediate 4 (0.17 g, 0.13 mmoles) was dissolved in methanol (5 ml) and sodium borohydride (0.01 g, 0.26 mmoles) was added with stirring. After stirring for 3 hours the reaction mixture was evaporated and the residue was partitioned between ethyl acetate and water. The ethyl acetate layer was separated and dried over anhydrous magnesium sulphate. The product was evaporated to give Intermediate 53.

1H NMR (CDCl$_3$, ppm) δ 7.57 (d, 1H, amide NH), 7.81 (d, 1H, amide NH), 7.72 (d, 1H, amide NH), 8.40 (d, 1H, amide NH).

Preparation of Intermediate 54

Intermediate 53 (0.18 g, 0.13 mmoles was dissolved in THF (2 ml) and deprotected by stirring overnight with 1M tetrabutylammonium fluoride (0.2 ml, 0.2 mmoles). The solvent was evaporated and the residue was taken up in dichloromethane, washed with water (×3) and dried over anhydrous magnesium sulphate. The solvent was removed by evaporation to give crude compound which was purified by MPLC to give the required Intermediate 54.

1H NMR (CDCl$_3$, ppm) δ 7.32 (d, 1H, amide NH), 7.53 (d, 1H, amide NH), 7.86 (d, 1H, amide NH), 8.17 (d, 1H, amide NH).

Preparation of Compound of Formula I from Intermediate 54

Intermediate 54 (0.07 g, 0.058 mmoles) was dissolved in DCM (1 ml) and 2-bromo-N,N-diethylethylamine hydrobromide (0.02 g, 0.058 mmoles) was added to the reaction mixture followed by 40% aqueous potassium hydroxide (1 ml) and the reaction mixture was stirred at room temperature overnight. The reaction mixture was diluted with water (15 mL) and more DCM (15 mL) was added then the DCM layer was separated and dried over anhydrous magnesium sulphate. The product was evaporated and the residue was purified using preparative thin layer chromatography (×2) to give a compound having Formula I (in this instance, [(3R,4R,5S)-4-Hydroxy-3-methyl-5-(methylamino)-1-2-(N,N-diethylamino)ethoxy-hexanoic acid]$^1$[(S)-thio-isopropyl-Sar]$^3$cyclosporin A (Compound AL)). Other alkyl halides such as iodomethane and 4-(2-chloroethyl) morpholine may be used in a similar manner to prepare other compounds of Formula I according to Scheme VII.

Compound AL

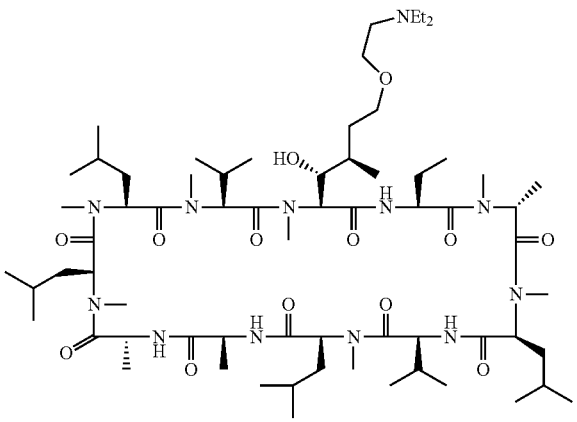

Scheme VIII

Procedure for obtaining a compound having Formula I, wherein R$^1$ is —CH$_2$CH$_3$, R$^{11}$ is O, n=0, m=0, and p=1. Scheme VIII:

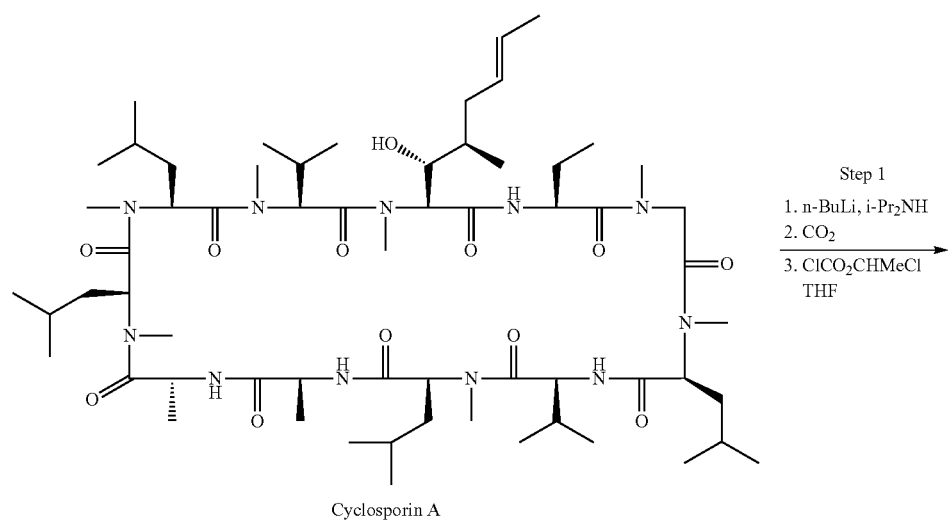

Cyclosporin A

Step 1
1. n-BuLi, i-Pr$_2$NH
2. CO$_2$
3. ClCO$_2$CHMeCl
   THF

-continued
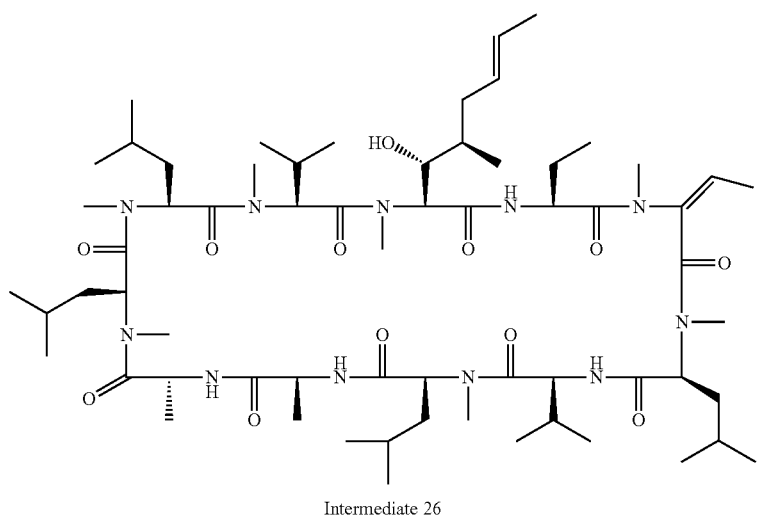
Intermediate 26
Step 2 / O₃
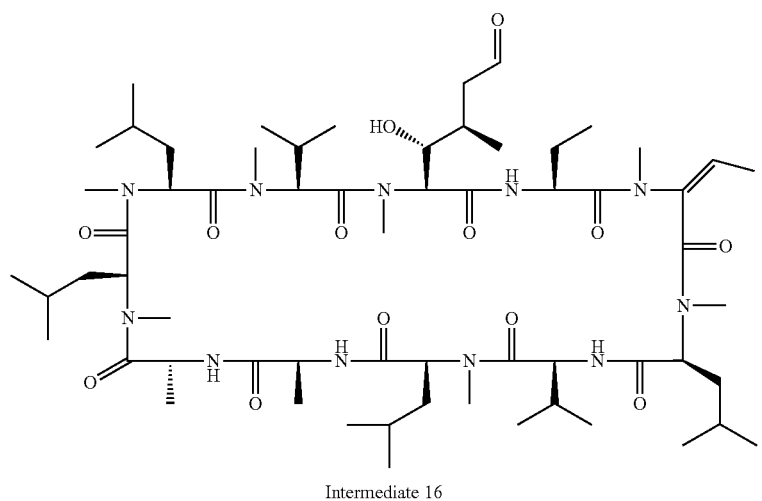
Intermediate 16
NaBHOAc₃
ClCH₂CH₂Cl
Step 3
(reductive
amination)

-continued

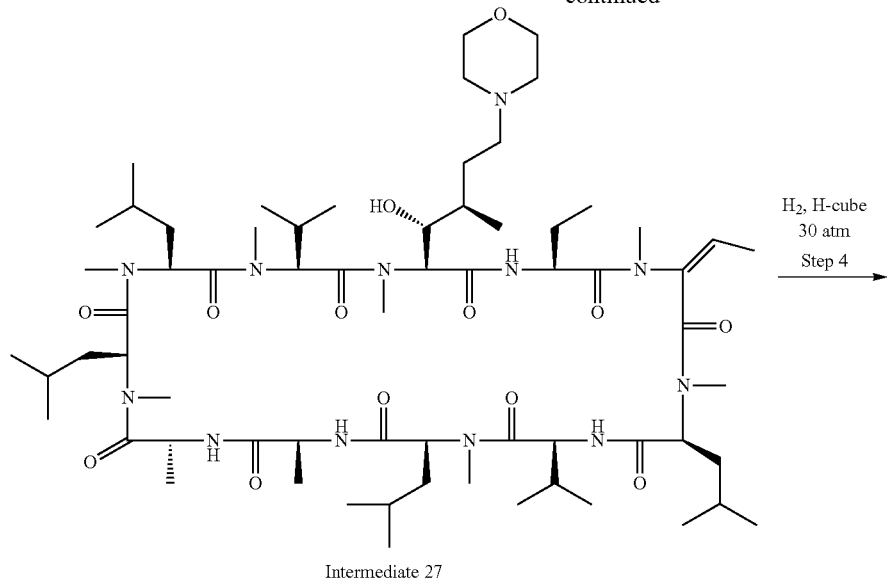

Intermediate 27

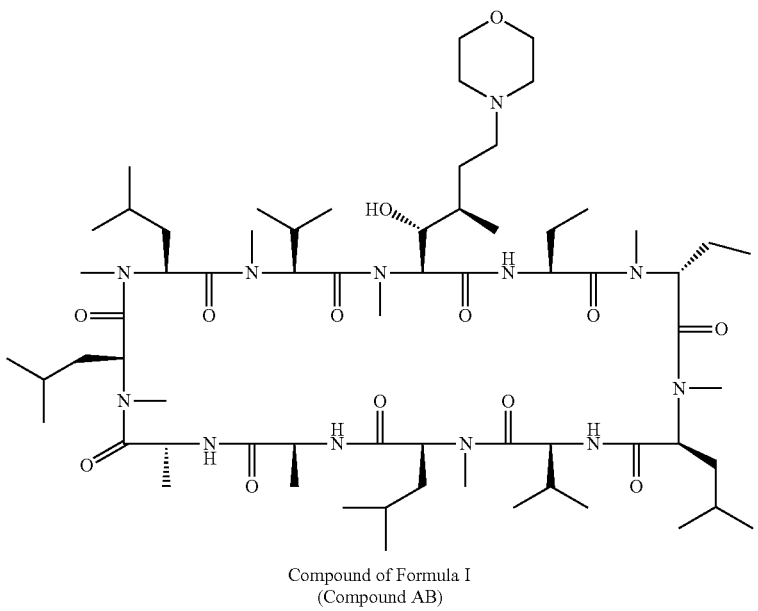

Compound of Formula I
(Compound AB)

Preparation of Intermediate 26 (Step 1)

Intermediate 26 is prepared according to the procedure used to prepare Intermediate 1 except that chloroethyl-chloro formate is used instead of chloromethly-chloro formate.

Preparation of Intermediate 16 (Step 2)

Step 2 in Scheme VIII above was carried out in an identical manner as described in step 2 Scheme 1 to give intermediate 16. Intermediate 16 may be substituted for Intermediate 1 in any of the schemes shown above to obtain compounds of Formula I in which $R^1$ is ethyl.

Preparation of Intermediate 27 (Step 3)

To a stirred solution of [(3R,4R,5S)-4-(hydroxy)-3-methyl-5-(methylamino)-1-oxo-hexanoic acid]$^1$[ethyl-2-ene-Sar]$^3$cyclosporin A (Intermediate 16) (0.219 g, 0.18 mmol) in dichloromethane (10 ml) was added morpholine (0.079 ml, 0.9 mmol) and sodium triacetoxyborohydride (0.160 g, 0.9 mmol) and the reaction mixture stirred at room temperature for 18 h. After this time, additional amounts of morpholine (0.079 ml, 0.9 mmol) and sodium triacetoxyborohydride (0.160 g, 0.9 mmol) were added and the reaction mixture stirred at 40° C. for 4.5 h. After this time, additional amounts of morpholine (0.025 ml, 0.28 mmol) and sodium triacetoxyborohydride (0.035 g, 0.2 mmol) were added and the reaction mixture stirred at 40° C. for 66 h. The reaction mixture was diluted with dichloromethane, washed with a saturated aqueous solution of sodium bicarbonate, brine then the organic phase was dried (Na$_2$SO$_4$), filtered and evaporated. [(3R,4R,5S)-4-(Hydroxy)-3-methyl-5-(methylamino)-1-N-morpholino-hexanoic acid]$^1$[ethyl-2-ene-Sar]$^3$cyclosporin A (Intermediate 27) was obtained as a white solid after purification by SCX chromatography using a solvent gradient of 100% methanol→0.14M ammonia in methanol.

ESMS MH$^+$ 1287.2

$^1$H NMR (CDCl$_3$, ppm) δ 7.15 (d, 1H, amide NH), 7.23 (d, 1H, amide NH), 7.72 (d, 1H, amide NH), 7.81 (d, 1H, amide NH).

Alternative compounds of Formula I may be produced according to Scheme VIII through the use of alternative heterocycles or amines at Step 3 in Scheme VIII.

Exemplary compounds that may be used in place of morpholine at step 3 in scheme VIII to produce compounds of the present invention include but are not limited to 2 methyloctahydropyrrolo[3,4c]pyrrole, piperidine, N-methyl piperazine, homomorpholine, and pyrrolidine.

Preparation of Compound AB

A solution of [(3R,4R,5S)-4-(hydroxy)-3-methyl-5-(methylamino)-1-N-morpholino-hexanoic acid]$^1$[ethyl-2-ene-Sar]$^3$cyclosporin A (Intermediate 27) (0.187 g, 0.145 mmol) in methanol (20 mL) was passed twice through a 10% palladium on carbon cartridge in a H-cube system at 30° C. under 30 atm of hydrogen. The reaction mixture was concentrated and the residue purified by MPLC chromatography using a solvent gradient of 100% dichloromethane→95% dichloromethane/5% methanol containing 10% aqueous ammonia (0.88) to give [(3R,4R,5S)-4-hydroxy-3-methyl-5-(methylamino)-1-N-morpholino-hexanoic acid]$^1$[(R)-ethyl-Sar]$^3$ cyclosporin A (Compound AB) as a white solid.

H-cube is a continuous flow reactor for carrying out hydrogenation under pressure. The hydrogenation is carried out using palladium on carbon catalyst at a hydrogen pressure of 30 atmospheres.

ESMS MH$^+$ 1289.5

$^1$H NMR (CDCl$_3$, ppm) 7.19 (d, 1H, amide NH), 7.37 (d, 1H, amide NH), 7.80 (d, 1H, amide NH), 7.98 (d, 1H, amide NH).

Scheme IX

Procedure for Obtaining a Compound Having Formula I, Wherein R$^1$ is —SCH$_3$, R$^{11}$ is O, n=0, m=0 and p=1, and wherein R$^9$, R$^{10}$, R$^{11}$, and the N to which R$^9$ and R$^{10}$ are attached taken together form

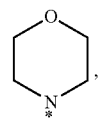

wherein "*" Represents the Point of attachment to R$^5$.

Scheme IX

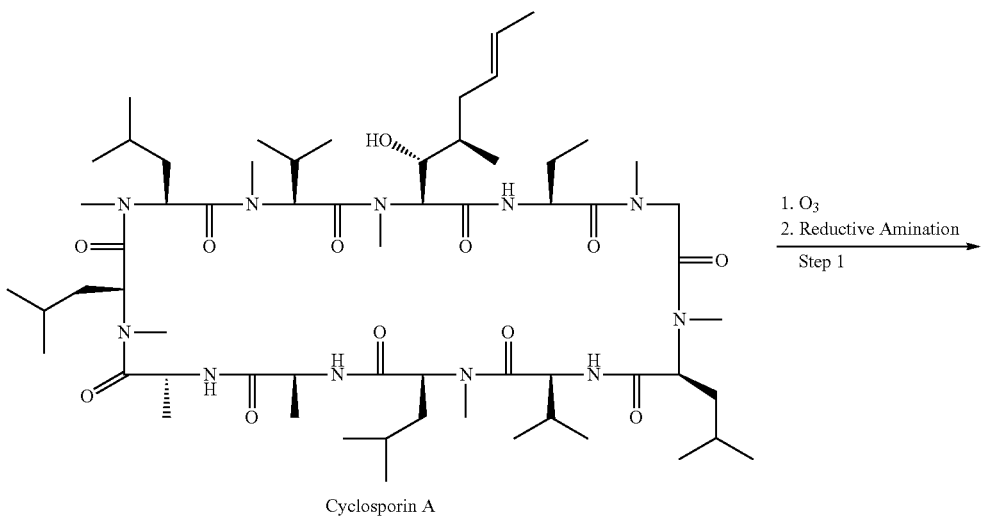

Cyclosporin A

1. O$_3$
2. Reductive Amination
   Step 1

-continued

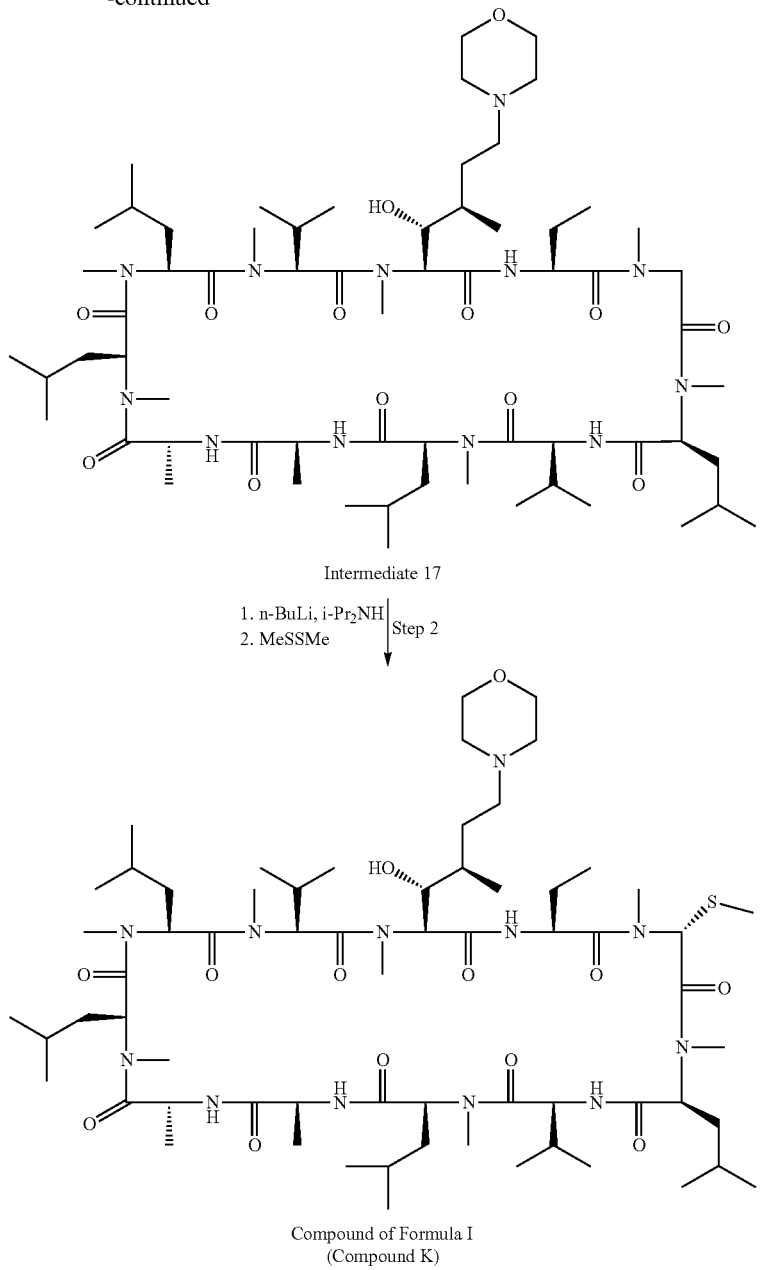

Preparation of Intermediate 17 (Compound A)

[(3R,4R,5S)-4-(hydroxy-3-methyl-5-(methylamino)-1-N-morpholino-hexanoic acid]¹cyclosporin A (Intermediate 17, Compound A) is prepared according to steps 2 and 3 of Scheme VIII using morpholine as the reactant in step 3.

ESMS MH⁺ 1261.59

$^1$H NMR (CDCl$_3$, ppm) δ 7.17 (d, 1H, amide NH), 7.40 (d, 1H, amide NH), 7.74 (d, 1H, amide NH), 7.91 (d, 1H, amide NH).

Compound LL (see table 2) [(3R,4R,5S)-4-(hydroxy-3-methyl-5-(methylamino)-1-N-methylpiperazinyl-hexanoic acid]¹cyclosporin A was prepared in a similar manner by using N-methylpiperazine as the reactant in step 3.

ESMS MH⁺ 1274.64

$^1$H NMR (CDCl$_3$, ppm) δ 7.17 (d, 1H, amide NH), 7.39 (d, 1H, amide NH), 7.75 (d, 1H, amide NH), 7.92 (d, 1H, amide NH).

Compound NN (see table 3) [(3R,4R,5S)-4-(hydroxy-3-methyl-5-(methylamino)-1-N-methylpiperazinyl-hexanoic acid]¹cyclosporin A was prepared in a similar manner by using ketopiperazine as the reactant in step 3.

ESMS MH⁺ 1274.71

$^1$H NMR (CDCl$_3$, ppm) δ 7.05 (d, 1H, amide NH), 8.05 (d, 1H, amide NH), 8.35 (d, 1H, amide NH), 8.41 (d, 1H, amide NH).

Compound AN (see table 19) [(3R,4R,5S)-4-(hydroxy-3-methyl-5-(methylamino)-1-N-morpholino-hexanoic acid]¹cyclosporin D was prepared in a similar manner by using Cyclosporin D as starting material and morpholine as the reactant in step 3.

ESMS MH+ 1275.78

$^1$H NMR (CDCl$_3$, ppm) δ 5.8 (s, 1H, (R)-Sar$^3$-H), 8.0 (d, 1H, amide NH), 7.75 (d, 1H, amide NH), 7.5 (d, 1H, amide NH), 7.15 (d, 1H, amide NH).

Compound A

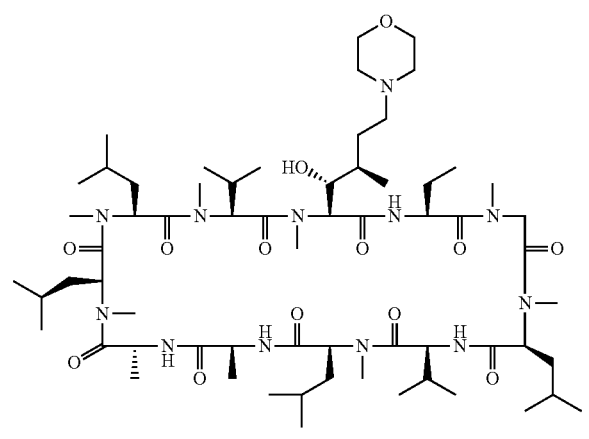

Compound LL

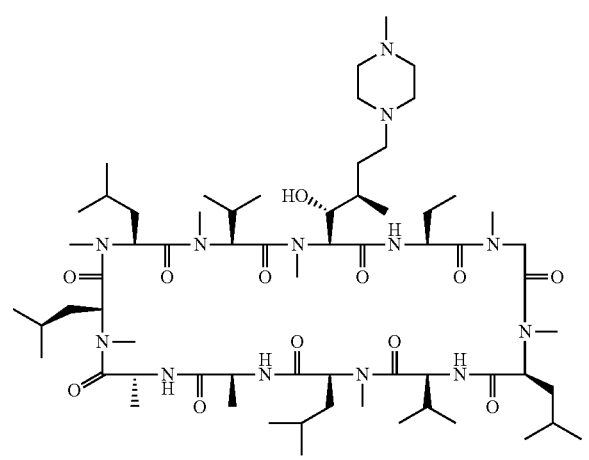

Compound NN

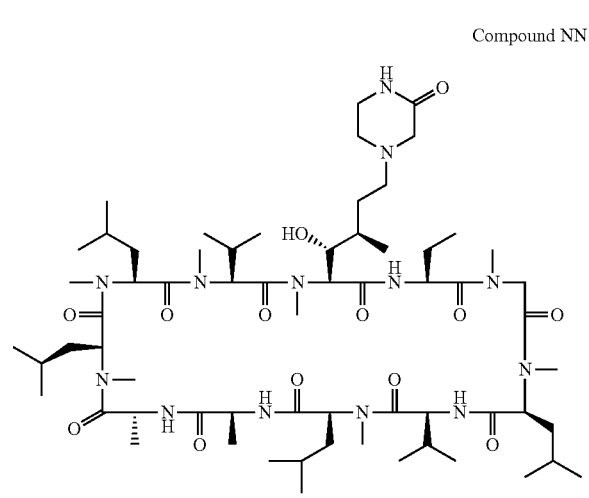

Compound AN

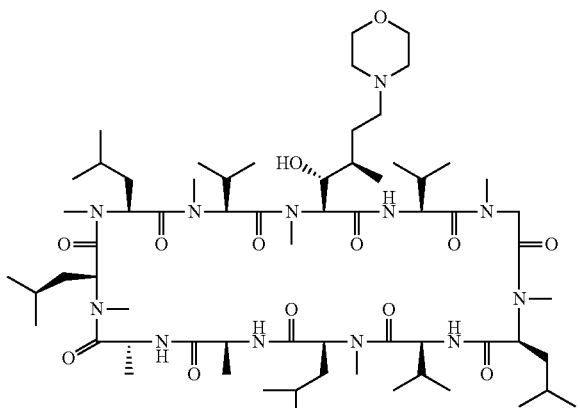

Preparation of Compound K

To a stirred solution of diisopropylamine (0.47 ml, 4.75 mmol) in THF (30 ml) at −78° C. under nitrogen was added dropwise n-butyl lithium (2.5M in hexane, 1.9 ml, 4.75 mmol) over 5 minutes. The reaction mixture was stirred at −78° C. for 1 hour, then [(3R,4R,5S)-4-(hydroxy-3-methyl-5-(methylamino)-1-N-morpholino-hexanoic acid]$^1$cyclosporin A (Intermediate 17) (0.6 g, 0.5 mmol) in THF (10 ml) was added dropwise over 5 minutes. The reaction mixture was stirred for a further 2 hours before methyl disulphide (0.42 ml, 4.75 mmol) was added and the reaction was allowed to warm to room temperature over 18 h. After this time the reaction mixture was quenched with ammonium hydroxide solution (100 ml) then extracted with ethyl acetate (2×50 ml). The combined organic phases were washed with saturated brine (100 ml), then dried (MgSO$_4$), filtered and evaporated. The crude orange solid obtained (0.4 g) was purified by passing through a 20 g silica column using 3% MeOH/dichloromethane as the eluent to obtain Compound K ([(3R,4R,5S)-4-hydroxy-3-methyl-5-(methylamino)-1-N-morpholino-hexanoic acid]$^1$[(S)-thiomethyl-Sar]$^3$cyclosporin A) as an off white solid.

ESMS MH+ 1308.02

$^1$H NMR (CDCl$_3$, ppm) δ 5.86 (s, 1H, (R)-Sar$^3$-H), 7.20 (m, 2H, 2× amide NH), 7.81 (m, 2H, 2× amide NH).

Other Compounds of Formula I in which R$^1$ is —SC$_{2-4}$ alkyl may be prepared using alternative disulphides in place of dimethyldisulphide (of MeSSMe) or by using other similar reagents such as MeSO$_2$SC$_{2-4}$ alkyl in place of MeSSMe at Step 2 in Scheme IX.

Using the procedure shown in Scheme IX with isopropyl disulphide in Step 2 Compound I was prepared Compound I (see Table 10), [(3R,4R,5S)-4-Hydroxy-3-methyl-5-(methylamino)-1-N-morpholino-hexanoic acid][1][(S)-thio-isopropyl-Sar][3]cyclosporin A

ESMS MH+ 1335.41

$^1$H NMR (CDCl$_3$, ppm) δ 7.12 (d, 1H, amide NH), 7.21 (d, 1H, amide NH), 7.81 (d, 1H, amide NH), 7.88 (d, 1H, amide NH).

Compound I

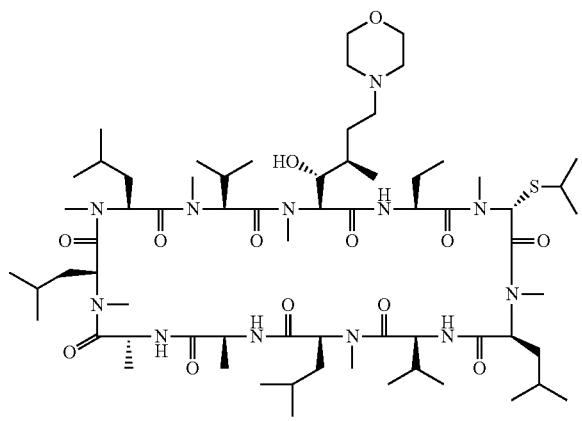

Using the procedure shown in Scheme IX with Cyclosporin D as the starting material instead of Cyclosporin A, Compound AM was prepared.

Compound AM (see Table 19), [(3R,4R,5S)-4-Hydroxy-3-methyl-5-(methylamino)-1-morpholino-hexanoic acid][1][(S)-thio-methyl-Sar][3]cyclosporin D

ESMS MH+ 1321.43

$^1$H NMR (CDCl$_3$, ppm) δ 7.9 (d, 1H, amide NH), 7.8 (d, 1H, amide NH), 7.3 (d, 1H, amide NH), 7.2 (d, 1H, amide NH).

Compound AM

Preparation of Intermediate 18

Intermediate 18 is a structural variant of cyclosporin A having an —OCH$_3$ at the position 3 α-carbon. Intermediate 18 can be used in place of cyclosporin A according to any of the schemes shown herein to produce compounds of Formula I (e.g., amines and amides of Formula I) in which R$^1$ is —OCH$_3$. Intermediate 18 can be prepared as described in Example 1 ((3-methoxycyclosporin) of US 2010/0167996. The chemical structure of Intermediate 18 is shown below.

Intermediate 18

For example, Compound B can be prepared from Intermediate 18 as shown below

Compound B (see Table 4), [(3R,4R,5S)-4-Hydroxy-3-methyl-5-(methylamino)-1-N-morpholino-hexanoic acid]¹[(S)-methoxy-Sar]³cyclosporin A

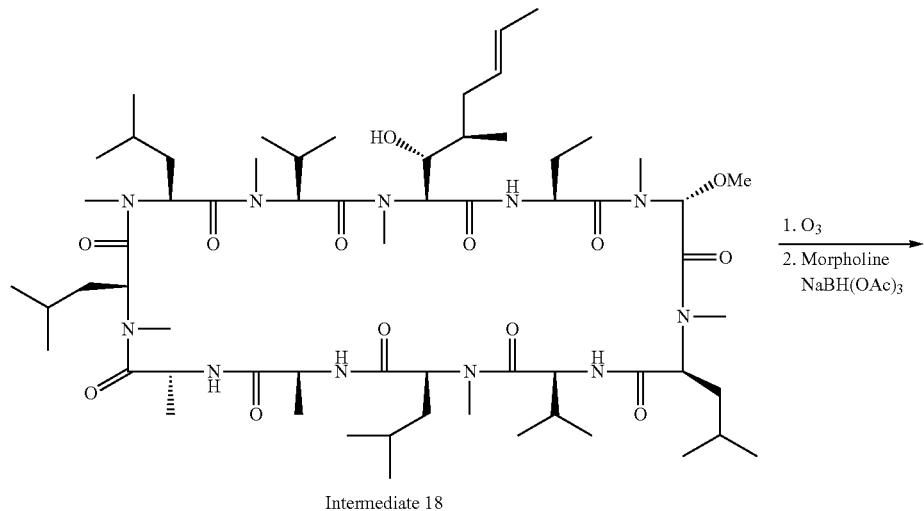

Intermediate 18

1. O₃
2. Morpholine
   NaBH(OAc)₃

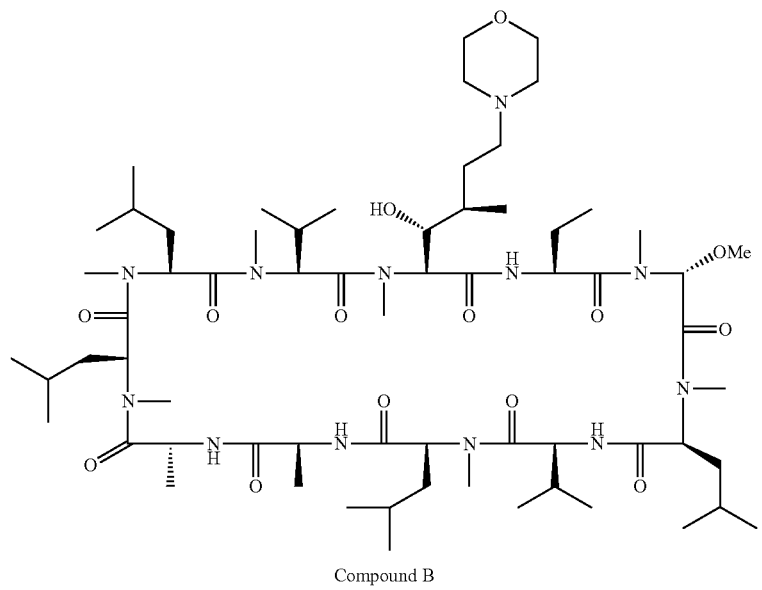

Compound B

ESMS MH⁺ 1291.9
¹H NMR (CDCl₃, ppm) δ 7.15 (d, 1H, amide NH), 7.19 (d, 1H, amide NH), 7.79 (d, 1H, amide NH), 7.85 (d, 1H, amide NH).

Preparation of Intermediate 23

Intermediate 23 is a structural variant of cyclosporine A having a —CH₂OCH₃ at the position 3 α-carbon. Intermediate 23 can be used in place of Cyclosporin A according to any of the schemes shown herein to produce compounds of Formula I (e.g., amines and amides of Formula I) in which R¹ is —CH₂OCH₃. The synthetic scheme for preparing Intermediate 23 is shown below.

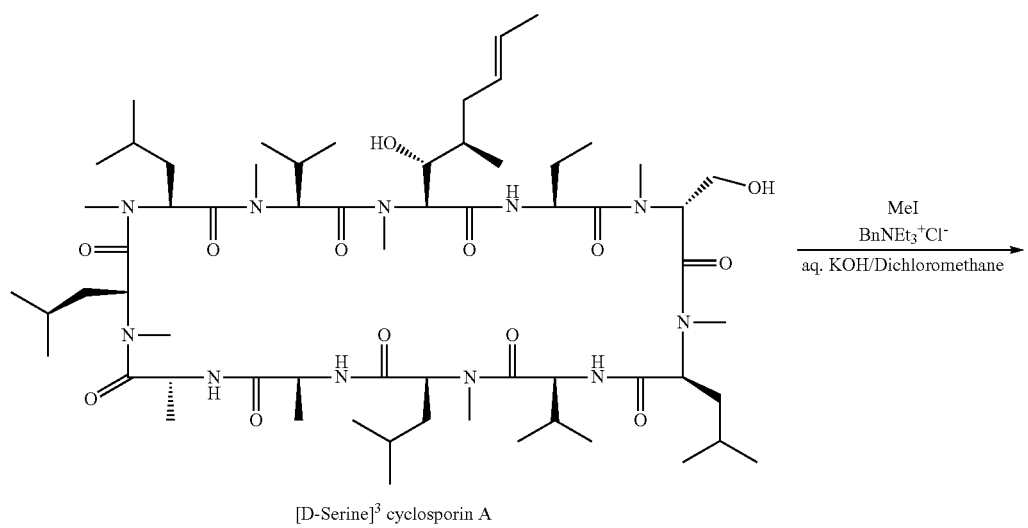

[D-Serine]³ cyclosporin A

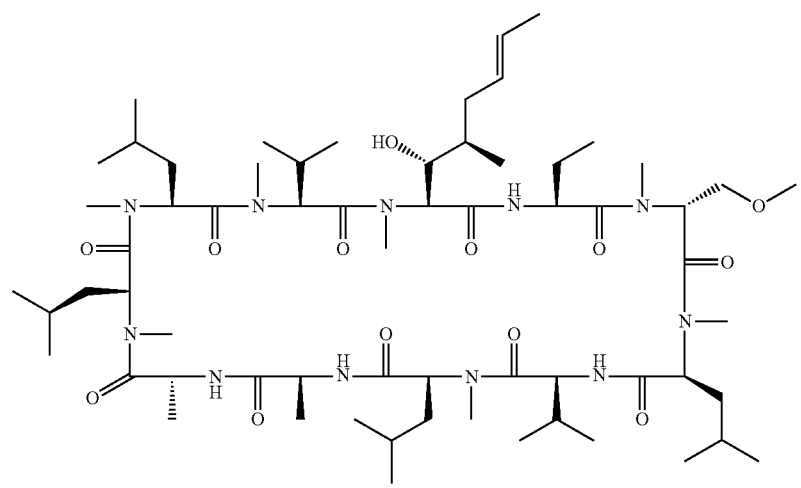

Intermediate 23

[(D)-Serine]³cyclosporin A is prepared as described by D. Seebach et al. (1993) Helvetica Chimica Acta 73(4): 1564-1590. To [(D)-Serine]³cyclosporin A (350 mg, 0.28 mmol) dissolved in dichloromethane (3 mL) was added benzyltriethylammonium chloride (65 mg, 0.28 mmol) and aqueous KOH solution (31%, 5.1 mL). Iodomethane (18 µL, 0.28 mmol) was added and the mixture stirred rapidly for 18 hours at room temperature. The reaction mixture was diluted with water (5 mL) and dichloromethane (5 mL) and the layers separated. The aqueous layer was further extracted with dichloromethane (3×10 mL) and the combined organic layers dried (MgSO₄) and evaporated in vacuo. The residue was purified by silicagel chromatography using 6% methanol in dichloromethane to provide [(R)-methoxymethylene-Sar]³ cyclosporin A (Intermediate 23) as an off-white solid.

ESMS MH⁺ 1246.87

¹H NMR (CDCl₃, ppm) δ 7.17 (d, 1H, amide NH), 7.44 (d, 1H, amide NH), 7.65 (d, 1H, amide NH), 8.03 (d, 1H, amide NH).

For example Compound D can be prepared from Intermediate 23 and similarly Compounds V, S and AD can be prepared from [(D)-Serine]³cyclosporin A as shown below.

Compound D (see Table 5), [(3R,4R,5S)-4-Hydroxy-3-methyl-5-(methylamino)-1-N-morpholino-hexanoic acid]¹[(R)-methoxymethylene-Sar]³cyclosporin A
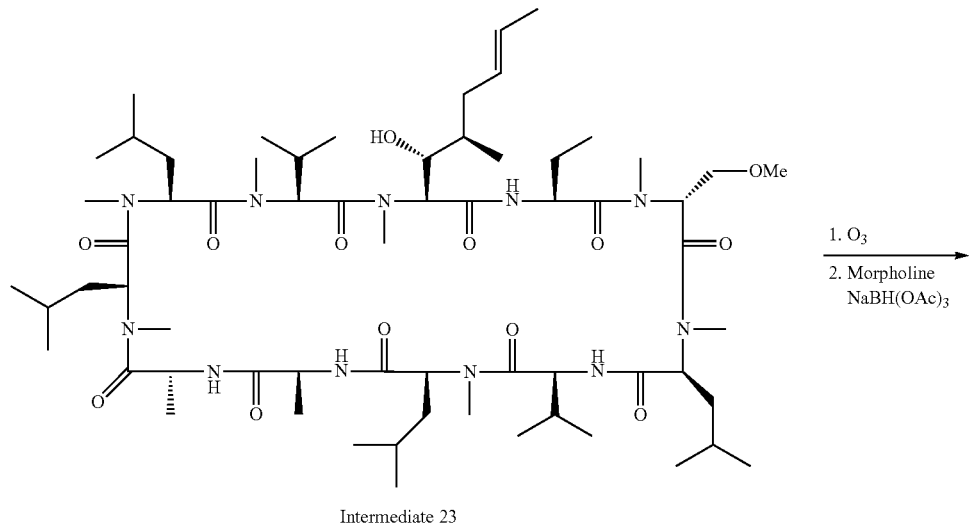
Intermediate 23
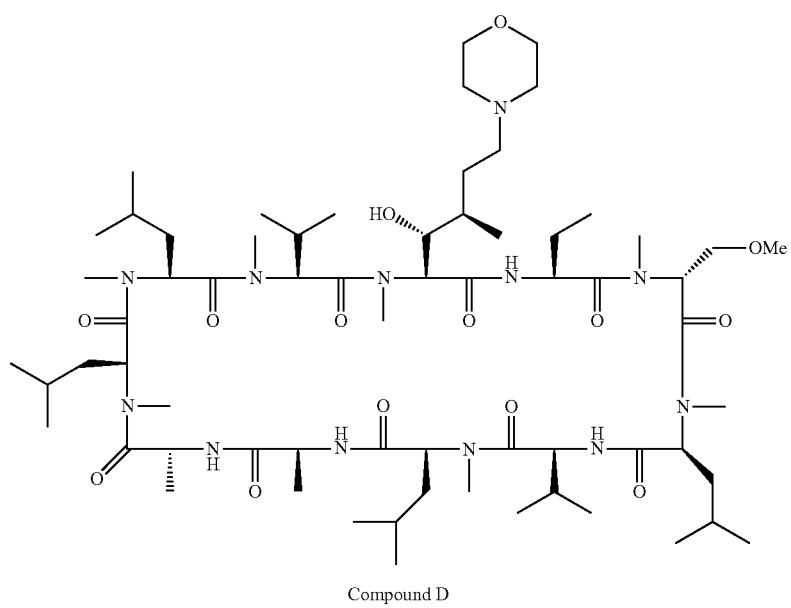
Compound D
ESMS MH⁺ 1305.8
¹H NMR (CDCl₃, ppm) δ 7.18 (d, 1H, amide NH), 7.37 (d, 1H, amide NH), 7.77 (d, 1H, amide NH), 7.95 (d, 1H, amide NH).

Compound V (see Table 13), [(3R,4R,5S)-4-Hydroxy-3-methyl-5-(methylamino)-1-N-morpholino-hexanoic acid]¹[(R)-hydroxymethyl-Sar]³cyclosporin A

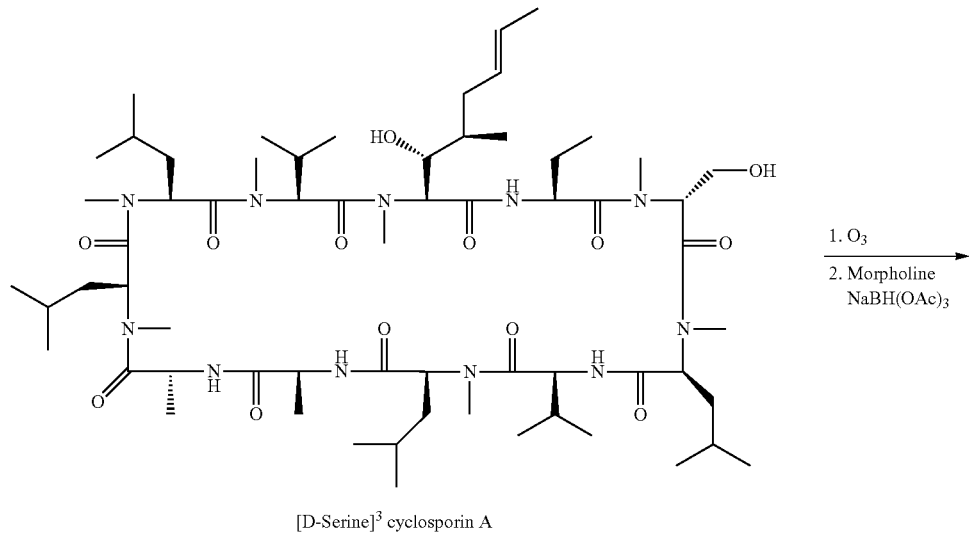

[D-Serine]³ cyclosporin A

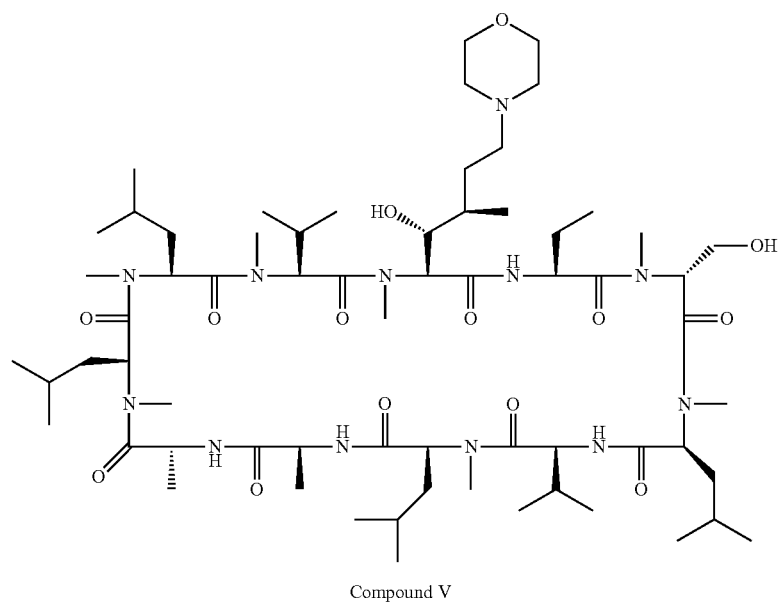

Compound V

ESMS MH⁺ 1291.5

¹H NMR (CDCl$_3$, ppm) δ 7.19 (d, 1H, amide NH), 7.41 (d, 1H, amide NH), 7.77 (d, 1H, amide NH), 7.99 (d, 1H, amide NH).

In a similar manner Compound EO and Compound EP can be prepared from [D-Serine]³cyclosporin A using 2,2,6,6-tetrafluoromorpholine or 3,3-difluoropyrrolidine as reagents.

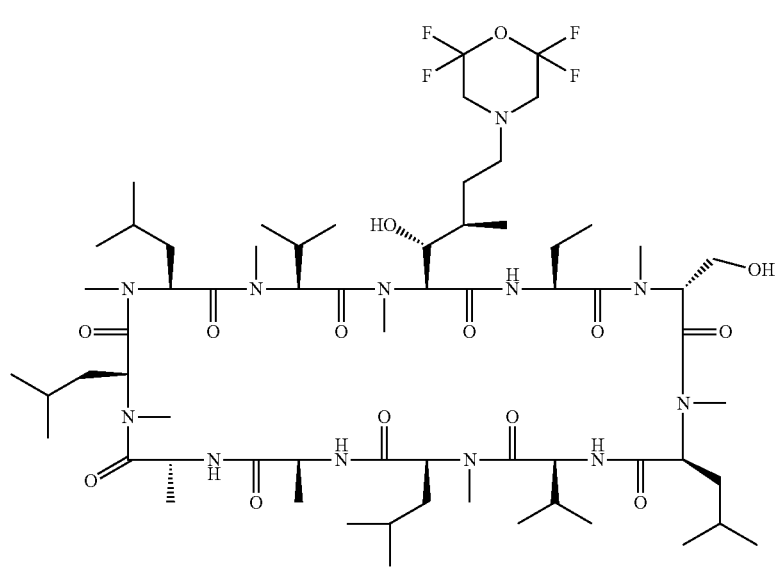

Compound EO

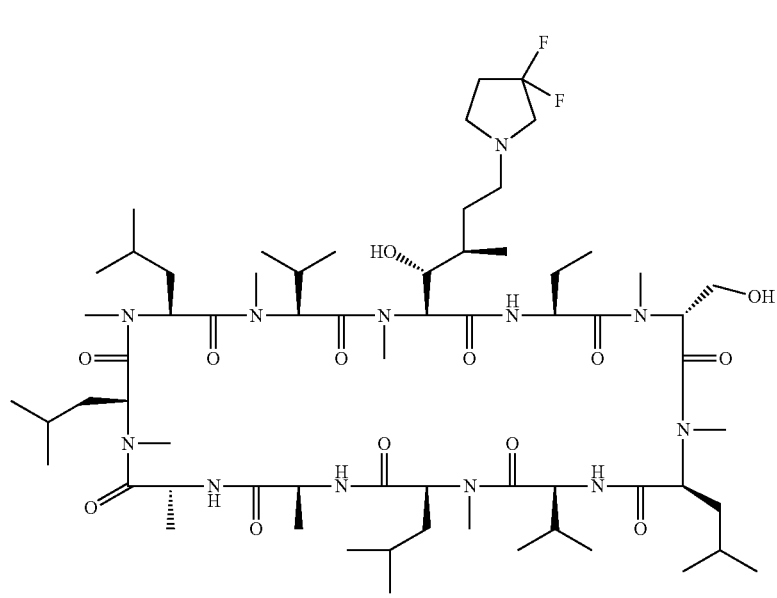

Compound EP

Compound EO (see table 13) (3R,4R,5S)-4-Hydroxy-3-methyl-5-(methylamino)-1-(2,2,6,6-tetrafluoro-morpholin-4-yl)-hexanoic acid]¹[D-Serine]³ cyclosporin A

ES/MS: 1364.0 MH⁺

¹H NMR (CDCl₃, ppm) δ 7.19 (d, 1H, amide NH), 7.52 (d, 1H, amide NH), 7.75 (d, 1H, amide NH), 8.18 (d, 1H, amide NH).

Compound EP (see table 13) (3R,4R,5S)-1-(3,3-Difluoro-pyrrolidin-1-yl)-4-hydroxy-3-methyl-5-(methylamino)-hexanoic acid]¹[D-Serine]³cyclosporin A

ES/MS: 1311.3 MH⁺

¹H NMR (CDCl₃, ppm) δ 7.19 (d, 1H, amide NH), 7.42 (d, 1H, amide NH), 7.77 (d, 1H, amide NH), 8.02 (d, 1H, amide NH).

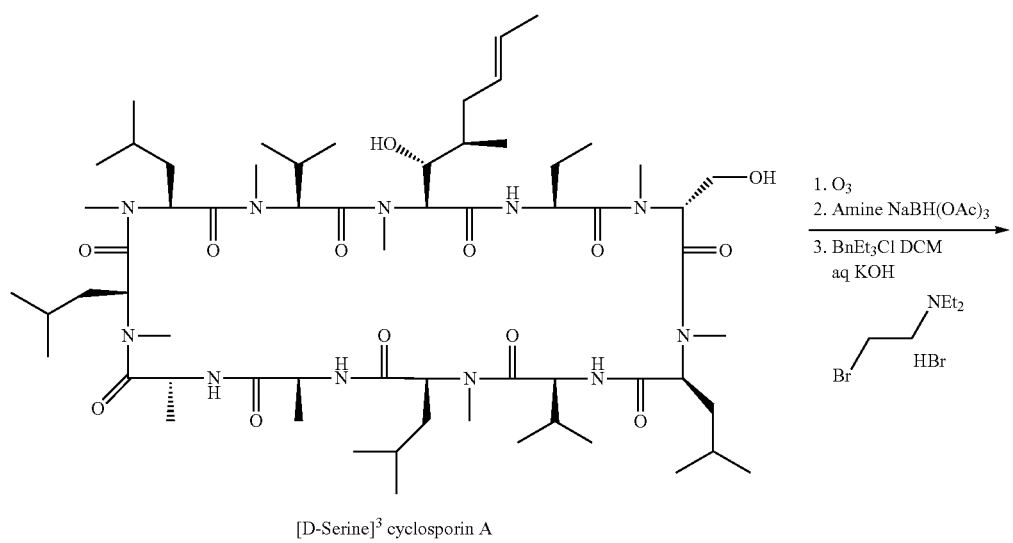

[D-Serine]³ cyclosporin A

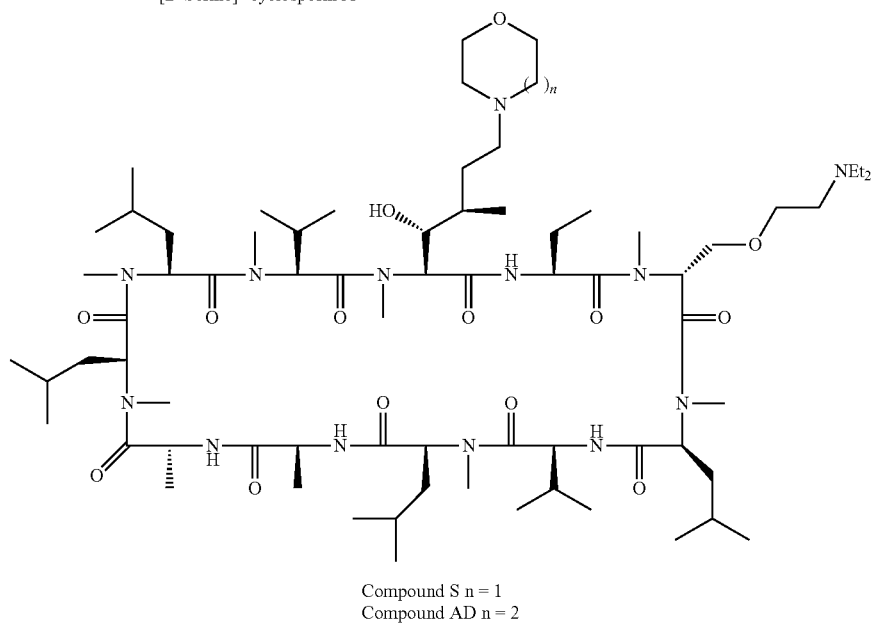

Compound S n = 1
Compound AD n = 2

Compound S (see Table 12), [(3R,4R,5S)-4-Hydroxy-3-methyl-5-(methylamino)-1-N-morpholino-hexanoic acid]¹[(R)-2-diethylamino ethyl oxymethyl-Sar]³cyclosporin A

ESMS MH⁺ 1390.7

¹H NMR (CDCl₃, ppm) δ 7.19 (d, 1H, amide NH), 7.48 (d, 1H, amide NH), 7.76 (d, 1H, amide NH), 7.96 (d, 1H, amide NH).

Compound AD (see Table 14), [(3R,4R,5S)-4-Hydroxy-3-methyl-5-(methylamino)-1-N-homomorpholino-hexanoic acid]¹[(R)-2-diethylamino 2 diethylamino ethyl oxymethyl-Sar]³cyclosporin A

ESMS MH⁺ 1404.7

¹H NMR (CDCl₃, ppm) δ 7.20 (d, 1H, amide NH), 7.39 (d, 1H, amide NH), 7.78 (d, 1H, amide NH), 7.98 (d, 1H, amide NH).

Scheme X

Procedure for Obtaining a Compound Having Formula I, Wherein $R^1$ is —$CH_3$, $R^2$ is —$CH_3$, $R^3$ is —$CH_2CH(CH_3)_2$, $R^4$ is —$CH_3$, $R^5$ is —$CH_2CH_2CH_2$—, $R^6$ is —$CH_2CH_3$, $R^8$ is $CH_2$, n=2, m=0, and p=0

Schemes X and Xa describe processes for the synthesis of amines of Formula I.

Scheme X describes the acylation of Intermediate 1 (Step 1) and bromination of Intermediate 29 by N-bromosuccinimide azobisisobutyrylnitrile in carbon tetrachloride (Step 2) carried out as described by M K Eberle et al. *J. Org. Chem.* 1992, 57, 2689-2691. Steps 3 and 4 are carried out as described in Steps 2 and 3 in Scheme II. Intermediate 1 is obtained as described in Scheme I. Step 5 is carried out by stirring Intermediate 32 in a solution of potassium carbonate in a mixture of methanol and water as described for Example 8 in US 2003/0212249.

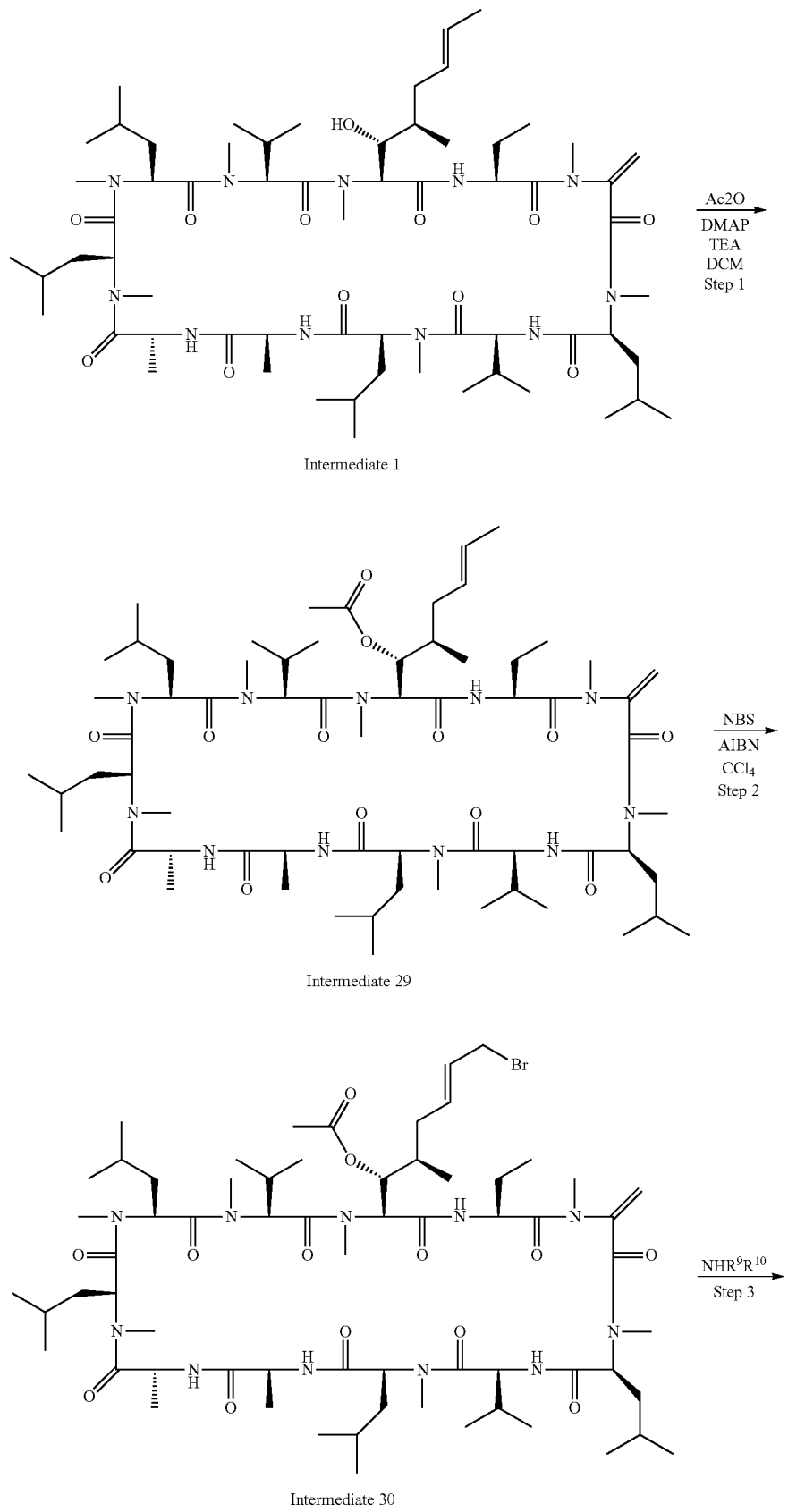
Scheme X
Intermediate 1
Intermediate 29
Intermediate 30

-continued
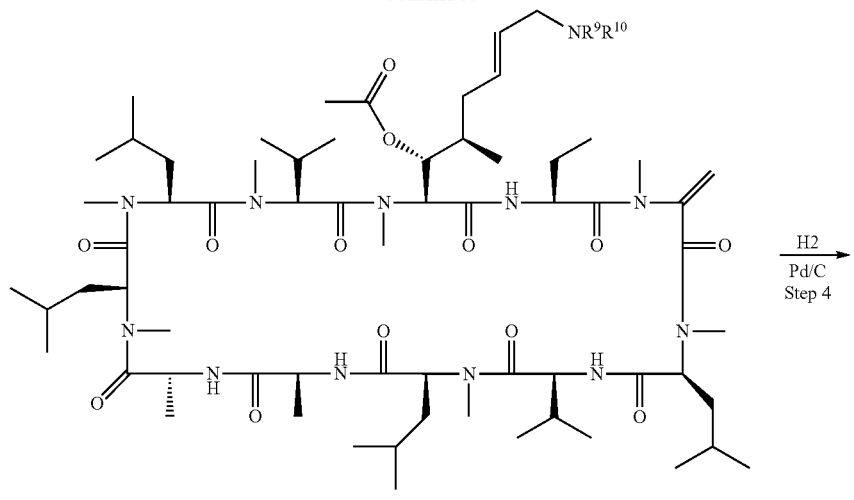
Intermediate 31
H2
Pd/C
Step 4
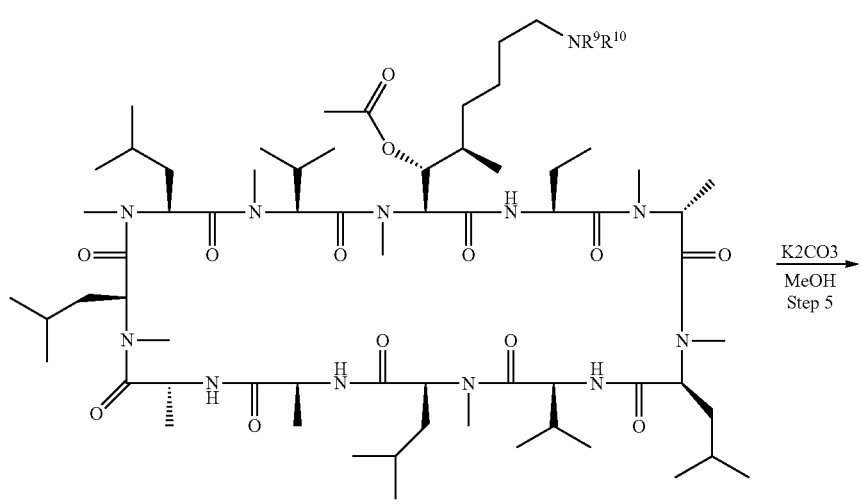
Intermediate 32
K2CO3
MeOH
Step 5
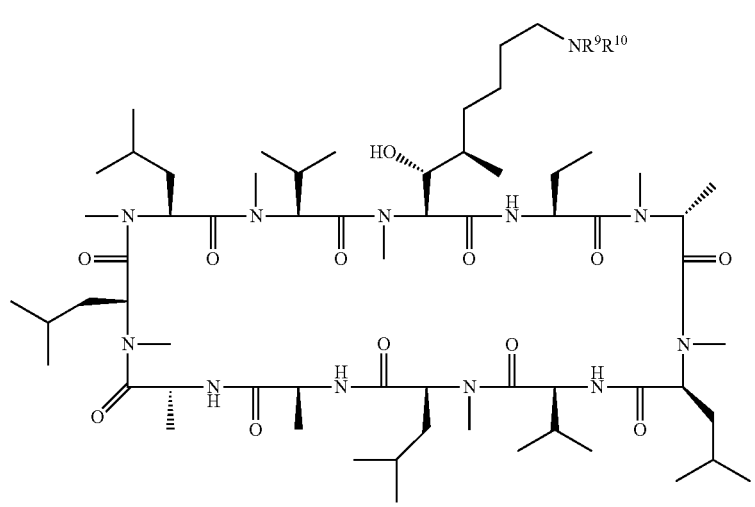
Compound of Formula I

Scheme Xa

Scheme Xa describes the use of Wittig chemistry on Intermediate 4 (Step 1). Intermediate 4 is obtained as described in Scheme I. Deprotection of Intermediate 35 and hydrogenation of Intermediate 36 are carried out as described in Steps 5 and 3, respectively, in Scheme I. Exemplary syntheses according to Scheme Xa are described below for the preparation of Compounds KF and KG.

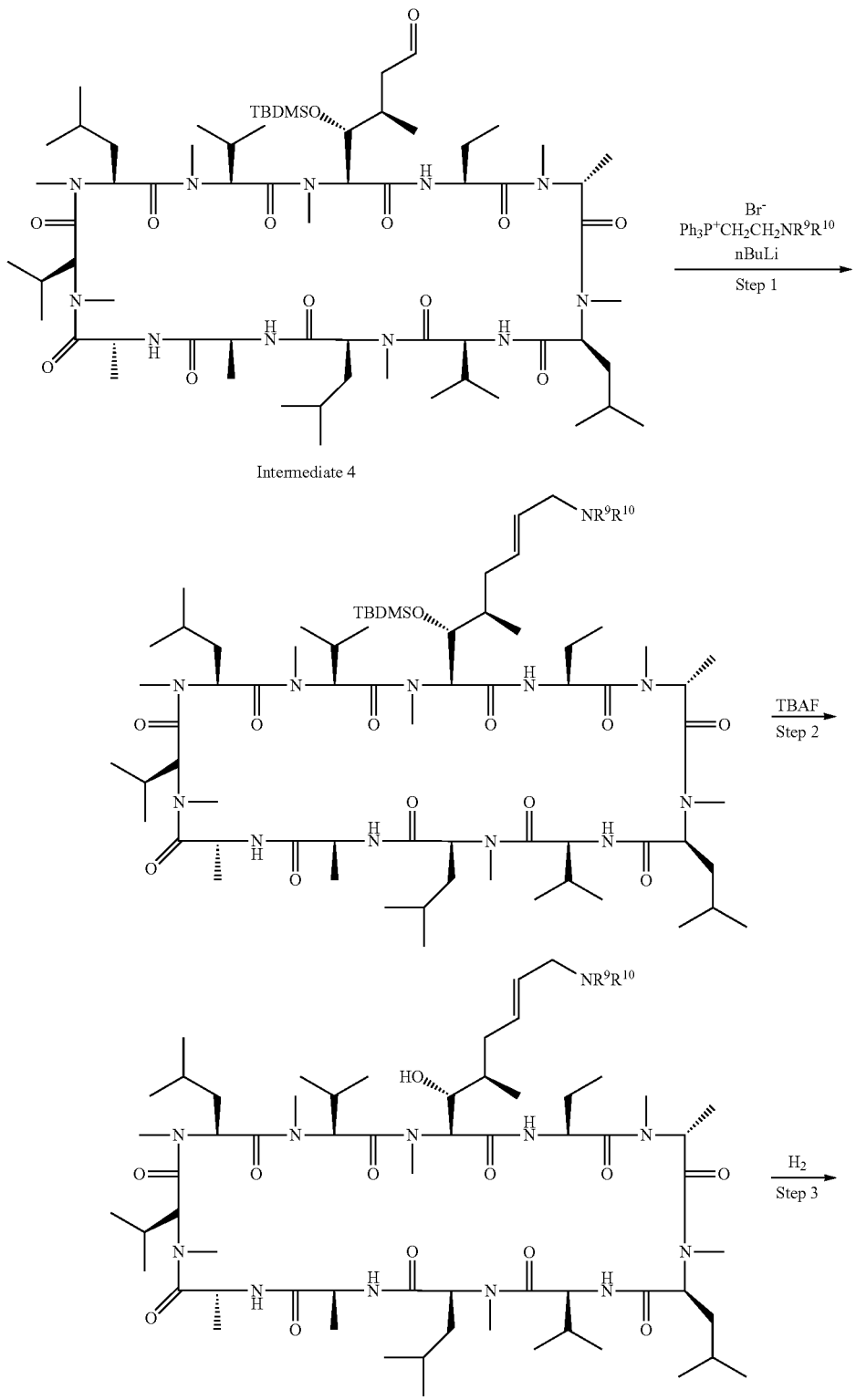

-continued
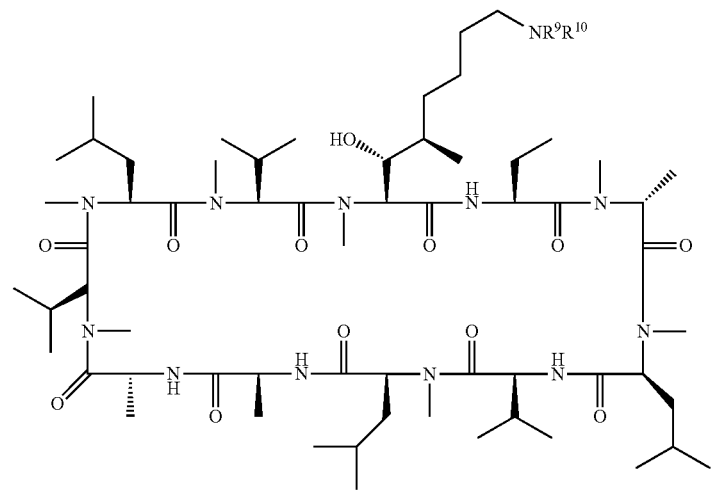
Compound of Formula I
Compound KF (NR$^9$R$^{10}$ = NMe$_2$)
Compound KG (NR$^9$R$^{10}$ = Morpholinyl)
Scheme Xa (Example 1)
Preparation of Compound KF
Compound KF
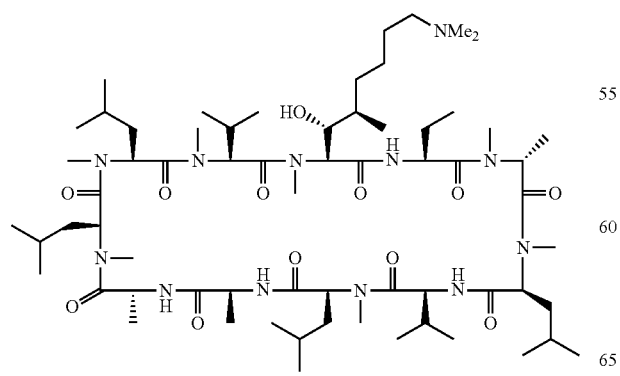

Step 1

Preparation of Intermediate 35

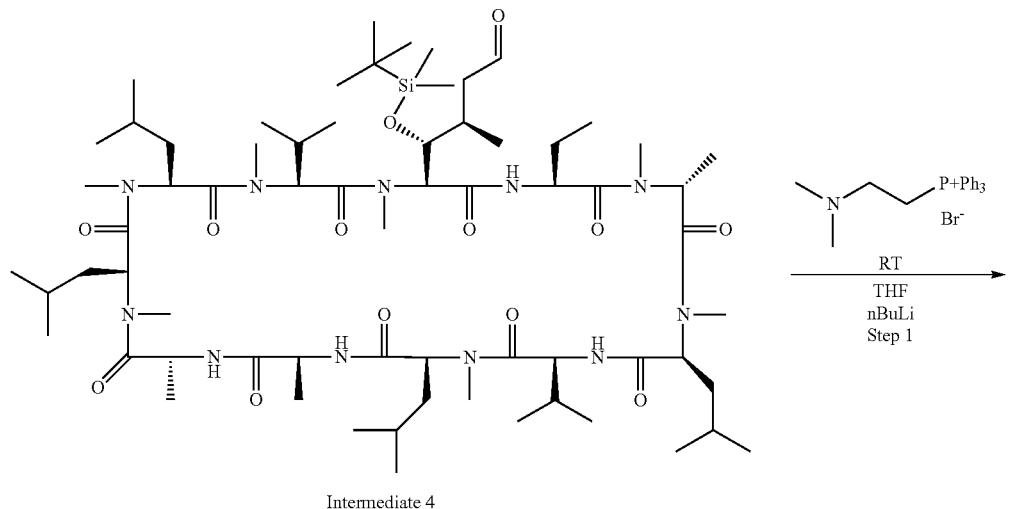

Intermediate 4

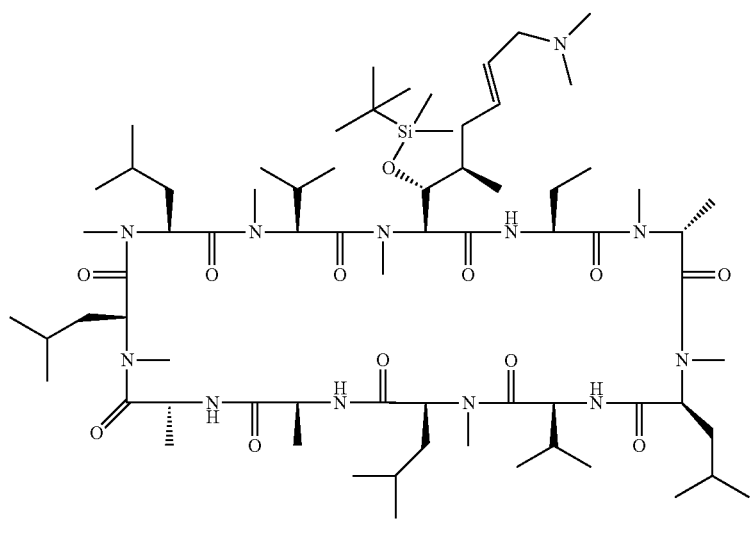

Intermediate 35

To an ice cooled suspension of (2-dimethylaminoethyl) triphenylphosphonium bromide (435 mg, 1.05 mmol) in dry tetrahydrofuran (6 mL) was added a solution of 2.5M n-butyl lithium in hexanes. The deep orange suspension was stirred under nitrogen for 50 minutes before the addition of a solution of [(3R,4R,5S)-4-(t-butyldimethylsilanyloxy)-3-methyl-5-(methylamino)-1-oxo-hexanoic acid][1][(R)-methyl-Sar][3]cyclosporin A (Intermediate 4) (198 mg, 0.15 mmol) in dry tetrahydrofuran (2 mL). The resulting yellow suspension was stirred at room temperature for 67 hours then concentrated in vacuo. The residue was partitioned between diethyl ether and water then the organic phase was dried over sodium sulphate and concentrated in vacuo. [(2E,5R,6R,7S)-6-(t-butyldimethylsilanyloxy)-1-(dimethylamino)-5-methyl-7-(methylamino)-oct-2-enoic acid][1][(R)-methyl-Sar][3]cyclosporin A (Intermediate 35) was obtained as a white solid after purification by SCX chromatography using a solvent gradient of 100% methanol→0.35M ammonia in methanol and used as such in the next step.

$^1$H NMR (CDCl$_3$, ppm) δ 7.20 (d, 1H, amide NH), 7.93 (d, 1H, amide NH), 8.07 (d, 1H, amide NH), 8.57 (d, 1H, amide NH).

Step 2

Preparation of Intermediate 36

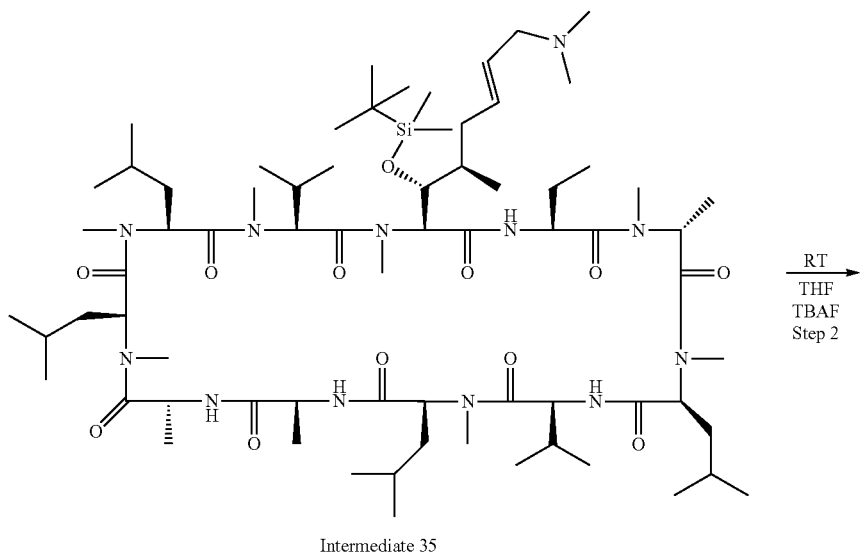

Intermediate 35

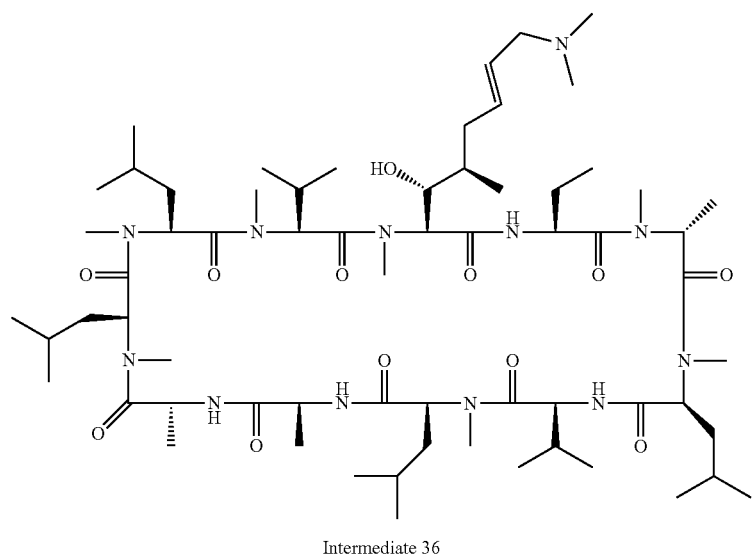

Intermediate 36

To a stirred solution of [(2E,5R,6R,7S)-6-(t-butyldimethylsilanyloxy)-1-(dimethylamino)-5-methyl-7-(methylamino)-oct-2-enoic acid]$^1$[(R)-methyl-Sar]$^3$cyclosporin A (Intermediate 35) (0.166 g, 0.12 mmol) in dry tetrahydrofuran (5 ml) was added tetrabutylammonium fluoride TBAF (1.0M solution in tetrahydrofuran, 0.6 ml, 0.6 mmol) and the yellow solution stirred at room temperature for 18 hours. The solvent was evaporated, the residue obtained dissolved in ethyl acetate and washed with $H_2O$. The organic phase was dried ($Na_2SO_4$), filtered and evaporated. The residue was purified by MPLC chromatography using a solvent gradient of 100% dichloromethane→95% dichloromethane/5% methanol containing 10% aqueous ammonia (0.88) to give [(2E,5R,6R,7S)-1-(dimethylamino)-6-hydroxy-5-methyl-7-(methylamino)-oct-2-enoic acid]$^1$[(R)-methyl-Sar]$^3$cyclosporin A (Intermediate 36) as a white solid.

ESMS MH$^+$ 1259.5

$^1$H NMR (CDCl$_3$, ppm) 7.21 (d, 1H, amide NH), 7.51 (d, 1H, amide NH), 7.74 (d, 1H, amide NH), 8.08 (d, 1H, amide NH).

Step 3

Preparation of Compound KF

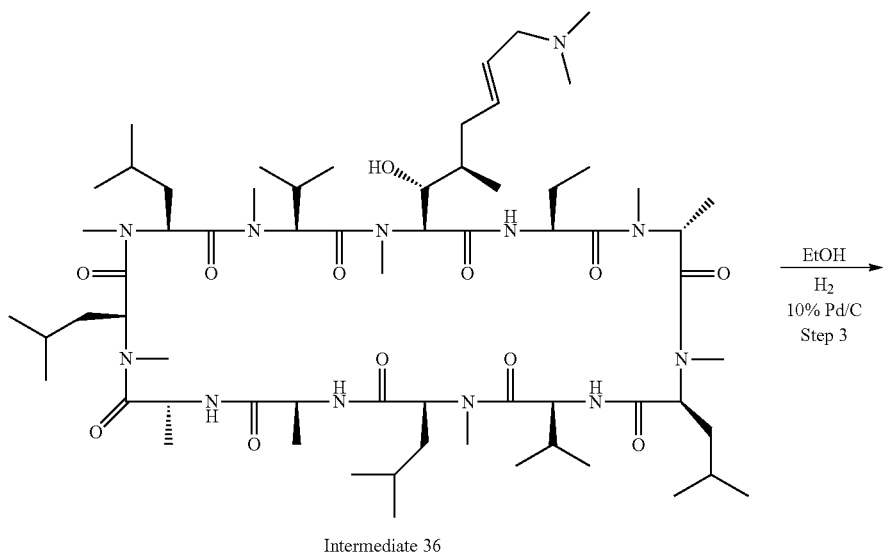

Intermediate 36

Compound of Formula I
(Compound KF)

[(2E,5R,6R,7S)-1-(Dimethylamino)-6-hydroxy-5-methyl-7-(methylamino)-oct-2-enoic acid]$^1$[(R)-methyl-Sar]$^3$cyclosporin A (Intermediate 36) (50 mg, 0.04 mmol) was dissolved in ethanol (10 mL), treated with 10% palladium on carbon (25 mg) then placed under a 1 atm atmosphere of hydrogen for 22 hours. The reaction mixture was filtered through celite then concentrated in vacuo. [(5R,6R,7S)-1-(dimethylamino)-6-hydroxy-5-methyl-7-(methylamino)-octanoic acid]$^1$[(R)-methyl-Sar]$^3$cyclosporin A (Compound KF) was obtained as a white solid after purification by SCX chromatography using a solvent gradient of 100% methanol→0.18M ammonia in methanol.

ESMS MH$^+$ 1261.2

$^1$H NMR (CDCl$_3$, ppm) δ 7.13 (d, 1H, amide NH), 7.49 (d, 1H, amide NH), 7.68 (d, 1H, amide NH), 7.93 (d, 1H, amide NH).

Scheme Xa (Example 2)
Preparation of Compound KG
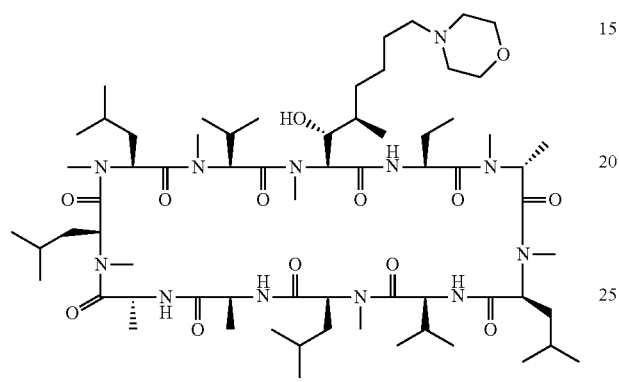
Compound KG
Step 1
Preparation of Intermediate 37
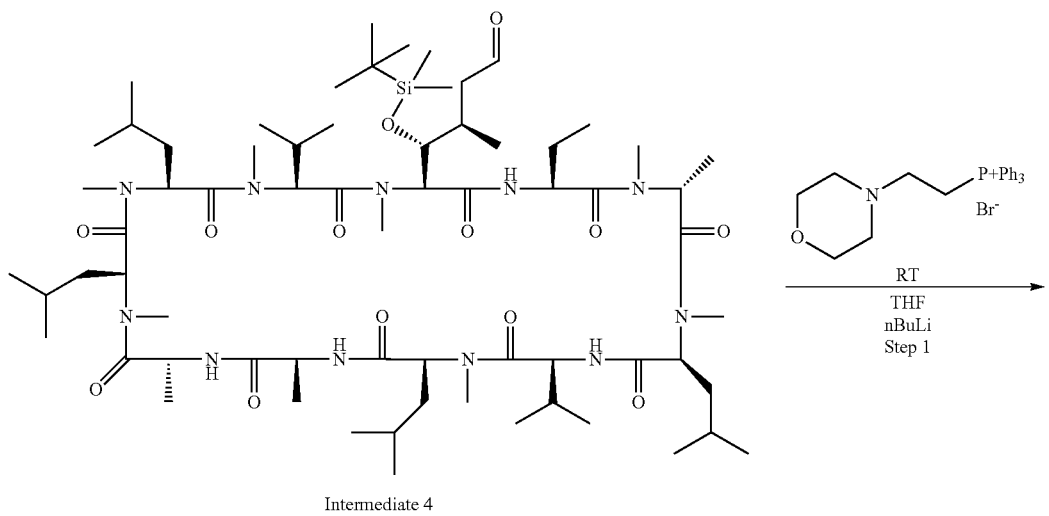
Intermediate 4

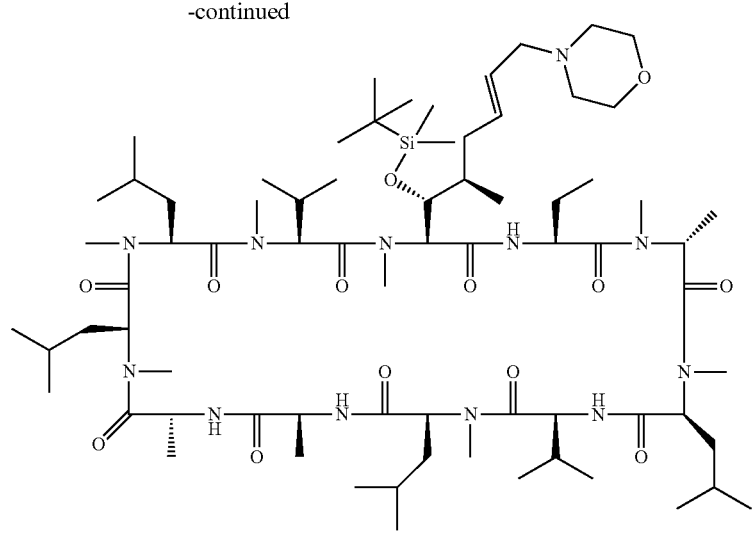

Intermediate 37

Using the procedure described above for the preparation of Intermediate 35 with (2-(N-morpholino)ethyl)triphenylphosphonium bromide (G. V. Rao et al. Tetrahedron Lett. 49 (2008) 824) as starting material, [(2E,5R,6R,7S)-6-(t-butyldimethylsilanyloxy)-5-methyl-7-(methylamino)-1-(N-morpholino)-oct-2-enoic acid]$^1$[(R)-methyl-Sar]$^3$cyclosporin A (Intermediate 37) was obtained as a white solid after purification by SCX chromatography using a solvent gradient of 100% methanol→0.14M ammonia in methanol and used as such in the next step.

Step 2

Preparation of Intermediate 38

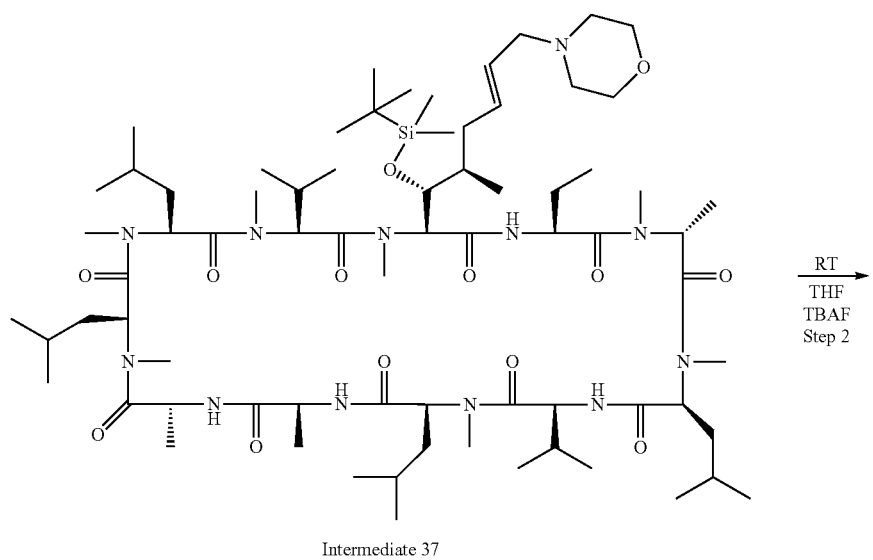

Intermediate 37

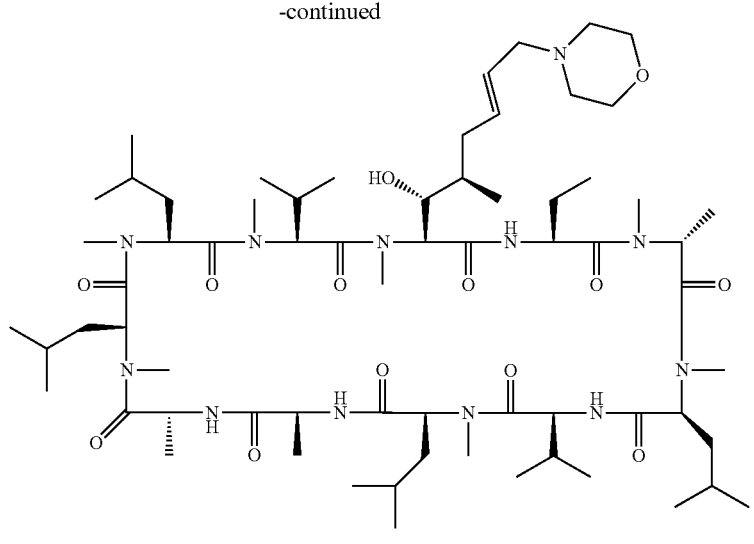

Intermediate 38

Using the procedure described above for the preparation of Intermediate 36 with [(2E,5R,6R,7S)-6-(t-butyldimethylsilanyloxy)-5-methyl-7-(methylamino)-1-(N-morpholino)-oct-2-enoic acid][1][(R)-methyl-Sar][3]cyclosporin A (Intermediate 37) as starting material, [(2E,5R,6R,7S)-6-hydroxy-5-methyl-7-(methylamino)-1-(N-morpholino)-oct-2-enoic acid][1] [(R)-methyl-Sar][3]cyclosporin A (Intermediate 38) was obtained as a white solid after purification by SCX chromatography using a solvent gradient of 100% methanol→0.35M ammonia in methanol.

ESMS MH⁺ 1301.3

$^1$H NMR (CDCl$_3$, ppm) δ 7.19 (d, 1H, amide NH), 7.52 (d, 1H, amide NH), 7.72 (d, 1H, amide NH), 8.06 (d, 1H, amide NH).

Step 3

Preparation of Compound KG

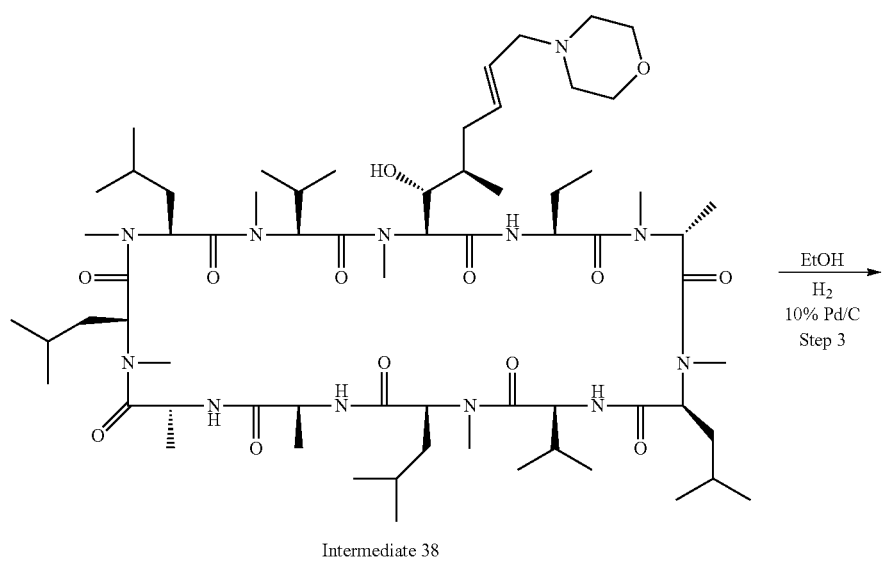

Intermediate 38

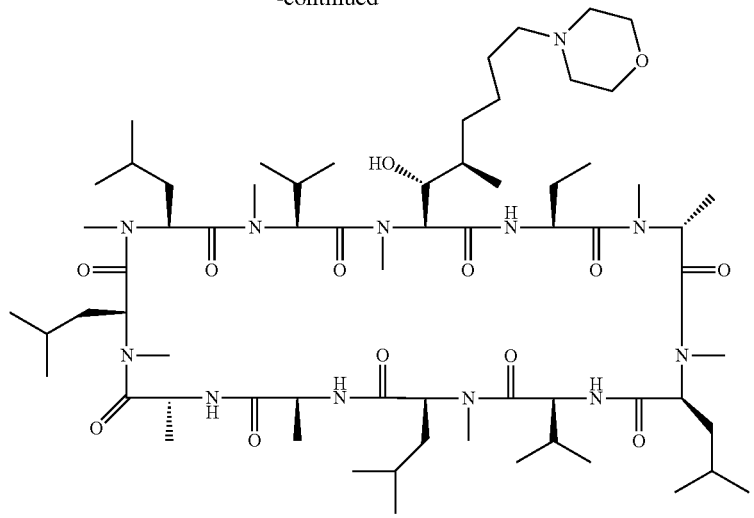

Compound of Formula I
(Compound KG)

Using the procedure described above for the preparation of Compound KF (Step 3) with [(2E,5R,6R,7S)-6-hydroxy-5-methyl-7-(methylamino)-1-(N-morpholino)-oct-2-enoic acid]¹[(R)-methyl-Sar]³cyclosporin A (Intermediate 38) as starting material, [(5R,6R,7S)-6-hydroxy-5-methyl-7-(methylamino)-1-(N-morpholino)-octanoic acid]¹[(R)-methyl-Sar]³cyclosporin A (Compound KG) was obtained as a white solid after purification by SCX chromatography using a solvent gradient of 100% methanol→0.35M ammonia in methanol.

ESMS MH⁺ 1303.4

¹H NMR (CDCl₃, ppm) δ 7.13 (d, 1H, amide NH), 7.50 (d, 1H, amide NH), 7.67 (d, 1H, amide NH), 7.91 (d, 1H, amide NH).

Scheme XI

Procedure for Obtaining a Compound Having Formula I, Wherein R¹ is —R¹³R¹⁴, R¹¹ is O, R¹¹ is CH₂S, R¹⁴ is —CH₂CH₂N(CH₂CH₃)₂, n=0, m=0 and p=1, and wherein R⁹, R¹⁰, R¹¹, and the N to which R⁹ and R¹⁰ are Attached Taken Together Form a Heterocycle

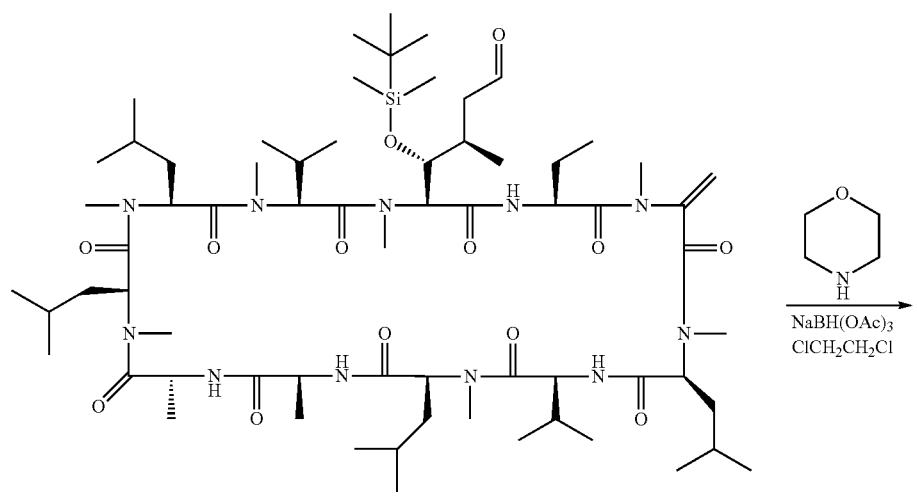

Intermediate 3

-continued
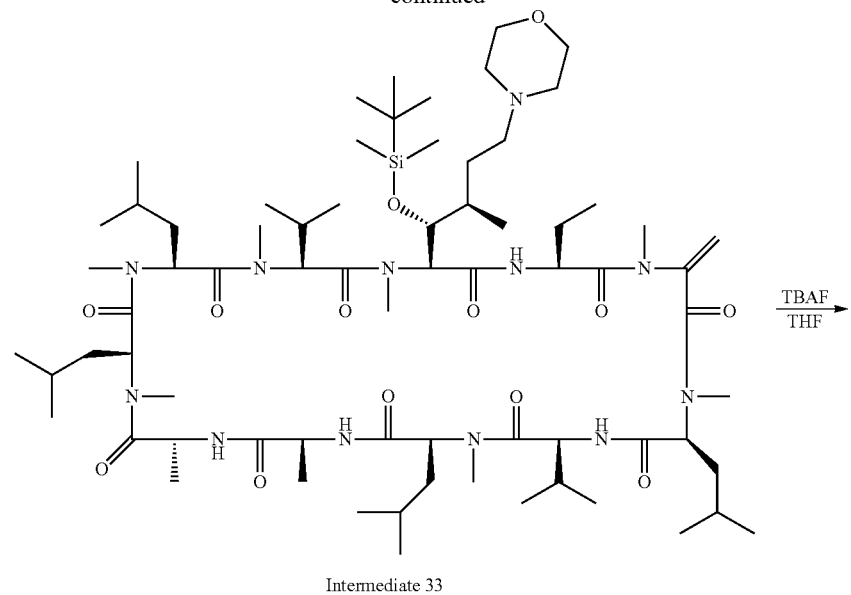
Intermediate 33
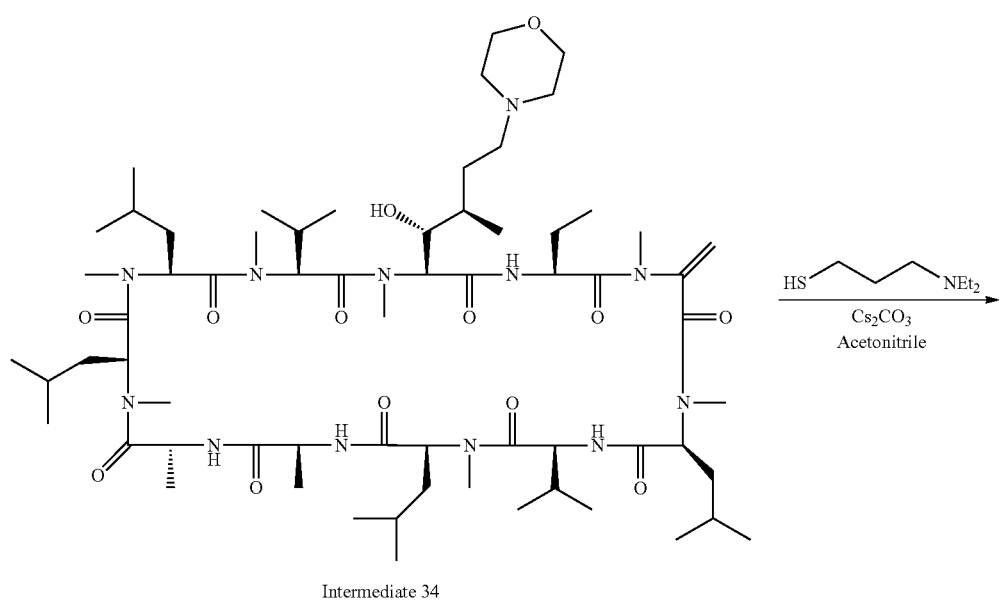
Intermediate 34

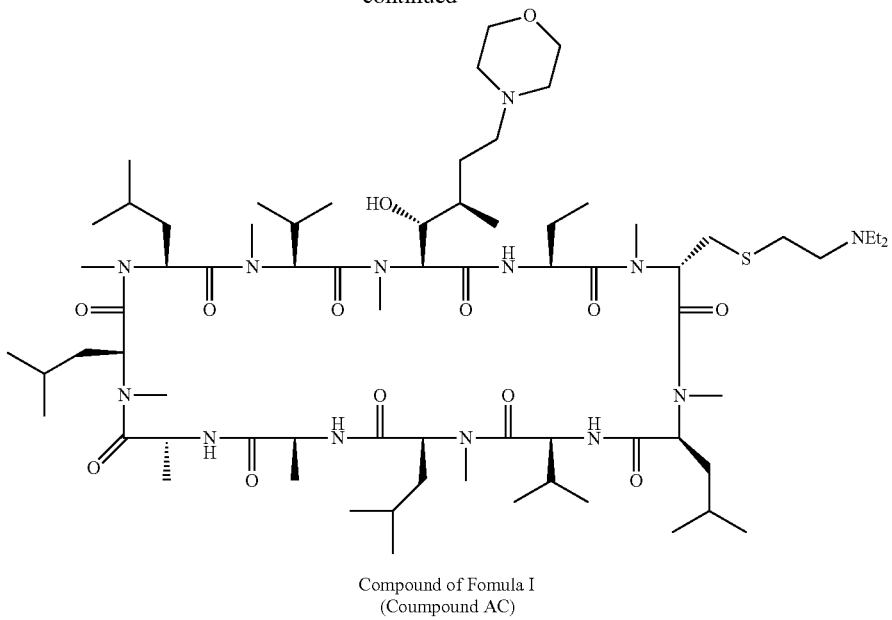

Compound of Formula I
(Coumpound AC)

Intermediate 3 is prepared as described in Scheme I. Intermediate 33 was prepared as described in Step 4 in Scheme I. Intermediate 34 was prepared as described in Step 5 in Scheme I.

Compound AC [(3R,4R,5S)-4-Hydroxy-3-methyl-5-(methylamino)-1-N-morpholino-hexanoic acid]$^1$[(S)-2-diethylaminoethylthiomethyl-Sar]$^3$cyclosporin A cyclosporinA was prepared in the following manner.

To a solution of [(3R,4R,5S)-4-hydroxy-3-methyl-5-(methylamino)-1-N-morpholino-hexanoic acid]$^1$[methylene-Sar]$^{33}$cyclosporin A (0.130 g, 0.1 mmol) (Intermediate 34) in acetonitrile (10 ml) was added cesium carbonate (0.332 g, 1 mmol) and the white suspension was bubbled through with nitrogen for one hour before adding diethylaminoethylthiol hydrochloride salt (0.087 g, 0.51 mmol). The reaction mixture was bubbled through with nitrogen overnight during which time the solvent had evaporated. Fresh acetonitrile (15 ml) and additional amounts of cesium carbonate (0.332 g, 1 mmol) were added, the resulting suspension was bubbled through with nitrogen for one hour before adding additional amounts of diethylaminoethylthiol hydrochloride salt (0.087 g, 0.51 mmol). The reaction mixture was bubbled through with nitrogen overnight during which time the solvent had evaporated. Fresh acetonitrile was added and the suspension filtered through a pad of sodium sulphate then concentrated to give 170 mg of a colourless oil. Purification by MPLC chromatography using a solvent gradient of 100% dichloromethane→95% dichloromethane/5% methanol containing 10% aqueous ammonia (0.88) followed by trituration with hexane in ultrasonic bath provided [(3R,4R,5S)-4-hydroxy-3-methyl-5-(methylamino)-1-N-morpholino-hexanoic acid]$^1$[(S)-2-diethylamino ethyl thiomethyl-Sar]$^3$cyclosporin A (Compound AC).

ESMS MH$^+$ 1406.5

$^1$H NMR (CDCl$_3$, ppm) δ 7.18 (1H, d, amide NH), 7.30 (1H, d, amide NH), 7.79 (1H, d, amide NH), 8.02 (1H, d, amide NH).

Other thiols such as morpholinoethylthiol, diethylaminopropylthiol, ethanethiol and morpholinopropylthiol may be reacted with Intermediate 34 in a similar manner to give the corresponding compounds of Formula I.

Preparation of [(3R,4R,5S)-4-Hydroxy-3-methyl-5-(methylamino)-1-({pyridin-2-ylmethyl}-methylamino)-hexanoic acid]$^1$[(R)-methyl-Sar]$^3$cyclosporin A (Compound DA)

ESMS MH$^+$ 1310.8

$^1$H NMR (CDCl$_3$, ppm) δ 7.20 (d, 2H, amide NH and pyridine CH), 7.45 (d, 1H, amide NH), 7.52 (m, 1H, pyridine CH), 7.69 (dd, 1H, pyridine CH), 7.80 (d, 1H, amide NH), 7.95 (d, 1H, amide NH), 8.53 (d, 1H, pyridine CH).

Compound DA is prepared from intermediate 4 according to Scheme I and the steps shown below. Compounds DB, DC, DD, DE, DF, DG, DH, DI, DJ, DK, DL, DM, DN, DO, DP, DQ, and DR are prepared in a similar manner according to Scheme I. The structures for each of these compounds along with their corresponding proton NMR and electron spray mass spectroscopy data are given below.

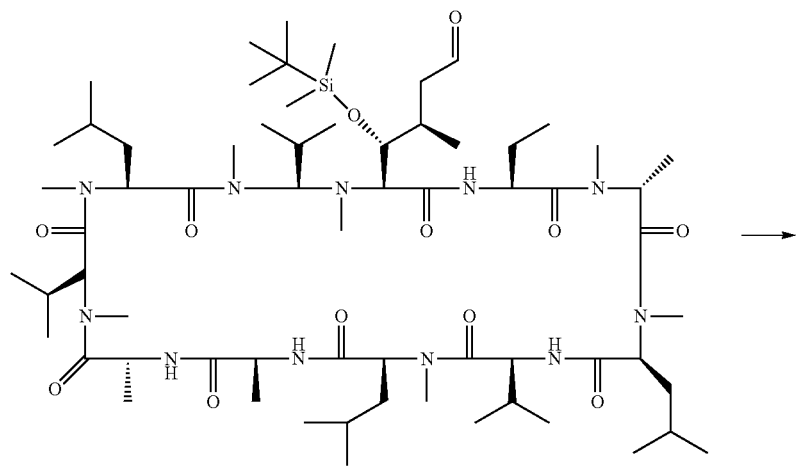
Intermediate 4
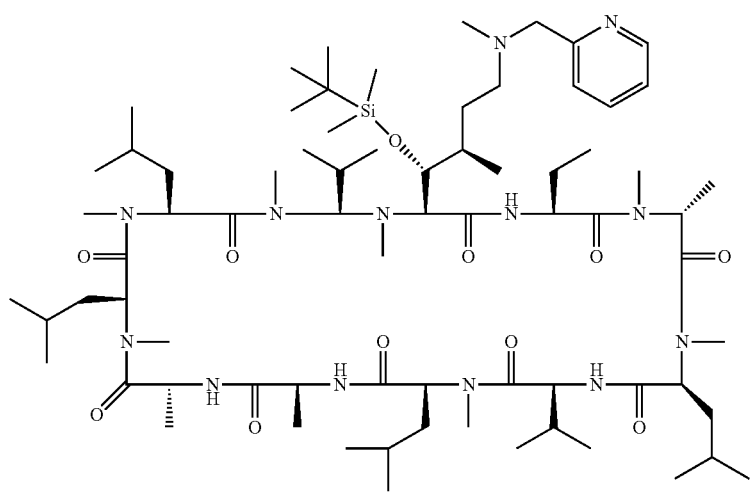
Intermediate 100
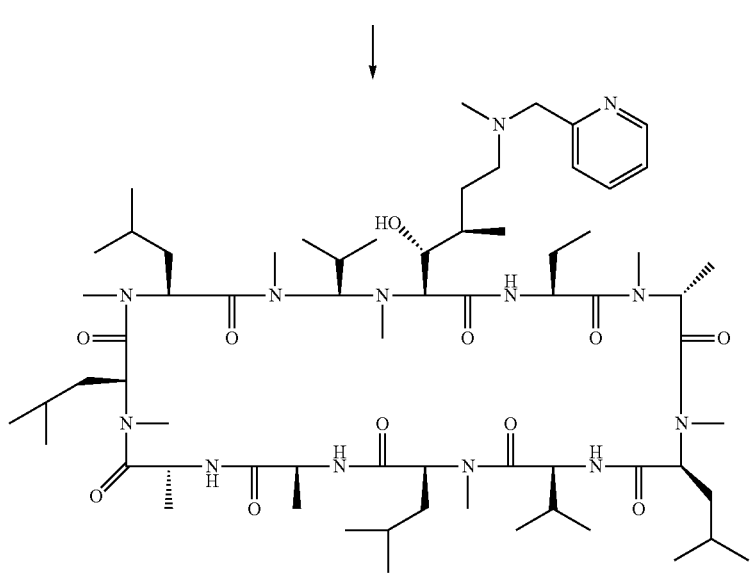
Compound DA

[(3R,4R,5S)-1-(Bis{pyridin-2-ylmethyl}amino)-4-hydroxy-3-methyl-5-(methylamino)-hexanoic acid]¹[(R)-methyl-Sar]³cyclosporin A (Compound DB)

ESMS MH⁺ 1387.8
¹H NMR (CDCl₃, ppm) δ 7.13 (m, 3H, amide 1NH and pyridine 2CH), 7.52 (m, 3H, amide 1NH and pyridine 2CH), 7.71 (m, 3H, amide 1NH and pyridine 2CH), 8.02 (d, 1H, amide NH), 8.53 (d, 2H, pyridine CH).

[(3R,4R,5S)-4-Hydroxy-3-methyl-5-(methylamino)-1-(methyl-phenyl-amino)-hexanoic acid]¹[(R)-methyl-Sar]³cyclosporin A (Compound DC)

ESMS MH⁺ 1295.8
¹H NMR (CDCl₃, ppm) δ 6.66 (m, 3H, phenyl CH), 7.11 (d, 1H, amide NH), 7.19 (dd, 2H, phenyl CH), 7.50 (d, 1H, amide NH), 7.70 (d, 1H, amide NH), 7.97 (d, 1H, amide NH).

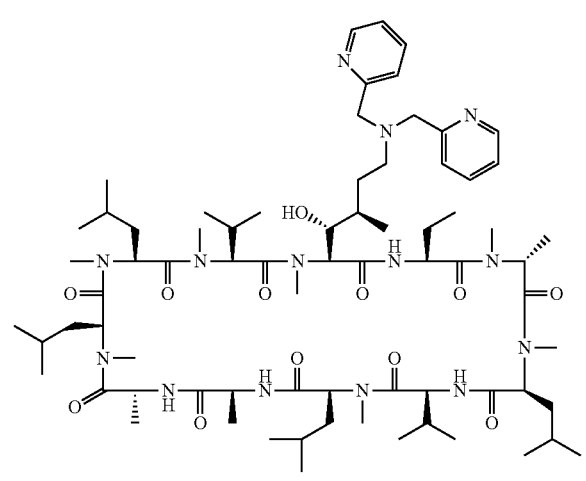

Compound DB

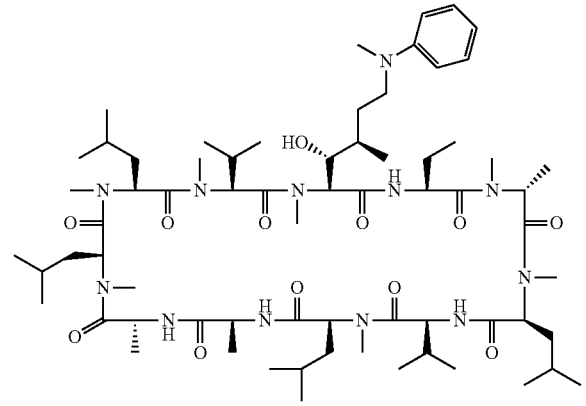

Compound DC

[(3R,4R,5S)-4-Hydroxy-3-methyl-5-(methylamino)-1-(methyl-pyridin-2-yl-amino)-hexanoic acid]¹[(R)-methyl-Sar]³cyclosporin A (Compound DD)

ESMS MH⁺ 1296.7
¹H NMR (CDCl₃, ppm) δ 6.49 (dd, 2H, pyridine CH), 7.17 (d, 1H, amide NH), 7.42 (dd, 1H, pyridine NH), 7.48 (d, 1H, amide NH), 7.80 (d, 1H, amide NH), 8.02 (d, 1H, amide NH), 8.1 (d, 1H, pyridine CH).

[(3R,4R,5S)-4-Hydroxy-3-methyl-5-(methylamino)-1-(2-sulfamoyl-ethyl)-methyl-amino)-hexanoic acid]¹[(R)-methyl-Sar]³cyclosporin A (Compound DE)

ESMS MH⁺ 1326.7
¹H NMR (CDCl₃, ppm) δ 7.12 (d, 1H, amide NH), 7.53 (d, 1H, amide NH), 7.71 (d, 1H, amide NH), 8.06 (d, 1H, amide NH).

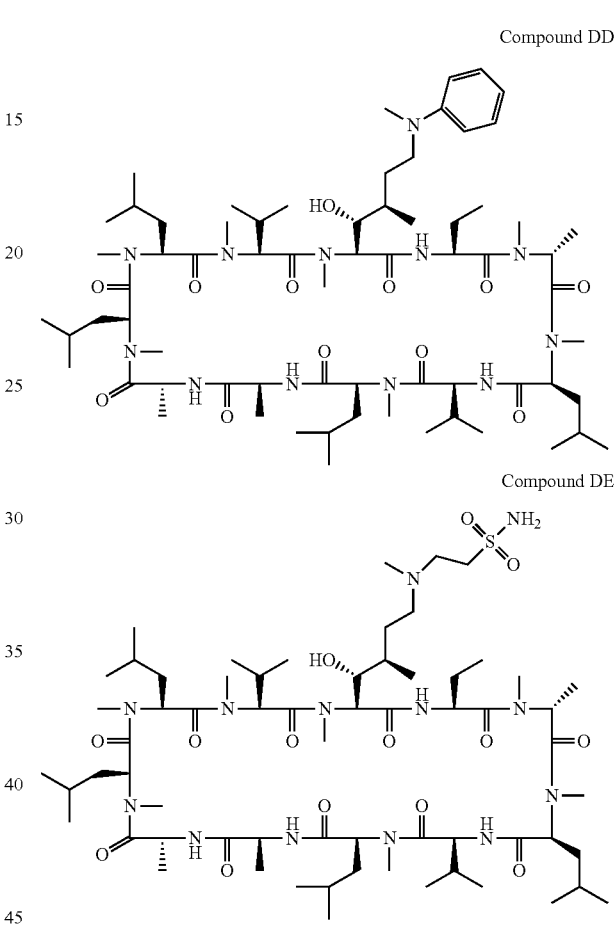

Compound DD

Compound DE

[(3R,4R,5S)-4-Hydroxy-3-methyl-5-(methylamino)-1-({pyridin-3-ylmethyl}-methylamino)-hexanoic acid]¹[(R)-methyl-Sar]³cyclosporin A (Compound DF)

ESMS MH⁺ 1310.5
¹H NMR (CDCl₃, ppm) δ 7.15 (d, 1H, amide NH), 7.25 (m, 1H, pyridine CH), 7.45 (d, 1H, amide NH), 7.70 (bd, 1H, pyridine CH), 7.74 (d, 1H, amide NH), 7.91 (d, 1H, amide NH), 8.48 (bs, 2H, pyridine CH).

[(3R,4R,5S)-4-Hydroxy-3-methyl-5-(methylamino)-1-({pyrimidin-2-ylmethyl}-methylamino)-hexanoic acid]¹[(R)-methyl-Sar]³cyclosporin A (Compound DG)

ESMS MH⁺ 1311.7
¹H NMR (CDCl₃, ppm) δ 7.18 (m, 2H, amide NH and pyrimidine CH), 7.42 (d, 1H, amide NH), 7.76 (d, 1H, amide NH), 7.93 (d, 1H, amide NH), 8.72 (d, 2H, pyrimidine CH).

Compound DF

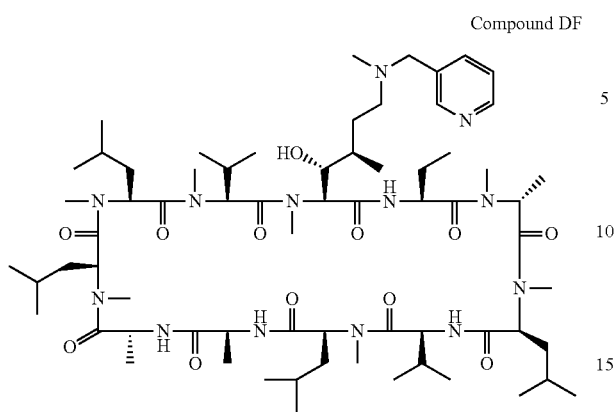

Compound DG

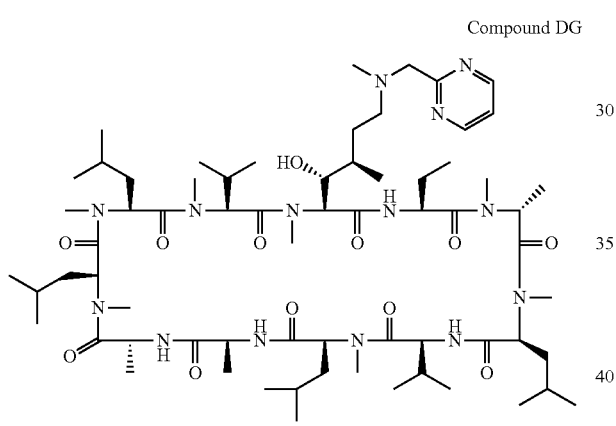

[(3R,4R,5S)-4-Hydroxy-3-methyl-5-(methylamino)-1-({pyrazin-2-ylmethyl}-methylamino)-hexanoic acid]¹[(R)-methyl-Sar]³cyclosporin A (Compound DH)

ESMS MH⁺ 1311.8

¹H NMR (CDCl₃, ppm) δ 7.14 (d, 1H, amide NH), 7.48 (d, 1H, amide NH), 7.74 (d, 1H, amide NH), 7.92 (d, 1H, amide NH), 8.48 (d, 2H, pyrazine CH), 8.7 (s, 1H, pyrazine CH).

[(3R,4R,5S)-4-Hydroxy-3-methyl-5-(methylamino)-1-({3-methyl-3H-imidazol-4-ylmethyl}-methylamino)-hexanoic acid]¹[(R)-methyl-Sar]³cyclosporin A (Compound DI)

ESMS MH⁺ 1313.6

¹H NMR (CDCl₃, ppm) δ 6.86 (s, 1H, imidazole CH), 7.12 (d, 1H, amide NH), 7.39 (s, 1H, imidazole CH), 7.49 (d, 1H, amide NH), 7.72 (d, 1H, amide NH), 7.93 (d, 1H, amide NH).

Compound DH

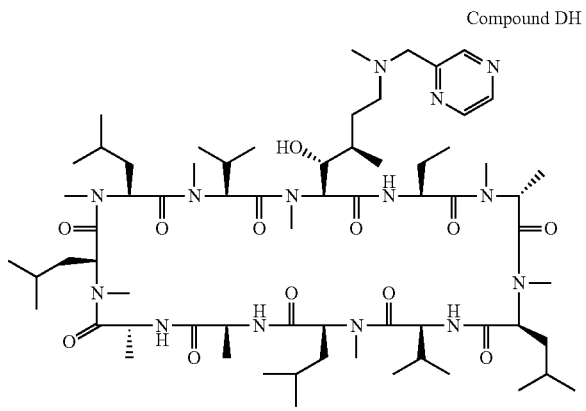

Compound DI

[(3R,4R,5S)-4-Hydroxy-3-methyl-5-(methylamino)-1-({2-methyl-2H-pyrazol-3-ylmethyl}-methylamino)-hexanoic acid]¹[(R)-methyl-Sar]³cyclosporin A (Compound DJ)

Compound DJ

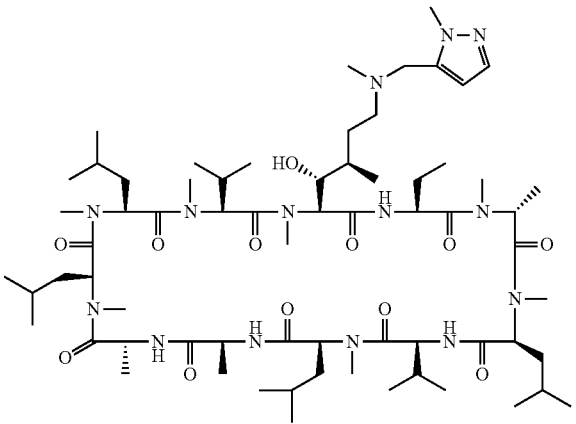

ESMS MH+ 1313.6

¹H NMR (CDCl₃, ppm) δ 6.10 (d, 1H, pyrazole CH), 7.12 (d, 1H, amide NH), 7.36 (d, 1H, pyrazole CH), 7.48 (d, 1H, amide NH), 7.72 (d, 1H, amide NH), 7.92 (d, 1H, amide NH).

[(3R,4R,5S)-1-({2-Cyano-propyl}-methyl-amino)-4-hydroxy-3-methyl-5-(methylamino)-hexanoic acid]¹[(R)-methyl-Sar]³cyclosporin A (Compound DK)

ESMS MH+ 1310.7

¹H NMR (CDCl₃, ppm) δ 7.15 (d, 1H, amide NH), 7.25 (d, 2H, pyridine CH), 7.47 (d, 1H, amide NH), 7.75 (d, 1H, amide NH), 7.92 (d, 1H, amide NH), 8.52 (d, 2H, pyridine CH).

[(3R,4R,5S)-4-Hydroxy-3-methyl-5-(methylamino)-1-({1-methyl-1H-pyrazol-4-ylmethyl}-methylamino)-hexanoic acid]¹[(R)-methyl-Sar]³cyclosporin A (Compound DM)

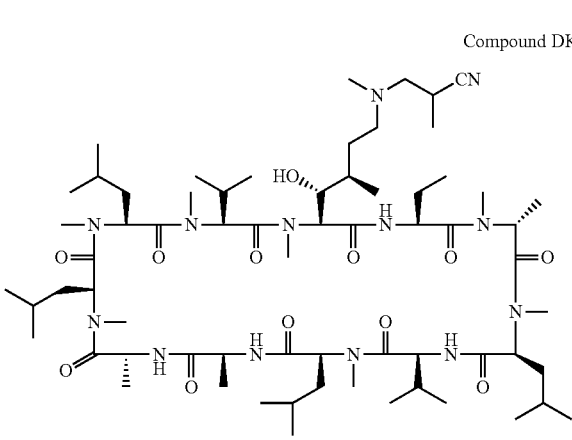

Compound DK

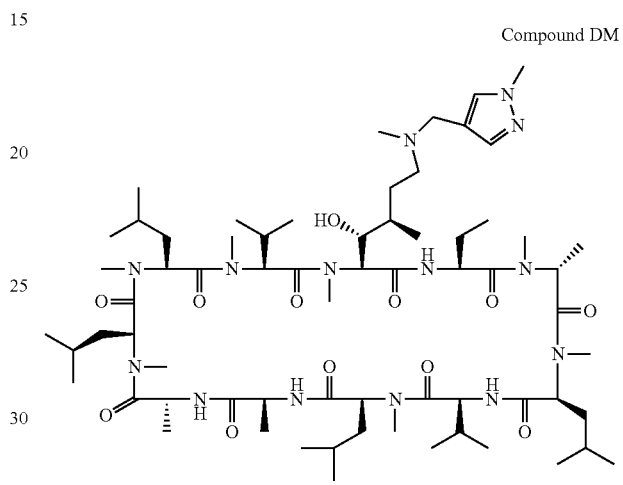

Compound DM

ESMS MH+ 1286.8

¹H NMR (CDCl₃, ppm) δ 7.12 (d, 1H, amide NH), 7.49 (d, 1H, amide NH), 7.70 (d, 1H, amide NH), 7.95 (d, 1H, amide NH).

[(3R,4R,5S)-4-Hydroxy-3-methyl-5-(methylamino)-1-({pyridin-4-ylmethyl}-methylamino)-hexanoic acid]¹[(R)-methyl-Sar]³cyclosporin A (Compound DL)

ESMS MH+ 1313.6

¹H NMR (CDCl₃, ppm) δ 7.21 (d, 1H, amide NH), 7.31 (s, 1H, pyrazole CH), 7.35 (s, 1H, pyrazole CH), 7.43 (d, 1H, amide NH), 7.84 (d, 1H, amide NH), 7.92 (d, 1H, amide NH).

[(3R,4R,5S)-4-Hydroxy-3-methyl-5-(methylamino)-1-({3,3,3-trifluoropropyl}-methyl-amino)-hexanoic acid]¹[(R)-methyl-Sar]³cyclosporin A (Compound DN)

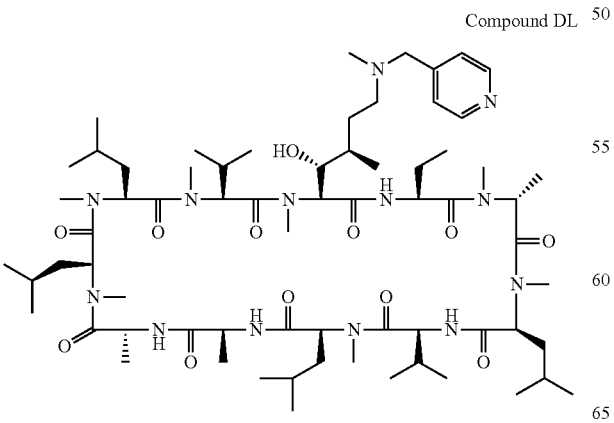

Compound DL

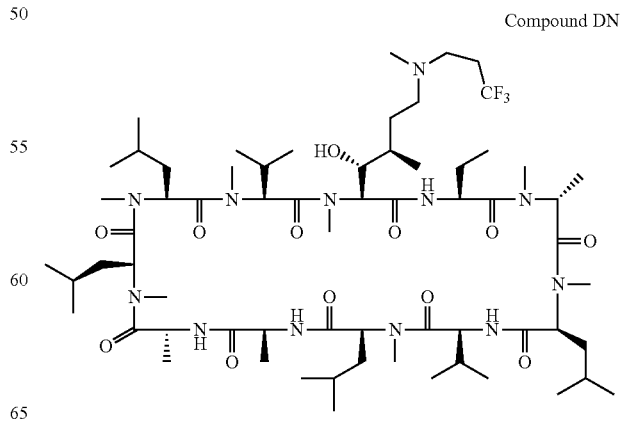

Compound DN

ESMS MH+ 1315.8

$^1$H NMR (CDCl$_3$, ppm) δ 7.15 (d, 1H, amide NH), 7.45 (d, 1H, amide NH), 7.75 (d, 1H, amide NH), 7.91 (d, 1H, amide NH).

[(3R,4R,5S)-4-Hydroxy-3-methyl-5-(methylamino)-1-({1-methyl-3-trifluoromethyl-2H-pyrazol-5-ylmethyl}-methylamino)-hexanoic acid]$^1$[(R)-methyl-Sar]$^3$cyclosporin A (Compound DO)

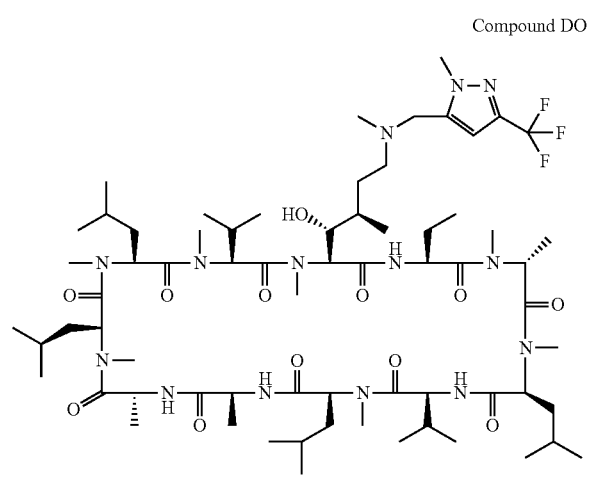

Compound DO

ESMS MH+ 1381.7

$^1$H NMR (CDCl$_3$, ppm) δ 6.38 (s, 1H, pyrazole CH), 7.11 (d, 1H, amide NH), 7.51 (d, 1H, amide NH), 7.70 (d, 1H, amide NH), 7.96 (d, 1H, amide NH).

[(3R,4R,5S)-4-Hydroxy-3-methyl-5-(methylamino)-1-({5-fluoro-pyridin-2-ylmethyl}-methylamino)-hexanoic acid]$^1$[(R)-methyl-Sar]$^3$cyclosporin A (Compound DP)

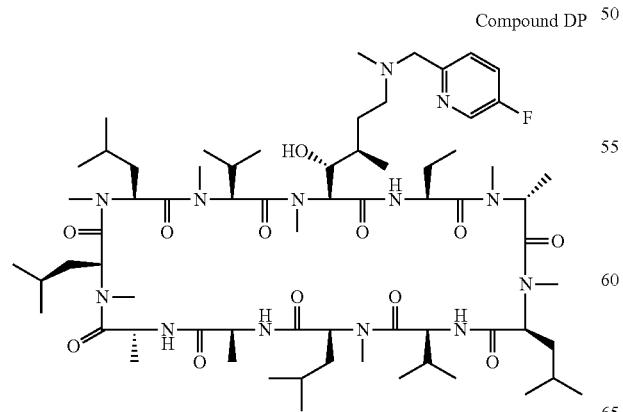

Compound DP

ESMS MH+ 1328.5

$^1$H NMR (CDCl$_3$, ppm) δ 7.17 (d, 1H, amide NH), 7.48 (m, 3H, amide 1NH and pyridine 2CH), 7.73 (d, 1H, amide NH), 7.94 (d, 1H, amide NH), 8.38 (d, 1H, pyridine CH).

[(3R,4R,5S)-4-Hydroxy-3-methyl-5-(methylamino)-1-({5-chloro-pyridin-2-ylmethyl}-methylamino)-hexanoic acid]$^1$[(R)-methyl-Sar]$^3$cyclosporin A (Compound DQ)

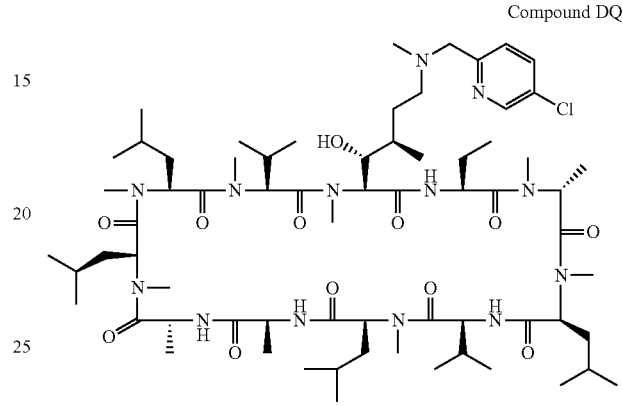

Compound DQ

ESMS MH+ 1344.6

$^1$H NMR (CDCl$_3$, ppm) δ 7.16 (d, 1H, amide NH), 7.48 (m, 2H, amide NH and pyridine CH), 7.68 (m, 1H, pyridine CH), 7.73 (d, 1H, amide NH), 7.93 (d, 1H, amide NH), 8.48 (d, 1H, pyridine CH).

[(3R,4R,5S)-4-Hydroxy-3-methyl-5-(methylamino)-1-({3-trifluoromethyl-pyridin-2-ylmethyl}-methylamino)-hexanoic acid]$^1$[(R)-methyl-Sar]$^3$cyclosporin A (Compound DR)

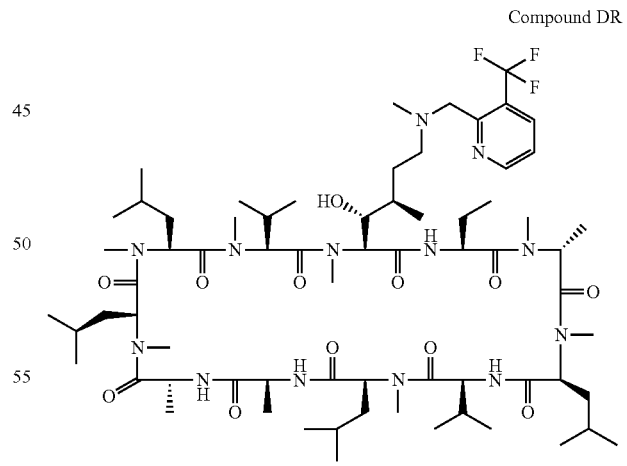

Compound DR

ESMS MH+ 1378.5

$^1$H NMR (CDCl$_3$, ppm) δ 7.14 (d, 1H, amide NH), 7.47 (d, 1H, amide NH), 7.54 (d, 1H, pyridine CH), 7.73 (m, 2H, amide NH and pyridine CH), 7.90 (m, 2H, amide NH and pyridine CH).

Compounds DS, DT, DU, DV, DW, DX, DZ, EA, EB, EC, ED, and EE are prepared by reaction of intermediate 4 with the appropriate cyclic amine according to Scheme I.

The structures and corresponding proton NMR and mass spectroscopy data for each compound are shown below.

[(3R,4R,5S)-1-(3,3-Dimethyl-morpholin-4-yl)-4-hydroxy-3-methyl-5-(methylamino)-hexanoic acid]¹ [(R)-methyl-Sar]³cyclosporin A (Compound DS)

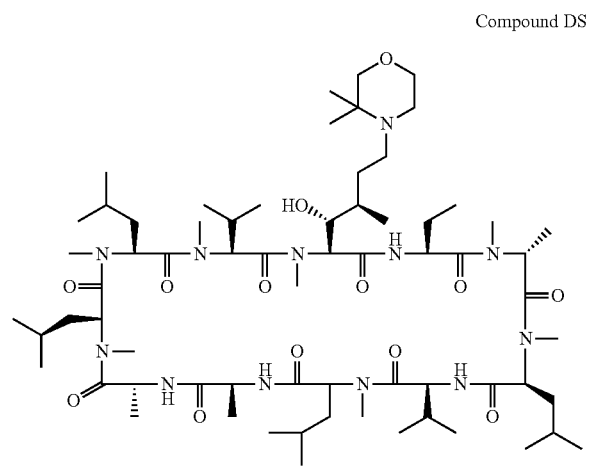

Compound DS

ESMS MH⁺ 1303.77

¹H NMR (CDCl₃, ppm) δ 7.13 (d, 1H, amide NH), 7.41 (d, 1H, amide NH), 7.75 (d, 1H, amide NH), 7.82 (d, 1H, amide NH).

[(3R,4R,5S)-4-Hydroxy-3-methyl-5-methylamino-((R)-3-methyl-morpholin-4-yl)-hexanoic acid]¹ [(R)-methyl-Sar]³cyclosporin A (Compound DT)

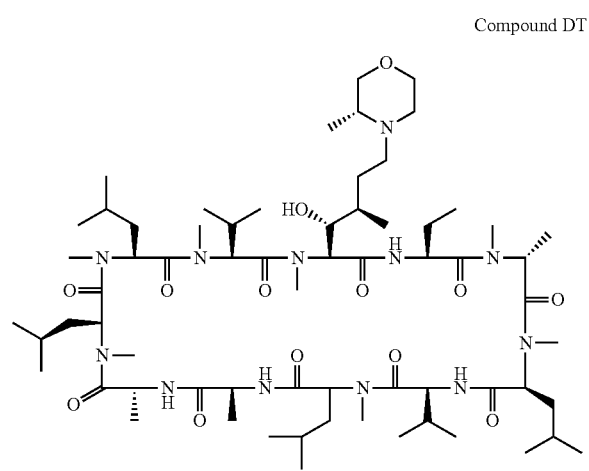

Compound DT

ESMS MH⁺ 1289.81

¹H NMR (CDCl₃, ppm) δ 7.14 (d, 1H, amide NH), 7.45 (d, 1H, amide NH), 7.72 (d, 1H, amide NH), 7.91 (d, 1H, amide NH).

[(3R,4R,5S)-1-(5,6-Dihydro-8H-[1,2,4]triazolo[4,3-a]pyrazin-7-yl)-4-Hydroxy-3-methyl-5-(methylamino)-hexanoic acid]¹[(R)-methyl-Sar]³cyclosporin A (Compound DU)

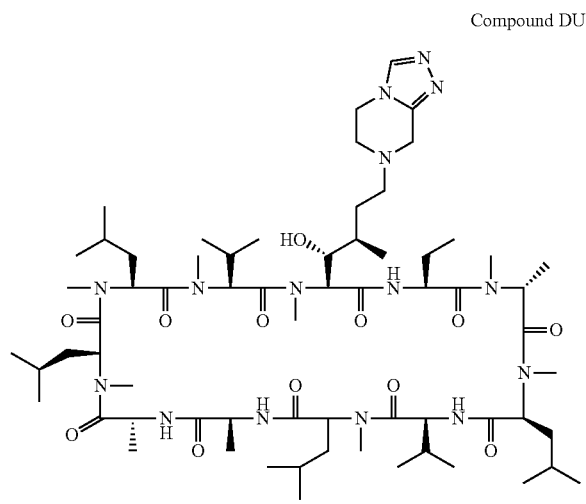

Compound DU

ESMS MH⁺ 1312.89

¹H NMR (CDCl₃, ppm) δ 7.22 (d, 1H, amide NH), 7.51 (d, 1H, amide NH), 7.81 (d, 1H, amide NH), 8.05 (d, 1H, amide NH), 8.10 (s, 1H, aromatic CH).

[(3R,4R,5S)-4-Hydroxy-3-methyl-5-(methylamino)-1-(8-oxa-3-aza-bicyclo[3.2.1]oct-3-yl)-hexanoic acid]¹[(R)-methyl-Sar]³cyclosporin A (Compound DV)

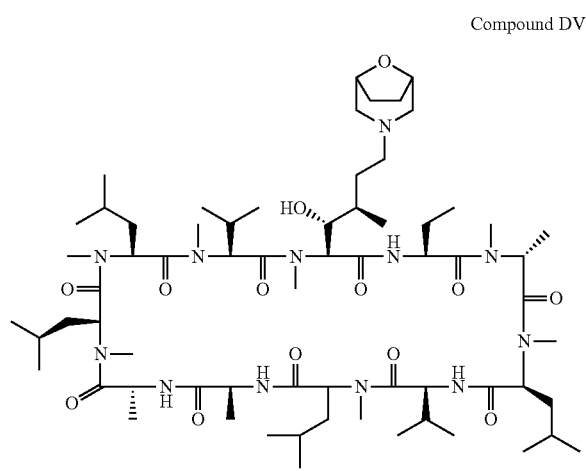

Compound DV

ESMS MH+ 1301.85

¹H NMR (CDCl₃, ppm) δ 7.18 (d, 1H, amide NH), 7.51 (d, 1H, amide NH), 7.77 (d, 1H, amide NH), 7.94 (d, 1H, amide NH).

[(3R,4R,5S)-4-Hydroxy-3-methyl-5-(methylamino)-1-((S)-3-methyl-morpholin-4-yl)-hexanoic acid]¹[(R)-methyl-Sar]³cyclosporin A (Compound DW)

Compound DW

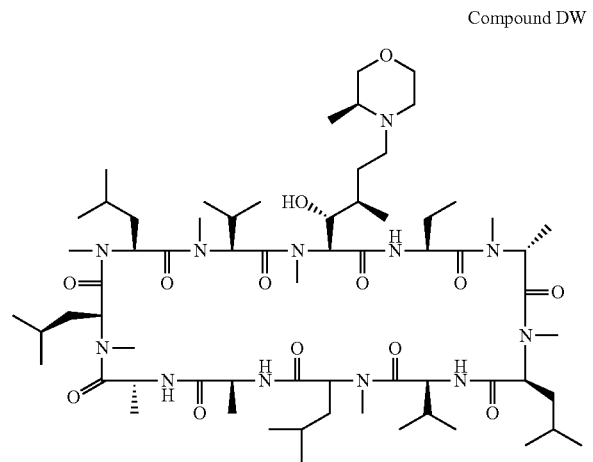

ESMS MH+ 1289.80

¹H NMR (CDCl₃, ppm) δ 7.15 (d, 1H, amide NH), 7.40 (d, 1H, amide NH), 7.75 (d, 1H, amide NH), 7.83 (d, 1H, amide NH).

[(3R,4R,5S)-1-(2,3-Dihydro-benzo[1,4]oxazin-4-yl)-4-Hydroxy-3-methyl-5-(methylamino)-hexanoic acid]¹[(R)-methyl-Sar]³cyclosporin A (Compound DX)

Compound DX

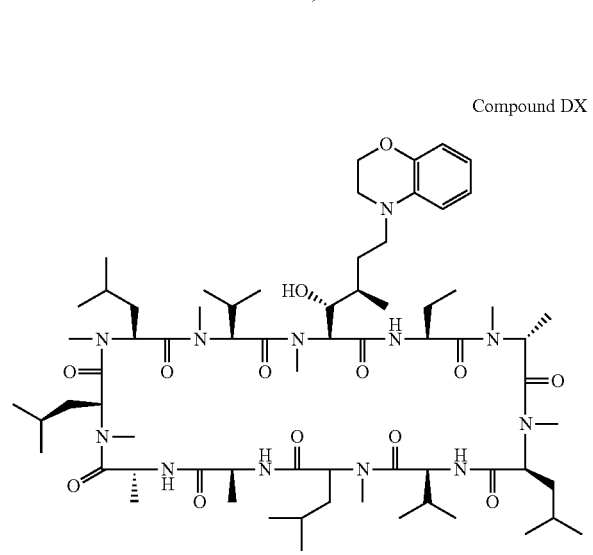

ESMS MH+ 1323.73

¹H NMR (CDCl₃, ppm) δ 7.12 (d, 1H, amide NH), 7.51 (d, 1H, amide NH), 7.71 (d, 1H, amide NH), 7.99 (d, 1H, amide NH).

[(3R,4R,5S)-1-(1,4-Dioxa-8-aza-spiro[4.5]dec-8-yl)-4-Hydroxy-3-methyl-5-(methylamino)-hexanoic acid]¹[(R)-methyl-Sar]³cyclosporin A (Compound DY)

Compound DY

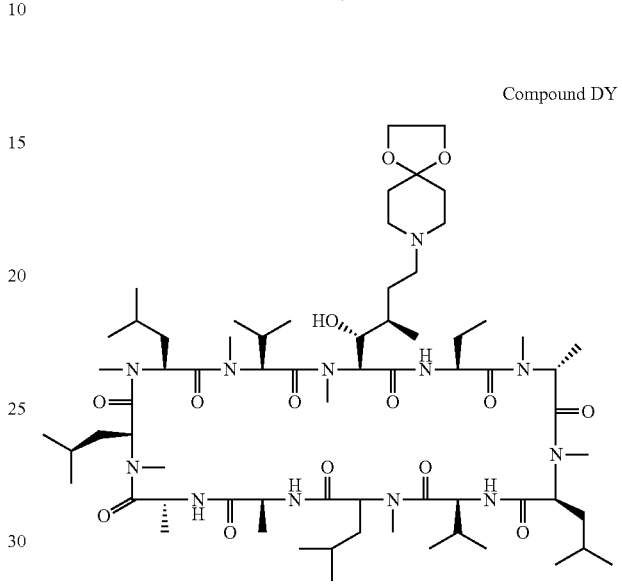

ESMS MH+ 1332.09

¹H NMR (CDCl₃, ppm) δ 7.20 (d, 1H, amide NH), 7.37 (d, 1H, amide NH), 7.79 (d, 1H, amide NH), 7.87 (d, 1H, amide NH).

[(3R,4R,5S)-4-Hydroxy-3-methyl-5-(methylamino)-1-(2-phenyl-morpholin-4-yl)-hexanoic acid]¹[(R)-methyl-Sar]³cyclosporin A (Compound DZ)

Compound DZ

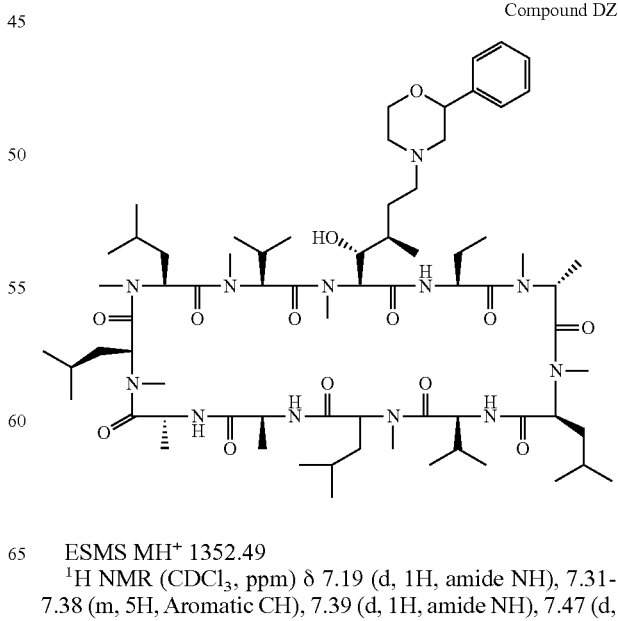

ESMS MH+ 1352.49

¹H NMR (CDCl₃, ppm) δ 7.19 (d, 1H, amide NH), 7.31-7.38 (m, 5H, Aromatic CH), 7.39 (d, 1H, amide NH), 7.47 (d, 1H, amide NH), 7.77 (d, 1H, amide NH), 7.78 (d, 1H, amide NH), 7.93 (d, 1H, amide NH), 8.01 (d, 1H, amide NH).

[(3R,4R,5S)-4-Hydroxy-3-methyl-5-(methylamino)-1-(piperidin-1-yl)-hexanoic acid]¹[(R)-methyl-Sar]³ cyclosporin A (Compound EA)

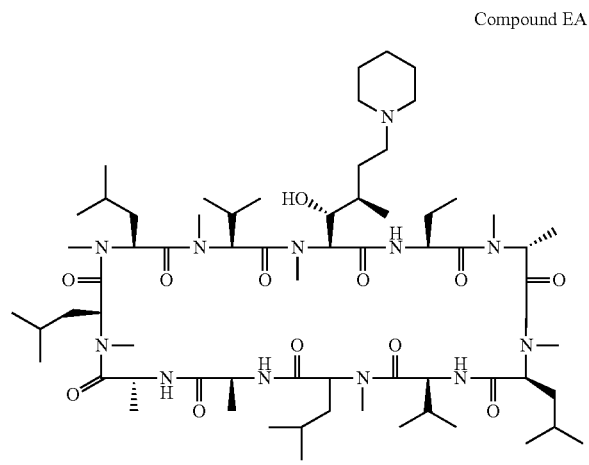 [SMILES: CC[C@H]1NC(=O)[C@@H]([C@H](O)[C@H](C)CCN2CCCCC2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)C(CC(C)C)N(C)C(=O)[C@@H](C(C)C)NC(=O)[C@H](CC(C)C)N(C)C(=O)[C@@H](C)N(C)C1=O]

Compound EA

ESMS MH⁺ 1273.69

¹H NMR (CDCl₃, ppm) δ 7.23 (d, 1H, amide NH), 7.37 (d, 1H, amide NH), 7.84 (d, 1H, amide NH), 7.90 (d, 1H, amide NH).

[(3R,4R,5S)-4-Hydroxy-3-methyl-5-(methylamino)-1-(pyrrolidin-1-yl)-hexanoic acid]¹[(R)-methyl-Sar]³cyclosporin A (Compound EF)

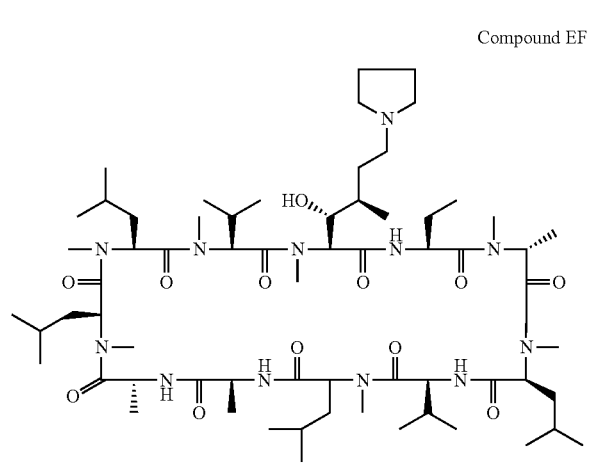 [SMILES: CC[C@H]1NC(=O)[C@@H]([C@H](O)[C@H](C)CCN2CCCC2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)C(CC(C)C)N(C)C(=O)[C@@H](C(C)C)NC(=O)[C@H](CC(C)C)N(C)C(=O)[C@@H](C)N(C)C1=O]

Compound EF

ESMS MH⁺ 1259.78

¹H NMR (CDCl₃, ppm) δ 7.21 (d, 1H, amide NH), 7.33 (d, 1H, amide NH), 7.81 (d, 1H, amide NH), 7.83 (d, 1H, amide NH).

[(3R,4R,5S)-4-Hydroxy-3-methyl-5-(methylamino)-1-(2-trifluoromethyl-piperidin-1-yl)-hexanoic acid]¹[(R)-methyl-Sar]³cyclosporin A (Compound EB)

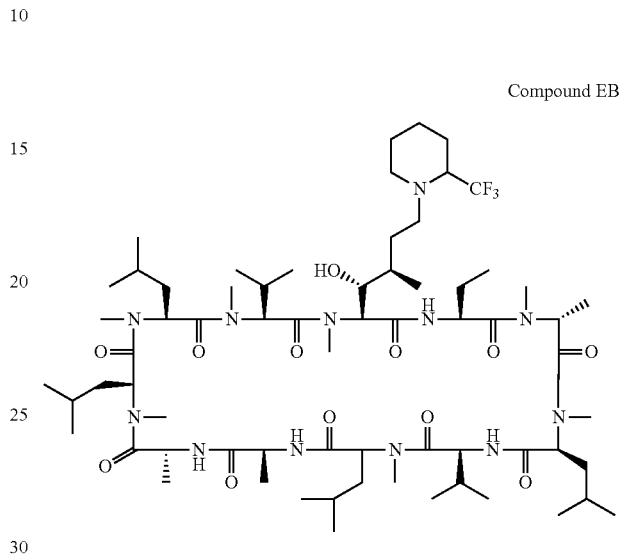

Compound EB

ESMS MH⁺ 1341.16

¹H NMR (CDCl₃, ppm) 2 isomers δ 7.13 (d, 1H, amide NH), 7.18 (d, 1H, amide NH), 7.45 (d, 1H, amide NH), 7.47 (d, 1H, amide NH), 7.70 (d, 1H, amide NH), 7.72 (d, 1H, amide NH), 7.95 (d, 1H, amide NH), 7.97 (d, 1H, amide NH).

[(3R,4R,5S)-4-Hydroxy-3-methyl-5-(methylamino)-1-(3-trifluoromethyl-morpholin-4-yl)-hexanoic acid]¹ [(R)-methyl-Sar]³cyclosporin A (Compound EC)

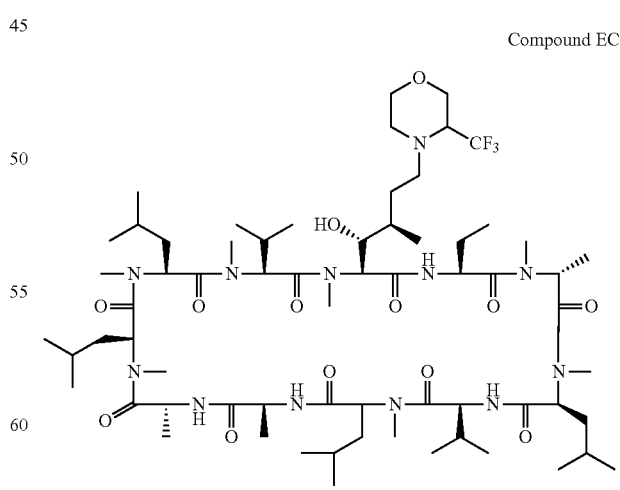

Compound EC

ESMS MH⁺ 1344.91

¹H NMR (CDCl₃, ppm) 2 isomers δ 7.11 (d, 1H, amide NH), 7.12 (d, 1H, amide NH), 7.49 (d, 1H, amide NH), 7.51

(d, 1H, amide NH), 7.67 (d, 1H, amide NH), 7.68 (d, 1H, amide NH), 7.97 (d, 1H, amide NH), 7.99 (d, 1H, amide NH).

[(3R,4R,5S)-4-Hydroxy-3-methyl-5-(methylamino)-1-([1,2]oxazinan-2-yl)-hexanoic acid]¹[(R)-methyl-Sar]³cyclosporin A (Compound ED)

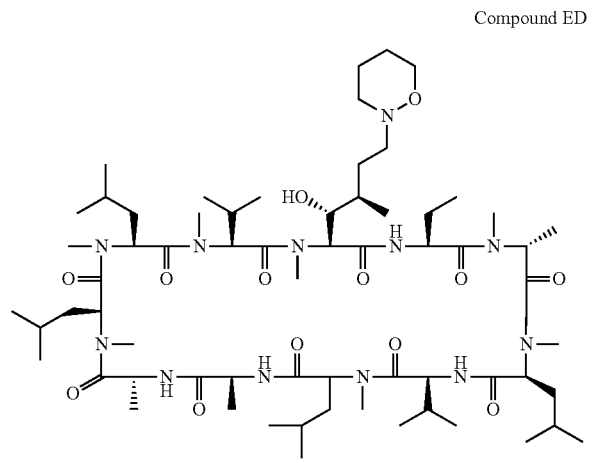 [SMILES: CC[C@H]1NC(=O)[C@@H]([C@H](O)[C@H](C)CCN2CCCCO2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)C(CC(C)C)N(C)C(=O)[C@@H](C(C)C)NC(=O)[C@H](CC(C)C)N(C)C(=O)[C@@H](C)N(C)C1=O]

Compound ED

ESMS MH⁺ 1276.43
¹H NMR (CDCl₃, ppm) δ 7.22 (d, 1H, amide NH), 7.40 (d, 1H, amide NH), 7.79 (d, 1H, amide NH), 8.05 (d, 1H, amide NH).

[(3R,4R,5S)-4-Hydroxy-3-methyl-5-(methylamino)-1-(2-trifluoromethyl-5,6-dihydro-8H-imidazo[1,2-a]pyrazin-7-yl)-hexanoic acid]¹[(R)-methyl-Sar]³cyclosporin A (Compound EE)

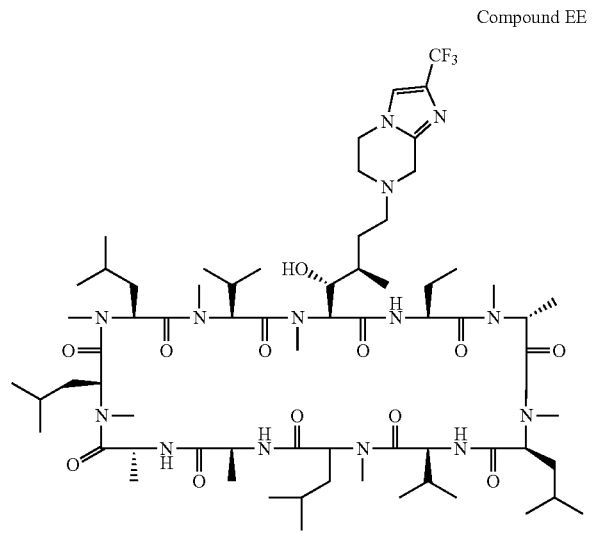 [SMILES: CC[C@H]1NC(=O)[C@@H]([C@H](O)[C@H](C)CCN2CCn3cc(C(F)(F)F)nc3C2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)C(CC(C)C)N(C)C(=O)[C@@H](C(C)C)NC(=O)[C@H](CC(C)C)N(C)C(=O)[C@@H](C)N(C)C1=O]

Compound EE

ESMS MH⁺ 1379.86
¹H NMR (CDCl₃, ppm) δ 7.15 (d, 1H, aromatic CH), 7.17 (d, 1H, amide NH), 7.51 (d, 1H, amide NH), 7.75 (d, 1H, amide NH), 7.98 (d, 1H, amide NH).
Compounds EG, EH, and EI are prepared according to Scheme I. Structures for each are shown below.

[[(3R,4R,5S)-4-Hydroxy-3-methyl-5-(methylamino)-1-(4-methyl-[1,4]diazepan-1-yl)-hexanoic acid]¹[(R)-methyl-Sar]³cyclosporin A (Compound EG)

ESMS MH⁺ 1302.5
¹H NMR (CDCl₃, ppm) δ 7.18 (d, 1H, amide NH), 7.46 (d, 1H, amide NH), 7.74 (d, 1H, amide NH), 7.96 (d, 1H, amide NH).

[[(3R,4R,5S)-4-Hydroxy-1-(3-methoxy-azetidin-1-yl)-3-methyl-5-(methylamino)-hexanoic acid]¹[(R)-methyl-Sar]³cyclosporin A (Compound EH)

ESMS MH⁺ 1275.9
¹H NMR (CDCl₃, ppm) δ 7.19 (d, 1H, amide NH), 7.36 (d, 1H, amide NH), 7.78 (d, 1H, amide NH), 7.88 (d, 1H, amide NH).

Compound [(4R,5R,6S)-5-Hydroxy-4-methyl-6-(methylamino)-1-(morpholin-4-yl)-heptanoic acid]¹cyclosporin A (Compound EI)

ESMS MH⁺ 1275.46
¹H NMR (CDCl₃, ppm) δ 7.15 (d, 1H, amide NH), 7.49 (d, 1H, amide NH), 7.69 (d, 1H, amide NH), 8.03 (d, 1H, amide NH).

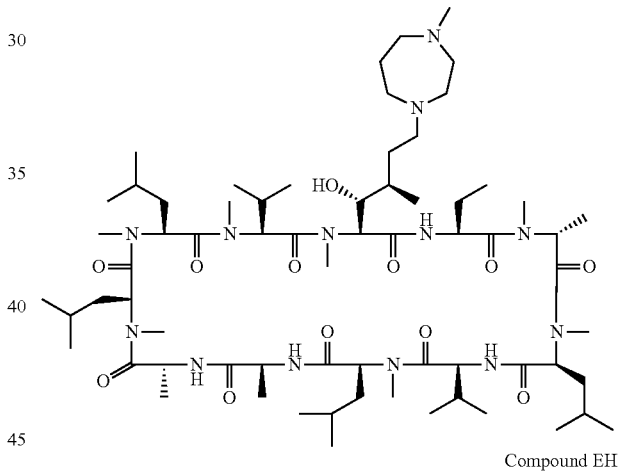

Compound EG

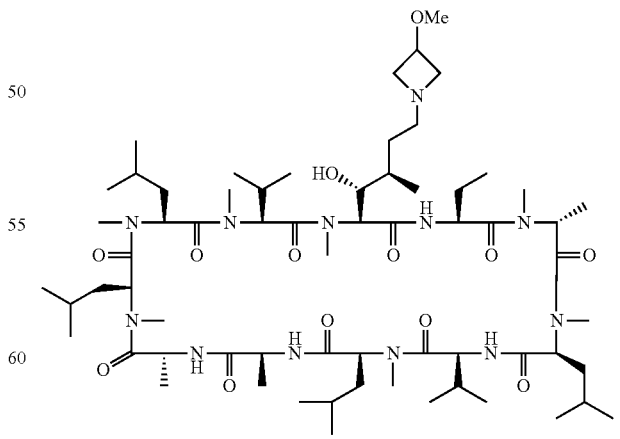

Compound EH

Compound EI is prepared from an intermediate similar to intermediate 15 by using Scheme Xa in a manner similar to that used to prepare Compound KG, as shown below.

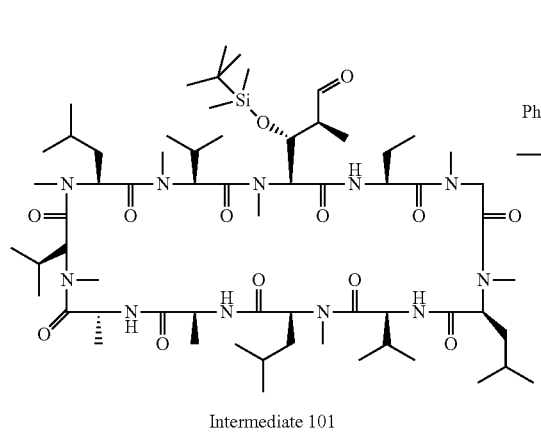

Intermediate 101

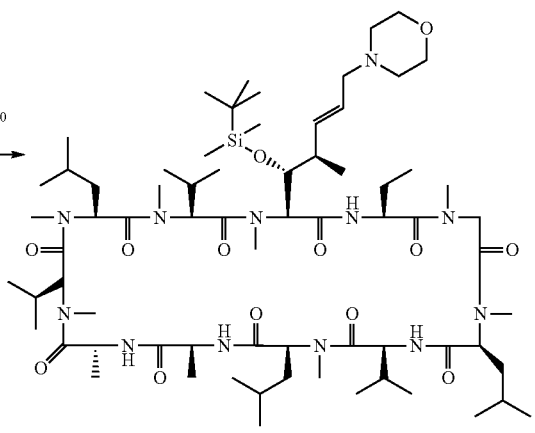

Intermediate 102

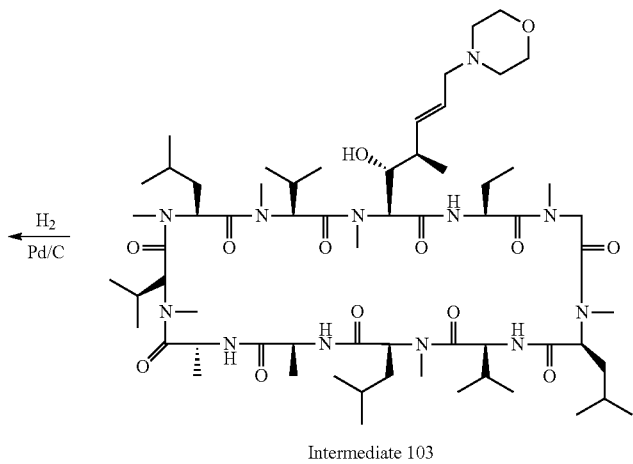

Intermediate 103

Compound EI

Intermediate 101 is prepared from CsA in a manner similar to that used to prepare intermediate 15 in Scheme VI, as shown by the scheme shown below.

Intermediate 104 is prepared in a similar manner to intermediate 2 in Scheme I.

Intermediate 105 is prepared in a similar manner to intermediate 3 in Scheme I.

Intermediate 106 is prepared in a similar manner to intermediate 14 in Scheme VI.

165
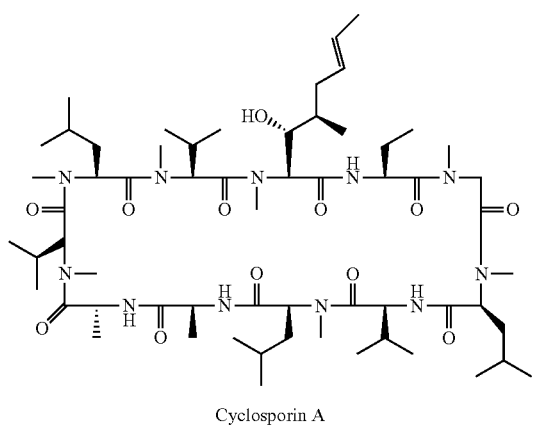
Cyclosporin A
166
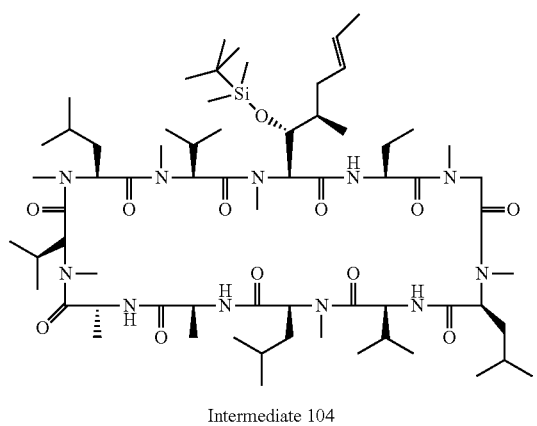
Intermediate 104
TBDMSOTf
Et₃N, DMF
O₃ | CH₂Cl₂
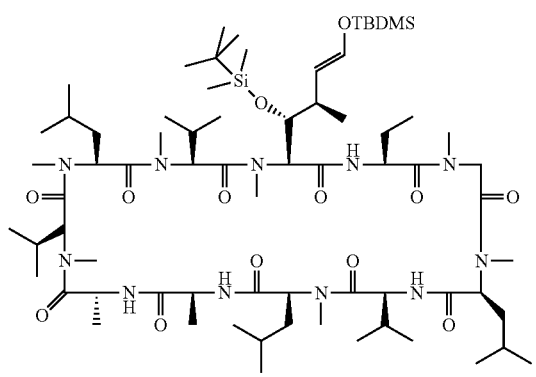
Intermediate 106
TBDMSOTf
DBU, DMF
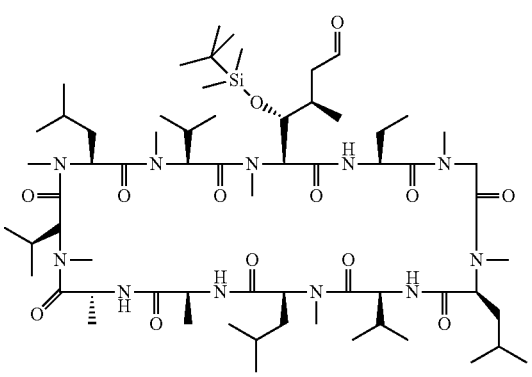
Intermediate 105
O₃ | CH₂Cl₂
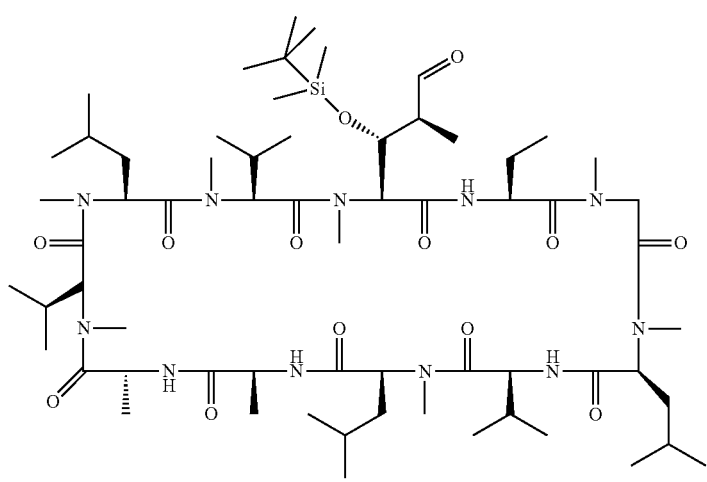
Intermediate 101

[(3R,4R,5S)-4-Hydroxy-3-methyl-1-(morpholin-4-yl)-hexanoic acid]¹[(R)-methyl-Sar]³[Ethyl-Val]⁴cyclosporin A (Compound EJ)

Compound EJ

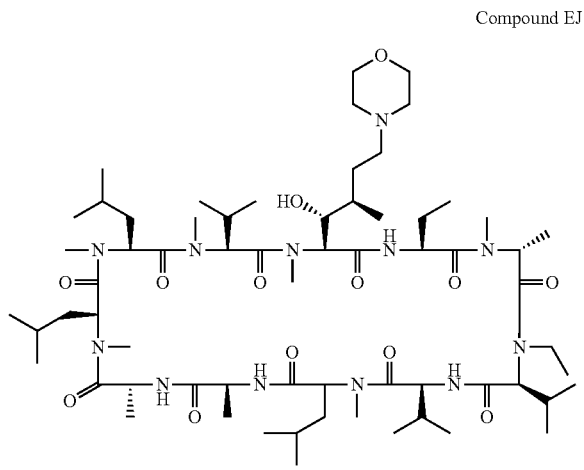 [SMILES: CC[C@H]1NC(=O)[C@@H]([C@H](O)[C@H](C)CCN2CCOCC2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)C(CC(C)C)N(C)C(=O)[C@@H](C(C)C)NC(=O)[C@H](C(C)C)N(CC)C(=O)[C@@H](C)N(C)C1=O]

ESMS MH⁺ 1275.77
¹H NMR (CDCl₃, ppm) δ 7.06 (d, 1H, amide NH), 7.17 (d, 1H, amide NH), 7.76 (d, 1H, amide NH), 7.79 (d, 1H, amide NH).

Biological and Physical Properties

Example Compounds of Formula I are listed and described in Tables 1-27, below. Compounds of the present invention include those listed and described in Tables 1-27, below, and their pharmaceutically acceptable salts.

Data Showing Cyclophilin A (Cyp A) Inhibitory Activity, immunosuppressive Potential, and aqueous solubility for select Compounds having Formula I are described in Tables 28-35. General procedures and assays used to obtain the data are given below.

The data shows that many compounds having Formula I, are potent inhibitors of cyclophilin A (Ki<10 nM), as measured by the protease-free PPIase assay. Many compounds having Formula I are also non-immunosuppressive, as measured by the MLR and CaN assays; and are more water soluble than unmodified Cyclosporin A, as measured by the Water Solubility Assay. Surprisingly, however, a sub-set of compounds having Formula I show more immunosuppressive potential than others. Examples include Compounds EK, EL, EM, EN, EQ, ER, EO, and EP.

General Procedures and Assays

*Protease-Free PPIase Assay

The protease-free PPIase assay measures the rate of cis to trans conversion of a peptide substrate catalyzed by the enzyme cyclophilin A. Addition of a cyclophilin A inhibitor (e.g., a test compound) slows the catalyzed rate and a $K_i$ value is obtained. A $K_i$ value of less than 10 nM demonstrates that the test compound is a potent inhibitor of cyclophilin A.
Materials
Assay Buffer:
35 mM HEPES pH 7.8, filtered through a 0.2 μm filter. 50 μM DTT was added prior to use each day and then the buffer was stored on ice.

Enzyme:
Human recombinant cyclophilin A (Cyp A) (Sigma C3805) enzyme was diluted to 1 μM with enzyme dilution buffer (20 mM HEPES pH 7.8, 40% glycerol, 50 μM DTT and 1 μM BSA) and stored at −20° C.
Substrate:
Succinimide-Ala-Ala-Pro-Phe-p-nitroanilide nitroanailide (SUC-AAPF-pNA) (from Bachem AG, L-1400), 20 mg/ml prepared in 0.5 M LiC1 in trifluoroethanol.
Method All readings were taken with an Agilent 8453 Spectrophotometer which consists of a cuvette holder, stirrer and chiller to maintain a stirred cuvette temperature of 10.0±0.1° C. The temperature is monitored by the use of temperature probe. To prevent UV degradation of test compounds, the light below 290 nm was blocked using a glass slide in the light path. 1.5 ml of assay buffer was put into a 3 ml quartz cuvette and cooled to 10.0±0.1° C. while stirring (vigorous but not so fast as to produce cavitation). The inhibitor was diluted in 100% DMSO, and then added to the assay to a maximum final concentration of 0.5% DMSO in the assay. A blank spectrum was obtained, then 3 μL of enzyme was added (2 nM final concentration) and then 3 μL substrate (60 μM final concentration) added. The absorbance was measured at 330 nm for 300 s or 500 s for blank runs (NOTE: the substrate must be added in one quick injection and the measurements started immediately to minimize mixing errors).

A first order rate equation was fitted to the absorbance data, for each concentration of inhibitor, to obtain the rate constant (the first 10 to 15 seconds were excluded as mixing causes errors in this portion of curve). The catalytic rate was calculated from the enzymatic rate constant minus the background rate constant. An exponential curve was generated using the catalytic rate constants versus the inhibitor concentration to obtain the $K_i$ value for the inhibitor. The $K_i$ value is indicative of the binding affinity between the test compound and cyclophilin A.

**Calcineurin Phosphatase (CaN) Assay

The calcineurin phosphatase assay is a means for estimating the immunosuppressive potential of a test compound. Calcineurin is a serine-threonine protein phosphatase that on activation dephosphorylates members of the nuclear factor of activated T cells (NFAT), which are important in T lymphocyte activation. Cyclosporin A (CsA) bound to cyclophilin A (Cyp A) inhibits calcineurin activity, thus resulting in immunosuppressive effects. Although CsA only inhibits calcineurin when bound to Cyp A, some Cyclosporin A (CsA) analogs will also bind calcineurin in the absence of Cyp A. Alternatively, some CsA analogs bind cyclophilin A but do not inhibit calcineurin activity.

To investigate the immunosuppressive potential of exemplary compounds of Formula I, which are cyclosporin analogs, their ability to inhibit calcineurin activity was measured in the presence and absence of Cyp A.

The CaN assay kit used is based on a colorimetric assay for measuring calcineurin phosphatase activity, and it is commercially available (Enzo Life Sciences and Calbiochem). Calmodulin is also required for calcineurin activity and RII phosphopeptide is used as an efficient peptide substrate for calcineurin. We have modified the method to enable measurement of Cyp A-dependent and Cyp A-independent inhibition of calcineurin through the addition of Cyp A in a 1:1 complex with the inhibitor. The detection of free phosphate released is based on the classic Malachite green assay.

Materials:
Enzo Life Sciences CaN Assay Kit: BML-AK804
2× Assay Buffer:
100 mM Tris, pH 7.5, 200 mM NaCl, 12 mM $MgCl_2$, 1 mM DTT, 0.05% NP-40, 1 mM $CaCl_2$
Malachite Green:
BIOMOL Green™ reagent
Calmodulin (Human, Recombinant):
was thawed on ice, diluted 1:50 with 2× assay buffer, and then stored on ice.
Calcineurin:
was thawed quickly, stored on ice immediately, diluted 1:12.5 with 1× assay buffer, and then stored on ice.
R-II Substrate:
915 µL ultrapure water (UPW) was added to the 1.5 mg vial substrate to give a final concentration of 0.75 mM.
Inhibitors:
2.5 mM inhibitor in 100% DMSO.
Cyp A:
recombinant human CypA (Sigma C3805), 1 mg/ml; Recombinant 6-his tagged CypA prepared by the Univ. of Edinburgh was also used. Comparison of the results showed that both enzymes gave identical results.
Method
Inhibitor Dilutions:
inhibitor compounds were diluted in UPW in polypropylene low-binding 96 well plates at 5× the final assay concentration. For samples 'without Cyp A', a 4-point dilution series of the inhibitor was prepared in duplicate to obtain a final assay concentration of 10, 1, 0.1 and 0.01 µM. For samples 'with Cyp A', a 7-point dilution series was prepared to obtain a 1:1 complex of the inhibitor with CypA; the inhibitor and Cyp A final assay concentrations of 10, 3.33, 1.11, 0.37, 0.12, 0.04, 0.014 µM were prepared. Cs A inhibitor controls were also prepared to obtain a final concentration of 10 µM Cs A with and without 10 µM Cyp A.
Assay Setup:
using the half area 96 well plates supplied with the kit, 10 µl UPW was added to duplicate wells to provide the non-inhibited control. 10 µl of the inhibitor or the inhibitor/Cyp A complex was added to the appropriate sample wells. 25 µl of the 2× assay buffer with CaM was added to all wells, then 5 µl of CaN was added to all wells (40 U per well final concentration) except duplicate 'no calcineurin blank' wells to which 50 µL, 1× assay buffer was added. The assay plate was placed in an oven at 30° C. for 15 minutes to equilibrate to the reaction temperature. The reaction was started by the addition of 10 µl RII-peptide (0.15 mM final concentration). The reaction was allowed to proceed at 30° C. for a time period in which the reaction is linear for about 60 minutes. The reaction was then terminated by adding 100 µl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no Calcineurin blank' from all the absorbance readings and plotting the background corrected absorbances against $Log_{10}$ inhibitor concentration. A sigmoidal-dose response curve was fitted to the data using GraphPad Prism Software.

Cyclosporin A is a potent inhibitor of calcineurin activity and therefore a potent immunosuppressive. It exerts its immunosuppressive activity by binding to cyclophilin A to form a complex, which then binds to calcineurin and thereby inhibits calcineurin activity. As shown in the tables, Cyclosporin A has a $IC_{50}$ value of 210 nM in the calcineurin/cyclophilin A assay. Thus, compounds with values higher than 210 nM in this assay will be predictably less immunosuppressive than cyclosporin A. As can be seen from the tables, many compounds of Formula I produce much higher values than 210 nM in this assay and so would be expected to be much less immunosuppressive than cyclosporin A. However, a sub-set of compounds of Formula I show immunosuppressive activity as measured by the Calcineurin phosphatase assay ($IC_{50}$ values between 225 nM and 4 µM)

***Mixed Lymphocyte Reaction ("MLR") Assay

The MLR assay is widely used in the field of immunology to measure T cell proliferation, and therefore is another means of estimating the immunosuppressive potential of test compounds. In the MLR assay, splenocytes isolated from two different strains of mice, termed Stimulator (e.g. BALB/c mice) and Responder (e.g. C57BL/6 mice), are mixed in cell culture, in turn eliciting an alloimmune response (immunity against antigens between individuals of the same species). Alloimmunity results in robust proliferation of T cells contained within the splenocyte cell population from both strains of mice. To ensure that T cell proliferation is restricted to only the Responder population (C57BL/6), the Stimulator cells (BALB/c) are first inactivated via x-irradiation before co-culture with Responder cells in the absence or presence of different concentrations of test compound. If the test compound present in the culture medium is immunosuppressive the proliferation of the responder cells is reduced. Total proliferation is quantified by the cellular uptake of $[^3H]$-thymidine, which occurs during cell division. Therefore, compounds that are less immunosuppressive than CsA will require a higher concentration to reduce T cell proliferation; and compounds that are not immunosuppressive will not affect T cell proliferation even at the highest concentrations tested.

Female C57BL/6 and BALB/c mice, 6-8 weeks of age, were obtained from the Frederick Cancer Research and Development Center of the National Cancer Institute (Frederick, Md.). Spleens were harvested aseptically from all mice and single cell suspensions were prepared by disaggregating the cells with frosted glass slides, allowing the debris to settle, and washing the cells twice with complete medium. Complete medium consists of RPMI 1640 medium containing 25 mM HEPES buffer (HyClone, Logan, Utah) supplemented with 10% heat-inactivated fetal bovine serum (FBS; Atlanta Biologicals, Lawrenceville, Ga.), 100 µg/mL streptomycin, 100 U/mL penicillin G, 0.25 µg/mL amphotericin B (HyClone), 2 mM L-glutamine dipeptide (HyClone), and $2×10^{-5}$ M 2-mercaptoethanol (Sigma). Cells were washed twice and resuspended in complete medium. Cell counts were performed using a Beckman Coulter Z-1 particle counter (Fullerton, Calif.). Cell viability was determined by propidium iodide (PI) staining using an Accuri C6 flow cytometer (Ann Arbor, Mich.).

Spleen cells from C57BL/6 ($H-2^b$) and BALB/c ($H-2^d$) were used as responder (R) and stimulator (S) cells, respectively. Cells were plated in triplicate in 96-well flat microtiter plates (Costar, Cambridge, Mass.) such that each well contained $2×10^5$ R and $8×10^5$ S cells. Cultures were incubated in the absence or presence of various concentrations of CsA, test compounds (e.g., a compound of Formula I), or medium at 37° C. in humidified 5% $CO_2$ for five days, pulsed with $^3H$-thymidine ($^3H$-TdR) for the final 16 hours of incubation, and harvested using a Brandel 96-well cell harvester (Gaithersburg, Md.). Proliferation was measured by counting the radioactivity on filter mats in a Wallac 1450 Microbeta TriLux scintillation counter (Turku, Finland). Controls to demonstrate effective inactivation by the x-irradiation were performed by incubating the S cells with 5 µg/mL of PHA at $2×10^5$ cells/well. These control cultures were incubated for 3 days under the same conditions as those described for the MLR; lymphoproliferation was determined in the same manner as described above.

****Water Solubility Assay (Measured in pH 7.8 Buffer)

The aqueous solubility of a compound of Formula I in buffer (pH 7.8) was measured by recording the onset of precipitation of the compound as a function of increasing concentration. The onset of precipitation, if it occurred, was detected by an increase in absorbance at 650 nm.

Materials

Assay Buffer:
35 mM HEPES pH 7.8
Stock solutions of Control and Test Compounds: 10 mM in 100% DMSO Method 10 mM stock solutions of control and test compounds were prepared in 100% DMSO. A series of dilutions were prepared from the stock in DMSO so that the final concentrations in the assay were 0, 3.33, 10, 25, 50, 75 and 100 μM and DMSO was limited to 1%.

Assay buffer (247.5 μl) was placed into flat bottomed transparent 96-well plate. For blank samples DMSO (2.5 μl) was added. For test and control samples 2.5 μl of the appropriate DMSO dilution stocks were added to the appropriate well. All test and control compounds were performed in triplicate.

The plates were sealed with adhesive plate seal and shaken at 250 rpm at 25° C. for 18 h on a plate shaker.

After incubation the plate seals were taken off and any bubbles observed in wells removed. The plates were read on a SpectraMaxM5 with a 5 s pre-shake at 650 nm.

Data files were transferred to the appropriate worksheet and the solubility range of the compounds was calculated from the data.

The values shown in the tables indicate the concentration in μM (micromolar) at which the compound remains in solution.

TABLE 1

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | | $R^{12}$ | n | m | p | q |
|---|---|---|---|---|---|---|---|---|
| F | —$CH_3$ | $R^{11}$ is O; and $R^9$, $R^{10}$, $R^{11}$, and the N to which $R^9$ and $R^{10}$ are attached taken together form: | 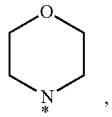 wherein "*" represents the point of attachment to $R^5$ | — | 0 | 0 | 1 | — |
| A | —H | $R^{11}$ is O; and $R^9$, $R^{10}$, $R^{11}$, and the N to which $R^9$ and $R^{10}$ are attached taken together form: | 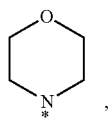 wherein "*" represents the point of attachment to $R^5$ | — | 0 | 0 | 1 | — |

TABLE 2

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | | $R^{12}$ | n | m | p | q |
|---|---|---|---|---|---|---|---|---|
| L | —$CH_3$ | $R^{11}$ is $NR^{12}$; and $R^9$, $R^{10}$, $R^{11}$, and the N to which $R^9$ and $R^{10}$ are attached taken together form: | 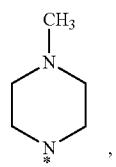 wherein "*" represents the point of attachment to $R^5$ | $CH_3$ | 0 | 0 | 1 | — |

TABLE 2-continued

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| LL | —H | $R^{11}$ is $NR^{12}$; and $R^9$, $R^{10}$, $R^{11}$, and the N to which $R^9$ and $R^{10}$ are attached taken together form: 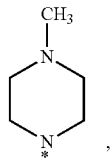 , wherein "*" represents the point of attachment to $R^5$ | $CH_3$ | 0 | 0 | 1 | — |

TABLE 3

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| N | —$CH_3$ | $R^{11}$ is $NR^{12}$; and $R^9$, $R^{10}$, $R^{11}$, and the N to which $R^9$ and $R^{10}$ are attached taken together form: 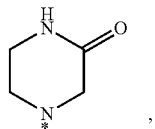 , wherein "*" represents the point of attachment to $R^5$ | H | 0 | 0 | 1 | — |
| NN | —H | $R^{11}$ is $NR^{12}$; and $R^9$, $R^{10}$, $R^{11}$, and the N to which $R^9$ and $R^{10}$ are attached taken together form: 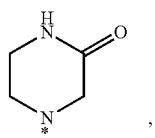 , wherein "*" represents the point of attachment to $R^5$ | H | 0 | 0 | 1 | — |

TABLE 4

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| B | —OCH$_3$ | $R^{11}$ is O; and $R^9$, $R^{10}$, $R^{11}$, and the N to which $R^9$ and $R^{10}$ are attached taken together form: 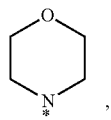 , wherein "*" represents the point of attachment to $R^5$ | — | 0 | 0 | 1 | — |
| C | —H | $R^{11}$ is O; and $R^9$, $R^{10}$, $R^{11}$, and the N to which $R^9$ and $R^{10}$ are attached taken together form: 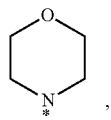 , wherein "*" represents the point of attachment to $R^5$ | — | 3 | 0 | 1 | — |

TABLE 5

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| G | —CH$_3$ | $R^{11}$ is O; and $R^9$, $R^{10}$, $R^{11}$, and the N to which $R^9$ and $R^{10}$ are attached taken together form: 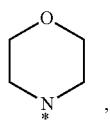 , wherein "*" represents the point of attachment to $R^5$ | — | 3 | 0 | 1 | — |
| D | —CH$_2$OCH$_3$ | $R^{11}$ is O; and $R^9$, $R^{10}$, $R^{11}$, and the N to which $R^9$ and $R^{10}$ are attached taken together form: 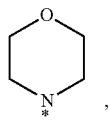 , wherein "*" represents the point of attachment to $R^5$ | — | 0 | 0 | 1 | — |

TABLE 6

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| H | —$CH_3$ | $R^{11}$ is O; and $R^9$, $R^{10}$, $R^{11}$, and the N to which $R^9$ and $R^{10}$ are attached taken together form: 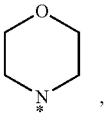, wherein "*" represents the point of attachment to $R^5$ | — | 1 | 1 | 1 | — |
| E | —H | $R^{11}$ is O; and $R^9$, $R^{10}$, $R^{11}$, and the N to which $R^9$ and $R^{10}$ are attached taken together form: 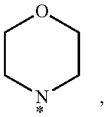, wherein "*" represents the point of attachment to $R^5$ | — | 1 | 1 | 1 | — |

TABLE 7

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| T | —$CH_3$ | $R^{11}$ is $NR^{12}$; and $R^9$, $R^{10}$, $R^{11}$, and the N to which $R^9$ and $R^{10}$ are attached taken together form: 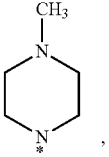, wherein "*" represents the point of attachment to $R^5$ | $CH_3$ | 1 | 1 | 1 | — |

TABLE 8

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| AB | —$CH_2CH_3$ | $R^{11}$ is O; and $R^9$, $R^{10}$, $R^{11}$, and the N to which $R^9$ and $R^{10}$ are attached taken together form: 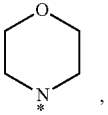, wherein "*" represents the point of attachment to $R^5$ | — | 0 | 0 | 1 | — |

TABLE 8-continued

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| Z | $-CH_3$ | $R^{11}$ is $S(O)_q$; and $R^9$, $R^{10}$, $R^{11}$, and the N to which $R^9$ and $R^{10}$ are attached taken together form: [structure], wherein "*" represents the point of attachment to $R^5$ | — | 1 | 1 | 1 | 2 |

TABLE 9

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| ZZ | $-CH_3$ | $R^9$, $R^{10}$, $R^{11}$, and the N to which $R^9$ and $R^{10}$ are attached taken together form: [structure], wherein "*" represents the point of attachment to $R^5$ | — | 1 | 1 | 1 | — |
| O | $-CH_3$ | $R^9$, $R^{10}$, $R^{11}$, and the N to which $R^9$ and $R^{10}$ are attached taken together form: [structure], wherein "*" represents the point of attachment to $R^5$ | — | 0 | 0 | 1 | — |

TABLE 10

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| I | $-SCH(CH_3)_2$ | $R^{11}$ is O; and $R^9$, $R^{10}$, $R^{11}$, and the N to which $R^9$ and $R^{10}$ are attached taken together form: [structure], wherein "*" represents the point of attachment to $R^5$ | — | 0 | 0 | 1 | — |

TABLE 10-continued

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| J | —$CH_3$ | $R^{11}$ is $S(O)_q$; and $R^9$, $R^{10}$, $R^{11}$, and the N to which $R^9$ and $R^{10}$ are attached taken together form: 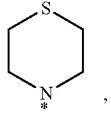 wherein "*" represents the point of attachment to $R^5$ | — | 0 | 0 | 1 | 0 |

TABLE 11

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| P | —$CH_3$ | $R^{11}$ is $S(O)_q$; and $R^9$, $R^{10}$, $R^{11}$, and the N to which $R^9$ and $R^{10}$ are attached taken together form: 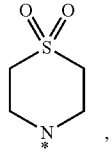 wherein "*" represents the point of attachment to $R^5$ | — | 0 | 0 | 1 | 2 |
| Q | —$CH_3$ | $R^{11}$ is $CH_2$; and $R^9$, $R^{10}$, $R^{11}$, and the N to which $R^9$ and $R^{10}$ are attached taken together form: 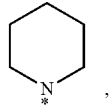 wherein "*" represents the point of attachment to $R^5$ | — | 1 | 1 | 1 | — |

TABLE 12

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| AC | 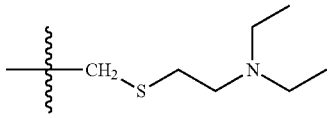 | $R^{11}$ is O; and $R^9$, $R^{10}$, $R^{11}$, and the N to which $R^9$ and $R^{10}$ are attached taken together form: 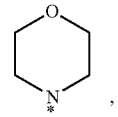, wherein "*" represents the point of attachment to $R^5$ | — | 0 | 0 | 1 | — |
| S | 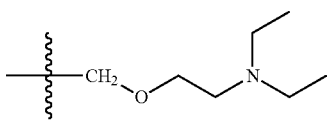 [SMILES: *COCCN(CC)CC] | $R^{11}$ is O; and $R^9$, $R^{10}$, $R^{11}$, and the N to which $R^9$ and $R^{10}$ are attached taken together form: 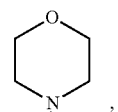, wherein "*" represents the point of attachment to $R^5$ | — | 0 | 0 | 1 | — |

TABLE 13

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| V | $-CH_2OH$ | $R^{11}$ is O; and $R^9$, $R^{10}$, $R^{11}$, and the N to which $R^9$ and $R^{10}$ are attached taken together form: 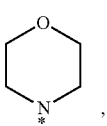, wherein "*" represents the point of attachement to $R^5$ | — | 0 | 0 | 1 | — |
| X | $-CH_3$ | $R^{11}$ is O; and $R^9$, $R^{10}$, $R^{11}$, and the N to which $R^9$ and $R^{10}$ are attached taken together form: 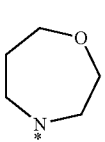, wherein "*" represents the point of attachment to $R^5$ | — | 0 | 0 | 1 | — |

TABLE 13-continued

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| EK | —$CH_3$ | $R^{11}$ is O; and $R^9$, $R^{10}$, $R^{11}$, and the N to which $R^9$ and $R^{10}$ are attached taken together form: [structure: 6-membered ring with O, N, and 4 F substituents], wherein "*" represents the point of attachment to $R^5$ | — | 0 | 0 | 1 | — |
| EL | —$CH_3$ | $R^{11}$ is $CF_2$; and $R^9$, $R^{10}$, $R^{11}$, and the N to which $R^9$ and $R^{10}$ are attached taken together form: [structure: pyrrolidine with $CF_2$], wherein "*" represents the point of attachment to $R^5$ | — | 0 | 0 | 1 | — |
| EM | —$CH_3$ | $R^{11}$ is $CF_2$; and $R^9$, $R^{10}$, $R^{11}$, and the N to which $R^9$ and $R^{10}$ are attached taken together form: [structure: azetidine with $CF_2$], wherein "*" represents the point of attachment to $R^5$ | — | 0 | 0 | 1 | — |
| EN | —$CH_3$ | $R^{11}$ is $CF_2$; and $R^9$, $R^{10}$, $R^{11}$, and the N to which $R^9$ and $R^{10}$ are attached taken together form: [structure: piperidine with $CF_2$], wherein "*" represents the point of attachment to $R^5$ | — | 0 | 0 | 1 | — |
| EO | —$CH_2OH$ | $R^{11}$ is O; and $R^9$, $R^{10}$, $R^{11}$, and the N to which $R^9$ and $R^{10}$ are attached taken together form: [structure: 6-membered ring with O, N, and 4 F substituents], wherein "*" represents the point of attachment to $R^5$ | — | 0 | 0 | 1 | — |

TABLE 13-continued

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| EP | —$CH_2OH$ | $R^{11}$ is $CF_2$; and $R^9$, $R^{10}$, $R^{11}$, and the N to which $R^9$ and $R^{10}$ are attached taken together form: [pyrrolidine with CF$_2$], wherein "*" represents the point of attachment to $R^5$ | — | 0 | 0 | 1 | — |
| ER | —$CH_3$ | $R^{11}$ is $CF_2$; and $R^9$, $R^{10}$, $R^{11}$, and the N to which $R^9$ and $R^{10}$ are attached taken together form: [pyrrolidine with two CF$_2$ groups], wherein "*" represents the point of attachment to $R^5$ | — | 0 | 0 | 1 | — |

TABLE 14

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| AD | —$CH_2$—O—$CH_2CH_2$—N(Et)— | $R^{11}$ is O; and $R^9$, $R^{10}$, $R^{11}$, and the N to which $R^9$ and $R^{10}$ are attached taken together form: [1,4-oxazepane], wherein "*" represents the point of attachment to $R^5$ | — | 0 | 0 | 1 | — |

TABLE 15

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| K | —$SCH_3$ | $R^{11}$ is O; and $R^9$, $R^{10}$, $R^{11}$, and the N to which $R^9$ and $R^{10}$ are attached taken together form: 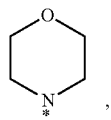 , wherein "*" represents the point of attachment to $R^5$ | — | 0 | 0 | 1 | — |

TABLE 16

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$ | $R^{10}$ | $R^{11}$ | $R^{12}$ | n | m | p | q |
|---|---|---|---|---|---|---|---|---|---|
| AF | —$CH_3$ | —H | —$CH_2CH_2OCH_3$ | — | — | 0 | 0 | 0 | — |
| AG | —$CH_3$ | —$CH_3$ | —$CH_2CH_2OCH_3$ | — | — | 0 | 0 | 0 | — |
| M | —$CH_3$ | —$CH_2CH_3$ | —$CH_2CH_3$ | — | — | 0 | 0 | 0 | — |
| U | —$CH_3$ | —$CH_2CH_3$ | —$CH_2CH_3$ | — | — | 1 | 1 | 0 | — |
| ZY | —$CH_3$ | —H | —$CH_2CH_2OCH_3$ | — | — | 1 | 1 | 0 | — |
| AH | —$CH_3$ | —$CH_2CH_3$ | —$CH_2CH_3$ | — | — | 3 | 0 | 0 | — |
| AI | —$CH_3$ | —H | —$CH_2CH_2OCH_3$ | — | — | 3 | 0 | 0 | — |
| AJ | —$CH_3$ | —$CH_3$ | 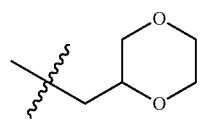 [SMILES: *CC1COCCO1] | — | — | 0 | 0 | 0 | — |
| ZX | —$CH_3$ | —H |  | — | — | 1 | 1 | 0 | — |
| Y | —$CH_3$ | —H | 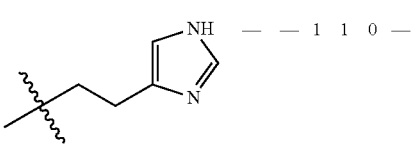 | — | — | 1 | 1 | 0 | — |

TABLE 17

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$ | $R^{10}$ | $R^{11}$ | $R^{12}$ | n | m | p | q |
|---|---|---|---|---|---|---|---|---|---|
| AK | —$CH_3$ | —H | 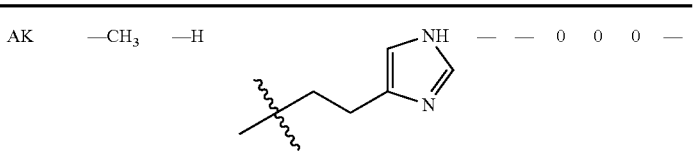 | — | — | 0 | 0 | 0 | — |

TABLE 17-continued

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$ | $R^{10}$ | $R^{11}$ | $R^{12}$ | n | m | p | q |
|---|---|---|---|---|---|---|---|---|---|
| W | —$CH_3$ | —H | 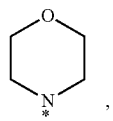 | — | — | 1 | 1 | 0 | — |
| KF | —$CH_3$ | —$CH_3$ | —$CH_3$ | — | — | 2 | 0 | 0 | — |

TABLE 18

Compounds having Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2O$

| Compound | $R^1$ | $R^9$ | $R^{10}$ | $R^{11}$ | $R^{12}$ | n | m | p | q |
|---|---|---|---|---|---|---|---|---|---|
| AL | —$CH_3$ | —$CH_2CH_3$ | —$CH_2CH_3$ | — | — | 2 | 0 | 0 | — |

TABLE 19

Compounds having Formula I, wherein: $R^2$ = —$CH_3$, $R^3$ = —$CH_2CH(CH_3)_2$, $R^4$ = —$CH_3$, $R^6$ = —$CH_2(CH_3)_2$, and $R^8$ = $CH_2$

| Compound | $R^1$ | $R^9$, $R^{10}$, and $R^{11}$ | $R^{12}$ | n | m | p | q |
|---|---|---|---|---|---|---|---|
| AM | —$SCH_3$ | $R^{11}$ is O; and $R^9$, $R^{10}$, $R^{11}$, and the N to which $R^9$ and $R^{10}$ are attached taken together form: 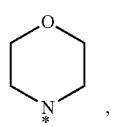 wherein "*" represents the point of attachment to $R^5$ | — | 0 | 0 | 1 | — |
| AN | —H | $R^{11}$ is O; and $R^9$, $R^{10}$, $R^{11}$, and the N to which $R^9$ and $R^{10}$ are attached taken together form: 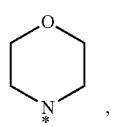 wherein "*" represents the point of attachment to $R^5$ | — | 0 | 0 | 1 | — |

TABLE 20

Compounds having Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| KG | —CH₃ | $R^{11}$ is O; and $R^9$, $R^{10}$, $R^{11}$, and the N to which $R^9$ and $R^{10}$ are attached taken together form: 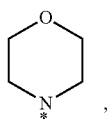, wherein "*" represents the point of attachment to $R^5$ | — | 2 | 0 | 1 | — |

TABLE 21

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$ | $R^{10}$ | $R^{11}$ | $R^{12}$ | n | m | p | q |
|---|---|---|---|---|---|---|---|---|---|
| DA | —CH₃ | —CH₃ | —CH₂Pyrid-2-yl | — | — | 0 | 0 | 0 | — |
| DB | —CH₃ | —CH₂Pyrid-2-yl | —CH₂Pyrid-2-yl | — | — | 0 | 0 | 0 | — |
| DC | —CH₃ | —CH₃ | -Phenyl | — | — | 0 | 0 | 0 | — |
| DD | —CH₃ | —CH₃ | -Pyrid-2-yl | — | — | 0 | 0 | 0 | — |
| DE | —CH₃ | —CH₃ | —CH₂CH₂SO₂NH₂ | — | — | 0 | 0 | 0 | — |
| DF | —CH₃ | —CH₃ | —CH₂Pyrid-3-yl | — | — | 0 | 0 | 0 | — |
| DG | —CH₃ | —CH₃ | —CH₂Pyrimidin-2-yl | — | — | 0 | 0 | 0 | — |
| DH | —CH₃ | —CH₃ | —CH₂Pyrazin-2-yl | — | — | 0 | 0 | 0 | — |
| DI | —CH₃ | —CH₃ | —CH₂-3-Me-Imidazol-4-yl | — | — | 0 | 0 | 0 | — |
| DJ | —CH₃ | —CH₃ | —CH₂-2-Me-Pyrazol-3-yl | — | — | 0 | 0 | 0 | — |
| DK | —CH₃ | —CH₃ | —CH₂CH(CH₃)CN | — | — | 0 | 0 | 0 | — |
| DL | —CH₃ | —CH₃ | —CH₂Pyrid-4-yl | — | — | 0 | 0 | 0 | — |
| DM | —CH₃ | —CH₃ | —CH₂-1-Me-Pyrazol-4-yl | — | — | 0 | 0 | 0 | — |
| DN | —CH₃ | —CH₃ | —CH₂CH₂CF₃ | — | — | 0 | 0 | 0 | — |
| DO | —CH₃ | —CH₃ | —CH₂-1-Me-3-CF₃-Pyrazol-5-yl | — | — | 0 | 0 | 0 | — |
| DP | —CH₃ | —CH₃ | —CH₂-5-F-Pyrid-2-yl | — | — | 0 | 0 | 0 | — |
| DQ | —CH₃ | —CH₃ | —CH₂-5-Cl-Pyrid-2-yl | — | — | 0 | 0 | 0 | — |
| DR | —CH₃ | —CH₃ | —CH₂-3-CF₃-Pyrid-2-yl | — | — | 0 | 0 | 0 | — |
| EQ | —CH₃ | —CH₂CH₂CF₃ | —CH₂CH₂CF₃ | — | — | 0 | 0 | 0 | — |

TABLE 22

Compounds of Formula I, wherein: $R^2 = -CH_3$, $R^3 = -CH_2CH(CH_3)_2$, $R^4 = -CH_3$, $R^6 = -CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| DS | —CH₃ | $R^{11}$ is O; and $R^9$, $R^{10}$, $R^{11}$, and the N to which $R^9$ and $R^{10}$ are attached taken together form: 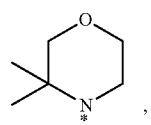, wherein "*" represents the point of attachment to $R^5$ | — | 0 | 0 | 1 | — |

TABLE 22-continued

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| DT | —$CH_3$ | $R^{11}$ is O; and $R^9$, $R^{10}$, $R^{11}$, and the N to which $R^9$ and $R^{10}$ are attached taken together form: 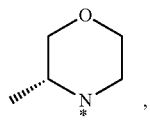, wherein "*" represents the point of attachment to $R^5$ | — | 0 | 0 | 1 | — |
| DU | —$CH_3$ | $R^{11}$ is N; and $R^9$, $R^{10}$, $R^{11}$, and the N to which $R^9$ and $R^{10}$ are attached taken together form: 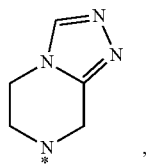, wherein "*" represents the point of attachment to $R^5$ | — | 0 | 0 | 1 | — |

TABLE 23

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| DV | —$CH_3$ | $R^{11}$ is O; and $R^9$, $R^{10}$, $R^{11}$, and the N to which $R^9$ and $R^{10}$ are attached taken together form: 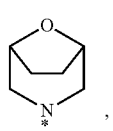, wherein "*" represents the point of attachment to $R^5$ | — | 0 | 0 | 1 | — |
| DW | —$CH_3$ | $R^{11}$ is O; and $R^9$, $R^{10}$, $R^{11}$, and the N to which $R^9$ and $R^{10}$ are attached taken together form: 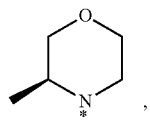, wherein "*" represents the point of attachment to $R^5$ | — | 0 | 0 | 1 | — |

TABLE 23-continued

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| DX | —$CH_3$ | $R^{11}$ is O; and $R^9$, $R^{10}$, $R^{11}$, and the N to which $R^9$ and $R^{10}$ are attached taken together form: 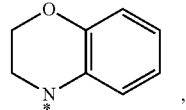 wherein "*" represents the point of attachment to $R^5$ | — | 0 | 0 | 1 | — |

TABLE 24

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| DY | —$CH_3$ | $R^9$, $R^{10}$, $R^{11}$, and the N to whch $R^9$ and $R^{10}$ are attached taken together form: 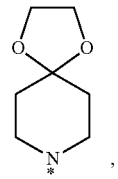 wherein "*" represents the point of attachment to $R^5$ | — | 0 | 0 | 1 | — |
| DZ | —$CH_3$ | $R^{11}$ is O; and $R^9$, $R^{10}$, $R^{11}$, and the N to which $R^9$ and $R^{10}$ are attached taken together form: 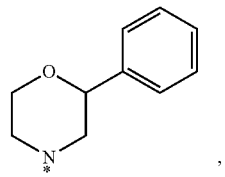 wherein "*" represents the point of attachment to $R^5$ | — | 0 | 0 | 1 | — |
| EA | —$CH_3$ | $R^{11}$ is O; and $R^9$, $R^{10}$, $R^{11}$, and the N to which $R^9$ and $R^{10}$ are attached taken together form: 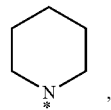 wherein "*" represents the point of attachment to $R^5$ | — | 0 | 0 | 1 | — |

TABLE 25

Compounds of Formula I, wherein: $R^2$ = —$CH_3$, $R^3$ = —$CH_2CH(CH_3)_2$, $R^4$ = —$CH_3$, $R^6$ = —$CH_2CH_3$, and $R^8$ = $CH_2$.

| Compound | $R^1$ | $R^9$, $R^{10}$, and $R^{11}$ | $R^{12}$ | n | m | p | q |
|---|---|---|---|---|---|---|---|
| EB | —$CH_3$ | $R^{11}$ is $CH_2$; and $R^9$, $R^{10}$, $R^{11}$, and the N to which $R^9$ and $R^{10}$ are attached taken together form: 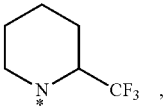 wherein "*" represents the point of attachment to $R^5$ | — | 0 | 0 | 1 | — |
| EC | —$CH_3$ | $R^{11}$ is O; and $R^9$, $R^{10}$, $R^{11}$, and the N to which $R^9$ and $R^{10}$ are attached taken together form: 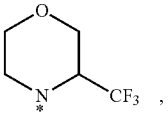 wherein "*" represents the point of attachment to $R^5$ | — | 0 | 0 | 1 | — |
| ED | —$CH_3$ | $R^{11}$ is O; and $R^9$, $R^{10}$, $R^{11}$, and the N to which $R^9$ and $R^{10}$ are attached taken together form: 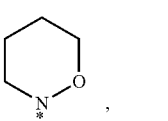 wherein "*" represents the point of attachment to $R^5$ | — | 0 | 0 | 1 | — |
| EE | —$CH_3$ | $R^{11}$ is N; and $R^9$, $R^{10}$, $R^{11}$, and the N to which $R^9$ and $R^{10}$ are attached taken together form: 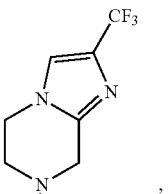 wherein "*" represents the point of attachment to $R^5$ | — | 0 | 0 | 1 | — |
| EF | —$CH_3$ | $R^{11}$ is $CH_2$; and $R^9$, $R^{10}$, $R^{11}$, and the N to which $R^9$ and $R^{10}$ are attached taken together form: 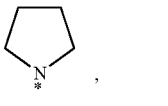 wherein "*" represents the point of attachment to $R^5$ | — | 0 | 0 | 1 | — |

TABLE 26

Compounds of Formula I, wherein: $R^2 =$ —$CH_3$, $R^3 =$ —$CH_2CH(CH_3)_2$, $R^4 =$ —$CH_3$, $R^6 =$ —$CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| EG | —$CH_3$ | $R^{11}$ is $NR^{12}$; and $R^9$, $R^{10}$, $R^{11}$, and the N to which $R^9$ and $R^{10}$ are attached taken together form: 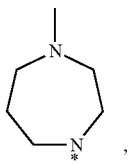, wherein "*" represents the point of attachment to $R^5$ | $CH_3$ | 0 | 0 | 1 | — |
| EH | —$CH_3$ | $R^{11}$ is $CH_2(OCH_3)$; and $R^9$, $R^{10}$, $R^{11}$, and the N to which $R^9$ and $R^{10}$ are attached taken together form: 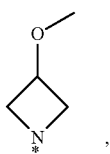, wherein "*" represents the point of attachment to $R^5$ | — | 0 | 0 | 1 | — |
| EI | —H | $R^{11}$ is O; and $R^9$, $R^{10}$, $R^{11}$, and the N to which $R^9$ and $R^{10}$ are attached taken together form: 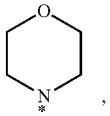, wherein "*" represents the point of attachment to $R^5$ | — | 1 | 0 | 1 | — |

TABLE 27

Compounds of Formula I, wherein: $R^2 =$ —$CH_2CH_3$, $R^3 =$ —$CH(CH_3)_2$, $R^4 =$ —$CH_3$, $R^6 =$ —$CH_2CH_3$, and $R^8 = CH_2$.

| Compound | $R^1$ | $R^9$, $R^{10}$, and $R^{11}$ | $R^{12}$ | n | m | p | q |
|---|---|---|---|---|---|---|---|
| EJ | —$CH_3$ | $R^{11}$ is O; and $R^9$, $R^{10}$, $R^{11}$, and the N to which $R^9$ and $R^{10}$ are attached taken together form: 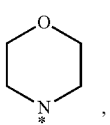, wherein "*" represents the point of attachment to $R^5$ | — | 0 | 0 | 1 | — |

TABLE 28

Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| Cyclosporin A | 1.5 | 210 | 1 | 10-25 |
| F | 4.5 | >10,000 | 144 | >100 |
| A | 23 | >10,000 | | >100 |
| L | 7.3 | >10,000 | 541 | >100 |
| LL | 46 | >10,000 | | |
| N | 6.1 | >10,000 | | <100 |
| NN | 120 | >10,000 | | |
| B | 8 | >10,000 | | >100 |
| G | 6.2 | >10,000 | 77 | >100 |
| C | 14 | >10,000 | 84 | >100 |
| M | 90 | | | 75-100 |
| D | 10 | >10,000 | >1000 | 75-100 |
| H | 3.9 | >10,000 | 418 | >100 |

TABLE 29

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| T | 5 | >10,000 | | >100 |
| U | 4 | >10,000 | | 75-100 |
| ZY | 5.7 | >10,000 | | 75-100 |
| K | 4.9 | >10,000 | >1000 | >100 |
| AB | 5.6 | >10,000 | | >100 |
| Y | 4.1 | >10,000 | >1000 | >100 |
| AK | 42 | >10,000 | | |
| W | 1.9 | >10,000 | | >100 |
| Z | 2 | >10,000 | | >100 |
| ZZ | 2.6 | >10,000 | | >100 |
| E | 24 | >10,000 | | |

TABLE 30

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| O | 8.2 | >10,000 | >1000 | >100 |
| AF | 28 | | | >100 |
| AG | 18 | | | >100 |
| I | 7.7 | >10,000 | >1000 | 25-50 |
| AH | 4.7 | >10,000 | | >100 |

TABLE 31

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| AI | 3.3 | >10,000 | | >100 |
| AJ | 12 | | | 50-75 |
| J | 3.7 | 6,300 | | 50-75 |
| P | 3.2 | >10,000 | | >100 |
| Q | 3.5 | >10,000 | | 50-75 |
| ZX | 2.3 | >10,000 | | >100 |

TABLE 32

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| AC | 7.5 | >10,000 | | >100 |
| S | 10 | >10,000 | | >100 |
| V | 4.5 | >10,000 | | >100 |
| X | 4.9 | >10,000 | | >100 |
| AD | 18 | >10,000 | | |
| AL | 27 | >10,000 | | >100 |
| AN | 15 | >10,000 | | |
| AM | 1.9 | >8,900 | | 25-50 |
| KF | 7.8 | >10,000 | | |
| KG | 3.8 | >10,000 | | |

TABLE 33

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| DA | 4.9 | >10,000 | | 75-100 |
| DB | 7.4 | >10,000 | | 75-100 |
| DC | 6.0 | >10,000 | | 10-25 |
| DD | 4.8 | >10,000 | | 25-50 |
| DE | 5.8 | >10,000 | | >100 |
| DF | 14 | >10,000 | | >100 |
| DG | 8.5 | >10,000 | | >100 |
| DH | 9.1 | >10,000 | | >100 |
| DI | 4.3 | >10,000 | | >100 |
| DJ | 5.4 | >10,000 | | >100 |
| DK | 13 | 6,300 | | >100 |
| DL | 5.7 | >10,000 | | >100 |
| DM | 23 | | | |
| DN | 5.5 | >10,000 | | 25-50 |
| DO | 2.8 | >10,000 | | 10-25 |
| DP | 16.2 | >10,000 | | |
| DQ | 11 | >10,000 | | |
| DR | 8.4 | >10,000 | | |

TABLE 34

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (μM) |
|---|---|---|---|---|
| DS | 12 | >10,000 | | 75-100 |
| DT | 4.7 | >10,000 | | >100 |
| DU | 9.2 | >10,000 | | >100 |
| DV | 4.3 | >10,000 | 250 | 50-75 |
| DW | 6.5 | >10,000 | | >100 |
| DX | 5.2 | 7,600 | 250 | 25-50 |
| DY | 13 | >10,000 | | >100 |
| DZ | 6.0 | >10,000 | | 25-50 |
| EA | 22 | >10,000 | | |
| EF | 40 | >10,000 | | |
| EB | 3.7 | >10,000 | | |
| EC | 5.2 | >10,000 | | |
| ED | 3.8 | >10,000 | | |
| EE | 9.1 | >10,000 | | |

TABLE 35

Data Showing Cyclophilin A (Cyp A) Inhibitory Activity, immunosuppressive potential, and aqueous solubility for select Compounds having Formula I

| Compound | Protease-free PPIase Assay* Ki (nM) | Calcineurin Phosphatase (CaN) Assay (+CypA)** IC50 (nM) | Mixed Lymphocyte Reaction (MLR) Assay*** | Water Solubility Assay**** (μM) |
|---|---|---|---|---|
| EJ | 9.0 | >10,000 | | >100 |
| EG | 8.2 | >10,000 | | >100 |
| EH | 17 | >10,000 | | >100 |
| EI | 14 | >10,000 | | >100 |
| EK | 12 | 225 | 10 | 25-50 |
| EL | 10 | 1,300 | 10 | 75-100 |
| EM | 9.5 | 655 | 10 | 75-100 |
| EN | 6.7 | 2,400 | 50 | 25-50 |
| EQ | 4.6 | 780 | 10 | 25-50 |
| ER | 6.7 | 1,600 | | 25-50 |
| EO | 13 | 1,500 | 50 | 10-25 |
| EP | 3.4 | 7,800 | | 50-75 |

In Tables 28-35:

* Data generated using the protease-free PPIase assay.

** Data generated using the Calcineurin Phosphatase (CaN) Assay. No significant inhibition of CaN was observed in the absence or presence of CypA. Data obtained in the presence of Cyp A (+CypA) are reported in the table.

*** Data generated using the Mixed Lymphocyte Reaction ("MLR") Assay. The values shown are expressed as the IC50 for the compound relative to the IC50 for Cyclosporin A. Thus, a value of 10, for example, indicates that the compound is about ten times less immunosuppressive than Cyclosporin A.

**** Data generated using the Water Solubility Assay.

What is claimed is:

1. A compound having Formula I:

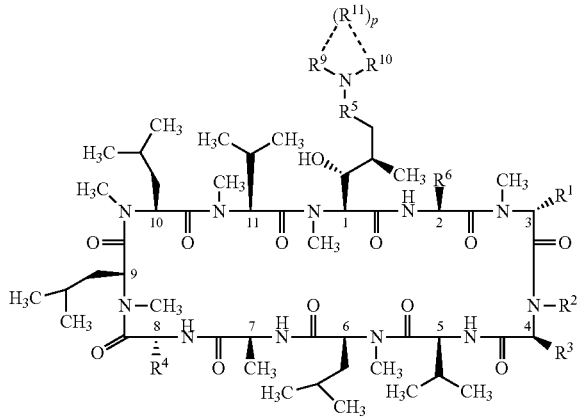

Formula I or a pharmaceutically acceptable salt thereof,
wherein:

$R^1$ is —H, —$C_{1-6}$alkyl, —$OC_{1-6}$alkyl, —$CH_2F$, —$CH_2OCH_3$, —$SC_{1-6}$alkyl, —$R^{13}R^{14}$,

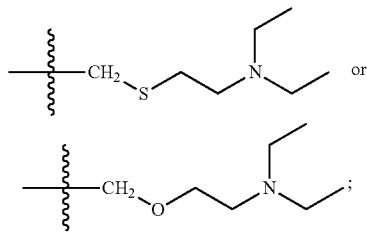

$R^2$ is —$CH_3$, —$CH_2CH_3$ or —$CH_2CH_2CH_3$;

$R^3$ is —$CH_2CH(CH_3)_2$, —$CH(CH_3)_2$, —$CH_2C(CH_3)_2(OH)$, —$CH(CH_3)(CH_2CH_3)$ or —$CH_2CH(R^7)(CH_2CH_3)$;

$R^4$ is —$CH_3$ or —$CH_2OH$;

$R^5$ is —$R^8(CH_2)_n(C=O)_m$—;

$R^6$ is —$CH_2CH_3$, —$CH(CH_3)(OH)$, —$CH(CH_3)_2$ or —$CH_2CH_2CH_3$;

$R^7$ is $OC_{1-5}$ alkyl;

$R^8$ is O, S, $CH_2O$, $CH_2S$ or $CH_2$;

$R^9$, $R^{10}$, $R^{11}$, and the N to which $R^9$ and $R^{10}$ are attached, together form a monocyclic or polycyclic non-aromatic heterocycle, wherein said heterocycle is optionally interrupted by a C=O, and the S and N atoms are optionally oxidized, and wherein said heterocycle is optionally substituted with halogen, nitro, cyano, —$OC_{1-6}$ alkyl, —$SC_{1-6}$ alkyl, —$C_{1-6}$ alkyl, —$C_{2-6}$ alkenyl, —$C_{2-6}$ alkynyl, carboxylic acid, ester, ketone, aldehyde, amide, amine, sulfonamide, $C_{3-8}$ cycloalkyl, hydroxyl or haloalkyl;

$R^{13}$ is O, S, $CH_2O$, $CH_2S$, $CH_2SO$ or $CH_2SO_2$;

$R^{14}$ is H, $C_{1-6}$alkyl, $C_{2-6}$alkenyl, $C_{2-6}$alkynyl, $C_{3-8}$cycloalkyl, $CH_2CH_2N(CH_2CH_3)_2$, $CH_2CH_2NH(CH_2CH_3)$, heterocycle or aryl;

n is 0, 1, 2, 3 or 4;
m is 0 or 1; and
p is 1;
wherein $R^{14}$ is optionally substituted with one or more groups independently selected from the group consisting of H, $C_{1-6}$alkyl, halogen, hydroxyl, ester, sulfonamide, ketone, aldehyde, cycloalkyl, heterocycle, aryl, amine, heterocycle, amide and guanidinyl; and
wherein "- - - - -" is a single bond.

2. A compound according to claim 1, wherein m is 0 and $R^1$ is not —H.

3. A compound according to claim 1, wherein m is 0.

4. A compound according to claim 1, wherein n is 0 or 3, and m is 0.

5. A compound according to claim 1, wherein $R^1$ is not —H.

6. A compound according to claim 1, wherein $R^2$ is —$CH_3$, $R^3$ is —$CH_2CH(CH_3)_2$, $R^4$ is —$CH_3$, $R^6$ is —$CH_2CH_3$ and $R^8$ is $CH_2$.

7. A compound according to claim 1, wherein $R^1$ is —$CH_3$, $R^6$ is —$CH_2CH_3$ or —$CH(CH_3)_2$, $R^8$ is $CH_2$, $R^{11}$ is O, and $R^9$, $R^{10}$, $R^{11}$, and the N to which $R^9$ and $R^{10}$ are attached taken together form a morpholinyl.

8. A compound according to claim 1, wherein $R^1$ is —$CH_3$, $R^2$ is —$CH_3$, $R^3$ is —$CH_2CH(CH_3)_2$, $R^4$ is —$CH_3$, $R^6$ is —$CH_2CH_3$, $R^8$ is $CH_2$, $R^{11}$ is O, n is 0 or 3, m is 0, and $R^9$, $R^{10}$, $R^{11}$, the N to which $R^9$ and $R^{10}$ are attached taken together form:

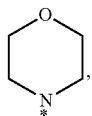

wherein "*" represents the point of attachment to $R^5$.

9. A compound according to claim 1, wherein the heterocycle formed from $R^9$, $R^{10}$, $R^{11}$ and the N to which $R^9$ and $R^{10}$ are attached is selected from the group consisting of morpholinyl, piperazinonyl, N-methylpiperazinyl,

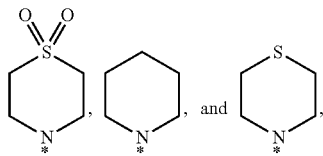

wherein "*" represents the point of attachment to $R^5$.

10. The compound according to claim 1 selected from the group consisting of:
[(3R,4R,5S)-4-(hydroxy)-3-methyl-5-(methylamino)-1-(morpholin-4-yl) hexanoic acid]$^1$[(R)-Me-Sar]$^3$cyclosporin A (Compound F);
[(3R,4R,5S)-4-hydroxy-3-methyl-5-(methylamino)-1-(4-methylpiperazino)-hexanoic acid]$^1$[(R)-Me-Sar]$^3$cyclosporin A (Compound L);
[(3R,4R,5S)-4-hydroxy-3-methyl-5-(methylamino)-1-(N-3-piperazinone)-hexanoic acid]$^1$[(R)-Me-Sar]$^3$cyclosporin A (Compound N);
[(3R,4R,5S)-4-Hydroxy-3-methyl-5-(methylamino)-1-(N-(3 aR*,6aS*)-2-methyloctahydropyrrolo[3,4-c]pyrrolo)-hexanoic acid]$^1$[(R)-methyl-Sar]$^3$cyclosporin A (Compound O);
[(3R,4R,5S)-4-Hydroxy-3-methyl-5-(methylamino)-1-(thiomorpholino)-hexanoic acid]$^1$[(R)-Me-Sar]$^3$cyclosporin A (Compound J);
[(3R,4R,5S)-4-Hydroxy-3-methyl-5-(methylamino)-1-(1,1-dioxo-thiomorpholino)-hexanoic acid]$^1$[(R)-Me-Sar]$^3$ cyclosporin A (Compound P);
[[(3R,4R,5S)-4-Hydroxy-3-methyl-5-(methylamino)-1-N-homomorpholino-hexanoic acid]$^1$[(R)-methyl-Sar]$^3$ cyclosporin A (Compound X);
[(6R,7R,8S)-7-hydroxy-6-methyl-8-(methylamino)-1-N-morpholino-nonanoic acid]$^1$[(R)-methyl-Sar]$^3$cyclosporin A (Compound G);
[(5R,6R,7S)-6-hydroxy-5-methyl-7-(methylamino)-1-N-morpholino-1-oxo-octanoic acid]$^1$[(R)-methyl-Sar]$^3$ cyclosporin A (Compound H);
[(5R,6R,7S)-6-hydroxy-5-methyl-7-(methylamino)-1-(4-methylpiperazin-1-yl)-1-oxo-octanoic acid]$^1$[(R)-methyl-Sar]$^3$cyclosporin A (Compound T);
[(5R,6R,7S)-6-hydroxy-5-methyl-7-(methylamino)-1-({1,1-dioxo}thiomorpholin-4-yl)-1-oxo-octanoic acid]$^1$ [(R)-methyl-Sar]$^3$cyclosporin A (Compound Z);
[(5R,6R,7S)-6-hydroxy-5-methyl-7-(methylamino)-1-(N-(3 aR*,6aS*)-2-methyloctahydropyrrolo[3,4-c]pyrrolo)-1-oxo-octanoic acid]1[(R)-methyl-Sar]3 cyclosporin A (Compound ZZ);
[(5R,6R,7S)-6-Hydroxy-5-methyl-7-(methylamino)-1-piperidino-1-oxo-octanoic acid]$^1$[(R)-methyl-Sar]$^3$cyclosporin A (Compound Q);
[(3R,4R,5S)-4-hydroxy-3-methyl-5-(methylamino)-1-N-morpholino-hexanoic acid]$^1$[(R)-ethyl-Sar]$^3$cyclosporin A (Compound AB);
[(3R,4R,5S)-4-hydroxy-3-methyl-5-(methylamino)-1-N-morpholino-hexanoic acid]$^1$[(S)-thiomethyl-Sar]$^3$cyclosporin A (Compound K);
[(3R,4R,5S)-4-Hydroxy-3-methyl-5-(methylamino)-1-N-morpholino-hexanoic acid]$^1$[(S)-thio-isopropyl-Sar]$^3$ cyclosporin A (Compound I);
[(3R,4R,5S)-4-Hydroxy-3-methyl-5-(methylamino)-1-N-morpholino-hexanoic acid]$^1$[(S)-methoxy-Sar]$^3$cyclosporin A (Compound B);
[(3R,4R,5S)-4-Hydroxy-3-methyl-5-(methylamino)-1-N-morpholino-hexanoic acid]$^1$[(R)-methoxymethylene-Sar]$^3$cyclosporin A (Compound D);
[(3R,4R,5S)-4-Hydroxy-3-methyl-5-(methylamino)-1-N-morpholino-hexanoic acid]$^1$[(R)-hydroxymethyl-Sar]$^3$ cyclosporin A (Compound V);
[(3R,4R,5S)-4-Hydroxy-3-methyl-5-(methylamino)-1-N-morpholino-hexanoic acid]$^1$[(R)2-diethylamino ethyl oxymethyl-Sar]$^3$cyclosporin A (Compound S);
[(3R,4R,5S)-4-Hydroxy-3-methyl-5-(methylamino)-1-N-homomorpholino-hexanoic acid]$^1$[(R)2 diethylamino ethyl oxymethyl-Sar]$^3$cyclosporin A (Compound AD);
[(5R,6R,7S)-6-hydroxy-5-methyl-7-(methylamino)-1-(N-morpholino)-octanoic acid]$^1$[(R)-methyl-Sar]$^3$cyclosporin A (Compound KG);
[(3R,4R,5S)-4-Hydroxy-3-methyl-5-(methylamino)-1-N-morpholino-hexanoic acid]$^1$[(S)-2-diethylaminoethylthiomethyl-Sar]$^3$cyclosporin A (Compound AC);
[(3R,4R,5S)-1-(3,3-Dimethyl-morpholin-4-yl)-4-hydroxy-3-methyl-5-(methylamino)-hexanoic acid]$^1$[(R)-methyl-Sar]$^3$cyclosporin A (Compound DS);
[(3R,4R,5S)-4-Hydroxy-3-methyl-5-methylamino((R)-3-methyl-morpholin-4-yl)-hexanoic acid]$^1$[(R)-methyl-Sar]$^3$cyclosporin A (Compound DT);
[(3R,4R,5S)-4-Hydroxy-3-methyl-5-(methylamino)-1-(8-oxa-3-aza-bicyclo[3.2.1]oct-3-yl)-hexanoic acid]$^1$[(R)-methyl-Sar]$^3$cyclosporin A (Compound DV);

[(3R,4R,5S)-4-Hydroxy-3-methyl-5-(methylamino)-1-(S)-3-methyl-morpholin-4-yl)-hexanoic acid]$^1$[(R)-methyl-Sar]$^3$cyclosporin A (Compound DW);
[(3R,4R,5S)-1-(1,4-Dioxa-8-aza-spiro[4.5]dec-8-yl)-4-Hydroxy-3-methyl-5-(methylamino)-hexanoic acid]$^1$[(R)-methyl-Sar]$^3$cyclosporin A (Compound DY);
[(3R,4R,5S)-4-Hydroxy-3-methyl-5-(methylamino)-1-(piperidin-1-yl)-hexanoic acid]$^1$[(R)-methyl-Sar]$^3$cyclosporin A (Compound EA);
[(3R,4R,5S)-4-Hydroxy-3-methyl-5-(methylamino)-1-(2-trifluoromethyl-piperidin-1-yl)-hexanoic acid]$^1$[(R)-methyl-Sar]$^3$cyclosporin A (Compound EB);
[(3R,4R,5S)-4-Hydroxy-3-methyl-5-(methylamino)-1-(3-trifluoromethyl-morpholin-4-yl)-hexanoic acid]$^1$[(R)-methyl-Sar]$^3$cyclosporin A (Compound EC);
[(3R,4R,5S)-4-Hydroxy-3-methyl-5-(methylamino)-1-([1,2]oxazinan-2-yl)-hexanoic acid]$^1$[(R)-methyl-Sar]$^3$cyclosporin A (Compound ED);
[(3R,4R,5S)-4-Hydroxy-3-methyl-5-(methylamino)-1-(pyrrolidin-1-yl)-hexanoic acid]$^1$[(R)-methyl-Sar]$^3$cyclosporin A (Compound EF);
[[(3R,4R,5S)-4-Hydroxy-3-methyl-5-(methylamino)-1-(4-methyl-[1,4]diazepan-1-yl)-hexanoic acid]$^1$[(R)-methyl-Sar]$^3$cyclosporin A (Compound EG);
[[(3R,4R,5S)-4-Hydroxy-1-(3-methoxy-azetidin-1-yl)-3-methyl-5-(methylamino)-hexanoic acid]$^1$[(R)-methyl-Sar]$^3$cyclosporin A (Compound EH);
[(4R,5R,6S)-5-Hydroxy-4-methyl-6-(methylamino)-1-(morpholin-4-yl)-heptanoic acid]$^1$cyclosporin A (Compound EI);
[(3R,4R,5S)-4-Hydroxy-3-methyl-1-(morpholin-4-yl)-hexanoic acid]$^1$[(R)-methyl-Sar]$^3$[Ethyl-Val]$^4$cyclosporin A (Compound EJ);
[(3R,4R,5S)-4-Hydroxy-3-methyl-5-(methylamino)-1-(2,2,6,6-tetrafluoro-morpholin-4-yl)-hexanoic acid]$^1$[(R)-methyl-Sar]$^3$cyclosporin A (Compound EK);
[(3R,4R,5S)-(3,3-Difluoro-pyrrolidin-1-yl)-4-Hydroxy-3-methyl-5-(methylamino)-1-hexanoic acid]$^1$[(R)-methyl-Sar]$^3$cyclosporin A (Compound EL);
[(3R,4R,5S)-(3,3-Difluoro-azetidin-1-yl)-4-hydroxy-3-methyl-5-(methylamino)-1-hexanoic acid]$^1$[(R)-methyl-Sar]$^3$cyclosporin A (Compound EM);
[(3R,4R,5S)-(4,4-Difluoro-piperidin-1-yl)-4-hydroxy-3-methyl-5-(methylamino)-1-hexanoic acid]$^1$[(R)-methyl-Sar]$^3$cyclosporin A (Compound EN);
[(3R,4R,5S)-4-Hydroxy-3-methyl-5-(methylamino)-1-(3,3,4,4-tetrafluoro-pyrrolidin-1-yl)-hexanoic acid]$^1$[(R)-methyl-Sar]$^3$cyclosporin A (Compound ER);
3R,4R,5S)-4-Hydroxy-3-methyl-5-(methylamino)-1-(2,2,6,6-tetrafluoro-morpholin-4-yl)-hexanoic acid]$^1$[(R)-hydroxymethyl-Sar]$^3$cyclosporin A (Compound EO);
(3R,4R,5S)-1-(3,3-Difluoro-pyrrolidin-1-yl)-4-hydroxy-3-methyl-5-(methylamino)-hexanoic acid]$^1$[(R)-hydroxymethyl-Sar]$^3$cyclosporin A (Compound EP);
[(3R,4R,5S)-4-(hydroxy-3-methyl-5-(methylamino)-1-N-morpholino-hexanoic acid]$^1$cyclosporin A (Compound A);
[(3R,4R,5S)-4-Hydroxy-3-methyl-5-(methylamino)-1-morpholino-hexanoic acid]$^1$[(S)-thio-methyl-Sar]$^3$cyclosporin D (Compound AM);
[(3R,4R,5S)-4-(hydroxy-3-methyl-5-(methylamino)-1-N-morpholino-hexanoic acid]$^1$cyclosporin D (Compound AN);
[(6R,7R,8S)-7-Hydroxy-6-methyl-8-(methylamino)-1-N-morpholinyl-nonanoic acid]$^1$cyclosporin A (Compound C);
[(5R,6R,7S)-6-hydroxy-5-methyl-7-(methylamino)-1-N-morpholino-1-oxo-octanoic acid]$^1$cyclosporin A (Compound E);
[(3R,4R,5S)-4-(hydroxy-3-methyl-5-(methylamino)-1-N-methylpiperazinyl-hexanoic acid]$^1$cyclosporin A (Compound LL); and
[(3R,4R,5S)-4-hydroxy-3-methyl-5-(methylamino)-1-N-methylpiperazinyl-hexanoic acid]$^1$cyclosporin A (Compound NN).

11. A pharmaceutical composition comprising as active ingredient a therapeutically effective amount of a compound according to claim 1, or a pharmaceutically acceptable salt thereof, and a pharmaceutically acceptable excipient.

12. The pharmaceutical composition of claim 11, wherein the composition is in the form of an emulsion or an aqueous solution.

13. The pharmaceutical composition of claim 11, wherein the composition is acceptable for administration to an eye of a mammal.

14. The compound of claim 1, wherein $R^1$ is —H, —CH$_2$F, —CH$_2$OCH$_3$, —CH$_3$, —CH$_2$CH$_3$, —SCH$_3$, —SCH(CH$_3$)$_2$, —CH$_2$OH, —OCH$_3$, —R$^{13}$R$^{14}$,

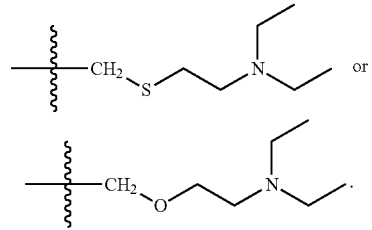

15. The compound of claim 14, wherein $R^1$ is —CH$_3$, —SCH$_3$, —OCH$_3$ or —CH$_2$OH; $R^8$ is CH$_2$; and m is 0.

16. The compound according to claim 15, wherein the heterocycle formed by $R^9$, $R^{10}$, $R^{11}$, and the N to which $R^9$ and $R^{11}$ are attached taken together is substituted by an alkyl, halogen or haloalkyl.

17. The compound according to claim 16, wherein said substituted heterocycle is substituted by —CF$_3$ or fluorine.

* * * * *